United States Patent
Gummadi et al.

(10) Patent No.: US 10,160,753 B2
(45) Date of Patent: Dec. 25, 2018

(54) INDAZOLE COMPOUNDS AS IRAK4 INHIBITORS

(71) Applicant: Aurigene Discovery Technologies Limited, Bangalore (IN)

(72) Inventors: Venkateshwar Rao Gummadi, Bangalore (IN); Susanta Samajdar, Bangalore (IN); Ajay Gupta, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 15/110,309

(22) PCT Filed: Jan. 7, 2015

(86) PCT No.: PCT/IB2015/050119
§ 371 (c)(1),
(2) Date: Jul. 7, 2016

(87) PCT Pub. No.: WO2015/104662
PCT Pub. Date: Jul. 16, 2015

(65) Prior Publication Data
US 2016/0326151 A1    Nov. 10, 2016

(30) Foreign Application Priority Data

Jan. 10, 2014  (IN) .............................. 146/CHE/2014
Jun. 20, 2014  (IN) ............................. 3018/CHE/2014

(51) Int. Cl.
| C07D 413/14 | (2006.01) |
| C07D 401/14 | (2006.01) |
| C07D 405/14 | (2006.01) |
| C07F 9/11   | (2006.01) |

(52) U.S. Cl.
CPC ......... *C07D 413/14* (2013.01); *C07D 401/14* (2013.01); *C07D 405/14* (2013.01); *C07F 9/11* (2013.01)

(58) Field of Classification Search
CPC ... C07D 413/14; C07D 401/14; C07D 405/14
See application file for complete search history.

(56) References Cited

U.S. PATENT DOCUMENTS

| 7,338,950 B2 | 3/2008 | Kelly et al. | |
| 9,732,095 B2 | 8/2017 | Gummadi et al. | |
| 9,855,273 B2 | 1/2018 | Starczynowski et al. | |
| 2006/0160861 A1* | 7/2006 | Bohlmann | C07D 403/14 514/338 |
| 2009/0069288 A1* | 3/2009 | Breinlinger | C07D 231/14 514/210.18 |
| 2010/0210619 A1* | 8/2010 | Bombrun | C07D 239/42 514/210.18 |
| 2011/0224137 A1* | 9/2011 | Ting | C07D 413/12 514/5.9 |
| 2012/0015962 A1 | 1/2012 | Arora et al. | |
| 2012/0053345 A1 | 3/2012 | Ericson et al. | |

FOREIGN PATENT DOCUMENTS

| EP | 1627869 A1 | 2/2006 |
| GB | 2406856 A | 4/2005 |
| WO | WO-2004/098518 A2 | 11/2004 |
| WO | WO-2004/108133 A2 | 12/2004 |
| WO | WO-2006/053227 A2 | 5/2006 |
| WO | WO-2007/095124 A2 | 8/2007 |
| WO | WO-2007/117465 A2 | 10/2007 |
| WO | WO-2008/030579 A2 | 3/2008 |
| WO | WO-2008/030584 A2 | 3/2008 |
| WO | WO-2008073825 A1 | 6/2008 |
| WO | WO-2009/12312 A1 | 1/2009 |
| WO | WO-2009/019167 A1 | 2/2009 |
| WO | WO-2010/071819 A1 | 6/2010 |
| WO | WO-2011/137219 A1 | 11/2011 |
| WO | WO-2012/084704 A1 | 6/2012 |
| WO | WO-2013/042137 A1 | 3/2013 |
| WO | WO-2013/068458 A1 | 5/2013 |
| WO | WO-2014/003483 A1 | 1/2014 |

(Continued)

OTHER PUBLICATIONS

Ex parte Cao, Decision rendered by the Board of Patent Appeals and Interferences in U.S. Appl. No. 10/696,862 on Sep. 21, 2011 (Year: 2011).*
International Search Report from published parent PCT application PCT/IB2015/050119 dated Mar. 19, 2015.
Alder, C. M. et al., "Identification of a Novel and Selective Series of Itk Inhibitors via a Template-Hopping Strategy", *Med. Chem. Lett.*, 4:948-952 (American Chemical Society, 2013).
International Search Report from parent PCT application PCT/IB2015/050217 dated Apr. 29, 2015.
Extended European Search Report issued by the European Patent Office in corresponding International Application No. PCT/IB2015/050217, dated May 2, 2017.
International Search Report from parent PCT application PCT/IB2015/054620 dated Oct. 19, 2015.
Extended European Search Report issued by the European Patent Office in corresponding Application No. PCT/IB2015054620 dated Jan. 16, 2018.

(Continued)

*Primary Examiner* — Matthew P Coughlin
(74) *Attorney, Agent, or Firm* — Foley Hoag LLP; David P. Halstead; Alexander J. Chatterley

(57) ABSTRACT

The present invention provides indazole compounds of formula (I), which are therapeutically useful as kinase inhibitors, particularly IRAK4 inhibitors, wherein $Z_1$, $Z_2$, $R_1$, $R_2$, $R_3$, 'm' and 'n' have the meanings given in the specification, and pharmaceutically acceptable salts or stereoisomers thereof that are useful in the treatment and prevention of diseases or disorders, in particular their use in diseases or disorders mediated by kinase enzyme, particularly IRAK4 enzyme. The present invention also provides pharmaceutical compositions comprising at least one of the compounds of the compound of formula (I) together with a pharmaceutically acceptable carrier, diluent or excipient.

42 Claims, No Drawings

(56) References Cited

FOREIGN PATENT DOCUMENTS

| WO | WO-2015/091426 A1 | 6/2015 |
| WO | WO-2015/104662 A1 | 7/2015 |
| WO | WO-2017/023941 A1 | 2/2017 |

OTHER PUBLICATIONS

International Search Report and Written Opinion for International Application No. PCT/IB2016/054203 dated Sep. 23, 2016.

* cited by examiner

INDAZOLE COMPOUNDS AS IRAK4 INHIBITORS

RELATED APPLICATIONS

This application is the U.S. national phase of International Patent Application No. PCT/IB2015/050119, filed Jan. 7, 2015, which claims the benefit of Indian provisional applications 146/CHE/2014 filed on Jan. 10, 2014, and 3018/CHE/2014 filed on Jun. 20, 2014, which are hereby incorporated by reference in their entirety.

FIELD OF THE INVENTION

This invention relates to compounds useful for treatment of cancer and inflammatory diseases associated with Interleukin-1 Receptor Associated Kinase (IRAK) and more particularly compounds that modulate the function of IRAK-4. The invention also provides pharmaceutically acceptable compositions comprising compounds of the present invention and methods of using said compositions in the treatment of diseases associated with IRAK-4.

BACKGROUND OF THE INVENTION

Interleukin-1 (IL-1) Receptor-Associated Kinase-4 (IRAK-4) is a serine/threonine kinase enzyme that plays an essential role in signal transduction by Toll/IL-1 receptors (TIRs). Diverse IRAK enzymes are key components in the signal transduction pathways mediated by interleukin-1 receptor (IL-1R) and Toll-like receptors (TLRs) (Janssens, S, et al. Mol. Cell. 11(2), 2003, 293-302). There are four members in the mammalian IRAK family: IRAK-1, IRAK-2, IRAK-M and IRAK-4. These proteins are characterized by a typical N-terminal death domain that mediates interaction with MyD88-family adaptor proteins and a centrally located kinase domain. The IRAK proteins, as well as MyD88, have been shown to play a role in transducing signals other than those originating from IL-1R receptors, including signals triggered by activation of IL-18 receptors (Kanakaraj, et al. J. Exp. Med. 189(7), 1999, 1129-38) and LPS receptors (Yang, et al., J. Immunol. 163(2), 1999, 639-643). Out of four members in the mammalian IRAK family, IRAK-4 is considered to be the "master IRAK". Under overexpression conditions, all IRAKs can mediate the activation of nuclear factor-κB (NF-κB) and stress-induced mitogen activated protein kinase (MAPK)-signaling cascades. However, only IRAK-1 and IRAK-4 have been shown to have active kinase activity. While IRAK-1 kinase activity could be dispensable for its function in IL-1-induced NF-κB activation (Kanakaraj et al, J. Exp. Med. 187(12), 1998, 2073-2079) and (Li, et al. Mol. Cell. Biol. 19(7), 1999, 4643-4652), IRAK-4 requires its kinase activity for signal transduction [(Li S, et al. Proc. Natl. Acad. Sci. USA 99(8), 2002, 5567-5572) and (Lye, E et al, J. Biol. Chem. 279(39); 2004, 40653-8)]. Given the central role of IRAK4 in Toll-like/IL-1R signalling and immunological protection, IRAK4 inhibitors have been implicated as valuable therapeutics in inflammatory diseases, sepsis and autoimmune disorders (Wietek C, et al, Mol. Interv. 2: 2002, 212-215).

Mice lacking IRAK-4 are viable and show complete abrogation of inflammatory cytokine production in response to IL-1, IL-18 or LPS (Suzuki et al. Nature, 416(6882), 2002, 750-756). Similarly, human patients lacking IRAK-4 are severely immunocompromised and are not responsive to these cytokines (Medvedev et al. J. Exp. Med., 198(4), 2003, 521-531 and Picard et al. Science 299(5615), 2003, 2076-2079). Knock-in mice containing inactive IRAK4 were completely resistant to lipopolysaccharide- and CpG-induced shock (Kim T W, et al. J. Exp. Med 204(5), 2007, 1025-36) and (Kawagoe T, et al. J. Exp. Med. 204(5): 2007, 1013-1024) and illustrated that IRAK4 kinase activity is essential for cytokine production, activation of MAPKs and induction of NF-κB regulated genes in response to TLR ligands (Koziczak-Holbro M, et al. J. Biol. Chem. 282(18): 2007; 13552-13560). Inactivation of IRAK4 kinase (IRAK4 KI) in mice leads to resistance to EAE due to reduction in infiltrating inflammatory cells into CNS and reduced antigen specific CD4+ T-cell mediated IL-17 production (Staschke et al. The Journal of Immunology, 183(1), 2009, 568-577).

The crystal structures revealed that IRAK-4 contains characteristic structural features of both serine/threonine and tyrosine kinases, as well as additional novel attributes, including the unique tyrosine gatekeeper residue. Structural analysis of IRAK-4 revealed the underlying similarity with kinase family; ATP-binding cleft sandwiched between a bilobal arrangements. The N-terminal lobe consists of mainly of a twisted five-stranded antiparallel beta-sheet and one alpha-helix, and the larger C-terminal lobe is predominantly alpha-helical. Yet, the structure reveals a few unique features for IRAK-4 kinase, including an additional alpha-helix from the N-terminal extension in the N-terminal lobe, a longer loop between helices alpha-D and alpha-E, and a significantly moved helix alpha G as well as its adjoining loops. The ATP-binding site in IRAK-4 has no deep pocket in the back but has a featured front pocket. This uniquely shaped binding pocket provides an excellent opportunity for designing IRAK-4 inhibitors.

The development of IRAK-4 kinase inhibitors has generated several novel classes of protein binders which includes thiazole and pyridine amides (George M Buckley, et al. Bioorg. Med. Chem. Lett., 18(11), 2008, 3211-3214), aminobenzimidazoles (Powers J P, et al. Bioorg. Med. Chem. Lett., 16(11), 2006, 2842-2845), Imidazo[1,2-a] pyridines (Buckley G M, et al. Bioorg. Med. Chem. Lett. 18(12), 2008, 3656-3660) and (Buckley G M, et al. Bioorg. Med. Chem. Lett. 18(11), 2008, 3291-3295), imidazo[1,2-b] pyridazines and benzimidazole-indazoles (WO2008030579; WO2008030584). Apparently, all of them are still in the early preclinical stage.

Despite various disclosures on different kinase inhibitors, however, with the rise in number of patients affected by kinase enzyme mediated diseases, there appears to be unmet need for newer drugs that can treat such diseases more effectively. There is still need for newer kinase inhibitors including multikinase inhibitors, which may be further useful in treatment of disorders owing to variations in various kinases activity and possessing broader role. They may also be useful as part of other therapeutic regimens for the treatment of disorders, alone or in combination with protein kinase compounds well known by the one skilled in the art.

OBJECTIVES OF THE INVENTION

One objective herein is to provide indazole compounds of formula (I) as kinase inhibitors, particularly IRAK4 inhibitors.

Another objective is to provide a pharmaceutical composition comprising the compound of formula (I) or pharmaceutically acceptable salt or stereoisomer thereof, and atleast one pharmaceutically acceptable excipient such as a pharmaceutically acceptable carrier or diluent.

Yet another objective is to provide a use of Indazole compound of formula (I) or pharmaceutically acceptable salt or stereoisomer thereof for the treatment and/or prevention of diseases or disorders, in particular their use in diseases or disorder mediated by kinase enzyme, more particularly IRAK4 enzyme.

SUMMARY OF THE INVENTION

Provided herein is a compound of formula (I),

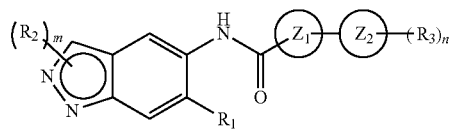

(I)

or a pharmaceutically acceptable salt or a stereoisomer thereof;
wherein,
Ring $Z_1$ is an optionally substituted heteroaryl;
Ring $Z_2$ is a optionally substituted heterocycloalkyl, optionally substituted heteroaryl or a direct bond;
$R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;
$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
$R_3$, at each occurrence, independently is hydrogen, halogen, alkyl, haloalkyl, haloalkoxy, alkoxy, —$NR_aR_b$, hydroxyl or hydroxyalkyl;
$R_a$ is hydrogen or alkyl;
$R_b$ is hydrogen, alkyl, acyl, hydroxyalkyl, —$SO_2$-alkyl or optionally substituted cycloalkyl;
'm' and 'n' are independently 1 or 2.
In yet another aspect, the present invention provides a pharmaceutical composition comprising the compound of formula (I) or a pharmaceutically acceptable salt or a stereoisomer thereof, and atleast one pharmaceutically acceptable excipient (such as a pharmaceutically acceptable carrier or diluent).

In yet further aspect of the present application, it provides use of compound of formula (I) or a pharmaceutically acceptable salt or a stereoisomer thereof for the treatment and prevention in diseases or disorder mediated by IRAK4 enzyme.

More particularly, the invention relates to the use of indazole compound of formula (I) or a pharmaceutically acceptable salt or a stereoisomer thereof, including mixtures thereof in all ratios as a medicament, by inhibiting IRAK or IRAK4 other related kinases.

The compound of formula (I) of the present invention possess therapeutic role of inhibiting IRAK or IRAK4 related kinases useful in the area of diseases and/or disorders include, but are not limited to cancers, allergic diseases and/or disorders, autoimmune diseases and/or disorders, inflammatory diseases and/or disorder and/or conditions associated with inflammation and pain, proliferative diseases, hematopoietic disorders, hematological malignancies, bone disorders, fibrosis diseases and/or disorders, metabolic disorders and/or diseases, muscle diseases and/or disorders respiratory diseases and/or disorders, pulmonary disorders, genetic developmental diseases and/or disorders, neurological and neurodegenerative diseases and/or disorders, chronic inflammatory demyelinating neuropathies, cardiovascular, vascular or heart diseases and/or disorders, ophthalmic/ocular diseases and/or disorders, wound repair, infection and viral diseases. Therefore, inhibition of one or more of kinases would have multiple therapeutic indications.

DETAILED DESCRIPTION OF THE INVENTION

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" refers to a group R—CO— wherein R is an alkyl group defined above. Examples of 'acyl' groups are, but not limited to, CH₃CO—, CH₃CH₂CO—, CH₃CH₂CH₂CO— or (CH₃)₂CHCO—.

As used herein, the term "alkoxy" refers to a straight or branched, saturated aliphatic $C_1$-$C_{10}$ hydrocarbon radical bonded to an oxygen atom that is attached to a core structure. Preferably, alkoxy groups have one to six carbon atoms. Examples of alkoxy groups include but are not limited to methoxy, ethoxy, propoxy, isopropoxy, butoxy, isobutoxy, tert-butoxy, pentoxy, 3-methyl butoxy and the like.

As used herein, the term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy (—OCHF₂), trifluoromethoxy (—OCF₃) or trifluoroethoxy (—OCH₂CF₃).

As used herein, the term "aryl" alone or in combination with other term(s) means a 6- to 10-membered carbocyclic aromatic system containing one or two rings wherein such rings may be fused. The term "fused" means that the second ring is attached or formed by having two adjacent atoms in common with the first ring. The term "fused" is equivalent to the term "condensed". Examples of aryl groups include but are not limited to phenyl, naphthyl or indanyl and the like. Unless otherwise specified, all aryl groups described herein may be optionally substituted.

As used herein, "amino" refers to an —NH₂ group.

As used herein, "aminoalkyl" refers to an amino group, as defined above, in which one or two hydrogen atoms are substituted with alkyl group.

As used herein, "nitro" refers to an —NO₂ group.

As used herein, "alkylamino" and "cycloalkylamino", refer to an —N-group, wherein nitrogen atom of said group being attached to alkyl or cycloalkyl respectively. Representative examples of an "Alkylamino" and "Cycloalkylamino" groups include, but are not limited to —NHCH₃ and —NH-cyclopropyl. An amino group can be optionally substituted with one or more of the suitable groups.

As used herein the term "cycloalkyl" alone or in combination with other term(s) means $C_3$-$C_{10}$ saturated cyclic hydrocarbon ring. A cycloalkyl may be a single ring, which typically contains from 3 to 7 carbon ring atoms. Examples of single-ring cycloalkyls include cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused, and spirocyclic carbocyclyls.

As used herein, the term "cyano" refers to —CN group.

As used herein, the term "hydroxy" or "hydroxyl" refers to —OH group.

As used herein the term "hydroxyalkyl" or "hydroxylalkyl" means alkyl substituted with one or more hydroxyl groups, wherein the alkyl groups are as defined above. Examples of "hydroxyalkyl" include but are not limited to hydroxymethyl, hydroxyethyl, hydroxypropyl, propan-2-ol and the like.

As used herein, the term "halo" or "halogen" alone or in combination with other term(s) means fluorine, chlorine, bromine or iodine.

As used herein, the term "heterocyclyl" includes definitions of "heterocycloalkyl" and "heteroaryl".

As used herein, the term "heterocycloalkyl" refers to a non-aromatic, saturated or partially saturated, monocyclic or polycyclic ring system of 3 to 15 member having at least one heteroatom or heterogroup selected from O, N, S, S(O), S(O)₂, NH or C(O) with the remaining ring atoms being independently selected from the group consisting of carbon, oxygen, nitrogen, and sulfur. Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-azabicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocycloalkyl" includes azetidinyl, pyrrolidinyl, morpholinyl and piperidinyl. All heterocycloalkyl are optionally substituted by one or more aforesaid groups.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Preferably "heteroaryl" refers to 5- to 6-membered ring selected from the group consisting of furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more aforesaid groups.

As used herein, the term 'compound(s)' comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

The phrase "pharmaceutically acceptable" refers to compounds or compositions that are physiologically tolerable and do not typically produce allergic or similar untoward reaction, including but not limited to gastric upset or dizziness when administered to mammal.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts, and the like. Certain compounds of the invention (compound of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium, or zinc, salts.

As used herein, the term "stereoisomer" is a term used for all isomers of individual compounds of compound of formula (I) that differ only in the orientation of their atoms in space. The term stereoisomer includes mirror image isomers (enantiomers) of compound of formula (I), mixtures of mirror image isomers (racemates, racemic mixtures) of compound of formula (I), geometric (cis/trans or E/Z, R/S) isomers of compound of formula (I) and isomers of compound of formula (I) with more than one chiral center that are not mirror images of one another (diastereoisomers).

As used herein, the term "composition" is intended to encompass a product comprising the specified ingredients in the specified amounts, as well as any product which results, directly or indirectly, from combination of the specified ingredients in the specified amounts.

As used herein, the term "pharmaceutical composition" refers to a composition(s) containing a therapeutically effective amount of at least one compound of formula (I) or its pharmaceutically acceptable salt; and a conventional pharmaceutically acceptable carrier.

The pharmaceutical composition(s) of the present invention can be administered orally, for example in the form of tablets, coated tablets, pills, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermals, in the form of patches, or in other ways, for example in the form of aerosols or nasal sprays.

The pharmaceutical composition(s) usually contain(s) about 1% to 99%, for example, about 5% to 75%, or from about 10% to about 30% by weight of the compound of formula (I) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. The examples of carriers, stabilizers and adjuvant are mentioned in literature like, Martin, Remington's Pharmaceutical Sciences, 15th Ed., Mack Publ. Co., Easton, Pa. [1975].

The term "treatment"/"treating" means any treatment of a disease in a mammal, including: (a) Inhibiting the disease, i.e., slowing or arresting the development of clinical symptoms; and/or (b) Relieving the disease, i.e., causing the regression of clinical symptoms and/or (c) alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" refers to an animal, preferably a mammal, and most preferably a human.

As used herein, the term, "therapeutically effective amount" refers to an amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a disease or disorder mediated by kinase enzymes, particularly IRAK or IRAK4 enzyme. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

In one embodiment, the present invention provides the compound of formula (I)

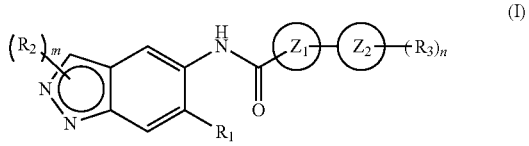

(I)

or a pharmaceutically acceptable salt or a stereoisomer thereof;
wherein,

Ring $Z_1$ is an optionally substituted heteroaryl;

Ring $Z_2$ is an optionally substituted heterocycloalkyl, optionally substituted heteroaryl or a direct bond;

$R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—CH$_2$—O-alkyl, —OP(O)(O-alkyl)$_2$ or —CH$_2$—OP(O)(O-alkyl)$_2$;

$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;

$R_3$, at each occurrence, independently is hydrogen, halogen, alkyl, haloalkyl, haloalkoxy, alkoxy, —$NR_aR_b$, hydroxyl or hydroxyalkyl;

$R_a$ is hydrogen or alkyl;

$R_b$ is hydrogen, alkyl, acyl, hydroxyalkyl, —SO$_2$-alkyl or optionally substituted cycloalkyl;

'm' and 'n' are independently 1 or 2.

In another embodiment, the present invention provides the compound of formula (I) or a pharmaceutically acceptable salt or a stereoisomer thereof; wherein, Ring $Z_1$ is a 5- or 6-membered optionally substituted heteroaryl.

In another embodiment, the present invention provides the compound of formula (I) or a pharmaceutically acceptable salt or a stereoisomer thereof; wherein Ring $Z_1$ is an optionally substituted heteroaryl; wherein the optional substituent is alkyl;

In another embodiment, the compound of formula (I) or a pharmaceutically acceptable salt thereof, wherein Ring $Z_1$ is selected from the group consisting of tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl and pyrazolyl.

In another embodiment, the compound of formula (I) or a pharmaceutically acceptable salt thereof, wherein Ring $Z_1$ is selected from the group consisting of pyridyl, oxazolyl and furanyl; wherein the pyridyl group is optionally substituted with alkyl; in particular alkyl is methyl.

In another embodiment, the compound of formula (I) or a pharmaceutically acceptable salt thereof, wherein Ring $Z_2$ is a 5- or 6-membered heteroaryl selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In another embodiment, the compound of formula (I) or a pharmaceutically acceptable salt thereof, wherein Ring $Z_2$ is a 5- or 6-membered heterocycloalkyl selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl or 1,4-dioxanyl.

In yet another embodiment, the compound of formula (I) or a pharmaceutically acceptable salt thereof, wherein Ring $Z_2$ is pyridyl, pyrazolyl or pyrrolidinyl.

In another embodiment, the compound of formula (I) or a pharmaceutically acceptable salt thereof, wherein Ring $Z_2$ is a direct bond.

In another embodiment, the compound of formula (I) is compound of formula (IA)

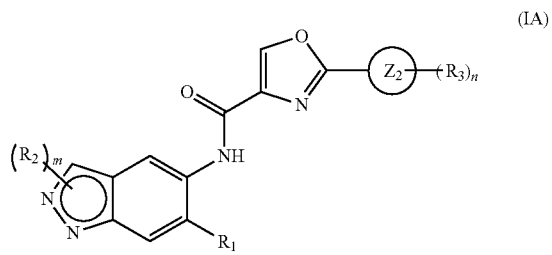

(IA)

or a pharmaceutically acceptable salt thereof;

wherein, $Z_2$, $R_1$, $R_2$, $R_3$, 'm' and 'n' are same as defined in compound of formula (I).

In yet another embodiment, the compound of formula (I) is compound of formula (IB)

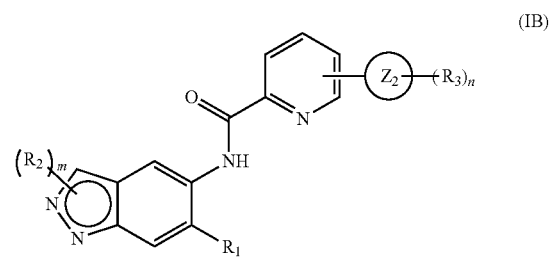

(IB)

or a pharmaceutically acceptable salt thereof;

wherein, $Z_2$, $R_1$, $R_2$, $R_3$, 'm' and 'n' are same as defined in compound of formula (I).

In yet another embodiment, the compound of formula (I) is compound of formula (IC)

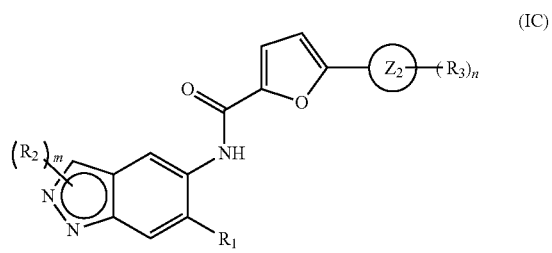

(IC)

or a pharmaceutically acceptable salt thereof;

wherein, $Z_2$, $R_1$, $R_2$, $R_3$, 'm' and 'n' are same as defined in compound of formula (I).

The embodiments below are illustrative of the present invention and are not intended to limit the claims to the specific embodiments exemplified.

According to one embodiment, specifically provided are compound of formula (I) wherein

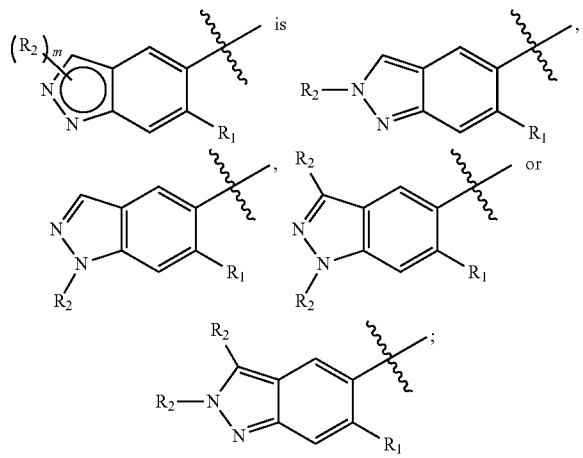

wherein $R_1$, $R_2$ and 'm' are same as defined in compound of formula (I).

According to one embodiment, specifically provided is compound of formula (I) or a pharmaceutically acceptable salt thereof, wherein Ring $Z_2$ is pyridyl.

According to one embodiment, specifically provided is compound of formula (I) or a pharmaceutically acceptable salt thereof, wherein Ring $Z_2$ is pyrazolyl.

According to one embodiment, specifically provided is compound of formula (I) or a pharmaceutically acceptable salt thereof, wherein Ring $Z_2$ is pyrrolidinyl.

According to one embodiment, specifically provided is compound of formula (I) or a pharmaceutically acceptable salt thereof, wherein $R_1$ is optionally substituted heterocyclyl; wherein the substituent is halogen, hydroxyl, hydroxyalkyl, amino, aminoalkyl, —OCO—$CH_2$—O-alkyl, —OP(O)(O-alkyl)$_2$ or —$CH_2$—OP(O)(O-alkyl)$_2$.

According to one embodiment, specifically provided is compound of formula (I) or a pharmaceutically acceptable salt thereof, wherein $R_1$ is optionally substituted azetidinyl, piperidinyl, morpholinyl, pyrrolidinyl or azepanyl; wherein the substituent is amino, halogen, hydroxyl, hydroxyalkyl, aminoalkyl, —OCO—$CH_2$—O-alkyl, —OP(O)(O-alkyl)$_2$ or —$CH_2$—OP(O)(O-alkyl)$_2$.

According to one embodiment, specifically provided is compound of formula (I) or a pharmaceutically acceptable salt thereof, wherein $R_1$ is optionally substituted piperidinyl; wherein the substituent is hydroxyl.

According to one embodiment, specifically provided is compound of formula (I) or a pharmaceutically acceptable salt thereof, wherein $R_1$ is optionally substituted phenyl; wherein the substituent is halogen.

According to one embodiment, specifically provided is compound of formula (I) or a pharmaceutically acceptable salt thereof, wherein $R_1$ is cycloalkyl.

According to one embodiment, specifically provided is compound of formula (I) or a pharmaceutically acceptable salt thereof, wherein $R_1$ is cyclopropyl or cyclohexyl.

According to one embodiment, specifically provided is compound of formula (I) or a pharmaceutically acceptable salt thereof, wherein $R_1$ is —$NR_aR_b$; $R_a$ is hydrogen; $R_b$ is optionally substituted cycloalkyl; wherein the substituent is hydroxyl.

According to one embodiment, specifically provided are compounds of formula (I) or a pharmaceutically acceptable salt thereof, wherein $R_1$ is cyano.

According to one embodiment, specifically provided is compound of formula (I) or a pharmaceutically acceptable salt thereof, wherein $R_2$ is optionally substituted alkyl; wherein substituent is alkoxy.

According to one embodiment, specifically provided is compound of formula (I) or a pharmaceutically acceptable salt thereof, wherein $R_2$ is cycloalkyl.

According to one embodiment, specifically provided is compound of formula (I) or a pharmaceutically acceptable salt thereof, wherein $R_3$ is hydrogen, halogen, alkyl, alkoxy, —$NR_aR_b$, hydroxyl or hydroxyalkyl; $R_a$ is hydrogen or alkyl; and $R_b$ is hydrogen, alkyl, acyl, hydroxyalkyl or —$SO_2$-alkyl.

According to one embodiment, specifically provided is compound of formula (I) or a pharmaceutically acceptable salt thereof, wherein Ring $Z_1$ is optionally substituted pyridyl; Ring $Z_2$ is pyridyl, pyrazolyl, pyrrolidinyl or direct bond; $R_1$ is an optionally substituted group selected from cyclopropyl, piperidinyl, morpholinyl or pyrrolidinyl; $R_2$ is optionally substituted alkyl or cycloalkyl; $R_3$ is hydrogen, halogen, alkyl, alkoxy, —$NR_aR_b$, hydroxyl or hydroxyalkyl; $R_a$ is hydrogen or alkyl; and $R_b$ is hydrogen or hydroxyalkyl.

According to one embodiment, specifically provided is compound of formula (I) or a pharmaceutically acceptable salt thereof, wherein Ring $Z_1$ is oxazolyl; Ring $Z_2$ is pyridyl, pyrazolyl or pyrrolidinyl; $R_1$ is cyano, —$NR_aR_b$, or an optionally substituted group selected from cyclopropyl, cyclohexyl, phenyl, azetidinyl, piperidinyl, morpholinyl or pyrrolidinyl; $R_2$ is optionally substituted alkyl or cycloalkyl; $R_3$ is hydrogen, halogen, alkyl, alkoxy, —$NR_aR_b$, hydroxyl or hydroxyalkyl; $R_a$ is hydrogen or alkyl; and $R_b$ is hydrogen, alkyl, acyl, hydroxyalkyl, —$SO_2$-alkyl or optionally substituted cycloalkyl.

According to one embodiment, specifically provided is compound of formula (I) or a pharmaceutically acceptable salt thereof, wherein $R_3$ is —$NR_aR_b$; $R_a$ is hydrogen or alkyl; and $R_b$ is hydrogen, alkyl, acyl, hydroxyalkyl, —$SO_2$-alkyl or optionally substituted cycloalkyl; wherein the optional substituent is hydroxyl;

According to one embodiment, specifically provided is compound of formula (I), wherein 'n' is 1.

According to one embodiment, specifically provided is compound of formula (I), wherein 'n' is 2.

According to one embodiment, specifically provided is compound of formula (I), wherein 'm' is 1.

According to one embodiment, specifically provided is compound of formula (I), wherein 'm' is 2.

In a further embodiment, the present invention relates to a process for preparing indazole compound of formula (I).

In a further embodiment, the present invention relates to a pharmaceutical composition, comprising at least one compound of formula (I), or a pharmaceutically acceptable salt or a stereoisomer thereof, and a pharmaceutically acceptable carrier or excipient.

In a further embodiment, the present invention relates to a compound or a pharmaceutically acceptable salt or a stereoisomer thereof, for use as a medicament.

In a further embodiment, the present invention relates to a method of treating IRAK4 mediated disorders or diseases or condition in a subject comprising administering a therapeutically effective amount of a compound of formula (I) or (IA) or (IB) or (IC).

In a further embodiment, the IRAK-mediated disorder or disease or condition is selected from the group consisting of a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder and a CNS disorder.

In a further embodiment, the IRAK-mediated disorder or disease or condition is selected from the group consisting of a cancer, an inflammatory disorder, a an autoimmune disease, metabolic disorder, a hereditary disorder, a hormone-related disease, immunodeficiency disorders, a condition associated with cell death, a destructive bone disorder, thrombin-induced platelet aggregation, liver disease, pathologic immune conditions involving T cell activation and a cardiovascular disorder.

In a further embodiment, wherein the cancer or proliferative disorder is selected the group consisting of a solid tumor, benign or malignant tumor, carcinoma of the brain, kidney, liver, stomach, vagina, ovaries, gastric tumors, breast, bladder colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, papillary carcinoma, seminoma, melanoma; hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulnemia (WM), splenic marginal zone lymphoma, intravascular large B-cell lymphoma, plasmacytoma and multiple myeloma.

In a further embodiment, the neurodegenerative disease is selected from the group consisting of Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy and graft versus host disease.

In a further embodiment, the inflammatory disorder is selected from the group consisting of ocular allergy, conjunctivitis, keratoconjunctivitis sicca, vernal conjunctivitis, allergic rhinitis, autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, primary biliary cirrhosis, uveitis (anterior and posterior), Sjogren's syndrome, interstitial lung fibrosis, psoriatic arthritis, systemic juvenile idiopathic arthritis, nephritis, vasculitis, diverticulitis, interstitial cystitis, glomerulonephritis (e.g. including idiopathic nephrotic syndrome or minimal change nephropathy), chronic granulomatous disease, endometriosis, leptospirosis renal disease, glaucoma, retinal disease, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, fibrositis, gastritis, gastroenteritis, nasal sinusitis, ocular allergy, silica induced diseases, chronic obstructive pulmonary disease (COPD), cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, juvenile rheumatoid arthritis, dermatomyositis, encephalitis, endocarditis, endometritis, enteritis, enterocolitis, epicondylitis, epididymitis, fasciitis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Cryopyrin Associated Periodic Syndrome (CAPS) and osteoarthritis.

In a further embodiment, a compound of formula (I) or (IA) or (IB) or (IC) or a pharmaceutically acceptable salt or a stereoisomer thereof, for use for the treatment of a cancer, an inflammatory disorder, a an autoimmune disease, metabolic disorder, a hereditary disorder, a hormone-related disease, immunodeficiency disorders, a condition associated with cell death, a destructive bone disorder, thrombin-induced platelet aggregation, liver disease, pathologic immune conditions involving T cell activation and a cardiovascular disorder.

In a further embodiment, use of the compound of formula (I) or (IA) or (IB) or (IC) or a pharmaceutically acceptable salt or a stereoisomer thereof, in the manufacture of a medicament for the treatment of cancer, an inflammatory disorder, a an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder.

An embodiment of the present invention provides the IRAK4 inhibitor compounds according to of formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures. Moreover, by utilizing the procedures described in detail, one of ordinary skill in the art can prepare additional compounds of the present invention claimed herein. All temperatures are in degrees Celsius (° C.) unless otherwise noted.

In a further embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2H$ ("D"), $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{15}F$, $^{36}Cl$, $^{123}I$ and $^{125}I$. Isotopically labeled compounds of the present inventions can generally be prepared by following procedures analogous to those disclosed in the Schemes and/or in the Examples herein below, by substituting an isotopically labeled reagent for a non-isotopically labeled reagent.

It is understood that substitution patterns and substituents on the compounds of the present invention can be selected by an ordinary skilled person in the art to provide compounds that are chemically stable and that can be readily synthesized by techniques known in the art, as well as those methods set forth below, from readily available starting materials. If a substituent itself is substituted with more than one group, it is understood that these multiple groups may be on the same carbon or on different carbons, as long as a stable structure is resulted.

The MS (Mass Spectral) data provided in the examples were obtained using the equipments—
API 2000 LC/MS/MS/Triplequad,
Agilent (1100) Technologies/LC/MS/DVL/Singlequad and
Shimadzu LCMS-2020/Singlequad.

The NMR data provided in the examples were obtained using the equipment—$^1H$-NMR: Varian—300, 400 and 600 MHz.

The abbreviations used in the entire specification may be summarized herein below with their particular meaning.

° C. (degree Celsius); δ (delta); % (percentage); $Ac_2O$ (Acetic anhydride); $(BOC)_2O$ (Bocanhydride); bs (Broad singlet); $CDCl_3$ (Deuterated chloroform); $CH_2Cl_2$/DCM (Dichloromethane); DAST (Diethylaminosulfur trifluoride); DMF (Dimethyl formamide); DMSO (Dimethyl sulphoxide); DIPEA/DIEA (N, N-Diisopropyl ethylamine); DMAP (Dimethyl amino pyridine); (DMSO-$d_6$) (Deuteriated DMSO); d (Doublet); dd (Doublet of doublet); EDCI.HCl (1-(3-Dimethyl aminopropyl)-3-carbodiimide hydrochloride); EtOAc (Ethyl acetate); EtOH (Ethanol); Fe (Iron powder); g or gm (gram); HATU (1-[bis(dimethylamino) methylene]-1H-1,2,3-triazolo[4,5-b]pyridinium 3-oxid hexafluorophosphate); H or $H_2$ (Hydrogen); $H_2O$ (Water); HOBt (1-Hydroxy benzotriazole); $H_2SO_4$ (Sulphuric acid); HCl (Hydrochloric acid); h or hr (Hours); Hz (Hertz); HPLC (High-performance liquid chromatography); J (Coupling constant); $K_2CO_3$ (Potassium carbonate); KOAc (Potassium Acetate); $KNO_3$ (Potassium nitrate); LiOH (Lithium hydroxide); NaHMDS (Sodiumbis(trimethylsilyl)amide); MeOH/$CH_3OH$ (Methanol); mmol (Millimol); M (Molar); ml (Milliliter); mg (Milli gram); m (Multiplet); mm (Millimeter); MHz (Megahertz); MS (ES) (Mass spectroscopy-electro spray); min (Minutes); NaH (Sodium hydride); $NaHCO_3$ (Sodium bicarbonate); $Na_2SO_4$ (Sodium sulphate); $N_2$ (Nitrogen); NMR (Nuclear magnetic resonance spectroscopy); NMP (N-Methyl-2-pyrrolidone); Pd/C (palladium carbon); $Pd(PPh_3)_2Cl_2$ (Bis(triphenylphosphine)palladium (II) dichloride); $Pd(OAc)_2$ (Palladium diacetate); Pd(dppf) $Cl_2$ (1,1'-Bis(diphenylphosphino)ferrocene) palladium(II) dichloride; $Pd_2(dba)_3$ (Tris(dibenzylideneacetone)dipalladium(0)); RT (Room Temperature); RM (Reaction mixture); S (Singlet); TBAF (Tetra-n-butylammonium fluoride); TBDMS (Tertiary butyl dimethyl silyl chloride); TEA (Triethyl amine); TFA (Trifluoroaceticacid); TLC (Thin Layer Chromatography); THF (Tetrahydrofuran); TFA (Trifluoro acetic acid); t (Triplet); $Zn(CN)_2$ (Zinc Cyanide).

General Modes of Preparation:

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

A general approach for the synthesis of compounds of general formula (I) is depicted in below schemes. The terms "$Z_1$", "$Z_2$", "$R_1$", "$R_2$", "$R_3$", "m" and "n" independently represents all the possible substitutions as disclosed in compound of formula (I).

Scheme -1:

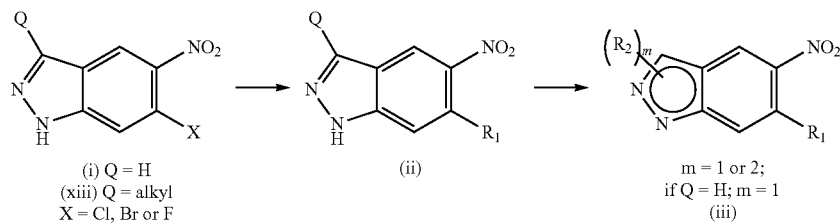

-continued

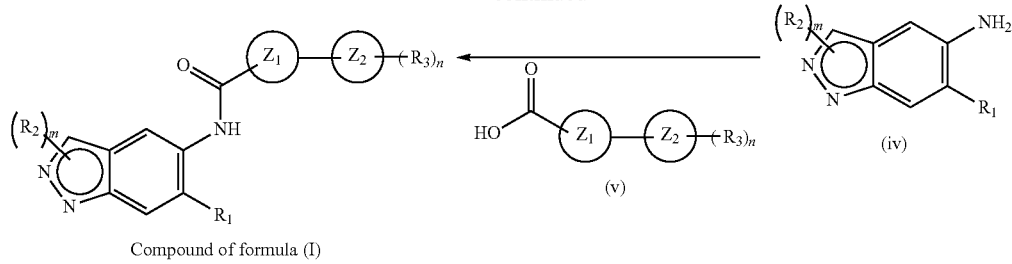

Compound of formula (I)

The first general approach for the synthesis of compounds of general formula (I) is depicted in scheme-1. Compound of formula (ii) can be obtained from compound of formula (i) or (xiii) by coupling with compounds including appropriate boronic acids and amines. Compound of formula (iii) can be obtained by the alkylation of compound of formula (ii) by using appropriate bases like potassium carbonate, or sodium hydride and suitable alkyl halides. Compound of formula (iii) can be reduced with suitable reducing reagents like Fe powder and HCl to give compound of formula (iv) which on amide coupling with a suitable acid of compound of formula (v) by using standard amide coupling reagent known in the literature can give compound of formula (I).

Scheme -2:

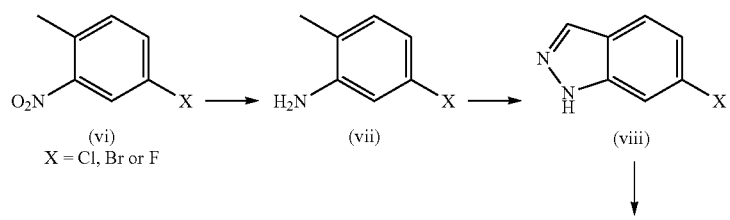

(vi) X = Cl, Br or F

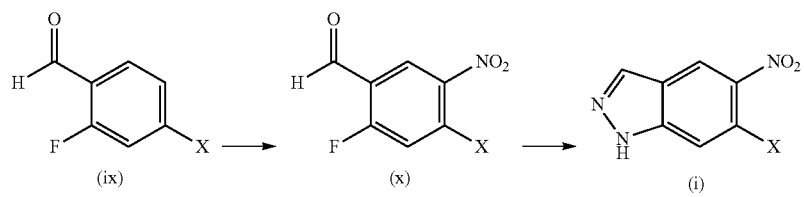

Synthesis of compound of formula (i) was achieved in two ways. A compound of formula (vi) can be reduced by using Fe powder and HCl to give compound of formula (vii) which on further reaction with $Ac_2O$, KOAc, Isoamylnitrate, at certain temperature can give compound of formula (viii). Compound of formula (viii) on nitration can give compound of formula (i). On the other hand compound of formula (ix) on nitration can give compound of formula (x) which can be reacted with hydrazine in suitable solvent like DMF, at 150° C. to give compound of formula (i).

Scheme -3:
Compound of formula (xiii) can be prepared as per the procedure given in Scheme -3.

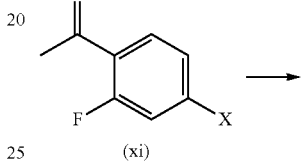

(xi)

-continued

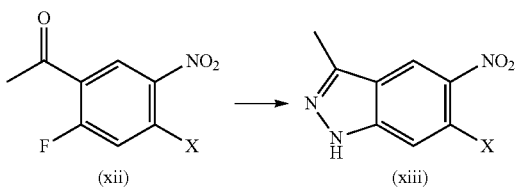

X = F

A compound of formula (xi) can be nitrated by potassium nitrate and sulphuric acid to give compound of formula (xii) which on further reaction with hydrazine at certain temperature can give compound of formula (xiii).

Intermediates

Intermediate 1

Synthesis of 6-(1-(tetrahydro-2H-pyran-2-yl)-1H-pyrazol-4-yl)picolinic acid

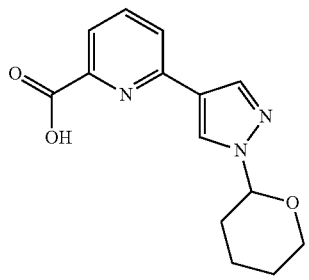 [SMILES: O=C(O)c1cccc(-c2cnn(C3CCCCO3)c2)n1]

Step 1: Preparation of methyl 6-(1-(tetrahydro-2H-pyran-2-yl)-1H-pyrazol-4-yl)picolinate In a sealed tube methyl 6-bromopicolinate (900 mg, 4.166 mmol) was coupled with 1-(tetrahydro-2H-pyran-2-yl)-4-(4,4,5,5-tetramethyl-1,3,2-dioxaborolan-2-yl)-1H-pyrazole (1.39 g, 5 mmol) using sodium carbonate (1.324 g, 12.49 mmol) and Pd(PPh$_3$)$_2$Cl$_2$ (339 mg, 0.416 mmol) in 1,2-dimethoxyethane (10 mL) and water (2 mL) and purged argon for 10 min, and heated at 95° C. overnight to get the crude product. The obtained crude was purified by 60-120 silica gel column chromatography using 30% ethyl acetate in hexane as eluent to obtain the title compound (450 mg, 38%). LCMS: m/z: 288.1 (M+1)$^+$.

Step 2: Preparation of 6-(1-(tetrahydro-2H-pyran-2-yl)-1H-pyrazol-4-yl)picolinic acid A solution of methyl 6-(1-(tetrahydro-2H-pyran-2-yl)-1H-pyrazol-4-yl)picolinate (450 mg, 1.567 mmol) and lithium hydroxide (500 mg, 7.839 mmol) in THF (10 mL) water (4 ml) was stirred at RT for 2 hrs. The reaction mixture was acidified with citric acid and extracted with DCM (2×100 mL), dried over sodium sulphate and distilled out the solvent to get the desired compound (300 mg, 70%). LCMS: m/z: 274.3 (M+1)$^+$.

Intermediate 2

Synthesis of 6-(1-methyl-1H-pyrazol-4-yl)picolinic acid

Step 1: Preparation of methyl 6-(1-methyl-1H-pyrazol-4-yl)picolinate

Using the same reaction conditions as described in step 1 of example 6, methyl 6-bromopicolinate (3.5 g, 16.28 mmol) was coupled with 1-methyl-4-(4,4,5,5-tetramethyl-1,3,2-dioxaborolan-2-yl)-1H-pyrazole (4.06 g, 19.53 mmol) using sodium carbonate (5.177 g, 48.846 mmol) and Pd(dppf)Cl$_2$ (1.328 g, 1.628 mmol) in 1,2-dimethoxyethane (20 mL) to get the crude product. The obtained crude was purified by 60-120 silica gel column chromatography using 30% ethyl acetate in hexane as eluent to obtain the title compound (1.2 g, 33.9%). LCMS: m/z: 218.2 (M+1)$^+$.

Step 2: Preparation of 6-(1-methyl-1H-pyrazol-4-yl)picolinic acid

The solution of methyl 6-(1-methyl-1H-pyrazol-4-yl)picolinate (1.2 g, 5.529 mmol), lithium hydroxide (696 mg, 16.58 mmol), methanol (2 mL), THF (8 mL) and water (1 mL) was stirred at RT for 2 h, acidified with 2N HCl, distilled the solvent and filtered the solid to get the title compound (900 mg, 80.3%).

Intermediate 3

Synthesis of 2-(6-methoxypyridin-3-yl)oxazole-4-carboxylic acid

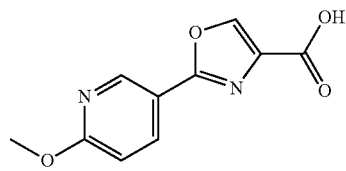 [SMILES: COc1ccc(-c2nc(C(=O)O)co2)cn1]

Step 1: Preparation of ethyl 2-(6-fluoropyridin-3-yl)oxazole-4-carboxylate

Using the same reaction conditions as described in step 1 of example 6, 2-fluoro-5-(4,4,5,5-tetramethyl-1,3,2-dioxaborolan-2-yl)pyridine (200 mg, 1.41 mmol) was coupled with ethyl 2-chlorooxazole-4-carboxylate (298 mg, 1.70 mmol) using sodium carbonate (451 mg, 4.25 mmol) and Pd(PPh$_3$)$_4$ (289 mg, 0.332 mmol) in 1,2-dimethoxyethane/water (15/3 mL) to get the crude product. The obtained crude was purified by 60-120 silica gel column chromatography using 20% ethyl acetate in hexane as eluent to obtain the title compound (200 mg, 59.8%).

Step 2: Preparation of 2-(6-methoxypyridin-3-yl)oxazole-4-carboxylic acid

Using the same reaction conditions as described in step 2 of intermediate 2, ethyl 2-(6-fluoropyridin-3-yl)oxazole-4-carboxylate (300 mg, 0.127 mmol) was hydrolyzed using lithium hydroxide (160 mg, 3.91 mmol) in THF/methanol/water (5/1/2 mL) at RT for 2 h to obtain the title compound (160 mg, 57.3%).
$^1$HNMR (DMSO-d$_6$, 300 MHz): δ 13.5-12.5 (bs, 1H), 8.85 (s, 1H), 8.80-8.79 (d, 1H), 8.26-8.23 (dd, 1H), 7.02-6.99 (dd, 1H), 3.95 (s, 3H). LCMS: m/z=221.1 (M+1)$^+$.

Intermediate 4

Synthesis of 2-(2-methylpyridin-3-yl)oxazole-4-carboxylic acid

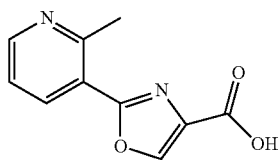

Step 1: Preparation of ethyl 2-(2-methylpyridin-3-yl)oxazole-4-carboxylate

Using the same reaction conditions as described in step 1 of example 6, 2-methyl-3-(4,4,5,5-tetramethyl-1,3,2-dioxaborolan-2-yl)pyridine (1 g, 7.09 mmol) was coupled with ethyl 2-chlorooxazole-4-carboxylate (1.86 g, 0.851 mmol) using sodium carbonate (2.25 g, 21.2 mmol) and Pd(dppf)Cl$_2$ (289 mg, 0.332 mmol) in 1,2-dimethoxyethane/water (30/6 mL) to get the crude product. The obtained crude was purified by 60-120 silica gel column chromatography using 20% ethyl acetate in hexane as eluent to obtain the title compound (1 g, 59.8%).

Step 2: Preparation of 2-(2-methylpyridin-3-yl)oxazole-4-carboxylic acid

Using the same reaction conditions as described in step 2 of intermediate 2, ethyl 2-(2-methylpyridin-3-yl)oxazole-4-carboxylate (1 g, 4.3 mmol) was hydrolyzed using lithium hydroxide (542 mg, 12.9 mmol) in THF/water (25/4 mL) at RT for 2 h to obtain the title compound (550 mg, 62.5%).

$^1$HNMR (400 MHz, DMSO-d$_6$,): δ 13.3 (s, 1H), 8.96 (s, 1H), 8.64-8.62 (dd, 1H), 8.32-8.03 (dd, 1H), 7.47-7.44 (q, 1H), 2.86 (s, 3H). LCMS: m/z=205.0 (M+1)$^+$.

Intermediate 5

Synthesis of 2-(2-hydroxypyridin-3-yl)oxazole-4-carboxylic acid

Step 1: Preparation of ethyl 2-(2-fluoropyridin-3-yl)oxazole-4-carboxylate

Using the same reaction conditions as described in step 1 of example 6, (2-fluoropyridin-3-yl)boronic acid (400 mg, 2.83 mmol) was coupled with ethyl 2-chlorooxazole-4-carboxylate (596 mg, 3.40 mmol) using sodium carbonate (902 mg, 8.51 mmol) and Pd(dppf)Cl$_2$ (115 mg, 0.141 mmol) in 1,2-dimethoxyethane/water (25/4 mL) to get the crude product. The obtained crude was purified by 60-120 silica gel column chromatography using 30% ethyl acetate in hexane as eluent to obtain the title compound (400 mg, 60.6%).

$^1$HNMR (400 MHz, DMSO-d$_6$): δ 9.11 (s, 1H), 8.64-8.59 (m, 1H), 8.48-8.47 (d, 1H), 7.62-7.59 (m, 1H), 4.38-4.33 (q, 2H), 1.35-1.32 (t, 3H).

Step 2: Preparation of 2-(2-hydroxypyridin-3-yl)oxazole-4-carboxylic acid

Using the same reaction conditions as described in step 2 of intermediate 2, ethyl 2-(2-fluoropyridin-3-yl)oxazole-4-carboxylate (400 mg, 1.69 mmol) was hydrolyzed using lithium hydroxide (213 mg, 5.07 mmol) in THF/water (10/2 mL) at RT for 2 h to obtain the title compound (250 mg, 71.6%).

$^1$H NMR (400 MHz, DMSO-d$_6$): δ 13.3-12.9 (bs, 1H), 12.4-12.2 (s, 1H), 8.81 (s, 1H), 8.20-8.17 (dd, 1H), 7.68-7.66 (dd, 1H), 6.41-6.37 (t, 1H). LCMS: m/z=207.1 (M+1)$^+$.

Intermediate 6

Synthesis of (R)-1-(4-(4,4,5,5-tetramethyl-1,3,2-dioxaborolan-2-yl)-1H-pyrazol-1-yl)propan-2-ol

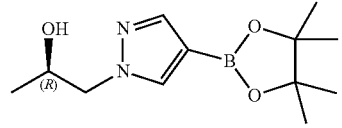

Step 1: Preparation of (R)-1-(4-iodo-1H-pyrazol-1-yl)propan-2-ol

Using the same reagents and conditions as described in example 34, 4-iodo-1H-pyrazole (500 mg, 2.577 mmol) was coupled with (R)-2-methyloxirane (275 mg, 5.154 mmol) using potassium hydroxide (433 mg, 7.731 mmol) in ethanol (5 mL) at 90° C. for 12 h to get the title compound (660 mg, 64.94%). LCMS: m/z=253.0 (M+1)$^+$.

Step 2: Preparation of (R)-1-(4-(4,4,5,5-tetramethyl-1,3,2-dioxaborolan-2-yl)-1H-pyrazol-1-yl)propan-2-ol Using the same reaction conditions as described in step 2 of example 9, (R)-1-(4-iodo-1H-pyrazol-1-yl)propan-2-ol (664 mg, 2.6349 mmol), was coupled with 4,4,4',4',5,5,5',5'-octamethyl-2,2'-bi(1,3,2-dioxaborolane) (1.338 gm, 5.269 mmol) using potassium acetate (646 mg, 6.587 mmol), and Pd(dppf)Cl$_2$ (96 mg, 0.1317 mmol) in DMSO (10 mL) at 80° C. for 45 min. The obtained crude was purified by 60-120 silica gel column chromatography using 1% methanol in DCM as eluent to obtain the title compound (110 mg, 16.56%). LCMS: m/z=253.2 (M+1)$^+$.

Intermediate 7

Synthesis of (S)-2-(3-((tert-butoxycarbonyl)amino)pyrrolidin-1-yl)oxazole-4-carboxylic acid

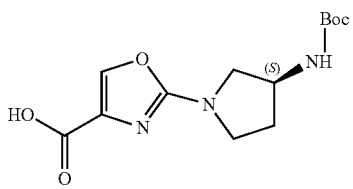

Step 1: Preparation of ethyl (S)-2-(3-((tert-butoxycarbonyl)amino)pyrrolidin-1-yl)oxazole-4-carboxylate The mixture of ethyl 2-chlorooxazole-4-carboxylate (100 mg, 0.5698 mmol), tert-butyl (S)-pyrrolidin-3-ylcarbamate (127 mg, 0.6837 mmol), DIPEA (0.284 mL, 1.4245 mmol) and DMF (5 mL) were heated at 120° C. for 2 h. The reaction mass was quenched with ice water and extracted with DCM. The solvent was distilled out to get the title compound (170 mg, 91.89%). LCMS: m/z=270.1 (M-t-butyl+1)$^+$.

Step 2: Preparation of (S)-2-(3-((tert-butoxycarbonyl)amino)pyrrolidin-1-yl)oxazole-4-carboxylic acid Using the same reaction conditions as described in step 2 of intermediate 2, ethyl (S)-2-(3-((tert-butoxycarbonyl)amino)pyrrolidin-1-yl)oxazole-4-carboxylate (170 mg, 0.5224 mmol) was hydrolyzed using lithium hydroxide (33 mg, 0.7837 mmol) in THF/methanol/water (10/1/2 mL) at RT for 12 h to obtain the title compound (150 mg, 96.77%). LCMS: m/z=242.0 (M-t-butyl+1)$^+$.

Intermediate 8

Synthesis of (S)-1-(4-(4,4,5,5-tetramethyl-1,3,2-dioxaborolan-2-yl)-1H-pyrazol-1-yl)propan-2-ol

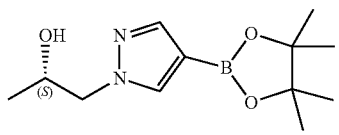

Step 1: Preparation of (S)-1-(4-iodo-1H-pyrazol-1-yl)propan-2-ol

Using the same reagents and conditions as described in example 34, 4-iodo-1H-pyrazole (500 mg, 2.577 mmol) was coupled with (S)-2-methyloxirane (273 mg, 5.15 mmol) using potassium hydroxide (433 mg, 7.731 mmol) in ethanol (6 mL) at 90° C. for 12 h to get the title compound (650 mg, 94.2%).

Step 2: Preparation of (S)-1-(4-(4,4,5,5-tetramethyl-1,3,2-dioxaborolan-2-yl)-1H-pyrazol-1-yl)propan-2-ol Using the same reaction conditions as described in step 2 of example 9, (S)-1-(4-iodo-1H-pyrazol-1-yl)propan-2-ol (650 mg, 2.57 mmol), was coupled with 4,4,4',4',5,5,5',5'-octamethyl-2,2'-bi(1,3,2-dioxaborolane) (1.31 g, 5.15 mmol) using potassium acetate (1.27 g, 6.43 mmol), and Pd(dppf)Cl$_2$ (95 mg, 0.128 mmol) in DMSO (4 mL) at 70° C. for 40 min to obtain the title compound (350 mg, 53.8%). LCMS: m/z=253.1 (M+1)$^+$.

Intermediate 9

Synthesis of (S)-2-(3-((tert-butyldimethylsilyl)oxy)pyrrolidin-1-yl)oxazole-4-carboxylic acid

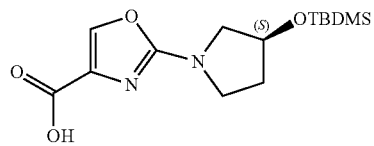

Step 1: Preparation of ethyl (S)-2-(3-hydroxypyrrolidin-1-yl)oxazole-4-carboxylate Using the same reaction conditions as described in step 1 of intermediate 7, ethyl 2-chlorooxazole-4-carboxylate (500 mg, 2.8490 mmol), was reacted with (S)-pyrrolidin-3-ol (298 mg, 3.4188 mmol), sodium carbonate (453 mg, 4.2735 mmol) in DMF (10 mL) to get the desired product (535 mg, 83.07%). LCMS: m/z=227.1 (M+1)$^+$.

Step 2: Preparation of ethyl (S)-2-(3-((tert-butyldimethylsilyl)oxy)pyrrolidin-1-yl)oxazole-4-carboxylate To the solution of ethyl (S)-2-(3-hydroxypyrrolidin-1-yl)oxazole-4-carboxylate (535 mg, 2.3672 mmol) in DMF (10 mL) was added DMAP (29 mg, 0.2367 mmol), TBDMS chloride (429 mg, 2.8407 mmol) and imidazole (396 mg, 5.8072 mmol) and stirred at RT for 2 h to get the crude product. The obtained crude was purified by 60-120 silica gel column chromatography using 20% ethyl acetate in hexane as eluent to obtain the title compound (520 mg, 64.5%). LCMS: m/z=341.2 (M+1)$^+$.

Step 3: Preparation of (S)-2-(3-((tert-butyldimethylsilyl)oxy)pyrrolidin-1-yl)oxazole-4-carboxylic acid Using the same reaction conditions as described in step 2 of intermediate 2, ethyl (S)-2-(3-((tert-butyldimethylsilyl)oxy)pyrrolidin-1-yl)oxazole-4-carboxylate (520 mg, 1.5294 mmol) was hydrolyzed using lithium hydroxide (97 mg, 2.2941 mmol) in THF/methanol/water (10/5/5 mL) at RT for 2 h to obtain the title compound (350 mg, 73.37%).

$^1$HNMR (400 MHz, CDCl$_3$): δ 7.88 (s, 1H), 4.55-4.50 (s, 1H), 3.75-3.60 (m, 3H), 3.5-3.4 (d, 1H), 2.05-1.90 (m, 2H), 0.9 (s, 9H). LCMS: m/z=313.1 (M+1)$^+$.

Intermediate 10

Synthesis of 2-(1-(tetrahydro-2H-pyran-2-yl)-1H-pyrazol-4-yl)oxazole-4-carboxylic acid

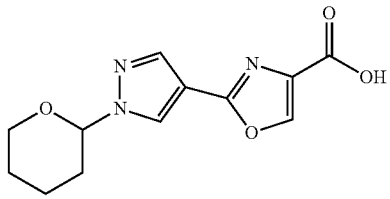 [SMILES: O=C(O)c1coc(-c2cnn(C3CCCCO3)c2)n1]

Step 1: Preparation of ethyl 2-(1-(tetrahydro-2H-pyran-2-yl)-1H-pyrazol-4-yl)oxazole-4-carboxylate Using the same reaction conditions as described in step 1 of example 6, 1-(tetrahydro-2H-pyran-2-yl)-4-(4,4,5,5-tetramethyl-1,3,2-dioxaborolan-2-yl)-1H-pyrazole (273 mg, 0.982 mmol) was coupled with ethyl 2-chlorooxazole-4-carboxylate (125 mg, 0.892 mmol) using sodium carbonate (283 mg, 2.676 mmol) and Pd(dppf)Cl$_2$ (65 mg, 0.089 mmol) in 1,2-dimethoxyethane/water (5/1 mL) to get the crude product. The obtained crude was purified by 60-120 silica gel column chromatography using 20% ethyl acetate in hexane as eluent to obtain the title compound (200 mg, 77.2%). LCMS: 95.44%, m/z=292.3 (M+1)$^+$.

Step 2: Preparation of 2-(1-(tetrahydro-2H-pyran-2-yl)-1H-pyrazol-4-yl)oxazole-4-carboxylic acid Using the same reaction conditions as described in step 2 of intermediate 2, ethyl 2-(1-(tetrahydro-2H-pyran-2-yl)-1H-pyrazol-4-yl)oxazole-4-carboxylate (200 mg, 0.784 mmol) was hydrolyzed using lithium hydroxide (50 mg, 1.176 mmol) in THF/methanol/water (5/2/1 mL) at RT for 1 h to obtain the title compound (206 mg, 100%).

Intermediate 11

Synthesis of 2'-fluoro-[2,3'-bipyridine]-6-carboxylic acid

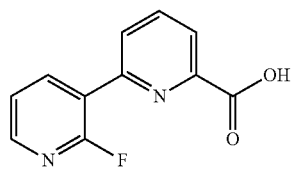 [SMILES: O=C(O)c1cccc(-c2cccnc2F)n1]

Step-1: Preparation of 2-fluoro-3-(4, 4, 5, 5-tetramethyl-1, 3, 2-dioxaborolan-2-yl) pyridine 3-Bromo-2-fluoropyridine (1.5 g, 8.52 mmol), potassium acetate (2.0 g, 21.30 mmol), bispinacolatodiboron (3.18 g, 13.21 mmol) and Pd(dppf)Cl$_2$ (340 mg, 0.42 mmol) were taken in 1, 4-dioxane (15 mL) and heated for 2 h at 90° C. The mixture was evaporated and used for next step without further purification (3.72 g).

$^1$HNMR (400 MHz, DMSO-d$_6$,): δ 8.36-8.35 (m, 1H), 8.20-8.15 (m, 1H), 7.37-7.35 (m, 1H), 1.35 (s, 12H). LCMS: 67%, m/z=224 (M+1)$^+$.

Step-2: Synthesis of methyl 2'-fluoro-[2,3'-bipyridine]-6-carboxylate

2-Fluoro-3-(4, 4, 5, 5-tetramethyl-1, 3, 2-dioxaborolan-2-yl) pyridine (1.9 g, 8.52 mmol), 2M K$_2$CO$_3$ (2.3 g, 17.0 mmol in 10 mL H$_2$O), methyl-6-bromopicolinate (2.2 g, 10.22 mmol) and Pd(dppf)Cl$_2$ (417 mg, 0.511 mmol) were taken in 1,4-Dioxan (10 mL) and heated for 2 h at 90° C. The mixture was evaporated and the residue was purified by silica gel column chromatography to give the title compound (1.38 g, 58%).

$^1$HNMR (400 MHz, DMSO-d$_6$,): δ 8.51 (t, 1H), 8.37 (d, 1H), 8.19-8.10 (m, 3H), 7.58 (t, 1H), 3.93 (s, 3H). LCMS: 100%, m/z=233 (M+1)$^+$.

Step-3: Synthesis of 2'-fluoro-[2,3'-bipyridine]-6-carboxylic acid

Using the same reaction conditions as described in step 2 of intermediate 2, methyl 2'-fluoro-[2, 3'-bipyridine]-6-carboxylate (1.38 g, 5.97 mmol) was hydrolysed using lithium hydroxide (502 mg, 11.95 mmol) in THF/methanol/water (10/10/10 mL) at RT for 12 h to obtain the title compound (643 mg, 49%).

$^1$HNMR (400 MHz, DMSO-d$_6$,): δ 13.29 (bs, 1H), 8.61 (t, 1H), 8.37-8.29 (m, 1H), 8.22-8.79 (m, 2H), 7.57 (t, 1H), 7.21-7.18 (m, 1H). LCMS: 100%, m/z=219 (M+1)$^+$.

Intermediate 12

Synthesis of 5-(2-methylpyridin-4-yl)furan-2-carboxylic acid

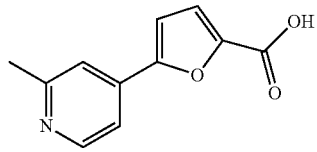

Step 1: Preparation of methyl 5-(2-methylpyridin-4-yl)furan-2-carboxylate

Using the similar reaction conditions as described in step 1 of example 6, methyl 5-bromofuran-2-carboxylate (214 mg, 1.0406 mmol) was coupled with 2-methyl-4-(4,4,5,5-tetramethyl-1,3,2-dioxaborolan-2-yl)pyridine (340 mg, 1.561 mmol) using potassium carbonate (288 mg, 2.08 mmol) TBAB (50 mg, 0.156 mmol) and Pd(dppf)Cl$_2$ (54 mg, 0.078 mmol) in dioxane/water (10/3 mL) to get the crude product. The obtained crude was purified by 60-120 silica gel column chromatography using 50% ethyl acetate in hexane as eluent to obtain the title compound (301 mg, 89%). LCMS: m/z=217.8 (M+1)$^+$.

Step 2: Preparation of 5-(2-methylpyridin-4-yl)furan-2-carboxylic acid

Using the same reaction conditions as described in step 2 of intermediate 2, methyl 5-(2-methylpyridin-4-yl)furan-2- carboxylate (300 mg, 1.38 mmol) was hydrolyzed using lithium hydroxide (116 mg, 2.76 mmol) in THF/methanol/water (10/5/5 mL) at 50° C. for 0.25 h to obtain the desired compound (260 mg, 92.8%). LCMS: m/z=204.1 (M+1)$^+$. HPLC: 95.85%.

Intermediate 13

Synthesis of 2-(2-acetamidopyridin-4-yl)oxazole-4-carboxylic acid

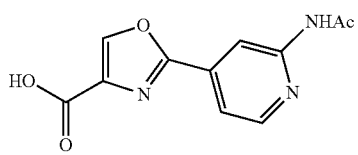 [SMILES: CC(=O)Nc1cc(-c2nc(C(=O)O)co2)ccn1]

Step 1: Preparation of ethyl 2-(2-acetamidopyridin-4-yl)oxazole-4-carboxylate

Using the same reaction conditions as described in step 1 of example 6, N-(5-(4,4,5,5-tetramethyl-1,3,2-dioxaborolan-2-yl)pyridin-2-yl)acetamide (2.78 g, 10.04 mmol) was coupled with ethyl 2-chlorooxazole-4-carboxylate (1 g, 7.09 mmol) using sodium carbonate (106 mg, 21.2 mmol) and Pd(dppf)Cl$_2$ (259 mg, 0.354 mmol) in 1,2-dimethoxyethane/water (30/5 mL) to get the crude product. The obtained crude was purified by 60-120 silica gel column chromatography using 50% ethyl acetate in hexane as eluent to obtain the title compound (680 mg, 36%). LCMS: 276.3 (M+1)$^+$.

Step 2: Preparation of 2-(2-acetamidopyridin-4-yl)oxazole-4-carboxylic acid

Using the same reaction conditions as described in step 2 of intermediate 2, ethyl 2-(2-acetamidopyridin-4-yl)oxazole-4-carboxylate (500 mg, 1.81 mmol) was hydrolyzed using lithium hydroxide (84 mg, 2 mmol) in THF/methanol/water (10/1/5 mL) at RT for 4 h to obtain the title compound (360 mg, 81.08%). LCMS: 248.1 (M+1)$^+$.

Intermediate 14

Synthesis of 2-(2-aminopyridin-4-yl)oxazole-4-carboxylic acid

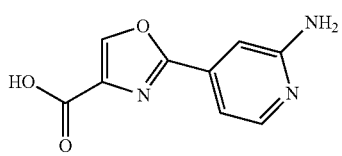 [SMILES: Nc1cc(-c2nc(C(=O)O)co2)ccn1]

Using the same reaction conditions as described in step 2 of intermediate 2, ethyl 2-(2-acetamidopyridin-4-yl)oxazole-4-carboxylate (product of step 1 of intermediate 13) (900 mg, 3.27 mmol) was hydrolyzed using lithium hydroxide (329 mg, 7.85 mmol) in THF/methanol/water (30/1/5 mL) at RT for 4 h to obtain the title compound (750 mg, 96%). LCMS: 206.2 (M+1)$^+$.

Intermediate 15

Synthesis of 2-(2-hydroxypyridin-4-yl)oxazole-4-carboxylic acid

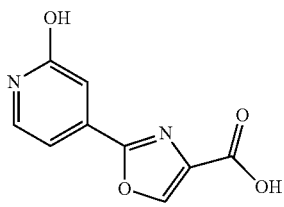 [SMILES: O=C(O)c1coc(-c2ccnc(O)c2)n1]

Step 1: Preparation of ethyl 2-(2-fluoropyridin-4-yl)oxazole-4-carboxylate

Using the same reaction conditions as described in step 1 of example 6, (2-fluoropyridin-4-yl)boronic acid (500 mg, 3.571 mmol) was coupled with ethyl 2-chlorooxazole-4-carboxylate (812 mg, 4.642 mmol) using sodium carbonate (1.18 g, 10.713 mmol) and Pd(dppf)Cl$_2$ (260 mg, 0.357 mmol) in 1,2-dimethoxyethane/water (8/2 mL) to get the crude product. The obtained crude was purified by flash chromatography using 20% ethyl acetate in hexane as eluent to obtain the title compound (550 mg, 65.4%).

Step 2: Preparation of 2-(2-hydroxypyridin-4-yl)oxazole-4-carboxylic acid

Using the same reaction conditions as described in step 2 of intermediate 2, ethyl 2-(2-fluoropyridin-4-yl)oxazole-4-carboxylate (100 mg, 0.349 mmol) was hydrolyzed using lithium hydroxide (80 mg, 1.398 mmol) in water (2 mL) at 70° C. for 14 h to obtain the crude title compound (80 mg). LCMS: 207.0 (M+1)$^+$.

Intermediate 16

Synthesis of 2-(2,6-dimethylpyridin-4-yl)oxazole-4-carboxylic acid

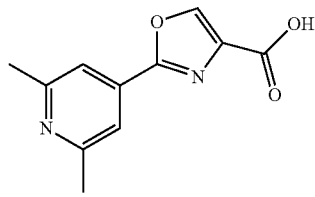 [SMILES: Cc1cc(-c2nc(C(=O)O)co2)cc(C)n1]

Step 1: Preparation of ethyl 2-(2,6-dimethylpyridin-4-yl)oxazole-4-carboxylate

Using the same reaction conditions as described in step 1 of example 6, 2,-(2,6-dimethylpyridin-4-yl)boronic acid (753 mg, 4.385 mmol) was coupled with ethyl 2-chlorooxaazole-4-carboxylate (500 mg, 3.321 mmol) using sodium carbonate (1.07 g, 9.965 mmol) and Pd(dppf)Cl$_2$ (246 mg, 0.329 mmol) in 1,2-dimethoxyethane/water (8/2 mL) to get the crude product. The obtained crude was purified by 60-120 silica gel column chromatography using 20% ethyl acetate in hexane as eluent to obtain the title compound (650 mg, 79.85%). LCMS: 247.3 (M+1)$^+$.

Step 2: Preparation of 2-(2,6-dimethylpyridin-4-yl)oxazole-4-carboxylic acid

Using the same reaction conditions as described in step 2 of intermediate 2, ethyl 2-(2,6-dimethylpyridin-4-yl)oxazole-4-carboxylate (650 mg, 2.642 mmol) was hydrolyzed using lithium hydroxide (216 mg, 5.28 mmol) in THF/water (4/2 mL) at RT for 2 h to obtain the title compound (400 mg, 69.8%). LCMS: 219.2 (M+1)$^+$.

Intermediate 17

Synthesis of 2-(2-(methyl amino) pyridin-4-yl) oxazole-4-carboxylic acid

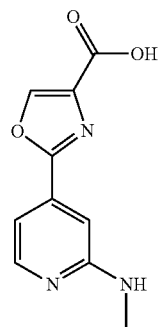 [SMILES: CNc1cc(-c2nc(C(=O)O)co2)ccn1]

Step-1: Preparation of methyl 2-(2-(N-methylacetamido) pyridin-4-yl)oxazole-4-carboxylate To a solution of 2-(2-acetamidopyridin-4-yl) oxazole-4-carboxylate (step-1 of intermediate 13) (500 mg 1.8 mmol) in DMF (5 ml) at 0° C. slowly added sodium hydride 60% (174 mg 3.60 mmol) and methyl iodide (510 mg 3.60 mmol) and allowed to come to RT stirred at RT for one hour, quenched the reaction mixture by aqueous NH$_4$Cl and extracted the compound to ethyl acetate dried and concentrated it, purified by column chromatography in 50% ethyl acetate in hexane to obtain the title compound (400 mg). LCMS: 276.3 (M+1)$^+$.

Step-2: Preparation of 2-(2-(methyl amino) pyridin-4-yl) oxazole-4-carboxylic acid To a solution of methyl 2-(2-(N-methylacetamido) pyridin-4-yl) oxazole-4-carboxylate (400 mg 1.4 mmol) in methanol (4 ml) and THF (4 ml) added aqueous LiOH (4 ml) (20% in H$_2$O), stirred at RT for 12 hours. slowly neutralized with 2M HCl, to get the light yellow solid, filtered and dried it, to obtain the title compound. (170 mg). LCMS: 220.2 (M+1)$^+$.

Intermediate 18

Synthesis of 2-(2-(dimethylamino) pyridin-4-yl) oxazole-4-carboxylic acid

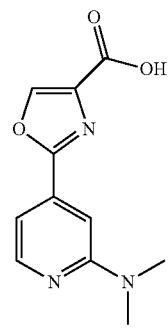 [SMILES: CN(C)c1cc(-c2nc(C(=O)O)co2)ccn1]

A solution of 2-(2-aminopyridin-4-yl)oxazole-4-carboxylic acid (intermediate 14) (300 mg 1.4 mmol) in aqueous formaldehyde, acetic acid (0.4 ml) and acetonitrile (3 ml) heated to 60° C. for two hours, cooled to 0° C. and NaCNBH$_3$ (1.65 g 2.6 mmol) was added slowly, stirred at RT for four hours, slowly quenched the reaction mixture by saturated NaHCO$_3$ solution, extracted the compound to 5% methanol in CHCl$_3$, dried and concentrated it, to obtain the title compound. (250 mg crude). LCMS: 234.2 (M+1)

Intermediate 19

Synthesis of 2-(2-(methylsulfonamido) pyridin-4-yl) oxazole-4-carboxylic acid

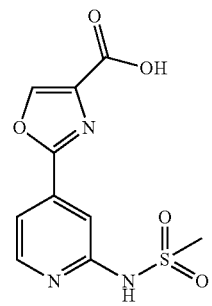 [SMILES: CS(=O)(=O)Nc1cc(-c2nc(C(=O)O)co2)ccn1]

Step-1: Preparation of methyl 2-(2-aminopyridin-4-yl)oxazole-4-carboxylate

A solution of 2-(2-acetamidopyridin-4-yl) oxazole-4-carboxylate (step-1 of intermediate 13) (1.2 g 4.3 mmol) in methanol (10 ml) at 0° C. added Conc. HCl (5 ml) stirred at 65° C. for 2 hours. The reaction mixture was concentrated, basified with NaHCO$_3$ solution, extracted to ethyl acetate and concentrated under reduced pressure, to obtain the title compound (950 mg).

Step-2: Preparation of methyl 2-(2-(methylsulfonamido) pyridin-4-yl) oxazole-4-carboxylate Methyl 2-(2-aminopyridin-4-yl)oxazole-4-carboxylate (144 mg 0.65 mmol) was taken in pyridine (5 ml) to this added methanesulfonylchloride (150 mg 1.31 mmol) at 0° C. stirred at RT for 12 hours. The reaction mixture was concentrated, completely dissolved in ethyl acetate, washed with water dried and concentrated under reduced pressure to get the title compound (183 mg).

Step-3: Preparation of 2-(2-(methylsulfonamido) pyridin-4-yl) oxazole-4-carboxylic acid Methyl 2-(2-(methylsulfonamido) pyridin-4-yl)oxazole-4-carboxylate (181 mg 0.609 mmol) was dissolved in methanol (5 ml) and THF (10 ml) and LiOH in water (25 mg/2 ml) was added and reaction mixture was stirred at RT for 12 hours, concentrated, completely dissolved in water (2 ml) acidified with Conc. HCl. The precipitate formed was filtered and dried it to get the title compound (83 mg).

$^1$HNMR (DMSO-$d_6$, 300 MHz): 8.97 (s, 1H), 8.50 (d, 1H), 7.50 (d, 2H), 3.343 (s, 6H) LCMS: 284.0 (M+1)$^+$.

EXAMPLES

Example 1

N-(2-methyl-6-(piperidin-1-yl)-2H-indazol-5-yl)-6-(1H-pyrazol-4-yl) picolinamide

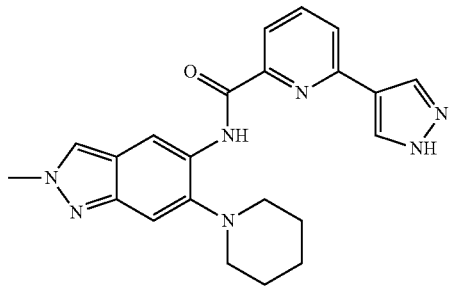 [SMILES: Cn1cc2cc(NC(=O)c3cccc(-c4cn[nH]c4)n3)c(N3CCCCC3)cc2n1]

Step-1: Synthesis of 5-fluoro-2-methylaniline

4-Fluoro-1-methyl-2-nitrobenzene (2.50 g, 16 mmol) was dissolved in ethanol (50 mL). To this solution, iron powder (4.50 g, 81 mmol) and 0.25 ml of HCl were added at 0° C. and the reaction mixture was refluxed for 12 h. After completion of reaction, reaction mixture was cooled to room temperature, diluted with ethyl acetate, filtered through Celite® and washed with ethyl acetate. Filtrate was basified with sodium bicarbonate solution; organic layer was washed with water followed by brine solution. Organic layer was dried over anhydrous Na$_2$SO$_4$ and concentrated under reduced pressure to obtain crude compound. The residue was purified by column chromatography (n-hexane/EtOAc 1:1) to give the title compound (1.4 g, 70%) as a light brown solid.

$^1$H NMR (400 MHz, DMSO-$d_6$): δ 6.87 (t, J=7.6 Hz, 1H), 6.38-6.34 (m, 1H), 6.22-6.18 (m, 1H), 5.11 (bs, 2H), 1.99 (s, 3H). MS (ES) m/e: 126 (M+1)$^+$.

Step-2: Synthesis of 6-fluoro-1H-indazole

A mixture of 5-fluoro-2-methylaniline (3 g, 0.024 mol), potassium acetate (2.8 g, 0.028 mol) and acetic anhydride (6.8 mL, 0.072 mol) in chloroform (30 mL) was heated at 40° C. for 0.5 h. At this temperature isoamylnitrate (3.8 mL, 0.028 mol) was added and stirred at 80° C. for 12 h. After completion of reaction, solvent was removed under reduced pressure, the residue was basified with sodium carbonate solution and was extracted with ethyl acetate. The organic layer was washed with water followed by brine solution and concentrated under reduced pressure to obtain crude compound. The residue was purified by column chromatography over silica gel (30% EtOAc:Hexane) to give the pure compound which was stirred with methanolic HCl (60 mL) for 30 min. The reaction mixture was concentrated under reduced pressure, basified with aqueous sodium carbonate solution and extracted with ethyl acetate. The organic layer was washed with water, brine and was dried over anhydrous Na$_2$SO$_4$ and concentrated under reduced pressure to obtain crude compound. The crude compound was purified by column chromatography (n-hexane/EtOAc 7:3) to give the title compound (2.0 g, 62%) as a pale yellow solid.

$^1$H NMR (400 MHz, DMSO-$d_6$): δ 13.1 (bs, 1H), 8.10 (s, 1H), 7.82-7.84 (m, 1H), 7.33-7.30 (m, 1H), 7.02-6.97 (m, 1H). MS (ES) m/e: 135 (M-1)$^+$.

Step-3: Synthesis of 6-fluoro-5-nitro-1H-indazole

To a stirred mixture of 6-fluoro-1H-indazole (1 g, 0.007 mol) and Conc. H$_2$SO$_4$ (22 mL), KNO$_3$ (0.74 g, 0.007 mol) was added portion wise at 0° C., and stirring was continued at RT for 10 min After completion of reaction, reaction mixture was cooled to 0° C., basified with saturated NaHCO$_3$ solution, extracted with EtOAc, washed with brine and the organic layer was dried over anhydrous Na$_2$SO$_4$. After concentration under reduced pressure, the crude residue was purified by flash chromatography (DCM/MeOH 9.8:0.2) to give the title compound (0.4 g, 30%) as a yellow solid.

$^1$H NMR (400 MHz, DMSO-$d_6$): δ 13.7 (bs, 1H), 8.78 (d, J=7.4 Hz, 1H), 8.34 (s, 1H), 7.68 (d, J=11.8 Hz, 1H). MS (ES) m/e: 180 (M-1)$^+$.

Step-4: Synthesis of 5-nitro-6-(piperidin-1-yl)-1H-indazole

A solution of 6-fluoro-5-nitro-1H-indazole (0.4 g, 2.20 mmol) and piperidine (2 mL) in a sealed tube was stirred at 80° C. for 14 h. After completion of reaction, reaction mixture was concentrated under reduced pressure. The crude compound was purified by column chromatography, eluting with a gradient (CH$_2$Cl$_2$:MeOH; 98:2) to give the title compound (0.37 g, 68%).

$^1$H NMR (400 MHz, CDCl$_3$): δ 10.4 (bs, 1H), 8.22 (s, 1H), 8.09 (s, 1H), 7.05 (s, 1H), 3.98-3.01 (m, 4H), 1.78-1.72 (m, 4H), 1.63-1.50 (m, 2H). MS (ES) m/e: 247 (M+1)$^+$.

Step-5: Synthesis of 2-methyl-5-nitro-6-(piperidin-1-yl)-2H-indazole and 1-methyl-5-nitro-6-(piperidin-1-yl)-1H-indazole To a solution of 5-nitro-6-(piperidin-1-yl)-1H-indazole (334 mg, 1.35 mmol) in DMF (10 mL) was added potassium carbonate (562 mg, 4.07 mmol) and the contents were stirred for 0.5 h at RT. The reaction mixture was again cooled to 0° C. and methyl iodide (0.169 mL, 2.71 mmol) was added drop wise and stirring, at room temperature, was continued for 2 h. The reaction mixture was diluted with EtOAc, washed with brine and dried over anhydrous Na$_2$SO$_4$. After concentration, the residue was purified by flash chromatography (n-hexane:EtOAc; 3:1) to give 1-methyl-5-nitro-6-(piperidin-1-yl)-2H-indazole (Isomer B) (215 mg, 61%) as a brown solid.

$^1$H NMR (400 MHz, CDCl$_3$): δ 8.20 (s, 1H), 7.98 (s, 1H), 6.87 (s, 1H), 4.04 (s, 3H), 3.03-3.00 (m, 4H), 1.79-1.73 (m, 4H), 1.64-1.58 (m, 2H). MS (ES) m/e 261 (M$^+$+1, 95%). Further elution of column with (n-hexane:EtOAc 3:1) afforded the 2-methyl-5-nitro-6-(piperidin-1-yl)-2H-indazole (Isomer A, 87 mg, 24%) as a brown solid.

$^1$H NMR (400 MHz, CDCl$_3$): δ 8.08 (s, 1H), 7.97 (s, 1H), 7.22 (s, 1H), 4.20 (s, 3H), 2.96-2.88 (m, 4H), 1.75-1.69 (m, 4H), 1.60-1.54 (m, 2H). MS (ES) m/e: 261 (M+1)$^+$.

Step-6: Synthesis of 2-methyl-6-(piperidin-1-yl)-2H-indazol-5-amine 2-methyl-5-nitro-6-(piperidin-1-yl)-2H-indazole (0.39 g, 1.5 mmol) was dissolved in ethanol (15 mL) To this solution, Fe powder (0.42 g, 7.5 mmol) and 0.4 mL of HCl were added at 0° C. and the reaction mixture was refluxed for 1 h. After completion of reaction, reaction mixture was cooled to room temperature and diluted with ethyl acetate and filtered through Celite®. The filtrate was basified with sodium bicarbonate solution, extracted with ethyl acetate and the organic layer washed with water followed by brine solution. The organic layer was dried over anhydrous Na$_2$SO$_4$ and concentrated under reduced pressure to obtain crude compound. The crude residue was purified by column chromatography (n-hexane:EtOAc; 1:4) to give the title compound (0.2 g, 58%) as a light brown liquid.

$^1$H NMR (400 MHz, DMSO-d$_6$): δ 7.79 (s, 1H), 6.96 (s, 1H), 6.67 (s, 1H), 4.55 (bs, 2H), 4.00 (s, 3H), 2.90-2.70 (m, 4H), 1.71-1.66 (m, 4H), 1.65-1.54 (m, 2H). MS (ES) m/e: 231 (M+1)$^+$.

Step-7: Synthesis of N-(2-methyl-6-(piperidin-1-yl)-2H-indazol-5-yl)-6-(1-(tetrahydro-2H-pyran-2-yl)-1H-pyrazol-4-yl)picolinamide To a solution of 2-methyl-6-(piperidin-1-yl)-2H-indazol-5-amine (0.100 g, 0.434 mmol) in DMF (10 mL) was added 6-(1-(tetrahydro-2H-pyran-2-yl)-1H-pyrazol-4-yl) picolinic acid (intermediate 1) (0.119 g, 0.434 mmol), EDCI.HCl (0.167 g, 0.869 mmol), HOBT (0.117 g, 0.869 mmol), and triethyl amine (0.132 g, 1.30 mmol). The reaction mixture was stirred for 12 h at room temperature. After completion of reaction, reaction mixture was diluted with EtOAc, washed with brine and dried over anhydrous Na$_2$SO$_4$. After concentration under reduced pressure, the residue was purified by flash chromatography (CH$_2$Cl$_2$:MeOH; 98.5:1.5) to give the title compound (0.090 g, 47%) as a brown solid.

$^1$H NMR (400 MHz, CDCl$_3$): δ 10.93 (bs, 1H), 8.73 (s, 1H), 8.62 (s, 1H), 8.28 (d, J=12.3 Hz, 2H), 8.09-7.95 (m, 3H), 7.34 (s, 1H), 5.76 (s, 1H), 5.49 (dd, J=2.7 and 9.5 Hz, 1H), 4.12 (s, 3H), 2.90-2.80 (m, 4H), 2.19-1.96 (m, 4H), 1.79-1.72 (m, 4H), 1.66-1.47 (m, 2H), 1.36-1.29 (m, 2H). MS (ES) m/e: 486.5 (M+1)$^+$.

Step-8: Synthesis of N-(2-methyl-6-(piperidin-1-yl)-2H-indazol-5-yl)-6-(1H-pyrazol-4-yl) picolinamide N-(2-methyl-6-(piperidin-1-yl)-2H-indazol-5-yl)-6-(1-(tetrahydro-2H-pyran-2-yl)-1H-pyrazol-4-yl) picolinamide (90 mg, 0.185 mmol) was dissolved in DCM (10 mL). To this solution ether-HCl (10 mL) was added and stirred at room temperature for 3 h. After completion of reaction, excess of solvent was removed under reduced pressure, basified with saturated sodium carbonate solution and diluted with ethyl acetate. The organic layer was washed with brine and dried over anhydrous Na$_2$SO$_4$. After concentration, the residue was purified by column chromatography (CH$_2$Cl$_2$: MeOH; 98:2) to give the title compound (25 mg, 34%) as off-white solid.

$^1$H NMR (400 MHz, DMSO-d$_6$): δ 13.27 (bs, 1H), 11.00 (s, 1H), 8.74 (s, 1H), 8.50 (s, 1H), 8.28-8.26 (m, 2H), 8.07-7.96 (m, 3H), 7.35 (s, 1H), 4.12 (s, 3H), 2.79-2.88 (m, 4H), 1.81-1.78 (m, 4H), 1.60-1.55 (m, 2H). MS (ES) m/e: 402 (M+1)$^+$.

Example 2

N-(2-methyl-6-(piperidin-1-yl)-2H-indazol-5-yl)-2-(2-methylpyridin-4-yl) oxazole-4-carboxamide

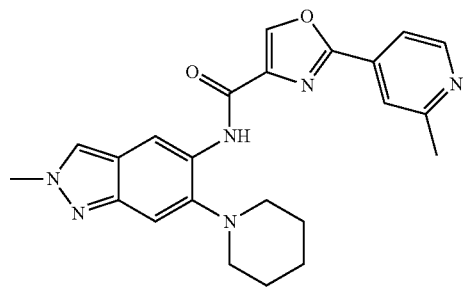 [SMILES: Cc1cc(-c2nc(C(=O)Nc3cc4cn(C)nc4cc3N3CCCCC3)co2)ccn1]

To a solution of 2-methyl-6-(piperidin-1-yl)-2H-indazol-5-amine (0.100 g, 0.434 mmol) (product of step 6 of example 1) in DMF (10 mL) were added 2-(2-methylpyridin-4-yl)oxazole-4-carboxylic acid [Source: PCT International Application. WO2011/043371, 14 Apr. 2011] (0.085 g, 0.434 mmol), EDCI.HCl (0.167 g, 0.869 mmol), HOBT (0.117 g, 0.869 mol), and triethylamine (0.132 g, 1.30 mmol). The reaction mixture was stirred for 12 h at room temperature and was diluted with EtOAc, washed with brine, and dried over Na$_2$SO$_4$. After concentration, the residue was purified by flash chromatography (CH$_2$Cl$_2$: MeOH; 98.5:1.5) to give the title compound (0.050 g, 28%) as a brown solid.

$^1$H NMR (400 MHz, DMSO-d$_6$) δ 10.42 (bs, 1H), 9.05 (s, 1H), 8.73 (d, J=4.9 Hz, 1H), 8.63 (s, 1H), 8.26 (s, 1H), 7.85 (s, 1H), 7.75 (d, J=4.9 Hz, 1H), 7.40 (s, 1H), 4.11 (s, 3H), 2.90-2.80 (m, 4H), 2.59 (s, 3H), 1.93-190 (m, 4H), 1.80-1.60 (m, 2H). MS (ES) m/e: 417 (M+1)$^+$.

Example 3

N-(1-methyl-6-(piperidin-1-yl)-1H-indazol-5-yl)-2-(2-methylpyridin-4-yl) oxazole-4-carboxamide

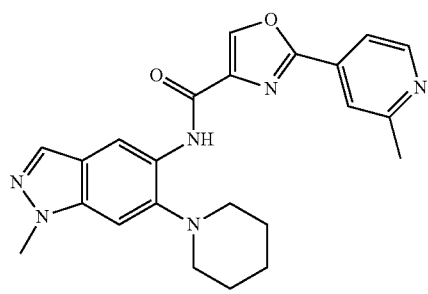 [SMILES: Cc1cc(-c2nc(C(=O)Nc3cc4cnn(C)c4cc3N3CCCCC3)co2)ccn1]

Step-1: Synthesis of 1-methyl-6-(piperidin-1-yl)-1H-indazol-5-amine 1-methyl-5-nitro-6-(piperidin-1-yl)-1H-indazole (0.215 g, 1.5 mmol) (product of step 5 in example 1 (Isomer B)) was dissolved in ethanol (15 mL). To this solution iron powder (0.463 g, 8.26 mmol) and 0.2 ml of HCl were added at 0° C. and the reaction mixture was refluxed for 1 h. After completion of reaction, reaction mixture was cooled to room temperature and diluted with ethyl acetate and filtered through Celite®. The filtrate was basified with sodium bicarbonate solution, organic layer washed with water followed by brine solution. The organic layer was dried over anhydrous $Na_2SO_4$ and concentrated under reduced pressure to obtain crude compound. The crude residue was purified by column chromatography (n-hexane: EtOAc; 3:7) to give the title compound (0.113 g, 59%) as a light brown liquid. $^1$H NMR (400 MHz, DMSO-$d_6$): δ 7.62 (s, 1H), 7.05 (s, 1H), 6.85 (s, 1H), 4.52 (bs, 2H), 3.32 (s, 3H), 2.90-2.80 (m, 4H), 1.71-1.67 (m, 4H), 1.62-1.50 (m, 2H). MS (ES) m/e: 231 (M+1)$^+$.

Step-2: Synthesis of N-(1-methyl-6-(piperidin-1-yl)-1H-indazol-5-yl)-2-(2-methylpyridin-4-yl) oxazole-4-carboxamide To a solution of 1-methyl-6-(piperidin-1-yl)-1H-indazol-5-amine (0.100 g, 0.434 mmol) in DMF (10 mL) was added 2-(2-methylpyridin-4-yl)oxazole-4-carboxylic acid (0.088 g, 0.434 mmol) (WO2011/043371), EDCI.HCl (0.167 g, 0.869 mmol), HOBT (0.117 g, 0.869 mmol), and triethyl amine (0.131 g, 1.30 mmol). The reaction mixture was stirred for 12 h at room temperature and was diluted with EtOAc and washed with brine. The organic layer was dried over anhydrous $Na_2SO_4$ and the residue was purified by flash chromatography ($CH_2Cl_2$:MeOH; 98:2) to give the title compound (90 mg, 50%) as an off white solid.

$^1$H NMR (400 MHz, DMSO-$d_6$): δ 10.32 (s, 1H), 9.05 (s, 1H), 8.73-8.70 (m, 2H), 8.00 (s, 1H), 7.85 (s, 1H), 7.75 (d, J=4.9 Hz, 1H), 7.54 (s, 1H), 4.02 (s, 3H), 2.96-2.93 (m, 4H), 2.59 (s, 3H), 2.00-1.85 (m, 4H), 1.70-1.80 (m, 2H). MS (ES) m/e: 417 (M+1)$^+$.

Example 4

N-(2-cyclopentyl-6-(piperidin-1-yl)-2H-indazol-5-yl)-2-(2-methylpyridin-4-yl) oxazole-4-carboxamide

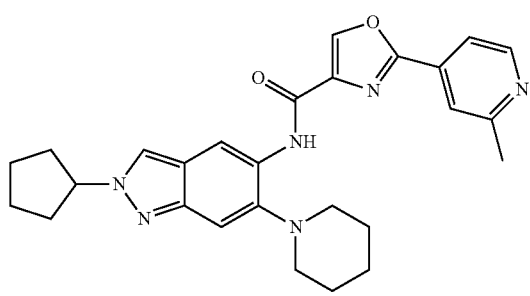 [SMILES: Cc1cc(-c2nc(C(=O)Nc3cc4cn(C5CCCC5)nc4cc3N3CCCCC3)co2)ccn1]

Step-1: Synthesis of 2-cyclopentyl-5-nitro-6-(piperidin-1-yl)-2H-indazole and 1-cyclopentyl-5-nitro-6-(piperidin-1-yl)-1H-indazole A suspension of sodium hydride (0.099 g, 4.14 mmol) in (5 mL) of DMF was cooled to 0° C. and 5-nitro-6-(piperidin-1-yl)-1H-indazole (0.850 g, 3.45 mmol) (product of step 4 in example 1) in DMF (5 mL) was added at the same temperature and stirred for 30 min Cyclopentyl bromide (0.616 g, 4.14 mmol) was added drop wise to the above mixture and continued stirring at 50° C. for 1 h. After completion of reaction, reaction mixture was cooled to 0° C. and crushed ice was added to the reaction mixture, diluted with EtOAc, washed with brine and dried over anhydrous $Na_2SO_4$. After concentration, the residue was purified by flash chromatography (n-hexane:EtOAc; 3:1) to give 2-cyclopentyl-5-nitro-6-(piperidin-1-yl)-2H-indazole (Isomer A, 0.279 g, 26%).

$^1$H NMR (400 MHz, DMSO-$d_6$): δ 8.58 (s, 1H), 8.26 (s, 1H), 7.29 (s, 1H), 5.08-5.01 (m, 1H), 2.88-2.86 (m, 4H), 2.23-2.15 (m, 2H), 2.09-1.91 (m, 2H), 1.89-1.71 (m, 2H), 1.63-1.70 (m, 2H), 1.51-1.60 (m, 4H), 1.42-1.50 (m, 2H). MS (ES) m/e: 315 (M$^+$+1, 100%).

Further elution of column with (n-hexane:EtOAc; 3:1) gave 1-cyclopentyl-5-nitro-6-(piperidin-1-yl)-1H-indazole (Isomer B, 0.058 g, 5.3%) as a brown solid.

$^1$H NMR (400 MHz, DMSO-$d_6$): δ 8.30 (s, 1H), 8.15 (s, 1H), 7.40 (s, 1H), 5.23-5.19 (m, 1H), 2.49-2.08 (m, 2H), 1.99-1.85 (m, 4H), 1.72-1.61 (m, 6H), 1.56-1.53 (m, 2H); MS (ES) m/e 315 (M$^+$+1, 100%).

Step-2: Synthesis of 2-cyclopentyl-6-(piperidin-1-yl)-2H-indazol-5-amine

2-Cyclopentyl-5-nitro-6-(piperidin-1-yl)-2H-indazole (0.279 g, 0.88 mmol) was dissolved in ethanol (10 mL) To this solution iron powder (0.497 g, 8.88 mmol) and 1 ml of HCl were added at 0° C. and refluxed for 1 h. After completion of reaction, reaction mixture was cooled to room temperature, diluted with ethyl acetate and filtered through Celite®. The filtrate was basified with sodium bicarbonate solution and organic layer was washed with water and brine solution. The organic layer was dried over $Na_2SO_4$ and concentrated under reduced pressure to obtain crude compound. The residue was purified by column chromatography (n-hexane:EtOAc; 3:1) to give the title compound (0.045 g, 18%) as a light brown liquid.

$^1$H NMR (400 MHz, DMSO-$d_6$): δ 7.63 (s, 1H), 7.26 (s, 1H), 6.78 (s, 1H), 4.87-4.73 (m, 1H), 4.10-3.90 (bs, 2H), 2.80-3.00 (m, 4H), 2.28-2.21 (m, 2H), 2.19-2.09 (m, 2H), 1.98-1.80 (m, 2H), 1.79-1.62 (m, 6H), 1.60-1.50 (m, 2H). MS (ES) m/e: 285 (M+1)$^+$.

Step-3: Synthesis of N-(2-cyclopentyl-6-(piperidin-1-yl)-2H-indazol-5-yl)-2-(2-methylpyridin-4-yl) oxazole-4-carboxamide To a solution of 2-cyclopentyl-6-(piperidin-1-yl)-2H-indazol-5-amine (0.045 g, 0.16 mol) in DMF (10 mL) was added 2-(2-methylpyridin-4-yl)oxazole-4-carboxylic acid (0.032 g, 0.16 mol), EDCI.HCl (0.030 g, 0.16 mol), HOBT (0.021 g, 0.16 mol), and DIPEA (0.041 g, 0.32 mol). The contents were stirred for 12 h at room temperature, diluted with EtOAc, washed with brine, and dried over $Na_2SO_4$. After concentration, the residue was purified by preparative HPLC to give the title compound (0.004 g, 6%) as a pale brown solid.

$^1$H NMR (400 MHz, DMSO-$d_6$): δ 10.43 (bs, 1H), 9.04 (s, 1H), 8.72 (d, J=4.9 Hz, 1H), 8.62 (s, 1H), 8.35 (s, 1H), 7.86 (s, 1H), 7.75 (d, J=4.9 Hz, 1H), 7.43 (s, 1H), 4.98-4.95 (m, 1H), 2.99-2.82 (m, 4H), 2.60 (s, 3H), 2.33-2.16 (m, 2H), 2.14-2.03 (m, 2H), 1.95-1.82 (m, 6H), 1.80-1.69 (m, 4H). MS (ES) m/e: 471 (M+1)$^+$.

Example 5

N-(6-cyano-2-cyclopentyl-2H-indazol-5-yl)-2-(2-methylpyridin-4-yl) oxazole-4-carboxamide

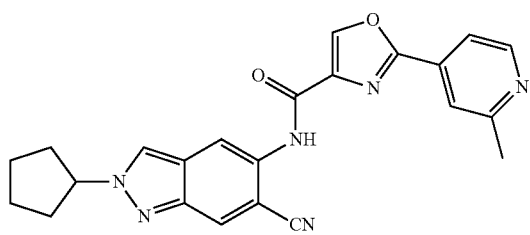 [SMILES: Cc1cc(-c2nc(C(=O)Nc3cc4cn(C5CCCC5)nc4cc3C#N)co2)ccn1]

Step-1: Synthesis of 4-bromo-2-fluoro-5-nitrobenzaldehyde 4-bromo-2-fluorobenzaldehyde (20 g, 98.57 mmol) was added to a mixture of $KNO_3$ (10.8 g, 107.7 mmol) and sulphuric acid (84 mL) at 0° C. After completion of reaction, reaction mixture was poured on crushed ice and stirred for 30 min at room temperature. The separated solid was filtered and washed with saturated $NaHCO_3$ solution followed by water. The solid was dried under vacuum to give the title compound (23 g, 94%) as a white solid.

$^1$H NMR (400 MHz, DMSO-$d_6$): δ 10.13 (s, 1H), 8.49 (d, J=6.8 Hz, 1H), 8.21 (d, J=9.8 Hz, 1H). LCMS: m/z: 246 (M−1)$^+$.

Step-2: Synthesis of 6-bromo-5-nitro-1H-indazole

To a solution of 4-bromo-2-fluoro-5-nitrobenzaldehyde (23 g, 93.11 mmol) in DMF (350 mL) was added hydrazine (6 mL, 102 mmol) and the contents were heated at 150° C. for 2 h. After completion of reaction, reaction mixture was cooled to room temperature, diluted with ethyl acetate. The organic layer was washed with water, brine solution and dried over anhydrous $Na_2SO_4$, concentrated under reduced pressure to obtain the title compound (20.0 g, 93%) as a yellow solid.

$^1$H NMR (400 MHz, DMSO-$d_6$): δ 13.70 (bs, 1H), 8.63 (s, 1H), 8.36 (s, 1H), 8.06 (s, 1H). LCMS: m/z: 240 (M−1)$^+$.

Step-3: Synthesis of 6-bromo-2-cyclopentyl-5-nitro-2H-indazole (Isomer A) and 6-bromo-1-cyclopentyl-5-nitro-1H-indazole (Isomer B)

A suspension of sodium hydride (0.160 g, 3.96 mmol) in dry DMF (5 mL) was cooled to 0° C. and 6-bromo-5-nitro-1H-indazole (0.8 g, 3.3 mmol) in dry DMF (5 mL) was added at the same temperature and stirred for 30 min. Cyclopentyl bromide (0.59 g, 3.96 mmol) was added drop wise to the above mixture and continued stirring at room temperature for 12 h. After completion of reaction, reaction mixture was poured on crushed ice, extracted with EtOAc. Ethyl acetate layer was washed with water followed by brine and dried over anhydrous $Na_2SO_4$. Organic layer was concentrated under reduced pressure to obtain crude compound, the crude residue was purified by flash chromatography (n-hexane:EtOAc; 9:1) to give 6-bromo-1-cyclopentyl-5-nitro-1H-indazole (Isomer B, 0.4 g, 40%) as a brown solid.

$^1$H NMR (400 MHz, DMSO-$d_6$): δ 8.60 (s, 1H), 8.38 (s, 1H), 8.35 (s, 1H), 5.31-5.28 (m, 1H), 2.18-2.11 (m, 2H), 2.01-1.86 (m, 4H), 1.73-1.67 (m, 2H). LCMS: m/z: 312 (M$^+$+1, 100%). Further elution of the column under the same conditions gave 6-bromo-2-cyclopentyl-5-nitro-2H-indazole (Isomer A, 0.3 g, 30%) as a brown solid.

$^1$H NMR (400 MHz, DMSO-$d_6$): δ 8.80 (s, 1H), 8.59 (s, 1H), 8.18 (s, 1H), 5.15-5.11 (m, 1H), 2.26-2.21 (m, 2H), 2.19-2.04 (m, 2H), 1.90-1.86 (m, 2H), 1.73-1.68 (m, 2H). LCMS: m/z: 312 (M+1)$^+$.

Step-4: Synthesis of 2-cyclopentyl-5-nitro-2H-indazole-6-carbonitrile

A solution of 6-bromo-2-cyclopentyl-5-nitro-2H-indazole (0.35 g, 1.12 mmol) in NMP (10 mL) was added Zn $(CN)_2$ (0.158 g, 1.35 mmol) and Pd(PPh$_3$)$_4$ (12 mg, 0.0112 mmol) and degassed with nitrogen for 30 min. The reaction mixture was heated at 90° C. for 1 h, was cooled to room temperature and diluted with ethyl acetate. The organic layer was washed with water followed by brine and dried over anhydrous $Na_2SO_4$. The organic layer was concentrated under reduced pressure to obtain crude compound, which was purified by column chromatography, eluting with a gradient (n-hexane:EtOAc; 1:1) to give the title compound (0.2 g, 69%).

$^1$H NMR (400 MHz, DMSO-$d_6$): δ 9.01 (s, 1H), 8.99 (s, 1H), 8.60 (s, 1H), 5.24-5.21 (m, 1H), 2.30-2.25 (m, 2H), 2.24-2.06 (m, 2H), 1.92-1.88 (m, 2H), 1.75-1.71 (m, 2H). LCMS: m/z: 257 (M+1)$^+$.

Step-5: Synthesis of 5-amino-2-cyclopentyl-2H-indazole-6-carbonitrile

1-Cyclopentyl-5-nitro-1H-indazole-6-carbonitrile (0.2 g, 0.78 mmol) was dissolved in ethanol (20 mL) To this solution iron powder (214 mg, 0.39 mmol) and 0.2 mL of HCl were added at 0° C. and the reaction mixture was refluxed for 2 h. After completion of reaction, the reaction mixture was cooled to room temperature, diluted with ethyl acetate, filtered through Celite® and the filtrate was basified with $NaHCO_3$ solution. The organic layer was washed with water followed by brine solution, dried over anhydrous $Na_2SO_4$ and concentrated under reduced pressure to obtain crude compound. The crude compound was purified by column chromatography (n-hexane:EtOAc; 1:1) to give the title compound (0.054 g, 30%) as a light brown solid.

$^1$H NMR (400 MHz, DMSO-$d_6$): δ 8.17 (s, 1H), 8.05 (s, 1H), 6.88 (s, 1H), 5.17 (bs, 2H), 4.99-4.93 (m, 1H), 2.19-216 (m, 2H), 2.14-2.00 (m, 2H), 1.99-1.80 (m, 2H), 1.73-1.64 (m, 2H). MS LCMS: m/z: 227 (M+1)$^+$.

Step-6: Synthesis of N-(6-cyano-2-cyclopentyl-2H-indazol-5-yl)-2-(2-methylpyridin-4-yl) oxazole-4-carboxamide To a solution of 2-(2-methylpyridin-4-yl) oxazole-4-carboxylic acid (0.060 g, 0.265 mmol) in DMF (5 mL) was added HATU (0.120 g, 0.318 mmol) and DIPEA (0.068 g, 0.53 mmol). The mixture was stirred at room temperature for 30 min and 5-amino-2-cyclopentyl-2H-indazole-6-carbonitrile (0.054 g, 0.265 mmol) was added and stirred for 2 h at room temperature. After completion of reaction, reaction mixture was diluted with ethyl acetate, washed with water followed by brine and the organic layer was dried over anhydrous $Na_2SO_4$ and concentrated under reduced pressure to obtain crude compound. The crude material was purified by preparative HPLC to give the title compound (0.006 g, 5.5%) as a brown solid.

$^1$H NMR (400 MHz, DMSO-d$_6$): δ 10.4 (bs, 1H), 9.00 (s, 1H), 8.69 (d, J=4.9 Hz, 1H), 8.61 (s, 1H), 8.37 (s, 1H), 7.94 (s, 1H), 7.88 (s, 1H), 7.79 (d, J=4.9 Hz, 1H), 5.20-5.12 (m, 1H), 2.60 (s, 3H), 2.33-2.22 (m, 2H), 2.12-2.09 (m, 2H), 1.91-1.88 (m, 2H), 1.74-1.71 (m, 2H). MS (ES) m/e: 413 (M+1)$^+$.

Example 6

N-(2-cyclopentyl-6-cyclopropyl-2H-indazol-5-yl)-2-(2-methylpyridin-4-yl) oxazole-4-carboxamide

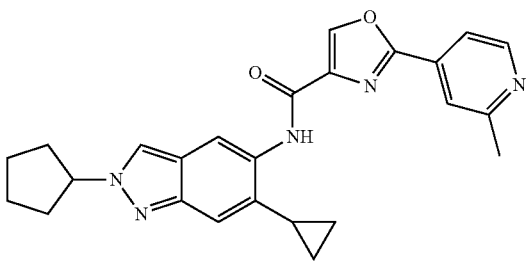 [SMILES: Cc1cc(-c2nc(C(=O)Nc3cc4cn(C5CCCC5)nc4cc3C3CC3)co2)ccn1]

Step-1: Synthesis of 2-cyclopentyl-6-cyclopropyl-5-nitro-2H-indazole

A solution of 6-bromo-2-cyclopentyl-5-nitro-2H-indazole (0.300 g, 0.967 mmol) (product of step 3 in example 5) in toluene:H$_2$O (12 mL, 3:1), cyclopropyl boronic acid (0.124 g, 1.45 mmol), Pd$_2$(dba)$_3$ (10 mg, 0.009 mmol), potassium carbonate (0.300 g, 2.901 mmol) and tricyclohexyl phosphine (16 mg, 0.058 mmol) were taken in a sealed tube under nitrogen atmosphere. The contents were heated at 90° C. for 12 h, cooled to room temperature and filtered through Celite®. The filtrate was diluted with ethyl acetate and the organic layer was washed with water, brine, dried over anhydrous Na$_2$SO$_4$ and concentrated under reduced pressure to obtain crude compound. The residue was purified by column chromatography (n-hexane:EtOAc; 7:3) to give the title compound (0.160 g, 61%) as a light brown solid.

$^1$H NMR (400 MHz, DMSO-d$_6$): δ8.69 (s, 1H), 8.43 (s, 1H), 7.50 (s, 1H), 5.12-5.05 (m, 1H), 2.33-2.20 (m, 3H), 2.19-2.01 (m, 2H), 1.93-1.83 (m, 2H), 1.75-1.65 (m, 2H), 0.94-0.79 (m, 2H), 0.73-0.69 (m, 2H). LCMS: m/z: 272 (M+1)$^+$.

Step-2: Synthesis of 2-cyclopentyl-6-cyclopropyl-2H-indazol-5-amine

2-Cyclopentyl-6-cyclopropyl-5-nitro-2H-indazole (0.300 g, 1.1 mmol) was dissolved in ethanol (15 mL) To this solution iron powder (0.302 mg, 5.5 mmol) and 0.3 mL of HCl were added at 0° C. and the contents were refluxed for 2 h. The reaction mixture was cooled to room temperature, diluted with ethyl acetate, filtered through Celite® and the filtrate was basified with NaHCO$_3$ solution. The organic layer was washed with water and brine solution, dried over anhydrous Na$_2$SO$_4$ and concentrated under reduced pressure to obtain crude compound which was purified by column chromatography (n-hexane:EtOAc; 1:1) to give the title compound (0.2 g, 75%) as a light brown solid.

$^1$H NMR (400 MHz, DMSO-d$_6$): δ 7.89 (s, 1H), 7.09 (s, 1H), 6.65 (s, 1H), 4.86-4.83 (m, 1H), 4.69 (bs, 2H), 2.14-2.09 (m, 3H), 2.08-1.95 (m, 2H), 1.85-1.77 (m, 2H), 1.76-1.63 (m, 2H), 0.91-0.86 (m, 2H), 0.57-0.54 (m, 2H). LCMS: m/z: 242 (M+1)$^+$.

Step-3: Synthesis of N-(2-cyclopentyl-6-cyclopropyl-2H-indazol-5-yl)-2-(2-methylpyridin-4-yl) oxazole-4-carboxamide To a solution of 2-(2-methylpyridin-4-yl) oxazole-4-carboxylic acid (0.1 g, 0.49 mmol) in DMF (10 mL) was added HATU (0.224 g, 0.588 mmol) and DIPEA (0.18 g, 0.98 mmol) and the mixture was stirred at room temperature for 30 min. To the above reaction mixture 2-cyclopentyl-6-cyclopropyl-2H-indazol-5-amine (0.118 g, 0.49 mmol) was added and stirred for 2 h at room temperature. After completion of reaction, reaction mixture was diluted with ethyl acetate, washed with water followed by brine and the organic layer was dried over anhydrous Na$_2$SO$_4$ and concentrated under reduced pressure to obtain crude compound. The crude material was purified by flash chromatography (CH$_2$Cl$_2$:MeOH; 99:1) to give the title compound (25 mg, 11%) as a brown solid.

$^1$H NMR (400 MHz, DMSO-d$_6$): δ 9.87 (bs, 1H), 9.03 (s, 1H), 8.69 (d, J=4.9 Hz, 1H), 8.37 (s, 1H), 8.30 (s, 1H), 7.81 (s, 1H), 7.79 (s, 1H), 7.43 (s, 1H), 5.00-4.97 (m, 1H), 2.60 (s, 3H), 2.19-2.10 (m, 3H), 2.09-2.06 (m, 2H), 1.87-1.80 (m, 2H), 1.78-1.60 (m, 2H), 1.10-1.08 (m, 2H), 0.76-0.75 (m, 2H). MS (ES) m/e: 428 (M+1)$^+$.

Example 7

N-(2-cyclopentyl-6-cyclopropyl-2H-indazol-5-yl)-6-(1H-pyrazol-4-yl) picolinamide

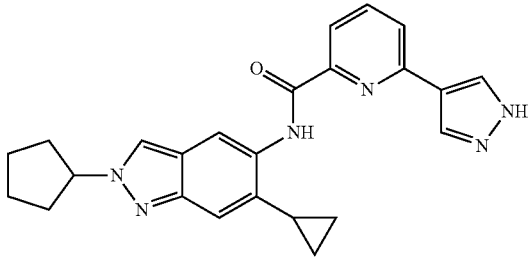 [SMILES: O=C(Nc1cc2cn(C3CCCC3)nc2cc1C1CC1)c1cccc(-c2cn[nH]c2)n1]

Step-1: Synthesis of N-(2-cyclopentyl-6-cyclopropyl-2H-indazol-5-yl)-6-(1-(tetrahydro-2H-pyran-2-yl)-1H-pyrazol-4-yl)picolinamide To a solution of 6-(1-(tetrahydro-2H-pyran-2-yl)-1H-pyrazol-4-yl) picolinic acid (intermediate 1) (0.1 g, 0.366 mmol) in DMF (6 mL) was added HATU (0.16 g, 0.43 mmol) and DIPEA (0.135 mL, 0.73 mmol) and the mixture was stirred room temperature for 30 min. To this reaction mixture 2-cyclopentyl-6-cyclopropyl-2H-indazol-5-amine (0.088 g, 0.366 mmol) (product of step 2 in example 6) was added and stirred for 2 h at room temperature. After completion of reaction, reaction mixture was diluted with ethyl acetate, washed with water followed by brine, the organic layer was dried over anhydrous Na$_2$SO$_4$ and concentrated under reduced pressure to obtain crude compound. The crude material was purified by flash chromatography (CH$_2$Cl$_2$:MeOH; 99:1) to give the title compound (0.100 g, 53%) as a off-white solid.

$^1$H NMR (400 MHz, DMSO-d$_6$): δ 10.84 (s, 1H), 8.66 (s, 1H), 8.49 (s, 1H), 8.38 (s, 1H), 8.21 (s, 1H), 8.09-7.95 (m, 3H), 7.45 (s, 1H), 5.49-5.47 (m, 1H), 5.01-4.97 (m, 1H), 4.00-3.95 (m, 1H), 3.71-3.37 (m, 1H), 2.22-2.11 (m, 2H), 2.09-1.95 (m, 3H), 1.89-1.86 (m, 2H), 1.76-1.72 (m, 2H), 1.70-1.69 (m, 2H), 1.59-1.47 (m, 2H), 1.45-1.42 (m, 2H), 1.05-1.00 (m, 2H), 0.90-0.78 (m, 2H). LCMS: m/z: 497 (M+1)$^+$.

Step-2: Synthesis of N-(2-cyclopentyl-6-cyclopropyl-2H-indazol-5-yl)-6-(1H-pyrazol-4-yl) picolinamide N-(2-cyclopentyl-6-cyclopropyl-2H-indazol-5-yl)-6-(1-(tetrahydro-2H-pyran-2-yl)-1H-pyrazol-4-yl) picolinamide (0.100 g, 0.195 mmol) was dissolved in DCM (10 mL). To this solution ether-HCl (1 mL) was added and stirring was continued at room temperature for 12 h. The reaction mixture was cooled to 0° C. and basified with saturated sodium carbonate solution followed by extraction with ethyl acetate. The organic layer was washed with water followed by brine and dried over anhydrous Na$_2$SO$_4$. The residue was purified by column chromatography (CH$_2$Cl$_2$:MeOH; 98:2) to give the title compound (6 mg, 7.5%) as an off-white solid.
$^1$H NMR (400 MHz, DMSO-d$_6$): δ 13.19 (bs, 1H), 10.79 (bs, 1H), 8.55 (s, 1H), 8.50 (s, 1H), 8.37 (s, 1H), 8.19 (s, 1H), 8.07-7.95 (m, 3H), 7.46 (s, 1H), 5.01-4.97 (m, 1H), 2.21-2.17 (m, 3H), 2.15-2.04 (m, 2H), 1.89-1.86 (m, 2H), 1.73-1.68 (m, 2H), 1.11-1.03 (m, 2H), 0.82-0.78 (m, 2H). MS (ES) m/e: 413 (M+1)$^+$.

Example 8

N-(2-cyclopentyl-6-morpholino-2H-indazol-5-yl)-2-(2-methylpyridin-4-yl) oxazole-4-carboxamide

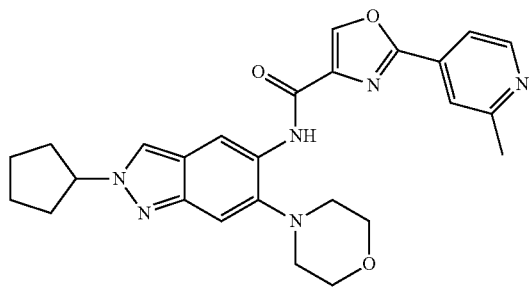 [SMILES: Cc1cc(-c2nc(C(=O)Nc3cc4cn(C5CCCC5)nc4cc3N3CCOCC3)co2)ccn1]

Step-1: Synthesis of 2-cyclopentyl-6-fluoro-5-nitro-2H-indazole and 1-cyclopentyl-6-fluoro-5-nitro-1H-indazole A suspension of sodium hydride (1 g, 44.16 mmol) in dry DMF (20 mL) was cooled at 0° C. and 6-fluoro-5-nitro-1H-indazole (4 g, 22.08 mmol) (product of step 3 in example 1) in dry DMF (20 mL) was added at the same temperature and stirred for 30 min Cyclopentyl bromide (3.94 g, 26.49 mmol) was added drop wise to the above mixture and continued stirring at room temperature for 12 h. After completion of reaction, reaction mixture was poured on crushed ice and was extracted with ethyl acetate. The organic layer was washed with water followed by brine and dried over anhydrous Na$_2$SO$_4$. Organic layer was concentrated under reduced pressure to obtain crude compound, the crude residue was purified by flash chromatography (n-hexane:EtOAc; 7:3) to give 1-cyclopentyl-6-fluoro-5-nitro-1H-indazole (Isomer B, 1.2 g, 21%) as a brown solid.
$^1$H NMR (400 MHz, DMSO-d$_6$): δ 8.49 (d, J=8 Hz, 1H), 8.09 (s, 1H), 7.19 (d, J=12 Hz, 1H), 4.86-4.79 (m, 1H), 2.14-2.11 (m, 4H), 2.09-1.87 (m, 2H), 1.75-1.60 (m, 2H). LCMS: m/z: 250 (M$^+$+1, 100%).
Further elution of the column afforded the required product 2-cyclopentyl-6-fluoro-5-nitro-2H-indazole (Isomer A, 0.9 g, 16%) as a brown solid.
$^1$H NMR (400 MHz, DMSO-d$_6$): δ 8.85 (s, 1H), 8.78 (d, J=8 Hz, 1H), 8.70 (d, J=12 Hz, 1H), 5.14-5.10 (m, 1H), 2.25-2.20 (m, 2H), 2.18-2.04 (m, 2H), 1.90-1.86 (m, 2H), 1.73-1.68 (m, 2H). LCMS: m/z: 250 (M+1)$^+$.

Step-2: Synthesis of 4-(2-cyclopentyl-5-nitro-2H-indazol-6-yl) morpholine 6-fluoro-2-cyclopentyl-5-nitro-2H-indazole (2 g, 1.61 mmol) was dissolved in morpholine (20 mL) and heated at 120° C. for 12 h. After completion of reaction, reaction mixture was cooled to room temperature, diluted with ethyl acetate and washed with water and brine. The organic layer was dried over anhydrous Na$_2$SO$_4$ and concentrated under reduced pressure to obtain crude compound. The residue was purified by column chromatography (CH$_2$Cl$_2$:MeOH; 95:5) to give the title compound (0.4 g, 19%) as a brown semi solid.
$^1$H NMR (400 MHz, DMSO-d$_6$): 8.62 (s, 1H), 8.32 (s, 1H), 7.39 (s, 1H), 5.08-5.04 (m, 1H), 3.78-3.68 (m, 4H), 2.93-2.91 (m, 4H), 2.33-2.21 (m, 2H), 2.19-2.01 (m, 2H), 1.99-1.83 (m, 2H), 1.74-1.66 (m, 2H). MS (ES) m/e: 317 (M+1)$^+$.

Step-3: Synthesis of 2-cyclopentyl-6-morpholino-2H-indazol-5-amine 4-(2-cyclopentyl-5-nitro-2H-indazol-6-yl) morpholine (0.400 g, 1.26 mmol) was dissolved in ethanol (20 mL). To this solution iron powder (0.040 g, 0.71 mmol) and 0.4 mL of HCl were added at 0° C. The reaction mixture was refluxed for 2 h, cooled to room temperature, diluted with ethyl acetate and filtered through Celite®. The filtrate was basified with NaHCO$_3$ solution and was washed with water followed by brine solution. The organic layer was dried over anhydrous Na$_2$SO$_4$ and concentrated under reduced pressure to obtain crude compound which was purified by column chromatography (n-hexane: EtOAc; 1:1) to give the title compound (0.150 g, 41%) as a light brown liquid.
$^1$H NMR (400 MHz, DMSO-d$_6$): δ 7.89 (s, 1H), 7.03 (s, 1H), 6.69 (s, 1H), 4.86-4.83 (m, 1H), 4.61 (bs, 2H), 3.78-3.76 (m, 4H), 2.90-2.80 (m, 4H), 2.14-2.05 (m, 2H), 2.04-1.98 (m, 2H), 1.85-1.80 (m, 2H), 1.68-1.64 (m, 2H). LCMS: m/z: 287 (M+1)$^+$.

Step-4: Synthesis of N-(2-cyclopentyl-6-morpholino-2H-indazol-5-yl)-2-(2-methylpyridin-4-yl) oxazole-4-carboxamide To a solution of 2-(2-methylpyridin-4-yl) oxazole-4-carboxylic acid (0.060 g, 0.294 mmol) in DMF (6 mL) was added HATU (0.134 g, 0.353 mmol) and DIPEA (0.075 g, 0.588 mmol) and the reaction mixture was stirred at room temperature for 30 min. To the above reaction mixture 2-cyclopentyl-6-morpholino-2H-indazol-5-amine (0.084 g, 0.294 mmol) was added and stirred for 2 h at room temperature. After completion of reaction, reaction mixture was diluted with ethyl acetate, washed with water followed by brine, dried over anhydrous Na₂SO₄ and concentrated under reduced pressure to obtain crude compound. The crude material was purified by preparative HPLC to give the title compound (30 mg, 21%) as a brown solid.

$^1$H NMR (400 MHz, DMSO-d₆): δ 10.32 (bs, 1H), 9.06 (s, 1H), 8.74 (d, J=5.4 Hz, 1H), 8.63 (s, 1H), 8.38 (s, 1H), 7.88 (s, 1H), 7.78 (d, J=4.9 Hz, 1H), 7.51 (s, 1H), 5.01-4.94 (m, 1H), 3.98-3.96 (m, 4H), 2.97-2.95 (m, 4H), 2.61 (s, 3H), 2.23-2.10 (m, 2H), 2.08-2.02 (m, 2H), 1.91-1.83 (m, 2H), 1.75-1.68 (m, 2H). LCMS: m/z: 473 (M+1)⁺.

Example 9

Synthesis of 6'-amino-N-(2-cyclopentyl-6-morpholino-2H-indazol-5-yl)-[2,3'-bipyridine]-6-carboxamide 2,2,2-trifluoroacetate

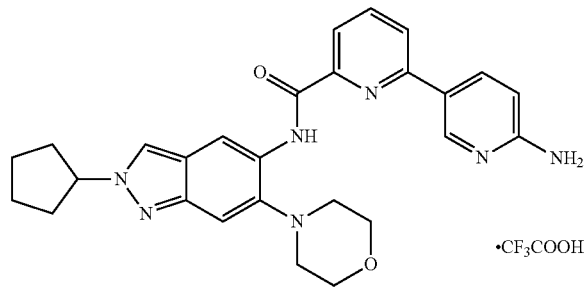 [SMILES: Nc1ccc(-c2cccc(C(=O)Nc3cc4cn(C5CCCC5)nc4cc3N3CCOCC3)n2)cn1 ; "·CF3COOH"]

Step-1: Synthesis of tert-butyl (5-bromopyridin-2-yl) carbamate

To a solution of 2-amino-5-bromopyridine (10 g, 57.8 mmol) in THF (200 mL) at 0° C. was added sodium bis(trimethylsilyl)amide (1M solution in THF, 120 mL, 655 mmol). After addition, the reaction was stirred at 0° C. for 5 min, and then di-tert-butyl dicarbonate (13.8 g, 63.3 mmol) was added in several portions. After addition, the reaction was stirred at RT for 30 min, and then diluted with water (100 mL) and neutralized by adding ice-cold 1N HCl to pH: 7-8. The resultant mixture was extracted with EtOAc (3×200 mL) and the combined organic layers were washed with brine solution. The organic layer was dried (Na₂SO₄), filtered and concentrated. The resulting residue was purified by silica gel column chromatography and elution with a gradient of EtOAc (0-50%) in hexane gave the title compound as an off-white solid (5.10 g, 32%).

$^1$H NMR (400 MHz, DMSO-d₆): δ 10.00 (s, 1H), 8.35 (s, 1H), 7.95-7.92 (m, 1H), 7.80-7.78 (m, 1H), 1.47 (s, 9H). MS (ES) m/e: 274 (M+1)⁺.

Step-2: Synthesis of tert-butyl (5-(4,4,5,5-tetramethyl-1,3,2-dioxaborolan-2-yl) pyridin-2-yl) carbamate 5-Bromo-2-[(tert-butoxycarbonyl) amino] pyridine (1.5 g, 5.51 mmol), potassium acetate (1.33 g, 13.62 mmol), Bispinacolatodiborane (2.06 g, 8.49 mmol) and Pd(dppf)Cl₂ (220 mg, 0.27 mmol) are dissolved in 1,4-dioxane (15 mL) and heated at 80° C. for 1 h. The solvent was evaporated and the residue was purified by silica gel flash chromatography to afford the boronate ester as a solid (1.24 g, 70%). MS (ES) m/e: 321 (M+1)⁺.

Step-3: Synthesis of methyl 6'-((tert-butoxycarbonyl) amino)-[2,3'-bipyridine]-6-carboxylate tert-butyl (5-(4,4,5,5-tetramethyl-1,3,2-dioxaborolan-2-yl)pyridin-2-yl) carbamate (0.940 g, 2.93 mmol), 2M Na₂CO₃ (0.757 g, 7.14 mmol) in 4 mL H₂O and the corresponding methyl 6-bromopicolinate (0.633 g, 2.93 mmol) and Pd(dppf)Cl₂ (0.143 g, 0.175 mmol) are dissolved in DME (10 mL) and heated at 90° C. for 1 h. The mixture was evaporated and the residue was purified by silica gel flash chromatography.

$^1$H NMR (400 MHz, DMSO-d₆): δ 10.04 (s, 1H), 8.99 (s, 1H), 8.46-8.44 (m, 1H), 8.25-8.23 (m, 1H), 8.10-7.94 (m, 3H), 3.92 (s, 3H), 1.49 (s, 9H). MS (ES) m/e: 330 (M+1)⁺.

Step-4: Synthesis of 6'-((tert-butoxycarbonyl) amino)-[2,3'-bipyridine]-6-carboxylic acid To a stirred solution of methyl 6'-((tert-butoxycarbonyl) amino)-[2,3'-bipyridine]-6-carboxylate (0.25 g, 0.759 mmol) in THF (10 mL), MeOH (10 mL) and water (10 mL) was added LiOH.H₂O (0.038 g, 0.911 mmol). The resulting reaction mixture was stirred at room temperature for 12 h and was concentrated under reduced pressure to remove volatiles. The residue was acidified with 2 N HCl and extracted with ethyl acetate. The organic layer was washed with brine, dried over anhydrous Na₂SO₄, concentrated under reduced pressure to give the title compound (0.120 g, 50%) as a white solid which was used in next step without further purification.

$^1$H NMR (400 MHz, DMSO-d₆): δ 13.20 (bs, 1H), 10.02 (s, 1H), 9.04 (s, 1H), 8.52-8.49 (m, 1H), 8.20-8.18 (m, 1H), 8.06-7.93 (m, 3H), 1.49 (s, 9H). MS (ES) m/e: 316 (M+1)⁺.

Step-5: Synthesis of 6'-amino-N-(2-cyclopentyl-6-morpholino-2H-indazol-5-yl)-[2,3'-bipyridine]-6-carboxamide 2,2,2-trifluoroacetate To a solution of 6'-((tert-butoxycarbonyl) amino)[2,3'-bipyridine]-6-carboxylic acid (0.1 g, 0.317 mmol) (product of step 4 of example 9) in DMF (6 mL) was added HATU (0.145 g, 0.380 mmol) and DIPEA (0.081 g, 0.634 mmol) and the mixture was stirred at room temperature for 30 min. To the above reaction mixture 2-cyclopentyl-6-morpholino-2H-indazol-5-amine (0.090 g, 0.317 mmol) (product of step 3 of example 8) was added and stirred for 2 h at room temperature. After completion of reaction, reaction mixture was diluted with EtOAc, washed with water followed by brine and the organic layer was dried over anhydrous Na₂SO₄ and concentrated under reduced pressure to obtain crude compound. The crude product is treated with TFA to deprotect Boc group at RT in DCM. The crude material was purified by preparative HPLC using mobile phase-A: 0.1% TFA (aq), mobile phase-B: acetonitrile to give the title compound (0.034 g, 22%) as a brown solid.

$^1$H NMR (400 MHz, DMSO-d₆): δ 11.02 (bs, 1H), 8.80-8.70 (m, 3H), 8.38 (s, 1H), 8.19-8.17 (m, 3H), 7.87 (bs, 2H), 7.48 (s, 1H), 7.21-7.04 (m, 1H), 5.02 (m, 1H), 3.75-3.80 (m, 4H), 2.91-2.85 (m, 4H), 2.32-2.18 (m, 2H), 2.17-2.02 (m, 2H), 1.91-1.83 (m, 2H), 1.75-1.68 (m, 2H). MS (ES) m/e: 483 (M+1)⁺.

Example 10

N-(6-(3-fluorophenyl)-2-methyl-2H-indazol-5-yl)-2-(2-methylpyridin-4-yl)oxazole-4-carboxamide

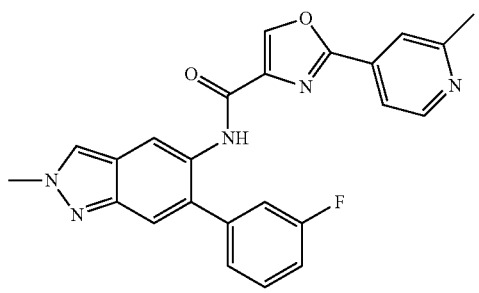

Step-1: Synthesis of 6-chloro-5-nitro-2H-indazole

In around bottomed flask taken 6-chloro-indazole (500 mg, 3.289 mmol) cooled to 0° C. Added 2 mL of Conc. sulphuric acid and stirred for 10 min. then added nitrating mixture (sulphuric acid:nitric acid: 1:1) drop wise at −10° C. and stirred at same temperature for 30 min. Then added ice water and filtered to get the crude product. This was purified by silica gel column chromatography and elution with DCM gave the title compound (310 mg, 65%).
$^1$HNMR (CDCl$_3$, 300 MHz): δ 10.5 (s, 1H), 8.43 (s, 1H), 8.24 (s, 1H), 7.69 (s, 1H). LCMS: 195.5 (M+1)$^+$.

Step-2: Synthesis of 6-chloro-2-methyl-5-nitro-2H-indazole

Using the same reagents and conditions as described in step 5 of example 1, 6-chloro-5-nitro-2H-indazole (500 mg, 2.55 mmol) was methylated using sodium hydride (220 mg, 5.35 mmol and methyl iodide (1.44 g, 10.70 mmol) in THF to get the crude product. This was purified by silica gel column chromatography and elution with DCM gave the title compound (236 mg, 44%). LCMS: 212.2 (M+1)$^+$.

Step-3: Synthesis of 6-(3-fluorophenyl)-2-methyl-5-nitro-2H-indazole

Using the same reagents and conditions as described in step 1 of example 6, 6-chloro-2-methyl-5-nitro-2H-indazole (35 mg, 0.142 mmol) was coupled with (3-fluorophenyl) boronic acid (30 mg, 0.213 mmol) using Pd$_2$(OAc)$_2$ (3 mg, 0.0106 mmol), potassium carbonate (59 mg, 0.426 mmol) and tricyclohexyl phosphine (6 mg, 0.0213 mmol) in toluene:H$_2$O (17 mL, 10:7) at 100° C. for 10 h to obtain desired compound (21 mg, 52%). LCMS: 272.0 (M+1)$^+$.

Step-4: Synthesis of 6-(3-fluorophenyl)-2-methyl-2H-indazol-5-amine

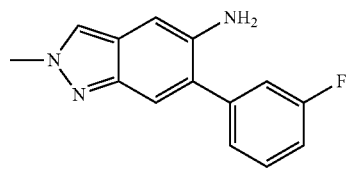 [SMILES: Cn1cc2cc(N)c(-c3cccc(F)c3)cc2n1]

The solution of 6-(3-fluorophenyl)-2-methyl-5-nitro-2H-indazole (200 mg, 0.738 mmol) and 10% Pd/C (40 mg) in methanol (20 mL) was stirred under hydrogen bladder for 2 h. Filtered through Celite® and concentrated to get the desired product (152 mg, 85%). LCMS: 242.3 (M+1)

Step-5: Synthesis of N-(6-(3-fluorophenyl)-2-methyl-2H-indazol-5-yl)-2-(2-methylpyridin-4-yl)oxazole-4-carboxamide Using the same reagents and conditions as described in step 7 of example 1, 6-(3-fluorophenyl)-2-methyl-2H-indazol-5-amine (127 mg, 0.622 mmol) was coupled with 2-(2-methylpyridin-4-yl)oxazole-4-carboxylic acid (150 mg, 0.622 mmol) using EDCI.HCl (178 mg, 0.931 mmol), HOBt (84 mg, 0.622 mmol), DIPEA (321 mg, 2.48 mmol) in DMF (5 mL) to get the crude compound. The crude material was purified by preparative HPLC to afford the desired compound (74 mg, 26%).
$^1$HNMR (CD$_3$OD, 300 MHz): δ 8.95-8.93 (m, 1H), 8.80 (s, 1H), 8.40-8.28 (m, 4H), 7.63 (s, 1H), 7.60-7.48 (m, 1H), 7.37-7.24 (m, 3H), 4.27 (s, 3H), 2.89 (s, 3H). LCMS: 96.61%, m/z=428.4 (M+1)$^+$. HPLC: 99.07%.

Example 11

N-(6-cyclohexyl-2-methyl-2H-indazol-5-yl)-2-(2-methylpyridin-4-yl)oxazole-4-carboxamide hydrochloride

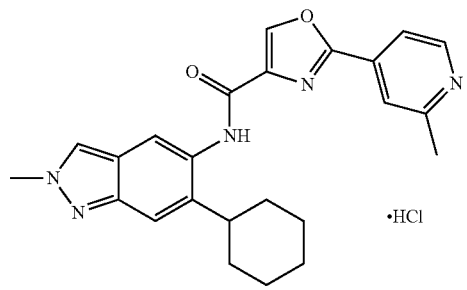 [SMILES: Cc1cc(-c2nc(C(=O)Nc3cc4cn(C)nc4cc3C3CCCCC3)co2)ccn1 ; Cl]

Step-1: Synthesis of 6-bromo-2-methyl-5-nitro-2H-indazole and 6-bromo-1-methyl-5-nitro-1H-indazole Using the same reagents and conditions as described in step 5 of example 1, 6-bromo-5-nitro-1H-indazole (product of step 2 of example 5) (2.5 g, 10.3 mmol) was methylated using sodium hydride (520 mg, 21.6 mmol) and methyl iodide (6.08 g, 42.3 mmol) in THF (25 mL) to get the crude product. This was purified by silica gel column chromatography and elution with 20% ethyl acetate in hexane gave the isomer A; 6-bromo-1-methyl-5-nitro-1H-indazole (1.4 g, 52.95%).
$^1$HNMR (CDCl$_3$, 300 MHz): δ 8.36 (s, 1H), 8.12 (s, 1H), 7.76 (s, 1H), 4.10 (s, 3H).
Further elution with 50% ethyl acetate in hexane gave the isomer B; 6-bromo-2-methyl-5-nitro-2H-indazole (1.1 g, 42.3%).
$^1$HNMR (DMSO-d$_6$, 300 MHz): δ 8.70 (s, 1H), 8.62 (s, 1H), 8.14 (s, 1H), 4.21 (s, 3H).

Step-2: Synthesis of 6-(cyclohex-1-en-1-yl)-2-methyl-5-nitro-2H-indazole

Using the same reagents and conditions as described in step 1 of example 6, 6-bromo-2-methyl-5-nitro-2H-indazole (100 mg, 0.390 mmol) was coupled with 2-(cyclohex-1-en-1-yl)-4,4,5,5-tetramethyl-1,3,2-dioxaborolane (97 mg, 0.465 mmol) using Pd(dppf)Cl$_2$.DCM (16 mg, 0.0195 mmol) and potassium carbonate (107 mg, 0.781 mmol) in 1,4-dioxane/H$_2$O (6/2 mL) at 90° C. for 5 h to obtain desired compound (21 mg, 52%). This was purified by silica gel column chromatography and elution with 50% ethyl acetate in hexane gave the title compound (100 mg, 83.3%). LCMS: 99.11%, m/z=258.1 (M+1)$^+$.

Step-3: Synthesis of 6-cyclohexyl-2-methyl-2H-indazol-5-amine

Using the same reagents and conditions as described in step 4 of example 10, 6-(cyclohex-1-en-1-yl)-2-methyl-5-nitro-2H-indazole (500 mg, 1.9455 mmol) was reduced using 10% Pd/C (100 mg) in methanol/ethyl acetate (10/10 mL) for 5 h to get the desired product (350 mg, 87.5%). LCMS: 85.11%, m/z=230.1 (M+1)$^+$.

Step-4: Synthesis of N-(6-cyclohexyl-2-methyl-2H-indazol-5-yl)-2-(2-methylpyridin-4-yl)oxazole-4-carboxamide hydrochloride Using the same reagents and conditions as described in step 7 of example 1, 6-cyclohexyl-2-methyl-2H-indazol-5-amine (200 mg, 0.873 mmol) was coupled with 2-(2-methylpyridin-4-yl)oxazole-4-carboxylic acid (178 mg, 0.873 mmol) using EDCI.HCl (250 mg, 0.131 mmol), HOBt (123 mg, 0.917 mmol), DIPEA (337 mg, 2.62 mmol) in DMF (8 mL) and further treated with ether HCl in DCM to afford the desired compound (280 mg, 91%).
$^1$HNMR (DMSO-d$_6$, 400 MHz): δ 9.88 (s, 1H), 9.11 (s, 1H), 8.86-8.85 (d, 1H), 8.29 (s, 1H), 8.20 (s, 1H), 8.09-8.08 (d, 1H), 7.74 (s, 1H), 7.46 (s, 1H), 4.15 (s, 3H), 2.73 (s, 3H), 1.90-1.65 (m, 5H), 1.50-1.20 (m, 6H). LCMS: 90.82%, m/z=416.2 (M+1)$^+$. HPLC: 98.39%.

Example 12

6'-fluoro-N-(2-methyl-6-(piperidin-1-yl)-2H-indazol-5-yl)-[2,3'-bipyridine]-6-carboxamide hydrochloride

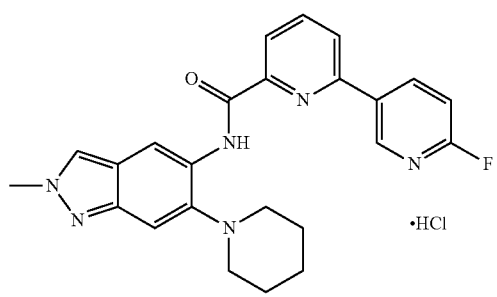 [SMILES: Cn1cc2cc(NC(=O)c3cccc(-c4ccc(F)nc4)n3)c(N3CCCCC3)cc2n1 ; Cl]

Step-1: Synthesis of 6-bromo-N-(2-methyl-6-(piperidin-1-yl)-2H-indazol-5-yl)picolinamide Using the same reaction conditions as described in step 7 of example 1, 2-methyl-6-(piperidin-1-yl)-2H-indazol-5-amine (product of step 6 of example 1) (450 mg, 1.953 mmol), was coupled with 6-bromopicolinic acid (474 mg, 2.3446 mmol) using EDCI.HCl (562 mg, 2.9308 mmol), HOBt (396 mg, 2.9308 mmol), DIPEA (1.361 mL, 7.8155 mmol) in DMF (20 mL) to afford the title compound (700 mg, 86.52%).
LCMS: 99.40%, m/z=416.2 (M+1)$^+$. HPLC: 95.18%.

Step-2: Synthesis of 6'-fluoro-N-(2-methyl-6-(piperidin-1-yl)-2H-indazol-5-yl)-[2,3'-bipyridine]-6-carboxamide hydrochloride Using the same reagents and conditions as described in step 1 of example 6, 6-bromo-N-(2-methyl-6-(piperidin-1-yl)-2H-indazol-5-yl)picolinamide (100 mg, 0.2413 mmol) was coupled with (6-fluoropyridin-3-yl)boronic acid (51 mg, 0.362 mmol) using Pd(dppf)Cl$_2$ (9 mg, 0.0120 mmol) and sodium carbonate (77 mg, 0.7241 mmol) in DME/H$_2$O (5/2 mL) at 90° C. for 12 h to obtain crude product. This was purified by prep HPLC and treated with ether HCl to get the title compound (70 mg, 62.50%).
$^1$HNMR (DMSO-d$_6$, 400 MHz): δ 11.17 (s, 1H), 9.14 (s, 1H), 8.80-8.78 (m, 2H), 8.33-8.24 (m, 4H), 7.43-7.40 (dd, 1H), 7.33 (s, 1H), 4.12 (s, 3H), 2.85 (s, 4H), 1.70-1.60 (m, 4H), 1.43 (s, 2H). LCMS: 98.08%, m/z=431.0 (M+1)$^+$. HPLC: 96.37%.

Example 13

N-(6-cyclohexyl-2-methyl-2H-indazol-5-yl)-6-(1H-pyrazol-4-yl)picolinamide hydrochloride

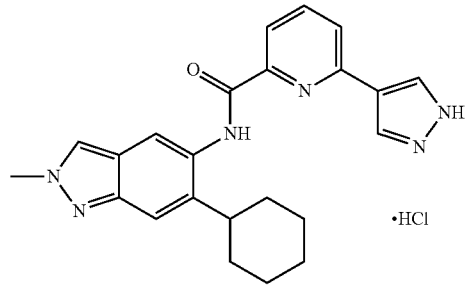 [SMILES: Cn1cc2cc(NC(=O)c3cccc(-c4cn[nH]c4)n3)c(C3CCCCC3)cc2n1 ; Cl]

Step-1: Synthesis of N-(6-cyclohexyl-2-methyl-2H-indazol-5-yl)-6-(1-(tetrahydro-2H-pyran-2-yl)-1H-pyrazol-4-yl)picolinamide Using the same reaction conditions as described in step 7 of example 1, 6-cyclohexyl-2-methyl-2H-indazol-5-amine (product of step 3 of example 11) (150 mg, 0.655 mmol), was coupled with 6-(1-(tetrahydro-2H-pyran-2-yl)-1H-pyrazol-4-yl) picolinic acid (intermediate 1) (214 mg, 0.786 mmol) using EDCI.HCl (187 mg, 0.982 mmol), HOBt (93 mg, 0.687 mmol), DIPEA (253 mg, 1.96 mmol) in DMF (6 mL) to afford the title compound (120 mg, 37.8%). LCMS: 96.95%, m/z=485.2 (M+1)$^+$. HPLC: 96.42%.

Step-2: Synthesis of N-(6-cyclohexyl-2-methyl-2H-indazol-5-yl)-6-(1H-pyrazol-4-yl)picolinamide hydrochloride Using the same reagents and conditions as described in step 8 of example 1, N-(6-cyclohexyl-2-methyl-2H-indazol-5-yl)-

6-(1-(tetrahydro-2H-pyran-2-yl)-1H-pyrazol-4-yl)picolinamide (120 mg, 0.2476 mmol) was deprotected using ether HCl (0.5 mL) in DCM (10 mL) to get the title compound (80 mg, 81%).

¹HNMR (DMSO-d₆, 400 MHz): δ 10.4 (s, 1H), 8.49 (s, 2H), 8.31 (s, 1H), 8.08 (s, 1H), 8.04-7.91 (m, 3H), 7.48 (s, 1H), 4.15 (s, 3H), 2.90-2.84 (t, 1H), 1.94-1.91 (d, 2H), 1.79-1.76 (d, 2H), 1.67-1.64 (d, 1H), 1.50-1.20 (m, 5H). LCMS: 94.20%, m/z=401.2 (M+1)⁺. HPLC: 97.15%.

Example 14

2'-fluoro-N-(2-methyl-6-(piperidin-1-yl)-2H-indazol-5-yl)-[2,3'-bipyridine]-6-carboxamide

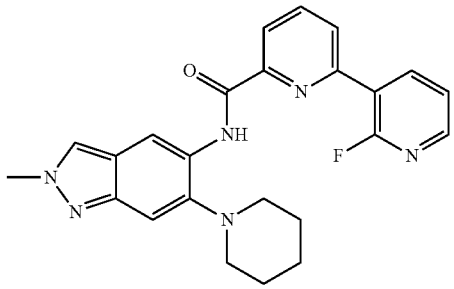 [SMILES: Cn1cc2cc(NC(=O)c3cccc(-c4cccnc4F)n3)c(N3CCCCC3)cc2n1]

Using the same reaction conditions as described in step 7 of example 1, 2-methyl-6-(piperidin-1-yl)-2H-indazol-5-amine (product of step 6 of example 1) (80 mg, 0.347 mmol), was coupled with 2'-fluoro-[2, 3'-bipyridine]-6-carboxylic acid (intermediate 11) (89 mg, 0.694 mmol) using EDCI.HCl (67 mg, 0.347 mmol), HOBt (47 mg, 0.347 mmol), DIPEA (89 mg, 0.694 mmol) in DMF (10 mL) to afford the crude product. This was purified by prep. HPLC to get the title compound (25 mg, 17%).

¹H NMR (DMSO-d₆, 400 MHz): δ 11.19 (bs, 1H), 8.78 (s, 1H), 8.61 (t, 1H), 8.43 (d, 1H), 8.27-8.24 (m, 3H), 8.20-8.11 (m, 1H), 7.60 (t, 1H), 7.34 (s, 1H), 4.12 (s, 3H), 2.81-2.75 (m, 4H), 1.56-1.50 (m, 4H), 1.40-1.30 (m, 2H). LCMS: 100%, m/z=431 (M+1).

Example 15

2-(2-chloropyridin-4-yl)-N-(2-methyl-6-(piperidin-1-yl)-2H-indazol-5-yl)oxazole-4-carboxamide hydrochloride

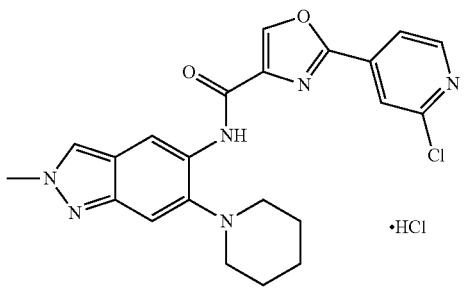 [SMILES: Cn1cc2cc(NC(=O)c3coc(-c4ccnc(Cl)c4)n3)c(N3CCCCC3)cc2n1 ; Cl]

Using the same reaction conditions as described in step 7 of example 1, 2-methyl-6-(piperidin-1-yl)-2H-indazol-5-amine (product of step 6 of example 1) (98 mg, 0.435 mmol), was coupled with 2-(2-chloropyridin-4-yl)oxazole-4-carboxylic acid (WO2011043371) (100 mg, 0.435 mmol) using EDCI.HCl (125 mg, 0.65 mmol), HOBt (59 mg, 0.435 mmol), DIPEA (170 mg, 1.305 mmol) in DMF (5 mL) to afford the crude compound which on treatment with methanolic HCl afforded the title compound (142 mg, 93.4%).

¹HNMR (DMSO-d₆, 300 MHz): δ 10.43 (s, 1H), 9.10 (s, 1H), 8.70-8.69 (d, 1H), 8.60 (s, 1H), 8.26 (s, 1H), 8.00 (s, 1H), 7.95-7.93 (d, 1H), 7.39 (s, 1H), 4.09 (s, 3H), 2.88 (s, 4H), 1.88 (s, 4H), 1.69 (s, 2H). LCMS: 97.79%, m/z=437.1 (M+1)⁺. HPLC: 96.69%.

Example 16

N-(6-cyclopropyl-2-methyl-2H-indazol-5-yl)-2-(2-methylpyridin-4-yl)oxazole-4-carboxamide hydrochloride

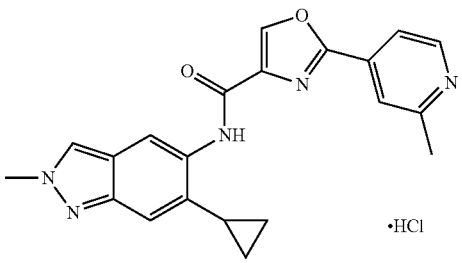 [SMILES: Cc1cc(-c2nc(C(=O)Nc3cc4cn(C)nc4cc3C3CC3)co2)ccn1 ; Cl]

Step-1: Synthesis of 6-cyclopropyl-2-methyl-5-nitro-2H-indazole

Using the same reagents and conditions as described in step 1 of example 6, 6-bromo-2-methyl-5-nitro-2H-indazole (product of step 1 of example 11) (1 gm, 3.9062 mmol) was coupled with cyclopropyl boronic acid (671 mg, 7.8125 mmol) using Pd(OAc)₂ (263 mg, 1.1718 mmol) tricyclohexyl phosphine (329 mg, 1.1718 mmol) and potassium phosphate (2.07 gm, 9.7656 mmol) in toluene/H₂O (50/10 mL) at 110° C. for 14 h to obtain crude product. This was purified by silica gel column chromatography and elution with 1% methanol in DCM to give the title compound (680 mg, 84.85%). LCMS: m/z=218.0 (M+1)⁺.

Step-2: Synthesis of 6-cyclopropyl-2-methyl-2H-indazol-5-amine

To a solution of 6-cyclopropyl-2-methyl-5-nitro-2H-indazole (680 mg, 3.1336 mmol) in THF (20 mL) was added ammonium chloride (2.681 gm, 50.1382 mmol) in water (5 mL) and zinc dust (1.639 gm, 25.0691 mmol) and stirred at RT for 30 min. Filtered the catalyst through Celite®, extracted with DCM (2×100 mL) and distilled out the solvent to get the crude product. This was purified by silica gel column chromatography and elution with 1% methanol in DCM to give the title compound (285 mg, 48.63%).

¹HNMR (CDCl₃, 300 MHz): δ 7.58 (s, 1H), 7.38 (s, 1H), 6.76 (s, 1H), 4.12 (s, 3H), 2.19-2.18 (m, 1H), 0.99-0.92 (m, 2H), 0.71-0.66 (m, 2H). LCMS: 100%, m/z=188.2 (M+1)⁺.

Step-3: Synthesis of N-(6-cyclopropyl-2-methyl-2H-indazol-5-yl)-2-(2-methylpyridin-4-yl)oxazole-4-carboxamide hydrochloride Using the same reagents and conditions as described in step 7 of example 1, 6-cyclopropyl-2-methyl-2H-indazol-5- amine (285 mg, 1.5240 mmol) was coupled with 2-(2-methylpyridin-4-yl)oxazole-4-carboxylic acid (373 mg, 1.8288 mmol) using EDCI.HCl (438 mg, 2.2860 mmol), HOBt (309 mg, 2.2860 mmol), DIPEA (1.061 mL, 6.0962 mmol) in DMF (12 mL) to afford the crude compound which on treatment with methanolic HCl afforded the title compound (396 mg, 63.46%).

$^1$HNMR (DMSO-$d_6$, 300 MHz): δ 9.88 (s, 1H), 9.13 (s, 1H), 8.80-8.78 (d, 1H), 8.28 (s, 2H), 8.10 (s, 1H), 8.03-8.02 (d, 1H), 7.39 (s, 1H), 4.12 (s, 3H), 2.69 (s, 3H), 2.10-2.00 (m, 1H), 1.09-1.04 (m, 2H), 0.74-0.73 (m, 2H). LCMS: 95.50%, m/z=374.1 (M+1)$^+$. HPLC: 97.02%.

Example 17

N-(1-cyclopentyl-6-cyclopropyl-1H-indazol-5-yl)-6-(1-methyl-1H-pyrazol-4-yl)picolinamide

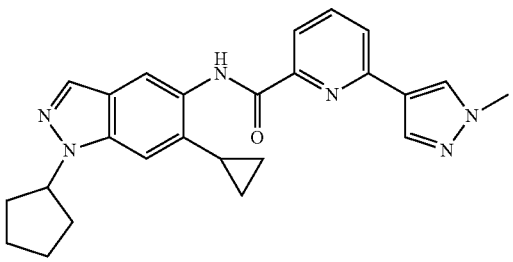 [SMILES: Cn1cc(-c2cccc(C(=O)Nc3cc4cnn(C5CCCC5)c4cc3C3CC3)n2)cn1]

Step-1: Synthesis of 6-chloro-1-cyclopentyl-5-nitro-1H-indazole and 6-chloro-2-cyclopentyl-5-nitro-2H-indazole Using the same reagents and conditions as described in step 5 of example 1, 6-chloro-5-nitro-2H-indazole (1 gm, 5.063 mmol) was alkylated with cyclopentylbromide (836 mg, 5.569 mmol) and potassium carbonate (2.1 gm, 15.189 mmol) in DMF (10 mL) to get the crude product. This was purified by silica gel column chromatography and elution with 10% ethyl acetate in hexane gave isomer A; 6-chloro-2-cyclopentyl-5-nitro-2H-indazole (500 mg, 73.4%). LCMS: 96.87%, m/z=265.9 (M+1) and further elution with 30% ethyl acetate in hexane gave the isomer B; 6-chloro-1-cyclopentyl-5-nitro-1H-indazole (500 mg, 73.4%). LCMS: 93.06%, m/z=266.0 (M+1)$^+$.

Step-2: Synthesis of 1-cyclopentyl-6-cyclopropyl-5-nitro-1H-indazole

Using the same reagents and conditions as described in step 1 of example 6, 6-chloro-1-cyclopentyl-5-nitro-1H-indazole (500 mg, 1.858 mmol) was coupled with cyclopropyl boronic acid (400 mg, 4.646 mmol) using Pd(OAc)$_2$ (127 mg, 0.557 mmol) tricyclohexyl phosphine (156 mg, 0.557 mmol) and potassium carbonate (770 mg, 5.57 mmol) in toluene/H$_2$O (15/2 mL) at 110° C. for 4 h to obtain crude product. This was purified by silica gel column chromatography and elution with 30% ethyl acetate in hexane gave the title compound (400 mg, 80%).

$^1$HNMR (CDCl$_3$, 300 MHz): δ 8.40 (s, 1H), 8.08 (s, 1H), 7.25 (s, 1H), 5.05-4.90 (m, 1H), 2.60-2.50 (m, 1H), 2.20-2.12m (, 4H), 2.02-1.95 (m, 2H), 1.79-1.73 (m, 2H), 1.09-1.03 (m, 2H), 0.74-0.69 (m, 2H). LCMS: 92.37%, m/z=272.1 (M+1)$^+$.

Step-3: Synthesis of 1-cyclopentyl-6-cyclopropyl-1H-indazol-5-amine

Using the same reaction conditions as described in step 2 of example 16, 1-cyclopentyl-6-cyclopropyl-5-nitro-1H-indazole (400 mg, 1.481 mmol) was reduced with zinc dust (770 mg, 11.84 mmol) and ammonium chloride (1.26 gm, 23.696 mmol) in THF/water (5/1 mL) to get the desired product (320 mg, 89.6%). LCMS: 95.13%, m/z=242.5 (M+1)$^+$.

Step-4: Synthesis of N-(1-cyclopentyl-6-cyclopropyl-1H-indazol-5-yl)-6-(1-methyl-1H-pyrazol-4-yl)picolinamide Using the same reagents and conditions as described in step 7 of example 1, 1-cyclopentyl-6-cyclopropyl-1H-indazol-5-amine (100 mg, 0.413 mmol) was coupled with 6-(1-methyl-1H-pyrazol-4-yl)picolinic acid (intermediate 2) (92 mg, 0.454 mmol) using EDCI.HCl (117 mg, 0.619 mmol), HOBt (84 mg, 0.619 mmol), DIPEA (160 mg, 1.239 mmol) in DMF (5 mL) to get the crude product. This was then purified by prep. HPLC to obtain the desired compound (85 mg, 54%).

$^1$HNMR (DMSO-$d_6$, 300 MHz): δ 10.70 (s, 1H), 8.46-8.44 (d, 2H), 8.14 (s, 1H), 8.03-7.88 (m, 4H), 7.52 (s, 1H), 5.20-5.10 (m, 1H), 3.90 (s, 3H), 2.30-1.80 (m, 7H), 1.70-1.60 (m, 2H), 1.10-1.00 (m, 2H), 0.84-0.83 (m, 2H). LCMS: 90.87%, m/z=427.1 (M+1)$^+$. HPLC: 98.67%.

Example 18

N-(2-cyclopentyl-6-cyclopropyl-2H-indazol-5-yl)-6-(1-methyl-1H-pyrazol-4-yl)picolinamide

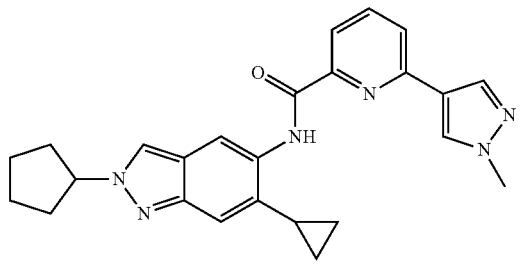 [SMILES: Cn1cc(-c2cccc(C(=O)Nc3cc4cn(C5CCCC5)nc4cc3C3CC3)n2)cn1]

Using the same reagents and conditions as described in step 7 of example 1, 2-cyclopentyl-6-cyclopropyl-2H-indazol-5-amine (product of step 2 of example 6) (100 mg, 0.413 mmol) was coupled with 6-(1-methyl-1H-pyrazol-4-yl)picolinic acid (intermediate 2) (92 mg, 0.454 mmol) using EDCI.HCl (117 mg, 0.619 mmol), HOBt (84 mg, 0.619 mmol), DIPEA (160 mg, 1.239 mmol) in DMF (5 mL) to get the crude product. This was then purified by prep. HPLC to obtain the desired compound (80 mg, 51%).

$^1$HNMR (DMSO-$d_6$, 400 MHz): δ 10.78 (s, 1H), 8.52 (s, 1H), 8.44 (s, 1H), 8.39 (s, 1H), 8.14 (s, 1H), 8.07-8.03 (t, 1H), 8.00-7.98 (d, 1H), 7.92-7.90 (d, 1H), 7.46 (s, 1H), 5.05-4.95 (m, 1H), 3.92 (s, 3H), 2.25-2.15 (m, 3H), 2.10-2.00 (m, 2H), 1.90-1.80 (m, 2H), 1.75-1.65 (m, 2H), 1.10-1.00 (m, 2H), 0.82-0.76 (m, 2H). LCMS: 92.47%, m/z=427.0 (M+1)$^+$. HPLC: 97.70%.

Example 19

6-(1-methyl-1H-pyrazol-4-yl)-N-(2-methyl-6-(piperidin-1-yl)-2H-indazol-5-yl)picolinamide

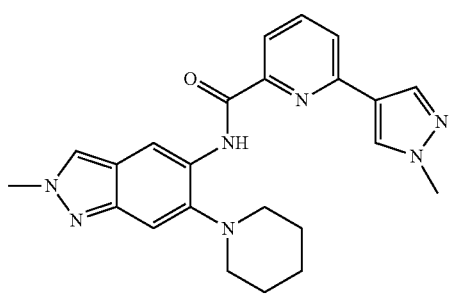 [SMILES: Cn1cc(-c2cccc(C(=O)Nc3cc4cn(C)nc4cc3N3CCCCC3)n2)cn1]

Using the same reaction conditions as described in step 7 of example 1, 2-methyl-6-(piperidin-1-yl)-2H-indazol-5-amine (product of step 6 of example 1) (80 mg, 0.347 mmol), was coupled with 6-(1-methyl-1H-pyrazol-4-yl)picolinic acid (intermediate 2) (64 mg, 0.313 mmol) using EDCI.HCl (99 mg, 0.521 mmol), HOBt (70 mg, 0.521 mmol), DIPEA (112 mg, 0.869 mmol) in DMF (2 mL) to afford the crude compound which after purification by prep HPLC afforded the title compound (50 mg, 34.7%).

$^1$HNMR (DMSO-$d_6$, 400 MHz): δ 11.00 (s, 1H), 8.72 (s, 1H), 8.47 (s, 1H), 8.30 (s, 1H), 8.23 (s, 1H), 8.07-7.99 (m, 2H), 7.93-7.91 (d, 1H), 7.40-7.30 (m, 1H), 4.13 (s, 3H), 3.93 (s, 3H), 2.89 (s, 4H), 1.80 (s, 4H), 1.55 (s, 2H). LCMS: 91.14%, m/z=416.2 (M+1)$^+$. HPLC: 95.37%.

Example 20

N-(2-cyclopentyl-6-cyclopropyl-2H-indazol-5-yl)-2-(6-methoxypyridin-3-yl)oxazole-4-carboxamide

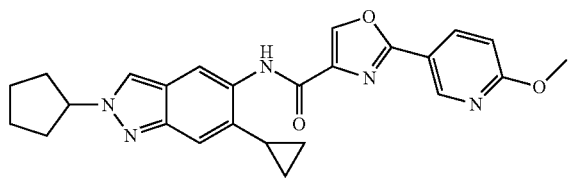 [SMILES: COc1ccc(-c2nc(C(=O)Nc3cc4cn(C5CCCC5)nc4cc3C3CC3)co2)cn1]

Using the same reagents and conditions as described in step 7 of example 1, 2-cyclopentyl-6-cyclopropyl-2H-indazol-5-amine (product of step 2 of example 6) (80 mg, 0.330 mmol) was coupled with 2-(6-methoxypyridin-3-yl)oxazole-4-carboxylic acid (intermediate 3) (73 mg, 0.330 mmol) using EDCI.HCl (95 mg, 0.4958 mmol), HOBt (47 mg, 0.3471 mmol), DIPEA (150 mg, 1.160 mmol) in DMF (5 mL) to obtain the desired compound (41 mg, 28%).

$^1$HNMR (DMSO-$d_6$, 300 MHz): δ 9.85 (s, 1H), 8.90-8.80 (d, 2H), 8.40-8.25 (m, 3H), 7.40 (s, 1H), 7.10-7.00 (d, 1H), 5.00-4.90 (m, 1H), 3.94 (s, 1H), 2.20-1.95 (m, 5H), 1.90-1.80 (m, 2H), 1.75-1.60 (m, 2H), 1.15-1.05 (m, 2H), 0.80-0.70 (m, 2H). LCMS: 98.34%, m/z=444.2 (M+1)$^+$. HPLC: 98.71%.

Example 21

2-(6-methoxypyridin-3-yl)-N-(2-methyl-6-(piperidin-1-yl)-2H-indazol-5-yl)oxazole-4-carboxamide

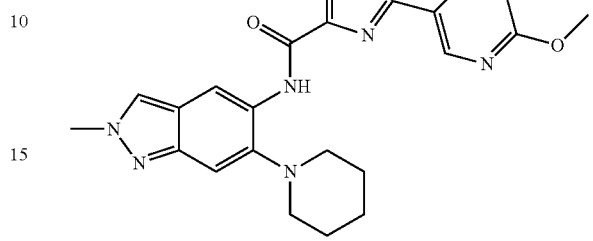

Using the same reaction conditions as described in step 7 of example 1, 2-methyl-6-(piperidin-1-yl)-2H-indazol-5-amine (product of step 6 of example 1) (90 mg, 0.390 mmol), was coupled with 2-(6-methoxypyridin-3-yl)oxazole-4-carboxylic acid (intermediate 3) (87 mg, 0.390 mmol) using EDCI.HCl (114 mg, 0.5892 mmol), HOBt (57 mg, 0.411 mmol), DIPEA (180 mg, 1.3779 mmol) in DMF (15 mL) to afford the title compound (141 mg, 84%).

$^1$HNMR (DMSO-$d_6$, 300 MHz): δ 10.30 (s, 1H), 8.94 (s, 1H), 8.86-8.85 (d, 1H), 8.30-8.20 (m, 2H), 7.35 (s, 1H), 7.14-7.06 (d, 1H), 4.09 (s, 3H), 3.94 (s, 3H), 2.40-2.30 (m, 4H), 1.90-1.80 (t, 4H), 1.65 (s, 2H). LCMS: 96.54%, m/z=433.3 (M+1)$^+$. HPLC: 98.67%.

Example 22

N-(2-methyl-6-(piperidin-1-yl)-2H-indazol-5-yl)-2-(3-methylpyridin-4-yl)oxazole-4-carboxamide

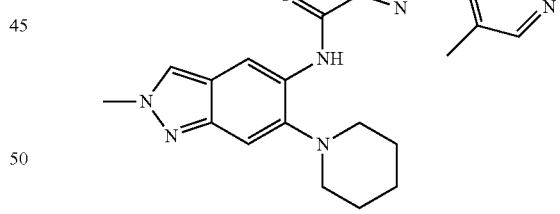

Using the same reagents and conditions as described in step 7 of example 1, 2-methyl-6-(piperidin-1-yl)-2H-indazol-5-amine (product of step 6 of example 1) (80 mg, 0.3478 mmol) was coupled with 2-(3-methylpyridin-4-yl)oxazole-4-carboxylic acid (PCT publication: WO2011043371 dated Apr. 14, 2011) (96 mg, 0.4695 mmol) using EDCI.HCl (135 mg, 0.7047 mmol), HOBt (64 mg, 0.4695 mmol), DIPEA (212 mg, 1.64 mmol) in DMF (5 mL) to obtain the desired compound (130 mg, 90.2%).

$^1$HNMR (DMSO-$d_6$, 300 MHz): δ 10.20 (s, 1H), 9.05 (s, 1H), 8.70 (s, 1H), 8.65 (s, 1H), 8.64-8.60 (d, 1H), 8.35 (s, 1H), 7.92-6.98 (d, 1H), 7.38 (s, 1H), 4.09 (s, 3H), 2.85 (s, 4H), 2.77 (s, 3H), 1.84-1.75 (t, 4H), 1.60 (s, 2H). LCMS: 95.66%, m/z=417.1 (M+1)$^+$. HPLC: 98.59%.

Example 23

6-bromo-N-(2-methyl-6-(piperidin-1-yl)-2H-indazol-5-yl)picolinamide

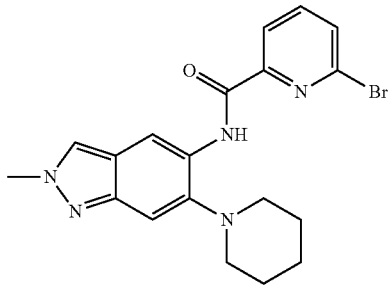 [SMILES: Cn1cc2cc(NC(=O)c3cccc(Br)n3)c(N3CCCCC3)cc2n1]

Using the same reagents and conditions as described in step 7 of example 1, 2-methyl-6-(piperidin-1-yl)-2H-indazol-5-amine (product of step 6 of example 1) (450 mg, 1.9538 mmol) was coupled with 6-bromopicolinic acid (474 mg, 2.344 mmol) using EDCI.HCl (562 mg, 2.9308 mmol), HOBt (396 mg, 2.9308 mmol), DIPEA (1.361 mL, 7.8155 mmol) in DMF (20 mL) to obtain the desired compound (700 mg, 86.52%).

$^1$HNMR (CDCl$_3$, 300 MHz): δ 11.30 (s, 1H), 8.81 (s, 1H), 8.28-8.25 (d, 1H), 7.81-7.74 (m, 2H), 7.66-7.63 (d, 1H), 7.40 (s, 1H), 4.17 (s, 1H), 3.20-2.80 (m, 5H), 2.10-1.80 (bs, 5H). LCMS: 99.40%, m/z=416.2 (M+2)$^+$. HPLC: 95.18%.

Example 24

6-chloro-5-methyl-N-(2-methyl-6-(piperidin-1-yl)-2H-indazol-5-yl)picolinamide

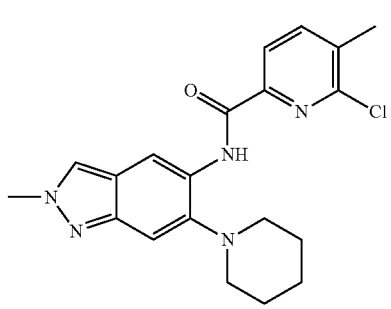

Using the same reagents and conditions as described in step 7 of example 1, 2-methyl-6-(piperidin-1-yl)-2H-indazol-5-amine (product of step 6 of example 1) (300 mg, 1.3025 mmol) was coupled with 6-chloro-5-methylpicolinic acid (269 mg, 1.5631 mmol) using EDCI.HCl (375 mg, 1.9538 mmol), HOBt (264 mg, 1.9538 mmol), DIPEA (0.907 mL, 5.2103 mmol) in DMF (15 mL) to obtain the desired compound (375 mg, 75.0%).

$^1$HNMR (CDCl$_3$, 300 MHz): δ 11.20 (s, 1H), 8.80 (s, 1H), 8.15-8.12 (d, 1H), 7.81 (s, 1H), 7.76-7.74 (d, 1H), 7.39 (s, 1H), 4.17 (s, 3H), 3.10-3.70 (m, 4H), 2.47 (s, 3H), 2.10-1.80 (bs, 4H). LCMS: 100%, m/z=383.9 (M+1)$^+$. HPLC: 96.01%.

Example 25

N-(2-methyl-6-(piperidin-1-yl)-2H-indazol-5-yl)-2-(6-methylpyridin-3-yl)oxazole-4-carboxamide

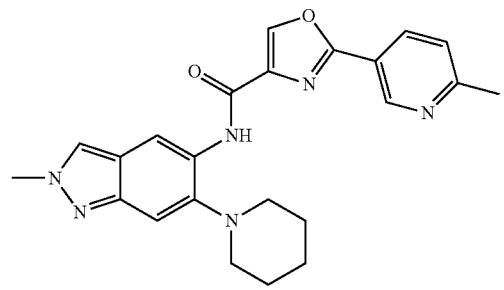

Using the same reagents and conditions as described in step 7 of example 1, 2-methyl-6-(piperidin-1-yl)-2H-indazol-5-amine (product of step 6 of example 1) (80 mg, 0.3478 mmol) was coupled with 2-(2-methylpyridin-5-yl)oxazole-4-carboxylic acid (96 mg, 0.4695 mmol) using EDCI.HCl (135 mg, 0.7047 mmol), HOBt (64 mg, 0.4695 mmol), DIPEA (212 mg, 1.64 mmol) in DMF (5 mL) to obtain the title compound (112 mg, 77%).

$^1$HNMR (DMSO-d$_6$, 400 MHz): δ 10.36 (s, 1H), 8.14 (s, 1H), 9.00 (s, 1H), 8.64 (s, 1H), 8.70-8.65 (m, 2H), 7.56-7.52 (d, 1H), 6.90 (s, 1H), 4.10 (s, 3H), 2.95-2.85 (m, 4H), 2.60 (s, 3H), 1.95-1.85 (m, 4H), 1.75-1.60 (m, 2H). LCMS: 98.42%, m/z=417.5 (M+1)$^+$. HPLC: 96.15%.

Example 26

N-(2-cyclopentyl-6-cyclopropyl-2H-indazol-5-yl)-2-(2-methylpyridin-3-yl)oxazole-4-carboxamide

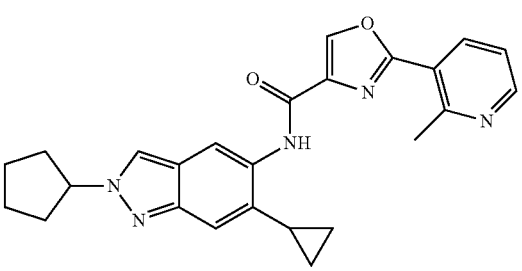 [SMILES: Cc1ncccc1-c1nc(C(=O)Nc2cc3cn(C4CCCC4)nc3cc2C2CC2)co1]

Using the same reagents and conditions as described in step 7 of example 1, 2-cyclopentyl-6-cyclopropyl-2H-indazol-5-amine (product of step 2 of example 6) (75 mg, 0.309 mmol) was coupled with 2-(2-methylpyridin-3-yl)oxazole-4-carboxylic acid (intermediate 4) (75 mg, 0.371 mmol) using EDCI.HCl (88 mg, 0.464 mmol), HOBt (42 mg, 0.309 mmol), DIPEA (0.3 mL, 1.236 mmol) in DMF (5 mL) to afford the crude compound which after purification by prep HPLC afforded the title compound (50 mg, 38%).

$^1$HNMR (DMSO-d$_6$, 300 MHz): δ 9.78 (s, 1H), 9.05 (s, 1H), 8.74-8.73 (d, 1H), 9.62-8.59 (d, 1H), 8.37-8.35 (d, 2H), 7.75-7.65 (m, 1H), 7.41 (s, 1H), 5.02-4.90 (m, 1H), 3.00 (s, 3H), 2.20-1.95 (m, 5H), 1.90-1.80 (m, 2H), 1.75-1.62 (m, 2H), 1.05-1.10 (m, 2H), 0.75-0.70 (m, 2H). LCMS: 99.64%, m/z=428.2 (M+1)$^+$. HPLC: 97.04%.

Example 27

N-(2-cyclopentyl-6-cyclopropyl-2H-indazol-5-yl)-2-(3-methylpyridin-4-yl)oxazole-4-carboxamide

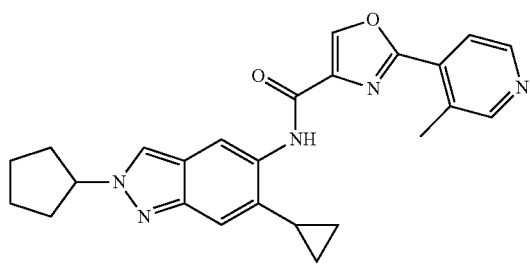 [SMILES: Cc1cnccc1-c1nc(C(=O)Nc2cc3cn(C4CCCC4)nc3cc2C2CC2)co1]

Using the same reagents and conditions as described in step 7 of example 1, 2-cyclopentyl-6-cyclopropyl-2H-indazol-5-amine (product of step 2 of example 6) (75 mg, 0.309 mmol) was coupled with 2-(3-methylpyridin-4-yl)oxazole-4-carboxylic acid (75 mg, 0.371 mmol) using EDCI.HCl (88 mg, 0.464 mmol), HOBt (42 mg, 0.309 mmol), DIPEA (0.3 mL, 1.236 mmol) in DMF (4 mL) to afford the crude compound which after purification by prep HPLC afforded the title compound (50 mg, 38%).

$^1$HNMR (DMSO-$d_6$, 300 MHz): δ 9.79 (s, 1H), 9.15 (s, 1H), 8.88 (s, 1H), 8.79-8.78 (d, 1H), 8.37 (s, 1H), 8.32 (s, 1H), 8.24-8.22 (d, 1H), 7.41 (s, 1H), 5.04-4.90 (m, 1H), 2.79 (s, 3H), 2.25-2.20 (m, 5H), 1.90-1.80 (m, 2H), 1.72-1.60 (m, 2H), 1.05-1.10 (m, 2H), 0.78-0.70 (m, 2H). LCMS: 99.40%, m/z=428.2 (M+1)$^+$. HPLC: 97.23%.

Example 28

N-(2-cyclopentyl-6-cyclopropyl-2H-indazol-5-yl)-2-(6-methylpyridin-3-yl)oxazole-4-carboxamide

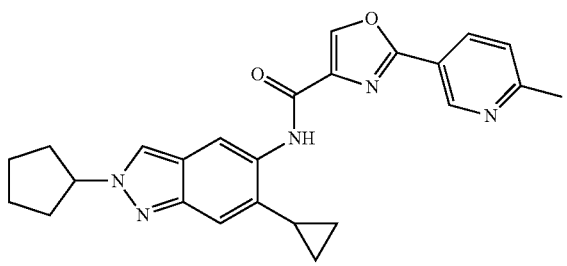 [SMILES: Cc1ccc(-c2nc(C(=O)Nc3cc4cn(C5CCCC5)nc4cc3C3CC3)co2)cn1]

Using the same reagents and conditions as described in step 7 of example 1, 2-cyclopentyl-6-cyclopropyl-2H-indazol-5-amine (product of step 2 of example 6) (100 mg, 0.4132 mmol) was coupled with 2-(2-methylpyridin-5-yl) oxazole-4-carboxylic acid (WO2011043371) (102 mg, 0.4958 mmol) using EDCI.HCl (119 mg, 0.6198 mmol), HOBt (84 mg, 0.6198 mmol), DIPEA (0.288 L, 1.6528 mmol) in DMF (2 mL) to afford the crude compound which after purification by prep HPLC afforded the title compound (70 mg, 36.64%).

$^1$HNMR (DMSO-$d_6$, 400 MHz): δ 9.80 (s, 1H), 9.11 (s, 1H), 8.95 (s, 1H), 8.34-8.30 (m, 3H), 7.53-7.51 (d, 1H), 7.39 (s, 1H), 5.00-4.90 (m, 1H), 2.56 (s, 3H), 2.16-2.12 (m, 5H), 1.90-1.80 (m, 2H), 1.70-1.60 (m, 2H), 1.10-1.00 (m, 2H), 0.75-0.70 (m, 2H). LCMS: 99.98%, m/z=428.2 (M+1)$^+$. HPLC: 98.41%.

Example 29

6'-amino-3-methyl-N-(2-methyl-6-(piperidin-1-yl)-2H-indazol-5-yl)-[2,3'-bipyridine]-6-carboxamide hydrochloride

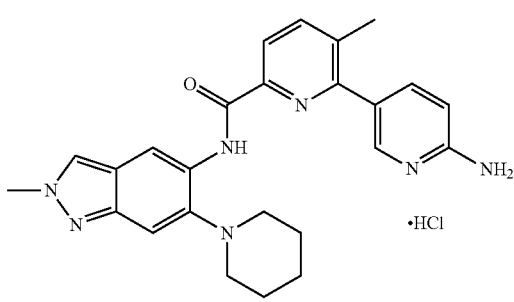 [SMILES: Cc1ccc(C(=O)Nc2cc3cn(C)nc3cc2N2CCCCC2)nc1-c1ccc(N)nc1 ; Cl]

Step-1: Synthesis of tert-butyl (3-methyl-6-((2-methyl-6-(piperidin-1-yl)-2H-indazol-5-yl)carbamoyl)-[2,3'-bipyridin]-6'-yl)carbamate Using the same reagents and conditions as described in step 1 of example 6, 6-chloro-5-methyl-N-(2-methyl-6-(piperidin-1-yl)-2H-indazol-5-yl)picolinamide (example 24) (100 mg, 0.2605 mmol) was coupled with tert-butyl (5-(4,4,5,5-tetramethyl-1,3,2-dioxaborolan-2-yl) pyridin-2-yl)carbamate (product of step 2 of example 9) (167 mg, 0.5210 mmol) using Pd(dppf)Cl$_2$ (10 mg, 0.0130 mmol) and sodium carbonate (69 mg, 0.6512 mmol) in DME/H$_2$O (5/2 mL) at 90° C. for 48 h to obtain crude product. This was purified by silica gel column chromatography and elution with 2% methanol in DCM gave the title compound (100 mg, 70.92%). LCMS: m/z=542.3 (M+1)$^+$.

Step-2: Synthesis of 6'-amino-3-methyl-N-(2-methyl-6-(piperidin-1-yl)-2H-indazol-5-yl)-[2,3'-bipyridine]-6-carboxamide hydrochloride Using the same reaction conditions as described in step 8 of example 1, tert-butyl (3-methyl-6-((2-methyl-6-(piperidin-1-yl)-2H-indazol-5-yl)carbamoyl)-[2,3'-bipyridin]-6'-yl)carbamate (100 mg, 0.1846 mmol) was deprotected using methanolic HCl (5 mL) and purified by prep HPLC to get the title compound (70 mg, 79.54%).

$^1$HNMR (DMSO-$d_6$, 400 MHz): δ 11.15 (s, 1H), 8.71 (s, 1H), 8.85-8.64 (m, 4H), 8.12-8.10 (d, 1H), 8.03-8.01 (d, 1H), 7.29 (s, 1H), 7.15-7.12 (d, 1H), 4.07 (s, 3H), 2.75 (s, 4H), 2.43 (s, 3H), 1.48 (s, 4H), 1.29 (s, 2H). LCMS: 98.73%, m/z=442.2 (M+1)$^+$. HPLC: 97.65%.

Example 30

5-methyl-6-(1-methyl-1H-pyrazol-4-yl)-N-(2-methyl-6-(piperidin-1-yl)-2H-indazol-5-yl)picolinamide

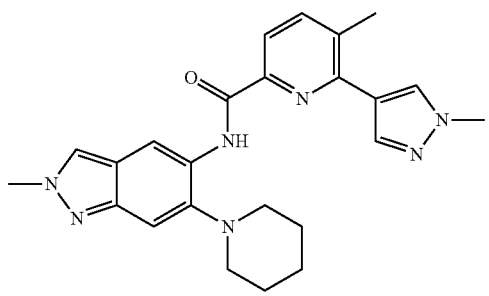

Using the same reagents and conditions as described in step 1 of example 6, 6-chloro-5-methyl-N-(2-methyl-6-(piperidin-1-yl)-2H-indazol-5-yl)picolinamide (example 24) (100 mg, 0.2605 mmol) was coupled with 1-methyl-4-(4,4,5,5-tetramethyl-1,3,2-dioxaborolan-2-yl)-1H-Pyrazole (109 mg, 0.5210 mmol) using Pd(dppf)Cl$_2$ (10 mg, 0.0130 mmol) and sodium carbonate (69 mg, 0.6512 mmol) in DME/H$_2$O (5/2 mL) at 90° C. for 12 h to obtain crude product. This was purified by silica gel column chromatography and elution with 2% methanol in DCM gave the title compound (30 mg, 24.79%).

$^1$HNMR (DMSO-d$_6$, 400 MHz): δ 11.00 (s, 1H), 8.70 (s, 1H), 8.31 (s, 1H), 8.25 (s, 1H), 8.15 (s, 1H), 7.93-7.89 (q, 2H), 7.30 (s, 1H), 4.08 (s, 3H), 3.91 (s, 3H), 2.81 (s, 4H), 2.50 (s, 3H), 1.67 (s, 4H), 1.42 (s, 2H). LCMS: 98.79%, m/z=430.0 (M+1)$^+$. HPLC: 97.80%.

Example 31

N-(1-cyclopropyl-6-(piperidin-1-yl)-1H-indazol-5-yl)-2-(2-methylpyridin-4-yl)oxazole-4-carboxamide hydrochloride

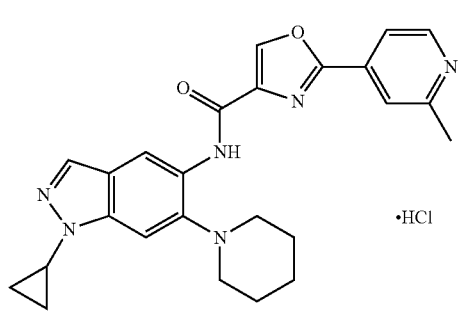 [SMILES: Cc1cc(-c2nc(C(=O)Nc3cc4cnn(C5CC5)c4cc3N3CCCCC3)co2)ccn1 ; Cl]

Step-1: Synthesis of 1-cyclopropyl-5-nitro-6-(piperidin-1-yl)-1H-indazole

Using the same reagents and conditions as described in step 1 of example 6, 5-nitro-6-(piperidin-1-yl)-1H-indazole (product of step 4 of example 1) (800 mg, 3.4060 mmol) was coupled with cyclopropyl boronic acid (837 mg, 9.7446 mmol) using Cu(OAc)$_2$ (708 mg, 3.8978 mmol), 2,2'-bipyridine (609 mg, 3.8978 mmol) and sodium carbonate (1.032 gm, 9.7446 mmol) in dichloroethane (50 mL) at 70° C. for 2 h to get the crude compound. This was purified by silica gel column chromatography and elution with 1% methanol in DCM gave the title compound (850 mg, 90.81%). LCMS: 98.64%, m/z=286.8 (M+1)$^+$. HPLC: 97.06%.

Step-2: Synthesis of 1-cyclopropyl-6-(piperidin-1-yl)-1H-indazol-5-amine

Using the same reaction conditions as described in step 2 of example 16, 1-cyclopropyl-5-nitro-6-(piperidin-1-yl)-1H-indazole (600 mg, 2.0979 mmol) was reduced with zinc dust (1.097 gm, 16.7832 mmol) and ammonium chloride (1.795 gm, 33.5664 mmol) in THF/water (50/10 mL) to get the desired product (500 mg, 93.10%). LCMS: 95.25%, m/z=257.1 (M+1)$^+$. HPLC: 86.70%.

Step-3: Synthesis of N-(1-cyclopropyl-6-(piperidin-1-yl)-1H-indazol-5-yl)-2-(2-methylpyridin-4-yl)oxazole-4-carboxamide hydrochloride Using the same reagents and conditions as described in step 7 of example 1, 1-cyclopropyl-6-(piperidin-1-yl)-1H-indazol-5-amine (100 mg, 0.3906 mmol) was coupled with 2-(2-methylpyridin-4-yl)oxazole-4-carboxylic acid (96 mg, 0.4687 mmol) using EDCI.HCl (113 mg, 0.5859 mmol), HOBt (80 mg, 1.5625 mmol), DIPEA (0.272 mL, 1.5625 mmol) in DMF (2 mL) to get the crude product. This was then purified by prep HPLC and treated with methanolic HCl to obtain the desired compound (70 mg, 37.43%).

$^1$HNMR (DMSO-d$_6$, 400 MHz): δ 10.29 (s, 1H), 9.19 (s, 1H), 8.90-8.88 (d, 1H), 8.70 (s, 1H), 8.13 (s, 1H), 8.05-7.98 (m, 2H), 7.54 (s, 1H), 3.77-3.73 (m, 1H), 2.97 (s, 4H), 2.72 (s, 3H), 1.92 (s, 4H), 1.71 (s, 2H), 1.13-1.10 (m, 4H). LCMS: 98.00%, m/z=443.2 (M+1)$^+$. HPLC: 98.74%.

Example 32

2-(2-hydroxypyridin-3-yl)-N-(2-methyl-6-(piperidin-1-yl)-2H-indazol-5-yl)oxazole-4-carboxamide

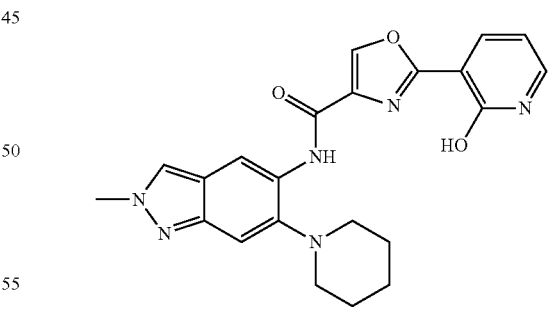

Using the same reagents and conditions as described in step 7 of example 1, 2-methyl-6-(piperidin-1-yl)-2H-indazol-5-amine (product of step 6 of example 1) (70 mg, 0.304 mmol) was coupled with 2-(2-hydroxypyridin-3-yl)oxazole-4-carboxylic acid (intermediate 5) (56 mg, 0.273 mmol) using EDCI.HCl (87 mg, 0.456 mmol), HOBt (62 mg, 0.456 mmol), DIPEA (98 mg, 0.76 mmol) in DMF (3 mL) to obtain the crude product. The obtained crude was purified by using prep HPLC to obtain the desired compound (9 mg, 7%).

¹HNMR (DMSO-d₆, 400 MHz): δ 12.30 (s, 1H), 8.82 (s, 1H), 8.59 (s, 1H), 8.28-8.18 (m, 2H), 7.66-7.65 (d, 1H), 7.32 (s, 1H), 6.40 (s, 1H), 4.07 (s, 3H), 2.82 (s, 4H), 1.82 (s, 4H), 1.60 (s, 2H). LCMS: 99.98%, m/z=419.1 (M+1)⁺. HPLC: 98.29%.

Example 33

(S)-6-(3-aminopyrrolidin-1-yl)-N-(2-methyl-6-(piperidin-1-yl)-2H-indazol-5-yl)picolinamide 2,2,2-trifluoroacetate

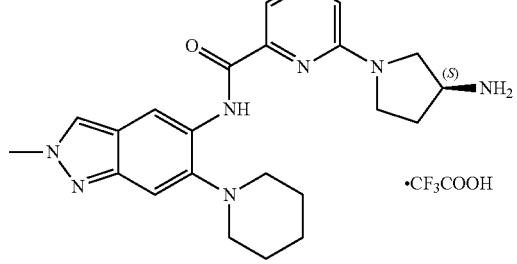

Step-1: Synthesis of tert-butyl (S)-(1-(6-((2-methyl-6-(piperidin-1-yl)-2H-indazol-5-yl)carbamoyl)pyridin-2-yl)pyrrolidin-3-yl)carbamate Using the same reagents and conditions as described in step 1 of example 6, 6-bromo-N-(2-methyl-6-(piperidin-1-yl)-2H-indazol-5-yl)picolinamide (example 23) (100 mg, 0.2413 mmol) was coupled with tert-butyl (S)-pyrrolidin-3-ylcarbamate (90 mg, 0.4827 mmol) using Pd(OAc)₂ (6 mg, 0.0241 mmol), xantphos (14 mg, 0.0241 mmol) and caesium carbonate (157 mg, 0.6034 mmol) in 1,4-dioxane (5 mL) at 110° C. for 12 h to obtain crude product. (60 mg, 48.0%). LCMS: m/z=520.3 (M+1)⁺.

Step-2: Synthesis of (S)-6-(3-aminopyrrolidin-1-yl)-N-(2-methyl-6-(piperidin-1-yl)-2H-indazol-5-yl)picolinamide 2,2,2-trifluoroacetate Using the same reaction conditions as described in step 8 of example 1, tert-butyl (S)-(1-(6-((2-methyl-6-(piperidin-1-yl)-2H-indazol-5-yl)carbamoyl)pyridin-2-yl)pyrrolidin-3-yl)carbamate (60 mg, 0.1154 mmol) was deprotected using methanolic HCl (2 mL), purified by prep HPLC and treated with TFA to get the title compound (12 mg, 19.67%).

¹HNMR (CD₃OD, 400 MHz): δ 8.58 (s, 1H), 8.24 (s, 1H), 7.81-7.78 (t, 1H), 7.60-7.59 (d, 1H), 7.46 (s, 1H), 6.84-6.82 (d, 1H), 4.22 (s, 3H), 4.14 (s, 1H), 4.00-3.96 (m, 1H), 3.91-3.82 (m, 3H), 3.05 (s, 4H), 2.62-2.52 (m, 1H), 2.80-2.70 (m, 1H), 1.95-1.80 (m, 4H), 1.75-1.65 (m, 2H). LCMS: 96.45%, m/z=420.2 (M+1)⁺. HPLC: 98.30%.

Example 34

(S)-6-(1-(2-hydroxypropyl)-1H-pyrazol-4-yl)-N-(2-methyl-6-(piperidin-1-yl)-2H-indazol-5-yl)picolinamide

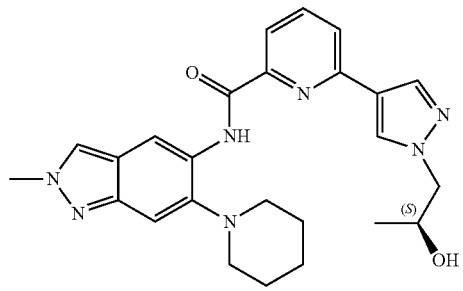

In a sealed tube, N-(2-methyl-6-(piperidin-1-yl)-2H-indazol-5-yl)-6-(1H-pyrazol-4-yl) picolinamide (example 1) (500 mg, 1.14 mmol), (S)-2-methyloxirane (133 mg, 2.29 mmol), sodium carbonate (607 mg, 5.73 mmol) and DMF (10 mL) were taken and heated at 140° C. for 4 h. The reaction was quenched with ice water and extracted with ethyl acetate. The obtained crude was purified by using prep. HPLC to get the title compound (295 mg, 56.08%).

¹HNMR (400 MHz, DMSO-d₆): δ 10.96 (s, 1H), 8.73 (s, 1H), 8.43 (s, 1H), 8.27-8.25 (d, 1H), 8.07-8.00 (m, 2H), 7.96-7.94 (d, 1H), 7.35 (s, 1H), 5.03-5.02 (d, 1H), 4.12 (s, 1H), 4.08-4.04 (m, 3H), 2.87 (s, 4H), 1.79 (s, 4H), 1.60-1.50 (m, 2H), 1.08-1.07 (d, 3H). LCMS: m/z=460.2 (M+1)⁺. HPLC: 98.51%.

Example 35

N-(1,6-dicyclopropyl-1H-indazol-5-yl)-2-(6-methoxypyridin-3-yl)oxazole-4-carboxamide

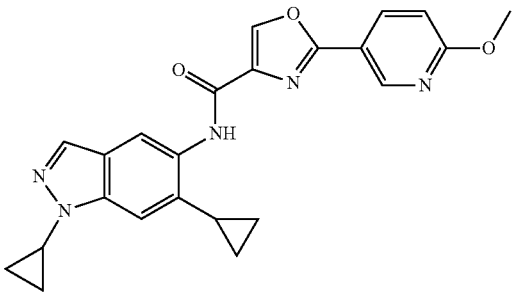 [SMILES: COc1ccc(-c2nc(C(=O)Nc3cc4cnn(C5CC5)c4cc3C3CC3)co2)cn1]

Step-1: Synthesis of 6-bromo-1-cyclopropyl-5-nitro-1H-indazole

Using the same reagents and conditions as described in step 1 of example 6, 6-bromo-5-nitro-1H-indazole (product of step 2 of example 5) (1 gm, 4.1322 mmol) was coupled with cyclopropyl boronic acid (710 mg, 8.2644 mmol) using Cu(OAc)₂ (901 mg, 4.9586 mmol), 2,2'-bipyridine (775 mg, 4.9586 mmol) and sodium carbonate (1.314 gm, 12.3966 mmol) in dichloroethane (20 mL) at 80° C. for 2 h to get the crude compound. This was purified by silica gel column chromatography and elution with 1% methanol in DCM gave the title compound (500 mg, 42.91%).

¹HNMR (CDCl₃, 300 MHz): δ 8.34 (s, 1H), 8.07 (s, 1H), 7.95 (s, 1H), 3.64-3.57 (m, 1H), 1.25-1.24 (m, 4H). LCMS: 89.33%, m/z=281.9 (M+1)⁺.

Step-2: Synthesis of 1,6-dicyclopropyl-5-nitro-1H-indazole

Using the same reagents and conditions as described in step 1 of example 6, 6-bromo-1-cyclopropyl-5-nitro-1H-indazole (400 mg, 1.4179 mmol) was coupled with cyclopropyl boronic acid (244 mg, 2.8359 mmol) using Pd(OAc)₂ (96 mg, 0.4253 mmol) tricyclohexyl phosphine (120 mg, 0.4253 mmol) and potassium phosphate (751 mg, 3.5449 mmol) in toluene/H₂O (10/2 mL) at 110° C. for 12 h to obtain crude product. This was purified by silica gel column chromatography and elution with 1% methanol in DCM gave the title compound (300 mg, 86.95%). LCMS: m/z=243.95 (M+1)⁺.

Step-3: Synthesis of 1,6-dicyclopropyl-1H-indazol-5-amine

Using the same reaction conditions as described in step 2 of example 16, 1,6-dicyclopropyl-5-nitro-1H-indazole (300 mg, 1.2396 mmol) was reduced with zinc dust (630 mg, 9.9173 mmol) and ammonium chloride (1.06 gm, 19.8347 mmol) in THF/water (20/10 mL) to get the desired product (260 mg, 98.48%). LCMS: m/z=214.1 (M+1)⁺.

Step-4: Synthesis of N-(1,6-dicyclopropyl-1H-indazol-5-yl)-2-(6-methoxypyridin-3-yl)oxazole-4-carboxamide Using the same reagents and conditions as described in step 7 of example 1, 1,6-dicyclopropyl-1H-indazol-5-amine (130 mg, 0.6095 mmol) was coupled with 2-(6-methoxypyridin-3-yl)oxazole-4-carboxylic acid (intermediate 3) (161 mg, 0.7314 mmol) using EDCI.HCl (175 mg, 0.9142 mmol), HOBt (124 mg, 0.9142 mmol), DIPEA (0.432 mL, 2.4381 mmol) in DMF (5 mL) to get the crude product. This was then purified by prep HPLC to obtain the desired compound (34 mg, 13.43%).

¹HNMR (400 MHz, DMSO-d₆): δ 9.90 (s, 1H), 8.93 (s, 1H), 8.896-8.891 (d, 1H), 8.34-8.31 (m, 2H), 7.98 (s, 1H), 7.47 (s, 1H), 7.07-7.05 (d, 1H), 3.96 (s, 3H), 3.80-3.70 (m, 1H), 2.20-2.10 (m, 1H), 1.20-1.10 (m, 6H), 0.84-0.78 (m, 2H). LCMS: 100%, m/z=416.1 (M+1)⁺. HPLC: 99.41%.

Example 36

N-(1,6-dicyclopropyl-1H-indazol-5-yl)-2-(2-methylpyridin-4-yl)oxazole-4-carboxamide hydrochloride

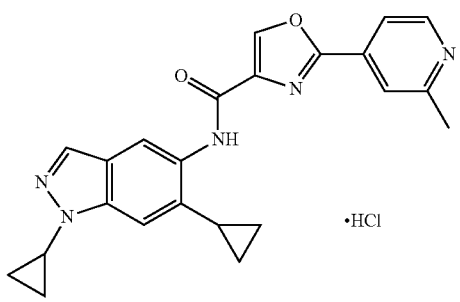 [SMILES: Cc1cc(-c2nc(C(=O)Nc3cc4cnn(C5CC5)c4cc3C3CC3)co2)ccn1 ; Cl]

Using the same reagents and conditions as described in step 7 of example 1, 1,6-dicyclopropyl-1H-indazol-5-amine (product of step 3 of example 35) (130 mg, 0.6132 mmol) was coupled with 2-(2-methylpyridin-4-yl)oxazole-4-carboxylic acid (150 mg, 0.7358 mmol) using EDCI.HCl (177 mg, 0.9198 mmol), HOBt (125 mg, 0.9198 mmol), DIPEA (0.428 mL, 2.4528 mmol) in DMF (2 mL) to get the crude product. This was then purified by prep HPLC and treated with methanolic HCl to obtain the desired compound (75 mg, 30.61%).

¹HNMR (400 MHz, DMSO-d₆): δ 9.97 (s, 1H), 9.16 (s, 1H), 8.84-8.83 (d, 1H), 8.22 (s, 1H), 8.18 (s, 1H), 8.10-8.08 (d, 1H), 7.99 (s, 1H), 7.45 (s, 1H), 3.80-3.70 (m, 1H), 2.73 (s, 3H), 2.20-2.10 (m, 1H), 1.12-1.09 (m, 6H), 0.81-0.80 (d, 2H). LCMS: 99.59%, m/z=400.2 (M+1)⁺. HPLC: 98.24%.

Example 37

(S)—N-(6-cyclopropyl-1-methyl-1H-indazol-5-yl)-6-(3-hydroxypyrrolidin-1-yl)picolinamide

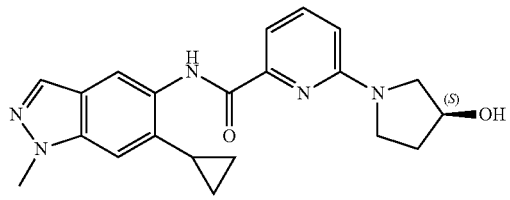

Step-1: Synthesis of 6-cyclopropyl-1-methyl-5-nitro-1H-indazole

Using the same reagents and conditions as described in step 1 of example 6, 6-bromo-1-methyl-5-nitro-1H-indazole (product of step 1 of example 11) (500 mg, 1.95 mmol) was coupled with cyclopropyl boronic acid (335 mg, 3.90 mmol) using Pd(OAc)₂ (44 mg, 1.95 mmol) tricyclohexyl phosphine (55 mg, 1.95 mmol) and potassium phosphate (1.03 gm, 4.88 mmol) in toluene/H₂O (8/2 mL) at 110° C. for 4 h to obtain crude product. This was purified by silica gel column chromatography and elution with 20% ethyl acetate in hexane to give the title compound (300 mg, 70.9%).

¹HNMR (400 MHz, CDCl₃): δ 8.35 (s, 1H), 8.08 (s, 1H), 7.19 (s, 1H), 4.09 (s, 3H), 2.60-2.50 (m, 1H), 1.10-1.05 (m, 2H), 0.75-0.71 (m, 2H). LCMS: 97.97%, m/z=218.0 (M+1)⁺. HPLC: 97.57%.

Step-2: Synthesis of 6-cyclopropyl-1-methyl-1H-indazol-5-amine

Using the same reagents and conditions as described in step 4 of example 10, 6-cyclopropyl-1-methyl-5-nitro-1H-indazole (300 mg, 1.3810 mmol) was reduced using 10% Pd/C (30 mg) in methanol (10 mL) for 4 h to get the desired product (240 mg, 85.7%). LCMS: 98.17%, m/z=188.1 (M+1)⁺.

Step-3: Synthesis of 6-bromo-N-(6-cyclopropyl-1-methyl-1H-indazol-5-yl)picolinamide Using the same reagents and conditions as described in step 7 of example 1, 6-cyclopropyl-1-methyl-1H-indazol-5-amine (240 mg, 1.28 mmol) was coupled with 6-bromopicolinic acid (311 mg, 1.54 mmol) using EDCI.HCl (368 mg, 1.94 mmol), HOBt (181 mg, 1.34 mmol), DIPEA (496 mg, 3.85 mmol) in DMF (5 mL) to obtain the desired compound (300 mg, 56.05%).

$^1$HNMR (400 MHz, CDCl$_3$): δ 10.77 (s, 1H), 8.83 (s, 1H), 8.30-8.28 (d, 1H), 7.95 (s, 1H), 7.82-7.78 (t, 1H), 7.68-7.66 (d, 1H), 7.27-7.26 (m, 1H), 4.06 (s, 3H), 2.09-2.05 (m, 1H), 1.32-1.27 (m, 2H), 0.87-0.83 (m, 2H). LCMS: 95.54%, m/z=373.0 (M+1)$^+$.

Step-4: Synthesis of (S)—N-(6-cyclopropyl-1-methyl-1H-indazol-5-yl)-6-(3-hydroxypyrrolidin-1-yl)picolinamide Using the same reagents and conditions as described in example 34, 6-bromo-N-(6-cyclopropyl-1-methyl-1H-indazol-5-yl)picolinamide (70 mg, 1.88 mmol) was substituted with (S)-pyrrolidin-3-ol (25 mg, 2.83 mmol) using sodium carbonate (80 mg, 0.754 mmol) in DMF (3 mL) at 140° C. for 4 h to get the title compound (55 mg, 71.4%).

$^1$HNMR (400 MHz, DMSO-d$_6$): δ 10.58 (s, 1H), 8.69 (s, 1H), 8.00 (s, 1H), 7.75-7.71 (t, 1H), 7.49 (s, 1H), 7.41-7.39 (d, 1H), 6.75-6.73 (d, 1H), 5.04-5.03 (d, 1H), 4.43 (s, 1H), 4.02 (s, 3H), 3.60-3.56 (m, 3H), 3.45-3.35 (m, 1H), 2.20-1.90 (m, 3H), 1.11-1.09 (d, 2H), 0.86-0.85 (d, 2H). LCMS: 94.25%, m/z=378.2 (M+1)$^+$. HPLC: 95.06%.

Example 38

(R)-6-(3-hydroxypyrrolidin-1-yl)-N-(2-methyl-6-(piperidin-1-yl)-2H-indazol-5-yl)picolinamide

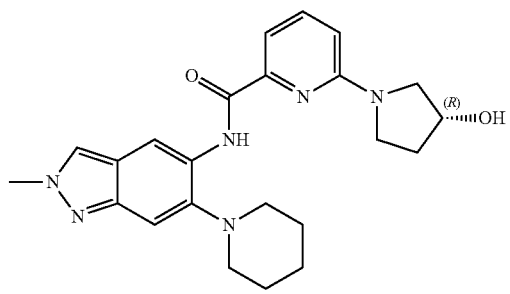

Using the same reagents and conditions as described in example 34, 6-bromo-N-(2-methyl-6-(piperidin-1-yl)-2H-indazol-5-yl)picolinamide (example 23) (45 mg, 0.1086 mmol) was substituted with (R)-pyrrolidin-3-ol (20 mg, 0.163 mmol) using sodium carbonate (34 mg, 0.326 mmol) in DMF (2 mL) at 140° C. for 14 h to get the crude product. This was purified by silica gel column chromatography and elution with 5% methanol in DCM gave the title compound (20 mg, 45%).

$^1$HNMR (300 MHz, DMSO-d$_6$): δ 10.74 (s, 1H), 8.67 (s, 1H), 8.22 (s, 1H), 7.72-7.67 (t, 1H), 7.39-7.37 (d, 1H), 7.31 (s, 1H), 6.71-6.68 (d, 1H), 5.02-5.00 (d, 1H), 4.42 (s, 1H), 4.08 (s, 3H), 3.65-3.48 (m, 5H), 2.81 (s, 4H), 2.00-1.90 (m, 1H), 1.74 (s, 4H), 1.56 (s, 2H). LCMS: 100%, m/z=421.2 (M+1)$^+$. HPLC: 95.42%.

Example 39

(S)-6-(3-hydroxypyrrolidin-1-yl)-N-(2-methyl-6-(piperidin-1-yl)-2H-indazol-5-yl)picolinamide

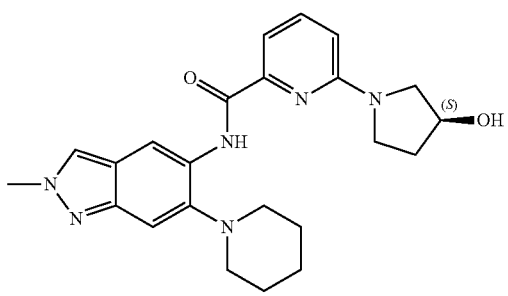

Using the same reagents and conditions as described in example 34, 6-bromo-N-(2-methyl-6-(piperidin-1-yl)-2H-indazol-5-yl)picolinamide (example 23) (150 mg, 0.362 mmol) was substituted with (S)-pyrrolidin-3-ol (66 mg, 0.543 mmol) using sodium carbonate (153 mg, 1.449 mmol) in DMF (5 mL) at 140° C. for 14 h to get the crude product. This was purified by silica gel column chromatography and elution with 5% methanol in DCM gave the title compound (75 mg, 50%).

$^1$HNMR (300 MHz, DMSO-d$_6$): δ 10.74 (s, 1H), 8.67 (s, 1H), 8.22 (s, 1H), 7.72-7.67 (t, 1H), 7.39-7.37 (d, 1H), 7.31 (s, 1H), 6.71-6.68 (d, 1H), 5.02-5.01 (d, 1H), 4.42 (s, 1H), 4.08 (s, 3H), 3.65-3.52 (m, 4H), 2.81 (s, 4H), 2.18-1.85 (m, 2H), 1.74 (s, 4H), 1.56 (s, 2H). LCMS: 97.7%, m/z=421.2 (M+1)$^+$. HPLC: 95.06%.

Example 40

6-(3-hydroxypyrrolidin-1-yl)-N-(2-methyl-6-(piperidin-1-yl)-2H-indazol-5-yl)picolinamide

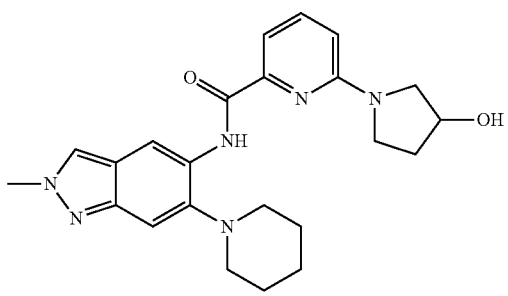 [SMILES: Cn1cc2cc(NC(=O)c3cccc(N4CCC(O)C4)n3)c(N3CCCCC3)cc2n1]

Using the same reagents and conditions as described in example 34, 6-bromo-N-(2-methyl-6-(piperidin-1-yl)-2H-indazol-5-yl)picolinamide (example 23) (20 mg, 0.483 mmol) was substituted with pyrrolidin-3-ol (9 mg, 0.0724 mmol) using sodium carbonate (15 mg, 0.1449 mmol) in DMF (2 mL) at 140° C. for 14 h to get the title compound (16 mg, 80%).

$^1$HNMR (300 MHz, DMSO-d$_6$): δ 10.74 (s, 1H), 8.67 (s, 1H), 8.22 (s, 1H), 7.72-7.67 (t, 1H), 7.39-7.37 (d, 1H), 7.31 (s, 1H), 6.71-6.69 (d, 1H), 5.02-5.01 (d, 1H), 4.42 (s, 1H), 4.08 (s, 3H), 3.70-3.45 (m, 4H), 2.81 (s, 4H), 2.10-2.00 (m,

1H), 2.00-1.90 (m, 1H), 1.74 (s, 4H), 1.56 (s, 2H). LCMS: 96.2%, m/z=421.3 (M+1)⁺. HPLC: 92.89%.

Example 41

(S)-6-(3-aminopyrrolidin-1-yl)-N-(6-cyclopropyl-1-methyl-1H-indazol-5-yl)picolinamide

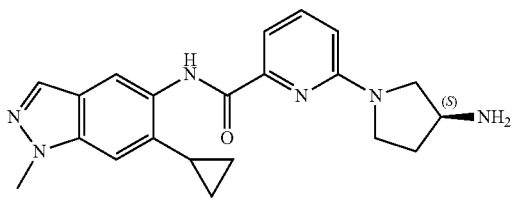

Using the same reagents and conditions as described in example 34, 6-bromo-N-(6-cyclopropyl-1-methyl-1H-indazol-5-yl)picolinamide (product of step 3 of example 37) (130 mg, 0.350 mmol) was substituted with tert-butyl (S)-pyrrolidin-3-ylcarbamate (98 mg, 0.525 mmol) using sodium carbonate (148 mg, 1.40 mmol) in DMF (3 mL) at 140° C. for 4 h to get the crude product. This was purified by silica gel column chromatography and elution with 1% methanol in DCM gave the required product. Using the same reaction conditions as described in step 8 of example 1 above product was deprotected using TFA/DCM (2/8 mL) to get the title compound (45 mg, 48%).

¹H NMR (400 MHz, CDCl₃,): δ 10.55 (s, 1H), 8.34 (s, 1H), 7.93 (s, 1H), 7.67-7.61 (m, 2H), 7.19 (s, 1H), 6.57-6.55 (dd, 1H), 4.04 (s, 3H), 3.80-3.69 (m, 3H), 3.62-3.58 (m, 1H), 3.29-3.26 (m, 1H), 2.28-2.23 (m, 1H), 2.10-2.05 (m, 1H), 1.90-1.85 (m, 1H), 1.16-1.12 (m, 2H), 0.86-0.82 (q, 2H). LCMS: 100%, m/z=377.1 (M+1)⁺. HPLC: 95.39%.

Example 42

(R)-6-(3-aminopyrrolidin-1-yl)-N-(2-methyl-6-(piperidin-1-yl)-2H-indazol-5-yl)picolinamide

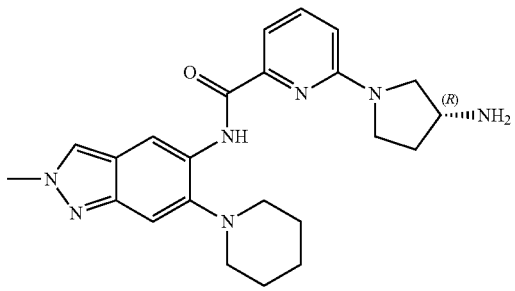

Using the same reagents and conditions as described in example 41, 6-bromo-N-(2-methyl-6-(piperidin-1-yl)-2H-indazol-5-yl)picolinamide (example 23) (75 mg, 0.1811 mmol) was substituted with tert-butyl (R)-pyrrolidin-3-ylcarbamate (68 mg, 0.362 mmol) using sodium carbonate (58 mg, 0.5434 mmol) in DMF (5 mL) at 140° C. for 14 h to get the crude product which was deprotected using TFA/DCM (1/3 mL) to get the title compound (35 mg, 61.87%).

¹HNMR (400 MHz, DMSO-d₆,): δ 10.75 (s, 1H), 8.68 (s, 1H), 8.23 (s, 1H), 7.72-7.68 (t, 1H), 7.39-7.37 (d, 1H), 7.32 (s, 1H), 6.70-6.68 (d, 1H), 4.10 (s, 3H), 3.75-3.45 (m, 3H), 2.82 (s, 4H), 2.15-1.90 (m, 2H), 1.85-1.70 (m, 6H), 1.65-1.54 (m, 2H). LCMS: 86.50%, m/z=420.2 (M+1)⁺. HPLC: 95.92%.

Example 43

(R)-6-(1-(2-hydroxypropyl)-1H-pyrazol-4-yl)-N-(2-methyl-6-(piperidin-1-yl)-2H-indazol-5-yl)picolinamide

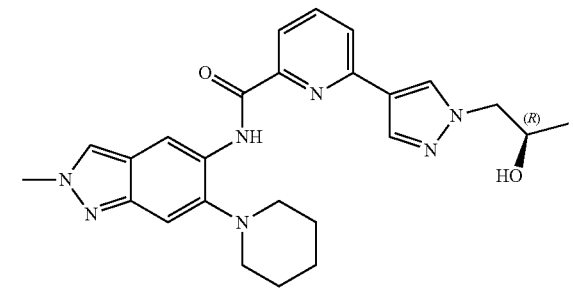

Using the same reaction conditions as described in step 6 of example 1, 6-bromo-N-(2-methyl-6-(piperidin-1-yl)-2H-indazol-5-yl)picolinamide (example 23) (75 mg, 0.18108 mmol) was coupled with (R)-1-(4-(4,4,5,5-tetramethyl-1,3,2-dioxaborolan-2-yl)-1H-pyrazol-1-yl)propan-2-ol (intermediate 6) (92 mg, 0.362 mmol) using sodium carbonate (48 mg, 0.452 mmol) and Pd(dppf)Cl₂ (7 mg, 0.009 mmol) in 1,2-dimethoxyethane/water (5/1 mL) to get the crude product. The obtained crude was purified by 60-120 silica gel column chromatography using 30% ethyl acetate in hexane as eluent to obtain the title compound (64 mg, 77.1%).

¹HNMR (400 MHz, DMSO-d₆,): δ 10.95 (s, 1H), 8.72 (s, 1H), 8.42 (s, 1H), 8.26-8.24 (d, 1H), 8.04-7.93 (m, 3H), 7.34 (s, 1H), 4.11 (s, 3H), 4.10-4.03 (m, 2H), 3.10-3.00 (m, 1H), 2.87 (s, 4H), 1.78 (s, 4H), 1.55 (s, 2H), 1.07-1.06 (d, 3H). LCMS: 96.34%, m/z=460.2 (M+1)⁺. HPLC: 96.89%.

Example 44

(S)-2-(3-aminopyrrolidin-1-yl)-N-(2-methyl-6-(piperidin-1-yl)-2H-indazol-5-yl)oxazole-4-carboxamide

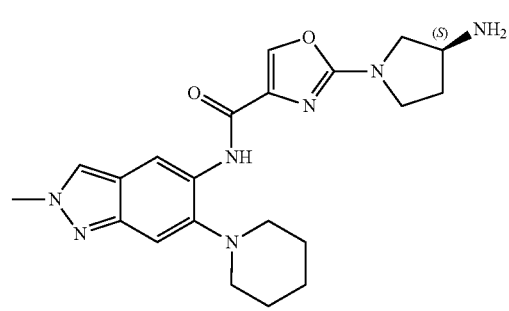

Using the same reagents and conditions as described in step 7 of example 1, 2-methyl-6-(piperidin-1-yl)-2H-indazol-5-amine (product of step 6 of example 1) (90 mg, 0.3913 mmol) was coupled with (S)-2-(3-((tert-butoxycarbonyl)amino)pyrrolidin-1-yl)oxazole-4-carboxylic acid (intermediate 7) (139 mg, 0.469 mmol) using EDCI.HCl (112 mg, 0.586 mmol), HOBt (79 mg, 0.5869 mmol), DIPEA (201 mg, 1.565 mmol) in DMF (2 mL) to obtain the crude product. Using the same reaction conditions as described in step 8 of example 1 above product was deprotected using TFA/DCM (2/2 mL) to get the title compound (60 mg, 86.95%).

¹HNMR (CDCl₃, 400 MHz): δ 10.2 (s, 1H), 8.73 (s, 1H), 7.83 (s, 1H), 7.79 (s, 1H), 7.35 (s, 1H), 4.16 (s, 3H), 3.80-3.70 (m, 3H), 3.65-3.58 (m, 1H), 3.30-3.25 (m, 1H), 3.10-2.60 (bs, 4H), 2.30-2.18 (m, 1H), 2.00-1.80 (m, 5H). LCMS: 100%, m/z=410.2 (M+1)⁺. HPLC: 98.69%.

Example 45

N-(6-cyclopropyl-1-methyl-1H-indazol-5-yl)-2-(2-methylpyridin-4-yl)oxazole-4-carboxamide

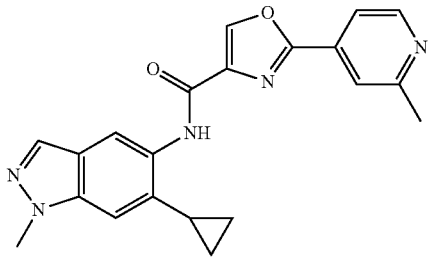 [SMILES: Cc1cc(-c2nc(C(=O)Nc3cc4cnn(C)c4cc3C3CC3)co2)ccn1]

Using the same reagents and conditions as described in step 7 of example 1, 6-cyclopropyl-1-methyl-1H-indazol-5-amine (product of step 2 of example 37) (130 mg, 0.83 mmol) was coupled with 2-(2-methylpyridin-4-yl)oxazole-4-carboxylic acid (170 mg, 1.54 mmol) using EDCI.HCl (199 mg, 1.0427 mmol), HOBt (94 mg, 0.069 mmol), DIPEA (358 mg, 2.78 mmol) in DMF (3 mL) to obtain the title compound (48 mg, 18.53%).

¹HNMR (CDCl₃, 300 MHz): δ 9.62 (s, 1H), 8.91 (s, 1H), 8.72 (s, 1H), 8.54 (s, 1H), 8.18-8.06 (m, 2H), 7.98 (s, 1H), 4.07 (s, 3H), 2.87 (s, 3H), 2.15-2.05 (m, 1H), 1.30-1.20 (m, 2H), 0.95-0.85 (m, 2H). LCMS: 99.48%, m/z=374.1 (M+1)⁺. HPLC: 97.42%.

Example 46

(S)—N-(6-cyclopropyl-1-methyl-1H-indazol-5-yl)-6-(1-(2-hydroxypropyl)-1H-pyrazol-4-yl)picolinamide

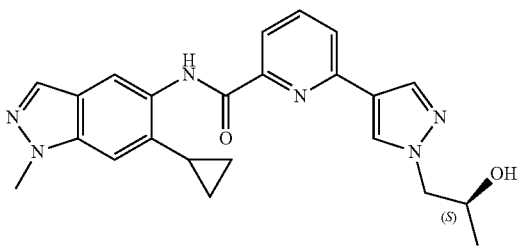

Using the same reaction conditions as described in step 6 of example 1, 6-bromo-N-(6-cyclopropyl-1-methyl-1H-indazol-5-yl)picolinamide (product of step 3 of example 37) (100 mg, 0.269 mmol) was coupled with (S)-1-(4-(4,4,5,5-tetramethyl-1,3,2-dioxaborolan-2-yl)-1H-pyrazol-1-yl)propan-2-ol (intermediate 8) (135 mg, 0.539 mmol) using sodium carbonate (72 mg, 0.673 mmol) and Pd(dppf)Cl₂ (10 mg, 0.134 mmol) in 1,2-dimethoxyethane/water (6/0.5 mL) at 90° C. for 4 h to get the crude product. The obtained crude was purified by 60-120 silica gel column chromatography using 2% methanol in DCM as eluent to obtain the title compound (22 mg, 19.6%).

¹HNMR (CDCl₃, 400 MHz): δ 10.75 (s, 1H), 8.85 (s, 1H), 8.20-8.18 (d, 1H), 8.08 (s, 1H), 7.99 (s, 1H), 7.96 (s, 1H), 7.93-7.89 (t, 1H), 7.64-7.62 (d, 1H), 4.28-4.25 (d, 2H), 4.12-4.08 (m, 1H), 4.06 (s, 3H), 2.20-2.10 (m, 1H), 1.30-1.28 (d, 3H), 1.22-1.20 (d, 2H), 1.90-0.89 (d, 2H). LCMS: 95.5%, m/z=417.2 (M+1)⁺. HPLC: 98.83%.

Example 47

(S)—N-(6-cyclopropyl-2-methyl-2H-indazol-5-yl)-6-(1-(2-hydroxypropyl)-1H-pyrazol-4-yl)picolinamide

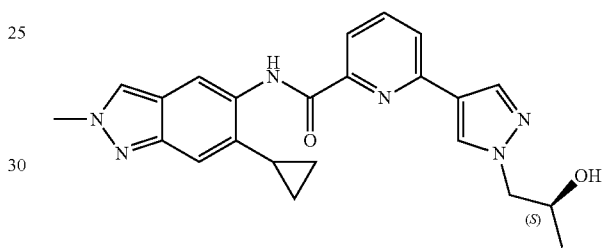

Step-1: Synthesis of 6-bromo-N-(6-cyclopropyl-2-methyl-2H-indazol-5-yl)picolinamide Using the same reagents and conditions as described in step 7 of example 1, 6-cyclopropyl-2-methyl-2H-indazol-5-amine (product of step 2 of example 16) (270 mg, 1.44 mmol) was coupled with 6-bromopicolinic acid (290 mg, 1.44 mmol) using EDCI.HCl (414 mg, 2.16 mmol), HOBt (204 mg, 1.51 mmol), DIPEA (750 mg, 5.76 mmol) in DMF (5 mL) to obtain the desired compound (434 mg, 81%). LCMS: 100%, m/z=373.0 (M+2)⁺. HPLC: 90.39%.

Step-2: Synthesis of N-(6-cyclopropyl-2-methyl-2H-indazol-5-yl)-6-(1-(tetrahydro-2H-pyran-2-yl)-1H-pyrazol-4-yl)picolinamide Using the same reagents and conditions as described in step 1 of example 6, 6-bromo-N-(6-cyclopropyl-2-methyl-2H-indazol-5-yl)picolinamide (150 mg, 0.4043 mmol) was coupled with 1-(tetrahydro-2H-pyran-2-yl)-4-(4,4,5,5-tetramethyl-1,3,2-dioxaborolan-2-yl)-1H-pyrazole (135 mg, 0.4851 mmol) using Pd(dppf)Cl₂ (15 mg, 0.0202 mmol) and sodium carbonate (128 mg, 1.212 mmol) in DME/H₂O (5/1 mL) at 85° C. for 6 h to obtain title product (148 mg, 83%). LCMS: 100%, m/z=443.1 (M+1)⁺.

Step-3: Synthesis of N-(6-cyclopropyl-2-methyl-2H-indazol-5-yl)-6-(1H-pyrazol-4-yl)picolinamide hydrochloride Using the same reaction conditions as described in step 8 of example 1, N-(6-cyclopropyl-2-methyl-2H-indazol-5-yl)-

6-(1-(tetrahydro-2H-pyran-2-yl)-1H-pyrazol-4-yl)picolinamide (148 mg, 0.334 mmol) was deprotected using ether HCl (5 mL) in methanol (5 mL) to get the title compound (104 mg, 79%). LCMS: 96.69%, m/z=359.1 (M+1)+.

Step-4: Synthesis of (S)—N-(6-cyclopropyl-2-methyl-2H-indazol-5-yl)-6-(1-(2-hydroxypropyl)-1H-pyrazol-4-yl)picolinamide Using the same reagents and conditions as described in example 34, N-(6-cyclopropyl-2-methyl-2H-indazol-5-yl)-6-(1H-pyrazol-4-yl)picolinamide hydrochloride (100 mg, 2.5 mmol) was substituted with (S)-2-methyloxirane (30 mg, 5 mmol) using sodium carbonate (133 mg, 12.5 mmol) in DMF (5 mL) at 100° C. for 14 h to get the title compound (19 mg, 18%).

$^1$HNMR (CDCl$_3$, 300 MHz): δ 10.84 (s, 1H), 8.08 (s, 1H), 8.18-8.16 (d, 1H), 8.07 (s, 1H), 7.98 (s, 1H), 7.92-7.87 (m, 2H), 7.85-7.63 (d, 1H), 7.55 (s, 1H), 4.28-4.23 (m, 2H), 4.19 (s, 3H), 4.12-4.04 (m, 1H), 3.06-3.04 (d, 1H), 2.15-2.05 (m, 1H), 1.29-1.27 (d, 3H), 1.18-1.14 (m, 2H) 0.89-0.84 (m, 2H). LCMS: 100%, m/z=417.2 (M+1)+. HPLC: 95.66%.

Example 48

(S)-6-(3-aminopyrrolidin-1-yl)-N-(6-cyclopropyl-2-methyl-2H-indazol-5-yl)picolinamide

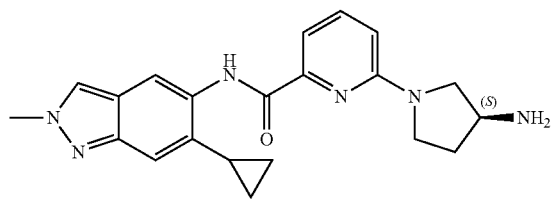

Step-1: Synthesis of tert-butyl (S)-(1-(6-((6-cyclopropyl-2-methyl-2H-indazol-5-yl)carbamoyl)pyridin-2-yl)pyrrolidin-3-yl)carbamate Using the same reagents and conditions as described in example 34, 6-bromo-N-(6-cyclopropyl-2-methyl-2H-indazol-5-yl)picolinamide (product of step 1 of example 47) (100 mg, 0.269 mmol) was substituted with tert-butyl (S)-pyrrolidin-3-ylcarbamate (75 mg, 0.404 mmol) using sodium carbonate (86 mg, 0.808 mmol) in DMF (5 mL) at 120° C. for 6 h to get the crude product.

Step-2: Synthesis of(S)-6-(3-aminopyrrolidin-1-yl)-N-(6-cyclopropyl-2-methyl-2H-indazol-5-yl)picolinamide Using the same reaction conditions as described in step 8 of example 1, it was deprotected using ether HCl/methanol (5/5 mL) to get the title compound (38 mg, 50.1%).

$^1$HNMR (CDCl$_3$, 300 MHz): δ 10.62 (s, 1H), 8.79 (s, 1H), 7.83 (s, 1H), 7.64-7.60 (m, 2H), 7.49 (s, 1H), 6.57-6.54 (dd, 1H), 4.18 (s, 3H), 3.80-3.59 (m, 4H), 3.27-3.25 (dd, 1H), 2.30-2.20 (m, 1H), 2.09-2.00 (m, 1H), 1.92-1.82 (m, 1H), 1.11-1.07 (m, 2H), 0.85-0.81 (m, 2H). LCMS: 377.8 (M+1)+. HPLC: 96.40%.

Example 49

(S)—N-(6-cyclopropyl-2-methyl-2H-indazol-5-yl)-6-(3-hydroxypyrrolidin-1-yl)picolinamide

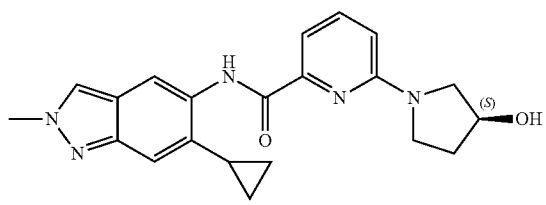

Using the same reagents and conditions as described in example 34, 6-bromo-N-(6-cyclopropyl-2-methyl-2H-indazol-5-yl)picolinamide (product of step 1 of example 47) (100 mg, 0.269 mmol) was substituted with (S)-pyrrolidin-3-ol (50 mg, 0.403 mmol) using sodium carbonate (114 mg, 1.076 mmol) in DMF (5 mL) at 120° C. for 6 h to get the title compound (34 mg, 34%).

$^1$HNMR (CDCl$_3$, 300 MHz): δ 10.61 (s, 1H), 8.80 (s, 1H), 7.83 (s, 1H), 7.65-7.60 (m, 2H), 7.50 (s, 1H), 6.59-6.56 (dd, 1H), 4.72-4.64 (m, 1H), 4.18 (s, 3H), 3.73-3.57 (m, 4H), 2.25-2.02 (m, 3H), 1.72-1.71 (d, 1H), 1.11-1.08 (m, 2H), 0.87-0.82 (m, 2H). LCMS: 368.2 (M+1)+. HPLC: 96.09%.

Example 50

(S)—N-(6-cyclopropyl-1-methyl-1H-indazol-5-yl)-2-(3-hydroxypyrrolidin-1-yl)oxazole-4-carboxamide

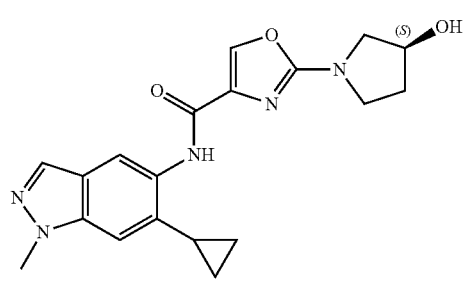

Step-1: Synthesis of (S)-2-(3-((tert-butyldimethylsilyl)oxy)pyrrolidin-1-yl)-N-(6-cyclopropyl-1-methyl-1H-indazol-5-yl)oxazole-4-carboxamide Using the same reagents and conditions as described in step 7 of example 1, 6-cyclopropyl-1-methyl-1H-indazol-5-amine (product of step 2 of example 37) (80 mg, 0.4278 mmol) was coupled with (S)-2-(3-((tert-butyldimethylsilyl)oxy)pyrrolidin-1-yl)oxazole-4-carboxylic acid (intermediate 9) (152 mg, 0.513 mmol) using EDCI.HCl (122 mg, 0.6417 mmol), HOBt (86 mg, 0.6417 mmol), DIPEA (220 mg, 1.7112 mmol) in DMF (2 mL) to obtain the crude product.

Step-2: Synthesis of (S)—N-(6-cyclopropyl-1-methyl-1H-indazol-5-yl)-2-(3-hydroxypyrrolidin-1-yl)oxazole-4-carboxamide Using the same reaction conditions as described in step 8 of example 1, (S)-2-(3-((tert-butyldimethylsilyl)oxy)pyrrolidin-1-yl)-N-(6-cyclopropyl-1-methyl-1H-indazol-5-yl)oxazole-4-carboxamide was deprotected using methanolic HCl (5 mL) to get the title compound (25 mg, 40.98%).

¹HNMR (CDCl₃, 400 MHz): δ 9.63 (s, 1H), 8.71 (s, 1H), 7.93 (s, 1H), 7.85 (s, 1H), 7.21 (s, 1H), 4.65 (s, 1H), 4.04 (s, 3H), 3.75-3.65 (m, 3H), 3.60-3.55 (m, 1H), 2.20-1.95 (m, 3H), 1.80 (s, 1H), 1.20-1.10 (m, 2H), 0.84-0.78 (m, 2H). LCMS: 100%, m/z=368.2 (M+1)⁺. HPLC: 97.06%

Example 51

(S)-2-(3-aminopyrrolidin-1-yl)-N-(6-cyclopropyl-1-methyl-1H-indazol-5-yl)oxazole-4-carboxamide

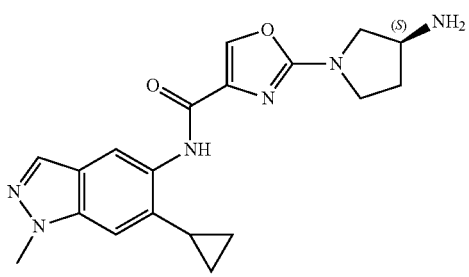

Using the same reagents and conditions as described in step 7 of example 1, 6-cyclopropyl-1-methyl-1H-indazol-5-amine (product of step 2 of example 37) (80 mg, 0.4278 mmol) was coupled with (S)-2-(3-((tert-butoxycarbonyl)amino)pyrrolidin-1-yl)oxazole-4-carboxylic acid (intermediate 7) (160 mg, 0.513 mmol) using EDCI.HCl (122 mg, 0.6417 mmol), HOBt (86 mg, 0.6417 mmol), DIPEA (220 mg, 1.711 mmol) in DMF (3 mL) to obtain the crude product. Using the same reaction conditions as described in step 8 of example 1, above crude product was deprotected using TFA/DCM (1/1 mL) to get the title compound (70 mg, 69.3%).

¹HNMR (CDCl₃, 400 MHz): δ 9.65 (s, 1H), 8.72 (s, 1H), 7.93 (s, 1H), 7.84 (s, 1H), 7.21 (s, 1H), 4.04 (s, 3H), 3.80-3.70 (m, 3H), 3.65-3.55 (m, 1H), 3.30-3.25 (d, 1H), 2.25-2.18 (m, 1H), 2.05-1.95 (m, 1H), 1.88-1.78 (m, 1H), 1.16-1.14 (d, 2H), 0.81-0.80 (d, 1H). LCMS: 366.81 (M+1)⁺. HPLC: 98.14%.

Example 52

(S)-2-(3-hydroxypyrrolidin-1-yl)-N-(2-methyl-6-(piperidin-1-yl)-2H-indazol-5-yl)oxazole-4-carboxamide

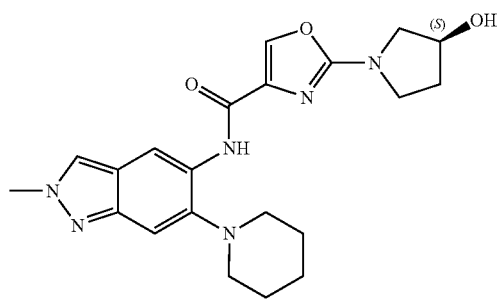

Using the same reagents and conditions as described in step 7 of example 1, 2-methyl-6-(piperidin-1-yl)-2H-indazol-5-amine (product of step 6 of example 1) (100 mg, 0.434 mmol) was coupled with (S)-2-(3-((tert-butyldimethylsilyl)oxy)pyrrolidin-1-yl)oxazole-4-carboxylic acid (intermediate 9) (162 mg, 0.5217 mmol) using EDCI.HCl (124 mg, 0.6521 mmol), HOBt (88 mg, 0.6521 mmol), DIPEA (224 mg, 1.739 mmol) in DMF (4 mL) to obtain the crude product. Using the same reaction conditions as described in step 8 of example 1 above crude product was deprotected using methanolic HCl/methanol (1/3 mL) to get the title compound (10 mg, 14.28%).

¹H NMR (CDCl₃, 400 MHz): δ 10.21 (s, 1H), 8.73 (s, 1H), 7.83 (s, 1H), 7.79 (s, 1H), 7.35 (s, 1H), 4.64 (s, 1H), 4.16 (s, 3H), 3.74-3.57 (m, 4H), 3.20-2.70 (bs, 4H), 2.20-2.00 (m, 3H), 2.0-1.80 (m, 6H). LCMS: 100%, m/z=411.2 (M+1)⁺. HPLC: 99.43%.

Example 53

(S)—N-(6-cyclopropyl-1-methyl-1H-indazol-5-yl)-2-(1-(2-hydroxypropyl)-1H-pyrazol-4-yl)oxazole-4-carboxamide

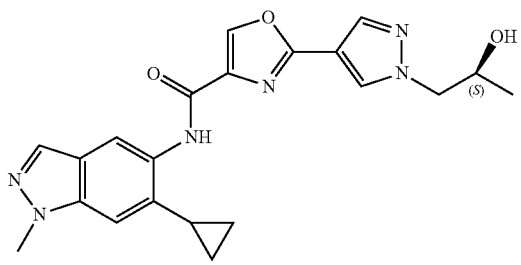

Step-1: Synthesis of N-(6-cyclopropyl-1-methyl-1H-indazol-5-yl)-2-(1-(tetrahydro-2H-pyran-2-yl)-1H-pyrazol-4-yl)oxazole-4-carboxamide Using the same reagents and conditions as described in step 7 of example 1, 6-cyclopropyl-1-methyl-1H-indazol-5-amine (product of step 2 of example 37) (100 mg, 0.534 mmol) was coupled with 2-(1-(tetrahydro-2H-pyran-2-yl)-1H-pyrazol-4-yl)oxazole-4-carboxylic acid (intermediate 10) (120 mg, 0.534 mmol) using EDCI.HCl (152 mg, 0.801 mmol), HOBt (108 mg, 0.801 mmol), DIPEA (275 mg, 2.136 mmol) in DMF (5 mL) to obtain the title compound (212 mg, 91.7%). LCMS: m/z=433.2 (M+1).

Step-2: Synthesis of N-(6-cyclopropyl-1-methyl-1H-indazol-5-yl)-2-(1H-pyrazol-4-yl)oxazole-4-carboxamide hydrochloride Using the same reaction conditions as described in step 8 of example 1, N-(6-cyclopropyl-1-methyl-1H-indazol-5-yl)-2-(1-(tetrahydro-2H-pyran-2-yl)-1H-pyrazol-4-yl)oxazole-4-carboxamide (212 mg, 0.490 mmol) was deprotected using methanolic HCl (5 mL) in methanol (1 mL) to get the title compound (180 mg, 95.7%).

Step-3: Synthesis of (S)—N-(6-cyclopropyl-1-methyl-1H-indazol-5-yl)-2-(1-(2-hydroxypropyl)-1H-pyrazol-4-yl)oxazole-4-carboxamide Using the same reagents and conditions as described in example 34, N-(6-cyclopropyl-1-methyl-1H-indazol-5-yl)-

2-(1H-pyrazol-4-yl)oxazole-4-carboxamide hydrochloride (180 mg, 0.517 mmol) was substituted with (S)-2-methyloxirane (60 mg, 1.034 mmol) using sodium carbonate (274 mg, 2.585 mmol) in DMF (5 mL) at 100° C. for 14 h to get the crude product. This was purified by prep HPLC to get the title compound (40 mg, 20%).

¹HNMR (CDCl₃, 400 MHz): δ 9.64 (s, 1H), 8.71 (s, 1H), 8.25 (s, 1H), 8.04 (s, 1H), 8.00 (s, 1H), 7.94 (s, 1H), 7.23 (s, 1H), 4.29-4.25 (d, 2H), 4.15-4.07 (m, 1H), 4.05 (s, 3H), 3.01-3.00 (d, 1H), 2.10-2.04 (m, 1H), 1.29-1.27 (d, 3H), 1.22-1.20 (d, 2H), 0.85-0.84 (d, 2H). LCMS: 99.33%, m/z=407.2 (M+1)⁺. HPLC: 97.39%.

Example 54

(S)-2-(3-aminopyrrolidin-1-yl)-N-(6-cyclopropyl-2-methyl-2H-indazol-5-yl)oxazole-4-carboxamide

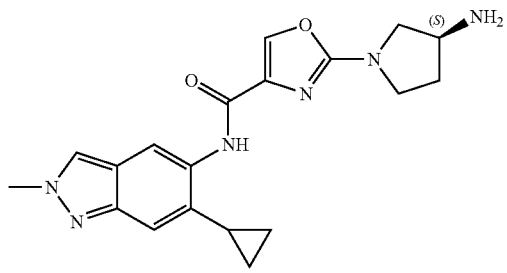

Step-1: Synthesis of tert-butyl (S)-(1-(4-((6-cyclopropyl-2-methyl-2H-indazol-5-yl)carbamoyl)oxazol-2-yl)pyrrolidin-3-yl)carbamate Using the same reagents and conditions as described in step 7 of example 1, 6-cyclopropyl-2-methyl-2H-indazol-5-amine (product of step 2 of example 16) (85 mg, 0.4545 mmol) was coupled with (S)-2-(3-((tert-butoxycarbonyl)amino)pyrrolidin-1-yl)oxazole-4-carboxylic acid (intermediate 7) (162 mg, 0.5454 mmol) using EDCI.HCl (157 mg, 0.8181 mmol), HOBt (77 mg, 0.5726 mmol), DIPEA (282 mg, 2.185 mmol) in DMF (5 mL) to obtain the desired compound (142 mg, 67%). LCMS: m/z=467.3 (M+1)⁺.

Step-2: Synthesis of (S)-2-(3-aminopyrrolidin-1-yl)-N-(6-cyclopropyl-2-methyl-2H-indazol-5-yl)oxazole-4-carboxamide Using the same reaction conditions as described in step 8 of example 1, tert-butyl (S)-(1-(4-(((6-cyclopropyl-2-methyl-2H-indazol-5-yl)carbamoyl)oxazol-2-yl)pyrrolidin-3-yl)carbamate (141 mg, 0.3025 mmol) was deprotected using ether HCl/methanol (5/5 mL) to get the title compound (32 mg, 29%).

¹HNMR (CDCl₃, 300 MHz): δ 9.73 (s, 1H), 8.66 (s, 1H), 7.83 (s, 1H), 7.82 (s, 1H), 7.50 (s, 1H), 4.17 (s, 3H), 3.75-3.59 (m, 4H), 3.28-3.26 (m, 1H), 2.30-2.20 (m, 1H), 2.20-1.75 (m, 2H), 1.16-1.06 (m, 2H), 0.81-0.77 (m, 2H). LCMS: 99.73%, m/z=367.3 (M+1)⁺.

Example 55

(S)—N-(6-cyclopropyl-2-methyl-2H-indazol-5-yl)-2-(3-hydroxypyrrolidin-1-yl)oxazole-4-carboxamide

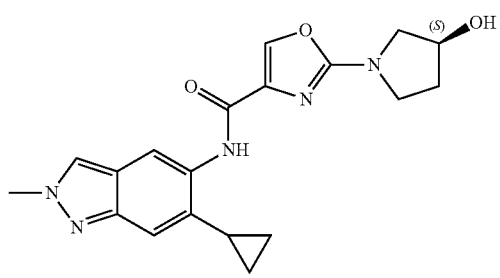

Step-1: Synthesis of (S)-2-(3-((tert-butyldimethylsilyl)oxy)pyrrolidin-1-yl)-N-(6-cyclopropyl-2-methyl-2H-indazol-5-yl)oxazole-4-carboxamide Using the same reagents and conditions as described in step 7 of example 1, 6-cyclopropyl-2-methyl-2H-indazol-5-amine (product of step 2 of example 16) (80 mg, 0.427 mmol) was coupled with (S)-2-(3-((tert-butyldimethylsilyl)oxy)pyrrolidin-1-yl)oxazole-4-carboxylic acid (intermediate 9) (133 mg, 0.427 mmol) using EDCI.HCl (123 mg, 0.64 mmol), HOBt (61 mg, 0.449 mmol), DIPEA (221 mg, 1.71 mmol) in DMF (5 mL) to obtain the desired compound (172 mg, 83%). LCMS: m/z=482.6 (M+1)⁺.

Step-2: Synthesis of (S)—N-(6-cyclopropyl-2-methyl-2H-indazol-5-yl)-2-(3-hydroxypyrrolidin-1-yl)oxazole-4-carboxamide Using the same reaction conditions as described in step 8 of example 1, (S)-2-(3-((tert-butyldimethylsilyl)oxy)pyrrolidin-1-yl)-N-(6-cyclopropyl-2-methyl-2H-indazol-5-yl)oxazole-4-carboxamide (170 mg, 0.353 mmol) was deprotected using 1M TBAF in THF (0.5/5 mL) to get the title compound (105 mg, 81%).

¹HNMR (CDCl₃, 300 MHz): δ 9.73 (s, 1H), 8.66 (s, 1H), 7.83 (s, 1H), 7.82 (s, 1H), 7.50 (s, 1H), 4.62 (s, 1H), 4.20 (s, 3H), 3.73-3.59 (m, 4H), 2.25-2.04 (m, 2H), 2.00-1.90 (m, 2H), 1.12-1.09 (m, 2H), 0.79-0.77 (m, 2H). LCMS: 100%, m/z=368.2 (M+1)⁺. HPLC: 96.00%.

Example 56

(S)-6-(1-(2-hydroxypropyl)-1H-pyrazol-4-yl)-N-(2-methyl-6-(piperidin-1-yl)-2H-indazol-5-yl)picolinamide

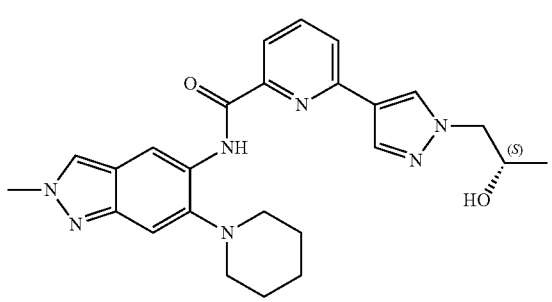

Step-1: Synthesis of N-(2-methyl-6-(piperidin-1-yl)-2H-indazol-5-yl)-6-(1-(tetrahydro-2H-pyran-2-yl)-1H-pyrazol-4-yl)picolinamide Using the same reagents and conditions as described in step 1 of example 6, 6-bromo-N-(2-methyl-6-(piperidin-1-yl)-2H-indazol-5-yl)picolinamide (product of step 1 of example 12) (180 mg, 0.4337 mmol) was coupled with 1-(tetrahydro-2H-pyran-2-yl)-4-(4,4,5,5-tetramethyl-1,3,2-dioxaborolan-2-yl)-1H-pyrazole (144 mg, 0.5204 mmol) (intermediate 1) using Pd(dppf)Cl$_2$ (31 mg, 0.0433 mmol) and sodium carbonate (137 mg, 1.3012 mmol) in DME/H$_2$O (5/1 mL) at 100° C. for 4 h to obtain crude product. The obtained crude was purified by 60-120 silica gel column chromatography using methanol in DCM as eluent to obtain the title compound (120 mg, 58%). LCMS: m/z=487.2 (M+1)$^+$.

Step-2: Synthesis of N-(2-methyl-6-(piperidin-1-yl)-2H-indazol-5-yl)-6-(1H-pyrazol-4-yl)picolinamide hydrochloride Using the same reaction conditions as described in step 8 of example 1, N-(2-methyl-6-(piperidin-1-yl)-2H-indazol-5-yl)-6-(1-(tetrahydro-2H-pyran-2-yl)-1H-pyrazol-4-yl)picolinamide (120 mg) was deprotected using methanolic HCl (5 mL) in methanol (10 mL) to get the title compound (100 mg, 98%). LCMS: m/z=403.2 (M+1)$^+$.

Step-3: Synthesis of (S)-6-(1-(2-hydroxypropyl)-1H-pyrazol-4-yl)-N-(2-methyl-6-(piperidin-1-yl)-2H-indazol-5-yl)picolinamide Using the same reagents and conditions as described in example 34, N-(2-methyl-6-(piperidin-1-yl)-2H-indazol-5-yl)-6-(1H-pyrazol-4-yl)picolinamide hydrochloride (100 mg, 0.2487 mmol) was reacted with (S)-2-methyloxirane (28 mg, 0.497 mmol) using sodium carbonate (131 mg, 1.243 mmol) in DMF (3 mL) at 100° C. for 14 h to get the crude product. The obtained crude was purified by 60-120 silica gel column chromatography using methanol in DCM as eluent to obtain the crude product. This was purified by prep HPLC to get the title compound (60 mg, 53%).

$^1$HNMR (DMSO-d$_6$, 400 MHz): δ 10.62 (s, 1H), 8.45 (s, 1H), 8.28-8.24 (d, 2H), 8.08-7.96 (m, 3H), 5.04-5.03 (d, 1H), 4.11-4.05 (m, 6H), 3.06 (s, 4H), 1.78 (s, 4H), 1.56 (s, 2H), 1.09-1.07 (d, 3H). LCMS: 99.12%, m/z=460.8 (M+1)$^+$. HPLC: 98.91%.

Example 57

6-((2-hydroxypropyl)amino)-N-(2-methyl-6-(piperidin-1-yl)-2H-indazol-5-yl)picolinamide

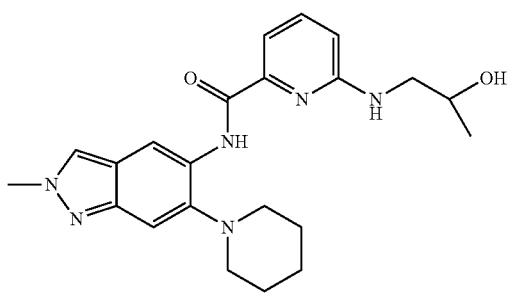 [SMILES: CC(O)CNc1cccc(C(=O)Nc2cc3cn(C)nc3cc2N2CCCCC2)n1]

The mixture of 6-bromo-N-(2-methyl-6-(piperidin-1-yl)-2H-indazol-5-yl)picolinamide (product of step 1 of example 12) (100 mg, 0.241 mmol), 1-aminopropan-2-ol (28 mg, 0.362 mmol), potassium carbonate (100 mg, 0.724 mmol) in DMSO (3 mL) was heated in sealed tube at 140° C. for 14 h. The reaction mass was quenched with ice water and extracted with ethyl acetate. The solvent was distilled out to get the crude product. This was purified by prep HPLC to get the title compound (35 mg, 35.7%).

$^1$H NMR (DMSO-d$_6$, 400 MHz): δ 10.6 (s, 1H), 8.64 (s, 1H), 8.23 (s, 1H), 7.59-7.56 (t, 1H), 7.33-7.30 (m, 2H), 6.85-6.83 (d, 1H), 6.69 (s, 1H), 4.83-4.82 (d, 1H), 4.10 (s, 3H), 3.90-3.80 (m, 1H), 2.82- (s, 4H), 1.78 (s, 4H), 1.58 (s, 2H), 1.15-1.14 (d, 3H). LCMS: 94.83%, m/z=408.9 (M+1)$^+$. HPLC: 98.44%.

Example 58

N-(6-(4-hydroxypiperidin-1-yl)-2-methyl-2H-indazol-5-yl)-2-(2-methylpyridin-4-yl)oxazole-4-carboxamide

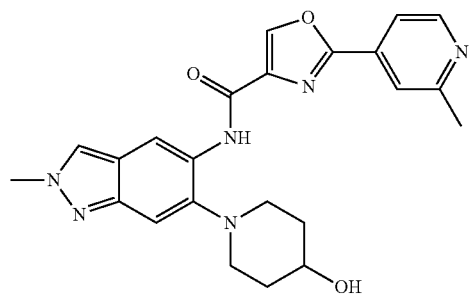

Step-1: Synthesis of 2-fluoro-4-(4-hydroxypiperidin-1-yl)-5-nitrobenzaldehyde To the solution of 2,4-difluoro-5-nitrobenzaldehyde (2 gm, 10.6 mmol) in DMF (mL) was added potassium carbonate (1.771 gm, 12.8 mmol) and 4-hydroxypiperidine (1.08 gm, 10.6 mmol) and the contents were stirred for 2 h at RT. The reaction mixture was quenched with ice water, extracted with EtOAc, washed with brine, dried over anhydrous Na$_2$SO$_4$ and distilled out the solvent. The obtained crude was purified by 60-120 silica gel column chromatography and compound eluted using ethyl acetate in hexane to give title compound (1.5 gm, 54%). LCMS: m/z=269.1 (M+1)$^+$.

Step-2: Synthesis of 4-(4-((tert-butyldimethylsilyl)oxy)piperidin-1-yl)-2-fluoro-5-nitrobenzaldehyde To the solution of 2-fluoro-4-(4-hydroxypiperidin-1-yl)-5-nitrobenzaldehyde (1.5 gm, 5.5 mmol) in DMF (10 mL) was added TBDMS chloride (1.007 gm, 6.7 mmol) and imidazole (951 mg, 13.9 mmol) and stirred at RT for 2 h. The reaction mass was quenched with water and extracted with ethyl acetate to get the crude product. The obtained crude was purified by 60-120 silica gel column chromatography using ethyl acetate in hexane as eluent to obtain the title compound (1 gm, 48%). LCMS: m/z=383.2 (M+1)$^+$.

Step-3: Synthesis of 6-(4-((tert-butyldimethylsilyl)oxy)piperidin-1-yl)-5-nitro-1H-indazole Using the similar reagents and conditions as described in step 2 of example 5, 4-(4-((tert-butyldimethylsilyl)oxy)piperidin-1-yl)-2-fluoro-5-nitrobenzaldehyde (1 gm, 2.61 mmol) was cyclized using hydrazine hydrate (261 mg, 5.2 mmol) in THF (15 mL) at 75° C. for 4 h to obtain the crude title compound (1 gm). LCMS: m/z=377.2 (M+1)+.

Step-4: Synthesis of 6-(4-((tert-butyldimethylsilyl)oxy)piperidin-1-yl)-1-methyl-5-nitro-1H-indazole and 6-(4-((tert-butyldimethylsilyl)oxy)piperidin-1-yl)-2-methyl-5-nitro-2H-indazole Using the same reagents and conditions as described in step 5 of example 1, 6-(4-((tert-butyldimethylsilyl)oxy)piperidin-1-yl)-5-nitro-1H-indazole (1 gm, 2.65 mmol) was methylated using sodium hydride (255 mg, 5.31 mmol) and methyl iodide (755 mg, 5.31 mmol) in THF at RT for 0.5 h to get the crude product. This was purified by silica gel column chromatography and elution with ethyl acetate in hexane resulted the title compound (isomer A 320 mg and isomer B 600 mg, 90%). LCMS: m/z=391.2 (M+1)+.

Step-5: Synthesis of 6-(4-((tert-butyldimethylsilyl)oxy)piperidin-1-yl)-2-methyl-2H-indazol-5-amine Using the same reaction conditions as described in step 2 of example 16, 6-(4-((tert-butyldimethylsilyl)oxy)piperidin-1-yl)-2-methyl-5-nitro-2H-indazole (320 mg, 0.820 mmol) was reduced with zinc dust (426 mg, 6.5641 mmol) and ammonium chloride (354 gm, 6.564 mmol) in THF/water (10/2 mL) to get the desired crude product (240 mg). LCMS: m/z=361.2 (M+1)+.

Step-6: Synthesis of N-(6-(4-((tert-butyldimethylsilyl)oxy)piperidin-1-yl)-2-methyl-2H-indazol-5-yl)-2-(2-methylpyridin-4-yl)oxazole-4-carboxamide Using the same reagents and conditions as described in step 7 of example 1, 6-(4-((tert-butyldimethylsilyl)oxy)piperidin-1-yl)-2-methyl-2H-indazol-5-amine (120 mg, 0.333 mmol) was coupled with 2-(2-methylpyridin-4-yl)oxazole-4-carboxylic acid (81 mg, 0.399 mmol) using EDCI.HCl (95 mg, 0.499 mmol), HOBt (44 mg, 0.333 mmol), DIPEA (0.3 mL, 1.03 mmol) in DMF (5 mL) to get the desired compound (160 mg, 84%). LCMS: m/z=547.3 (M+1)+.

Step-7: Synthesis of N-(6-(4-hydroxypiperidin-1-yl)-2-methyl-2H-indazol-5-yl)-2-(2-methylpyridin-4-yl)oxazole-4-carboxamide TBAF (1 mL) was added to the stirred solution of N-(6-(4-((tert-butyldimethylsilyl)oxy)piperidin-1-yl)-2-methyl-2H-indazol-5-yl)-2-(2-methylpyridin-4-yl)oxazole-4-carboxamide (160 mg, 0.2930 mmol) in THF (5 mL) and stirred at RT for 4 h. The reaction mass was diluted with saturated ammonium chloride solution and the solid was filtered and dried to get the title compound (50 mg, 40%).
1HNMR (DMSO-d6, 400 MHz): δ 10.4 (s, 1H), 9.03 (s, 1H), 8.68-8.67 (d, 1H), 8.62 (s, 1H), 7.91 (s, 1H), 7.80-7.97 (d, 1H), 7.40 (s, 1H), 4.96 (s, 1H), 4.11 (s, 3H), 3.78 (s, 1H), 3.06-3.03 (d, 2H), 2.85-2.82 (t, 2H), 2.61 (s, 3H), 2.06-2.03 (m, 2H), 1.95-1.88 (m, 2H). LCMS: 99.27%, m/z=433.2 (M+1)+. HPLC: 95.43%.

Example 59

N-(6-(azetidin-1-yl)-1-methyl-1H-indazol-5-yl)-2-(2-methylpyridin-4-yl)oxazole-4-carboxamide

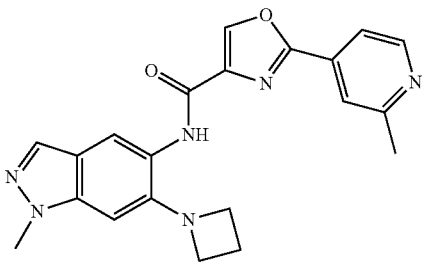 [SMILES: Cc1cc(-c2nc(C(=O)Nc3cc4cnn(C)c4cc3N3CCC3)co2)ccn1]

Step-1: Synthesis of 4-(azetidin-1-yl)-2-fluoro-5-nitrobenzaldehyde

Using the similar reagents and conditions as described in step 1 of example 58, 2,4-difluoro-5-nitrobenzaldehyde (2.3 gm, 12.2 mmol) was reacted with azetidine (772 mg, 13.5 mmol) using potassium carbonate (2.54 gm, 18.4 mmol) in DMF (10 mL) at RT for 2 h to get the crude compound. The obtained crude was purified by 60-120 silica gel column chromatography and compound eluted using 10% ethyl acetate in hexane to give title compound (2.2 gm, 81%). LCMS: m/z=225.2 (M+1)+.

Step-2: Synthesis of 6-(azetidin-1-yl)-5-nitro-1H-indazole

Using the similar reagents and conditions as described in step 2 of example 5, 4-(azetidin-1-yl)-2-fluoro-5-nitrobenzaldehyde (2.2 gm, 9.82 mmol) was cyclized using hydrazine hydrate (50 mg, 1.96 mmol) in THF (10 mL) at 60° C. for 1 h to obtain the crude title compound. The obtained crude was purified by 60-120 silica gel column chromatography and compound eluted using 20% ethyl acetate in hexane to give title compound (1.2 gm, 61%). LCMS: m/z=219.1 (M+1)+.

Step-3: Synthesis of 6-(azetidin-1-yl)-1-methyl-5-nitro-1H-indazole (Isomer A) and 6-(azetidin-1-yl)-2-methyl-5-nitro-2H-indazole (Isomer B)

Using the same reagents and conditions as described in step 5 of example 1, 6-(azetidin-1-yl)-5-nitro-1H-indazole (1.2 gm, 5.17 mmol) was methylated using sodium hydride (260 mg, 10.8 mmol) and methyl iodide (3.01 gm, 29.2 mmol) in THF (15 mL) at RT for 0.5 h to get the crude product. This was purified by silica gel column chromatography and elution with 50% ethyl acetate in hexane gave the title compound (isomer A 600 mg and isomer B 300 mg, 70%). LCMS: m/z=233.0 (M+1)+.

Step-4: Synthesis of 6-(azetidin-1-yl)-1-methyl-1H-indazol-5-amine

Using the same reaction conditions as described in step 2 of example 16, 6-(azetidin-1-yl)-1-methyl-5-nitro-1H-indazole (600 mg, 3.48 mmol) was reduced with zinc dust (2.26 gm, 34.8 mmol) and ammonium chloride (1.888 gm, 34.8 mmol) in THF/water (10/2.5 mL) to get the desired crude product (500 mg). LCMS: m/z=203.2 (M+1)+.

Step-5: Synthesis of N-(6-(azetidin-1-yl)-1-methyl-1H-indazol-5-yl)-2-(2-methylpyridin-4-yl)oxazole-4-carboxamide Using the similar reagents and conditions as described in step 7 of example 1, 6-(azetidin-1-yl)-1-methyl-1H-indazol-5-amine (250 mg, 0.23 mmol) was coupled with 2-(2-methylpyridin-4-yl)oxazole-4-carboxylic acid (302 mg, 0.248 mmol) using HATU (705 mg, 1.85 mmol), DIPEA (638 mg, 4.955 mmol) in DMF (8 mL) to get the desired compound (100 mg, 32%).

¹HNMR (DMSO-d₆, 400 MHz): δ 9.54 (s, 1H), 8.99 (s, 1H), 8.70-8.69 (d, 1H), 7.87-7.86 (d, 2H), 7.79-7.85 (d, 1H), 7.73 (s, 1H), 6.65 (s, 1H), 3.96-3.93 (m, 7H), 2.60 (s, 3H), 2.26-2.24 (m, 2H). 99.70%, LCMS: 99.70%, m/z=389.2 (M+1)+. HPLC: 98.73%.

Example 60

N-(6-(azetidin-1-yl)-2-methyl-2H-indazol-5-yl)-2-(2-methylpyridin-4-yl)oxazole-4-carboxamide

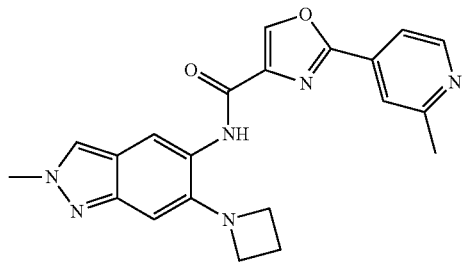 [SMILES: Cc1cc(-c2nc(C(=O)Nc3cc4cn(C)nc4cc3N3CCC3)co2)ccn1]

Step-1: Synthesis of 6-(azetidin-1-yl)-2-methyl-2H-indazol-5-amine

Using the same reaction conditions as described in step 2 of example 16, 6-(azetidin-1-yl)-2-methyl-5-nitro-2H-indazole (300 mg, 1.74 mmol) (product of step 3 of example 59) was reduced with zinc dust (1.13 gm, 17.4 mmol) and ammonium chloride (941 mg, 17.4 mmol) in THF/water (10/2 mL) to get the desired crude product (250 mg). LCMS: m/z=203.2 (M+1)+.

Step-2: Synthesis of N-(6-(azetidin-1-yl)-2-methyl-2H-indazol-5-yl)-2-(2-methylpyridin-4-yl)oxazole-4-carboxamide Using the similar reagents and conditions as described in step 7 of example 1, 6-(azetidin-1-yl)-2-methyl-2H-indazol-5-amine (250 mg, 1.23 mmol) was coupled with 2-(2-methylpyridin-4-yl)oxazole-4-carboxylic acid (302 mg, 1.48 mmol) using HATU (705 mg, 1.85 mmol), DIPEA (638 mg, 4.95 mmol) in DMF (10 mL) to get the desired compound (27 mg, 9%).

¹H NMR (DMSO-d₆, 400 MHz): δ 9.46 (s, 1H), 9.01 (s, 1H), 8.71-8.69 (d, 1H), 8.18 (s, 1H), 7.91-7.87 (m, 2H), 7.80-7.78 (d, 1H), 6.69 (s, 1H), 4.08 (s, 3H), 3.90-3.86 (t, 4H), 2.61 (s, 3H), 2.33-2.24 (m, 2H). LCMS: 100%, m/z=389.1 (M+1)+. HPLC: 96.16%.

Example 61

N-(6-(3-hydroxyazetidin-1-yl)-2-methyl-2H-indazol-5-yl)-2-(2-methylpyridin-4-yl)oxazole-4-carboxamide

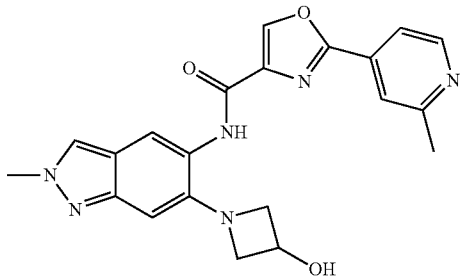 [SMILES: Cc1cc(-c2nc(C(=O)Nc3cc4cn(C)nc4cc3N3CC(O)C3)co2)ccn1]

Step-1: Synthesis of 2-fluoro-4-(3-hydroxyazetidin-1-yl)-5-nitrobenzaldehyde

Using the similar reagents and conditions as described in step 1 of example 58, 2,4-difluoro-5-nitrobenzaldehyde (2 gm, 10.6951 mmol) was substituted with azetidin-3-ol hydrochloride (1.277 mg, 11.7647 mmol) using potassium carbonate (4.434 gm, 32.0855 mmol) in DMF (20 mL) at 0° C. for 0.5 h to get the crude compound. The obtained crude was purified by 60-120 silica gel column chromatography and compound eluted using 1% methanol in DCM to give title compound (2.5 gm, 97.35%). LCMS: m/z=241.3 (M+1)+.

Step-2: Synthesis of 4-(3-((tert-butyldimethylsilyl)oxy)azetidin-1-yl)-2-fluoro-5-nitrobenzaldehyde Using the similar reagents and conditions as described in step 2 of example 58, 2-fluoro-4-(3-hydroxyazetidin-1-yl)-5-nitrobenzaldehyde (2.5 gm, 10.4084 mmol) was protected using TBDMS chloride (2.365 gm, 15.6903 mmol), imidazole (1.78 mg, 20.1506 mmol) and DMAP (1.533 gm, 12.5523 mmol) in DMF (10 mL) at RT for 0.5 h to obtain the title compound (2.7 gm, 73.19%). LCMS: m/z=355.1 (M+1)+.

Step-3: Synthesis of 1-(5-nitro-1H-indazol-6-yl)azetidin-3-ol

Using the similar reagents and conditions as described in step 2 of example 5, 4-(3-((tert-butyldimethylsilyl)oxy)azetidin-1-yl)-2-fluoro-5-nitrobenzaldehyde (2.7 gm, 7.6174 mmol) was cyclized using hydrazine hydrate (762 mg, 15.2348 mmol) in THF (20 mL) at 80° C. for 14 h to obtain the title compound (1.4 gm, 79.54%). LCMS: m/z=236.0 (M+1)+.

Step-4: Synthesis of 6-(3-((tert-butyldimethylsilyl)oxy)azetidin-1-yl)-5-nitro-1H-indazole Using the similar reagents and conditions as described in step 2 of example 58, 1-(5-nitro-1H-indazol-6-yl)azetidin-3-ol (1.4 gm, 6.0344 mmol) was protected using TBDMS chloride (1.364 gm, 9.0517 mmol), imidazole (1.027 mg, 15.0862 mmol) and DMAP (884 mg, 7.2413 mmol) in DMF (10 mL) at RT for 1 h to obtain the title compound (1.8 gm, 85.71%). LCMS: m/z=349.1 (M+1)⁺.

Step-5: Synthesis of 6-(3-((tert-butyldimethylsilyl) oxy)azetidin-1-yl)-1-methyl-5-nitro-1H-indazole compound and 6-(3-((tert-butyldimethylsilyl)oxy) azetidin-1-yl)-2-methyl-5-nitro-2H-indazole Using the same reagents and conditions as described in step 5 of example 1, 6-(3-((tert-butyldimethylsilyl)oxy)azetidin-1-yl)-5-nitro-1H-indazole (1.8 gm, 5.1652 mmol) was methylated using sodium hydride (416 mg, 10.4046 mmol) and methyl iodide (0.65 mL), 10.4046 mmol) in THF (20 mL) at 0° C. for 1 h to get the crude product. This was purified by silica gel column chromatography and elution with 30% ethyl acetate in hexane gave 6-(3-((tert-butyldimethylsilyl)oxy)azetidin-1-yl)-1-methyl-5-nitro-1H-indazole (1.2 gm, 64.10%) and further elution with 80% ethyl acetate in hexane gave 6-(3-((tert-butyldimethylsilyl)oxy)azetidin-1-yl)-2-methyl-5-nitro-1H-indazole (500 mg, 26.70%). LCMS: m/z=363.2 (M+1)⁺.

Step-6: Synthesis of 6-(3-((tert-butyldimethylsilyl) oxy)azetidin-1-yl)-2-methyl-2H-indazol-5-amine Using the same reaction conditions as described in step 2 of example 16, 6-(3-((tert-butyldimethylsilyl)oxy)azetidin-1-yl)-2-methyl-5-nitro-2H-indazole (500 mg, 1.3888 mmol) was reduced with zinc dust (726 mg, 11.11 mmol) and ammonium chloride (1.189 gm, 22.22 mmol) in THF/water (10/2 mL) to get the title product (320 mg, 69.86%). LCMS: m/z=333.2 (M+1)⁺.

Step-7: Synthesis of N-(6-(3-((tert-butyldimethylsilyl)oxy)azetidin-1-yl)-2-methyl-2H-indazol-5-yl)-2-(2-methylpyridin-4-yl)oxazole-4-carboxamide Using the similar reagents and conditions as described in step 7 of example 1, 6-(3-((tert-butyldimethylsilyl)oxy)azetidin-1-yl)-2-methyl-2H-indazol-5-amine (200 mg, 0.6014 mmol) was coupled with 2-(2-methylpyridin-4-yl)oxazole-4-carboxylic acid (186 mg, 0.9090 mmol) using HATU (461 mg, 1.2121 mmol) and DIPEA (0.423 mL, 2.4242 mmol) in DMF (5 mL) to get the desired compound (200 mg, 64.10%). LCMS: m/z=519.2 (M+1)⁺.

Step-8: Synthesis of N-(6-(3-hydroxyazetidin-1-yl)-2-methyl-2H-indazol-5-yl)-2-(2-methylpyridin-4-yl) oxazole-4-carboxamide Using the same reagents and conditions as described in step 7 of example 58, N-(6-(3-((tert-butyldimethylsilyl)oxy) azetidin-1-yl)-2-methyl-2H-indazol-5-yl)-2-(2-methylpyridin-4-yl)oxazole-4-carboxamide (100 mg, 0.1927 mmol) was deprotected using 0.1M TBAF in THF (0.5/10 mL) at RT for 0.5 h to get the title compound (37 mg, 47.43%).

¹HNMR (300 MHz, DMSO-d₆): δ 9.5 (s, 1H), 9.00 (s, 1H), 8.60-8.70 (d, 1H), 7.94 (s, 1H), 7.89 (s, 1H), 7.81-7.79 (d, 1H), 6.73 (s, 1H), 5.62-5.60 (d, 1H), 4.57-4.53 (m, 1H), 4.16-4.08 (m, 6H), 3.60-3.56 (t, 2H), 2.61 (s, 3H). 100%, LCMS: 100%, m/z=405.1 (M+1)⁺. HPLC: 97.35%.

Example 62

N-(1-methyl-6-(pyrrolidin-1-yl)-1H-indazol-5-yl)-2-(2-methylpyridin-4-yl)oxazole-4-carboxamide

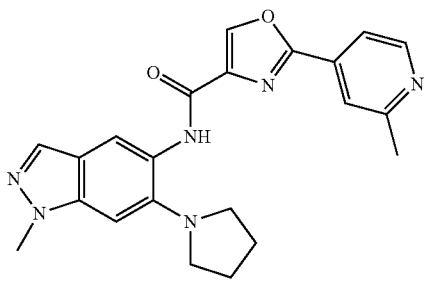 [SMILES: Cc1cc(-c2nc(C(=O)Nc3cc4cnn(C)c4cc3N3CCCC3)co2)ccn1]

Step-1: Synthesis of 2-fluoro-5-nitro-4-(pyrrolidin-1-yl)benzaldehyde

Using the similar reagents and conditions as described in step 1 of example 58, 2,4-difluoro-5-nitrobenzaldehyde (2.85 gm, 15.2 mmol) was substituted with pyrrolidine (1.192 gm, 16.7 mmol) using potassium carbonate (3.159 gm, 22.8 mmol) in DMF (20 mL) at 0° C. for 10 min to get the crude compound. The obtained crude was purified by 60-120 silica gel column chromatography and compound eluted using 30% ethyl acetate in hexane to give title compound (2.7 gm, 74.38%). LCMS: m/z=239.0 (M+1)⁺.

Step-2: Synthesis of 5-nitro-6-(pyrrolidin-1-yl)-1H-indazole

Using the similar reagents and conditions as described in step 2 of example 5, 2-fluoro-5-nitro-4-(pyrrolidin-1-yl) benzaldehyde (2.7 gm, 11.3 mmol) was cyclized using hydrazine hydrate (1.135 gm, 2.26 mmol) in THF (20 mL) at 80° C. for 14 h to obtain the crude title compound. The obtained crude was purified by 60-120 silica gel column chromatography and compound eluted using 50% ethyl acetate in hexane to give title compound (2.15 gm, 81.74%). LCMS: m/z=233.0 (M+1)⁺.

Step-3: Synthesis of 1-methyl-5-nitro-6-(pyrrolidin-1-yl)-1H-indazole and 2-methyl-5-nitro-6-(pyrrolidin-1-yl)-2H-indazole Using the same reagents and conditions as described in step 5 of example 1, 5-nitro-6-(pyrrolidin-1-yl)-1H-indazole (2.15 gm, 9.4298 mmol) was methylated using sodium hydride (754 mg, 18.8596 mmol) and methyl iodide (1.179 mL, 18.8596 mmol) in THF (80 mL) at RT for 3 h to get the crude product. This was purified by silica gel column chromatography and with 40% ethyl acetate in hexane gave 1-methyl-5-nitro-6-(pyrrolidin-1-yl)-1H-indazole (1.5 gm, 64.59%) and further elution with 80% ethyl acetate in hexane gave 2-methyl-5-nitro-6-(pyrrolidin-1-yl)-2H-indazole (800 mg, 34.45%). LCMS: m/z=247.1 (M+1)⁺.

Step-4: Synthesis of 1-methyl-6-(pyrrolidin-1-yl)-1H-indazol-5-amine

Using the same reagents and conditions as described in step 4 of example 10, 1-methyl-5-nitro-6-(pyrrolidin-1-yl)-

1H-indazole (1.5 gm, 6.0908 mmol) was reduced using 10% Pd/C (500 mg) in methanol (30 mL) for 14 h to get the title product (1.2 gm, 91.11%). LCMS: m/z=217.3 (M+1)⁺.

Step-5: Synthesis of N-(1-methyl-6-(pyrrolidin-1-yl)-1H-indazol-5-yl)-2-(2-methylpyridin-4-yl)oxazole-4-carboxamide Using the similar reagents and conditions as described in step 7 of example 1, 1-methyl-6-(pyrrolidin-1-yl)-1H-indazol-5-amine (150 mg, 0.6935 mmol) was coupled with 2-(2-methylpyridin-4-yl)oxazole-4-carboxylic acid (170 mg, 0.8322 mmol) using HATU (343 mg, 0.9015 mmol), DIPEA (0.483 mL, 2.7740 mmol) in DMF (3 mL) to get the title compound (70 mg, 25.17%).

¹HNMR (DMSO-d₆, 300 MHz): δ 9.91 (s, 1H), 9.04 (s, 1H), 8.72-8.70 (d, 1H), 8.33 (s, 1H), 7.95 (s, 1H), 7.83 (s, 1H), 7.76-7.74 (d, 1H), 4.00 (s, 3H), 3.28-3.21 (t, 4H), 2.60 (s, 3H), 2.02 (s, 4H). LCMS: 98.42%, m/z=403.2 (M+1)⁺. HPLC: 94.55%.

Example 63

N-(2-methyl-6-(pyrrolidin-1-yl)-2H-indazol-5-yl)-2-(2-methylpyridin-4-yl)oxazole-4-carboxamide

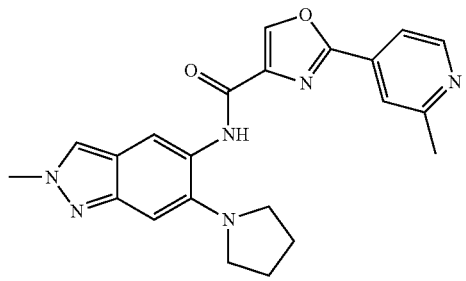 [SMILES: Cc1cc(-c2nc(C(=O)Nc3cc4cn(C)nc4cc3N3CCCC3)co2)ccn1]

Step-1: Synthesis of 2-methyl-6-(pyrrolidin-1-yl)-1H-indazol-5-amine

Using the same reagents and conditions as described in step 4 of example 10, 2-methyl-5-nitro-6-(pyrrolidin-1-yl)-1H-indazole (product of step 3 of example 62) (800 mg, 3.2484 mmol) was reduced using 10% Pd/C (300 mg) in methanol (30 mL) for 14 h to get the desired product (250 mg, 35.61%). LCMS: m/z=217.3 (M+1)⁺.

Step-2: Synthesis of N-(2-methyl-6-(pyrrolidin-1-yl)-1H-indazol-5-yl)-2-(2-methylpyridin-4-yl)oxazole-4-carboxamide Using the similar reagents and conditions as described in step 7 of example 1, 2-methyl-6-(pyrrolidin-1-yl)-1H-indazol-5-amine (170 mg, 0.7859 mmol) was coupled with 2-(2-methylpyridin-4-yl)oxazole-4-carboxylic acid (193 mg, 0.9431 mmol) using HATU (388 mg, 1.0217 mmol), DIPEA (0.548 mL, 3.1439 mmol) in DMF (3 mL) to get the desired compound (70 mg, 22.22%).

¹HNMR (DMSO-d₆, 300 MHz): δ 10.04 (s, 1H), 9.04 (s, 1H), 8.72-8.70 (d, 1H), 8.47 (s, 1H), 8.25 (s, 1H), 7.82 (s, 1H), 7.74-7.73 (d, 1H), 7.35 (s, 1H), 4.10 (s, 3H), 3.11 (s, 4H), 2.59 (s, 3H), 2.50 (s, 4H). 100%. LCMS: m/z=403.2 (M+1)⁺.

Example 64

(S)—N-(6-(3-hydroxypyrrolidin-1-yl)-2-methyl-2H-indazol-5-yl)-2-(2-methylpyridin-4-yl)oxazole-4-carboxamide

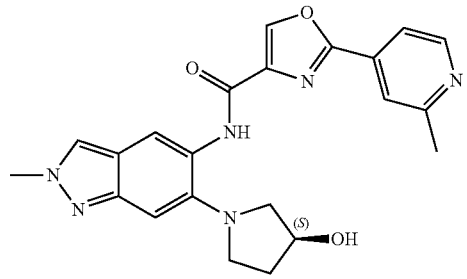

Step-1: Synthesis of 6-fluoro-1-methyl-5-nitro-1H-indazole (Isomer A) and 6-fluoro-2-methyl-5-nitro-2H-indazole (Isomer B)

Using the same reagents and conditions as described in step 5 of example 1, 6-fluoro-5-nitro-1H-indazole (product of step 3 of example 1) (2.5 gm, 13.6 mmol) was methylated using sodium hydride (696 mg, 29.0 mmol and methyl iodide (8.04 gm, 56.6 mmol) in THF (20 mL) at RT for 0.5 h to get the crude product. This was purified by silica gel column chromatography and elution with 50% ethyl acetate in hexane gave the title compound (isomer B 800 mg and isomer A 1.1 gm, 90%).

Step-2: Synthesis of (S)-1-(2-methyl-5-nitro-2H-indazol-6-yl)pyrrolidin-3-ol

Using the similar reagents and conditions as described in step 1 of example 58, 6-fluoro-2-methyl-5-nitro-2H-indazole (250 mg, 1.28 mmol) was substituted with (S)-pyrrolidin-3-olhydrochloride (189 mg, 1.53 mmol) using potassium carbonate (530 mg, 0.384 mmol) in DMF (10 mL) at 0° C. for 0.5 h to get the crude compound. The obtained crude was purified by 60-120 silica gel column chromatography and compound eluted using 50% ethyl acetate in hexane to give title compound (200 mg, 60.6%).

Step-3: Synthesis of (S)-6-(3-((tert-butyldimethylsilyl)oxy)pyrrolidin-1-yl)-2-methyl-5-nitro-2H-indazole Using the similar reagents and conditions as described in step 2 of example 58, (S)-1-(2-methyl-5-nitro-2H-indazol-6-yl)pyrrolidin-3-ol (200 mg, 0.763 mmol) was protected using TBDMS chloride (137 mg, 0.916 mmol), imidazole (129 mg, 1.90 mmol) and DMAP (102 mg, 0.839 mmol) in DMF (7 mL) at RT for 1 h to obtain the title compound (150 mg, 53.1%). LCMS: m/z=377.2 (M+1)⁺.

Step-4: Synthesis of (S)-6-(3-((tert-butyldimethylsilyl)oxy)pyrrolidin-1-yl)-2-methyl-2H-indazol-5-amine Using the same reaction conditions as described in step 2 of example 16, (S)-6-(3-((tert-butyldimethylsilyl)oxy)pyrrolidin-1-yl)-2-methyl-5-nitro-2H-indazole (150 mg, 0.474 mmol) was reduced with zinc dust (308 mg, 4.74 mmol) and ammonium chloride (256 gm, 4.74 mmol) in THF/water (8/1 mL) to get the desired product (135 mg, 97.8%).

Step-5: Synthesis of (S)—N-(6-(3-((tert-butyldimethylsilyl)oxy)pyrrolidin-1-yl)-2-methyl-2H-indazol-5-yl)-2-(2-methylpyridin-4-yl)oxazole-4-carboxamide Using the same reagents and conditions as described in step 7 of example 1, (S)-6-(3-((tert-butyldimethylsilyl)oxy)pyrrolidin-1-yl)-2-methyl-2H-indazol-5-amine (100 mg, 0.289 mmol) was coupled with 2-(2-methylpyridin-4-yl)oxazole-4-carboxylic acid (71 mg, 0.346 mmol) using EDCI.HCl (82 mg, 0.433 mmol), HOBt (41 mg, 0.303 mmol), DIPEA (111 mg, 0.867 mmol) in DMF (5 mL) to get the title compound (60 mg, 50%).

Step-6: Synthesis of (S)—N-(6-(3-hydroxypyrrolidin-1-yl)-2-methyl-2H-indazol-5-yl)-2-(2-methylpyridin-4-yl)oxazole-4-carboxamide Using the same reaction conditions as described in step 8 of example 1, (S)—N-(6-(3-((tert-butyldimethylsilyl)oxy)pyrrolidin-1-yl)-2-methyl-2H-indazol-5-yl)-2-(2-methylpyridin-4-yl)oxazole-4-carboxamide (60 mg, 0.112 mmol) was deprotected using methanolic HCl/methanol (3/3 mL) and purified by prep HPLC to get the title compound (15 mg, 31.9%).
$^1$HNMR (DMSO-$d_6$, 400 MHz): δ 9.04 (s, 1H), 8.69-8.68 (d, 1H), 8.44 (s, 1H), 8.24 (s, 1H), 7.93 (s, 1H), 7.82-7.80 (d, 1H), 7.30 (s, 1H), 5.09 (s, 1H), 4.51 (s, 1H), 4.10 (s, 3H), 3.03-2.99 (m, 2H), 2.60 (s, 3H), 2.30-2.26 (m, 2H), 2.00-1.90 (m, 1H). 100%, LCMS: 100%, m/z=419.1 (M+1)$^+$. HPLC: 99.14%.

Example 65

(R)—N-(6-(3-hydroxypyrrolidin-1-yl)-2-methyl-2H-indazol-5-yl)-2-(2-methylpyridin-4-yl)oxazole-4-carboxamide

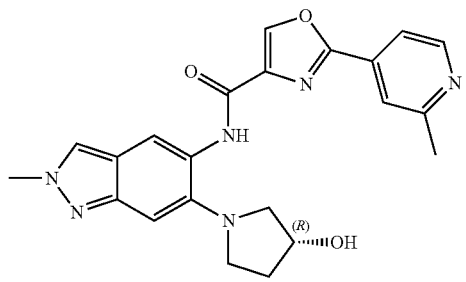

Step-1: Synthesis of (R)-1-(2-methyl-5-nitro-2H-indazol-6-yl)pyrrolidin-3-ol

Using the similar reagents and conditions as described in step 1 of example 58, 6-fluoro-2-methyl-5-nitro-2H-indazole (product of step 1 of example 64) (250 mg, 1.28 mmol) was substituted with (R)-pyrrolidin-3-ol (133 mg, 1.52 mmol) using potassium carbonate (530 mg, 0.384 mmol) in DMF (10 mL) at 100° C. for 12 h to get the crude compound. The obtained crude was purified by 60-120 silica gel column chromatography and compound eluted using 50% ethyl acetate in hexane to give title compound (200 mg, 60.6%). LCMS: m/z=263.1 (M+1)$^+$.

Step-2: Synthesis of (R)-6-(3-((tert-butyldimethylsilyl)oxy)pyrrolidin-1-yl)-2-methyl-5-nitro-2H-indazole Using the similar reagents and conditions as described in step 2 of example 58, (R)-1-(2-methyl-5-nitro-2H-indazol-6-yl)pyrrolidin-3-ol (200 mg, 0.763 mmol) was protected using TBDMS chloride (137 mg, 0.916 mmol), imidazole (129 mg, 1.90 mmol) and DMAP (102 mg, 0.839 mmol) in DMF (7 mL) at RT for 1 h to obtain the title compound (200 mg, 43%). LCMS: m/z=377.1 (M+1)$^+$.

Step-3: Synthesis of (R)-6-(3-((tert-butyldimethylsilyl)oxy)pyrrolidin-1-yl)-2-methyl-2H-indazol-5-amine Using the same reaction conditions as described in step 2 of example 16, (R)-6-(3-((tert-butyldimethylsilyl)oxy)pyrrolidin-1-yl)-2-methyl-5-nitro-2H-indazole (200 mg, 0.570 mmol) was reduced with zinc dust (375 mg, 5.70 mmol) and ammonium chloride (312 gm, 5.70 mmol) in THF/water (10/1 mL) to get the desired product (150 mg, 84.5%). LCMS: m/z=347.2 (M+1)$^+$.

Step-4: Synthesis of (R)—N-(6-(3-((tert-butyldimethylsilyl)oxy)pyrrolidin-1-yl)-2-methyl-2H-indazol-5-yl)-2-(2-methylpyridin-4-yl)oxazole-4-carboxamide Using the same reagents and conditions as described in step 7 of example 1, (R)-6-(3-((tert-butyldimethylsilyl)oxy)pyrrolidin-1-yl)-2-methyl-2H-indazol-5-amine (150 mg, 0.433 mmol) was coupled with 2-(2-methylpyridin-4-yl)oxazole-4-carboxylic acid (106 mg, 0.520 mmol) using HATU (247 mg, 0.850 mmol) and DIPEA (223 mg, 1.73 mmol) in DMF (8 mL) to get the desired compound (120 mg, 45%). LCMS: m/z=533.2 (M+1)$^+$.

Step-5: Synthesis of (R)—N-(6-(3-hydroxypyrrolidin-1-yl)-2-methyl-2H-indazol-5-yl)-2-(2-methylpyridin-4-yl)oxazole-4-carboxamide Using the same reaction conditions as described in step 8 of example 1, (R)—N-(6-(3-((tert-butyldimethylsilyl)oxy)pyrrolidin-1-yl)-2-methyl-2H-indazol-5-yl)-2-(2-methylpyridin-4-yl)oxazole-4-carboxamide (120 mg, 0.287 mmol) was deprotected using methanolic HCl/methanol (5/5 mL) to get the title compound (95 mg, 92%).
$^1$HNMR (DMSO-$d_6$, 400 MHz): δ 9.04 (s, 1H), 8.69-8.68 (d, 1H), 8.44 (s, 1H), 8.24 (s, 1H), 7.92 (s, 1H), 7.81-7.80 (d, 1H), 7.30 (s, 1H), 5.10 (s, 1H), 4.51 (s, 1H), 4.01 (s, 3H), 3.05-2.95 (m, 2H), 2.60 (s, 3H), 2.50-2.27 (m, 2H), 2.00-1.90 (s, 1H). LCMS: 96.05%, m/z=419.2 (M+1)$^+$. HPLC: 95.17%.

Example 66

N-(2-methyl-6-(piperidin-1-yl)-2H-indazol-5-yl)-5-(2-methylpyridin-4-yl)furan-2-carboxamide

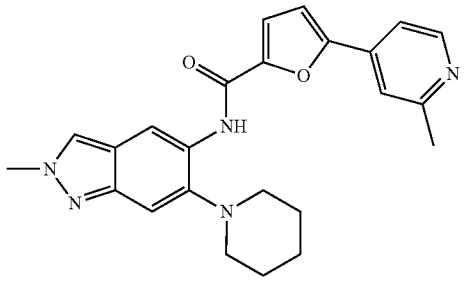 [SMILES: Cc1cc(-c2ccc(C(=O)Nc3cc4cn(C)nc4cc3N3CCCCC3)o2)ccn1]

Using the same reaction conditions as described in step 7 of example 1, 2-methyl-6-(piperidin-1-yl)-2H-indazol-5-amine (product of step 6 of example 1) (100 mg, 0.434 mmol), was coupled with 5-(2-methylpyridin-4-yl)furan-2-carboxylic acid (intermediate 12) (105 mg, 1.02 mmol) using HATU (247 mg, 0.652 mmol) and DIPEA (224 mg, 1.73 mmol) in DMF (8 mL) to afford the title compound (55 mg, 30.5%).

$^1$H NMR (DMSO-$d_6$, 400 MHz): δ 8.57-8.56 (m, 2H), 8.27 (s, 1H), 7.73 (s, 1H), 7.67-7.66 (d, 1H), 7.509-7.500 (d, 1H), 7.43 (s, 2H), 4.12 (s, 3H), 2.89 (s, 4H), 2.55 (s, 3H), 1.84-1.82 (t, 4H), 1.64 (s, 2H). LCMS: 97.29%, m/z=416.2 (M+1)$^+$. HPLC: 95.83%.

Example 67

N-(6-(4-hydroxypiperidin-1-yl)-2-methyl-2H-indazol-5-yl)-5-(2-methylpyridin-4-yl)furan-2-carboxamide

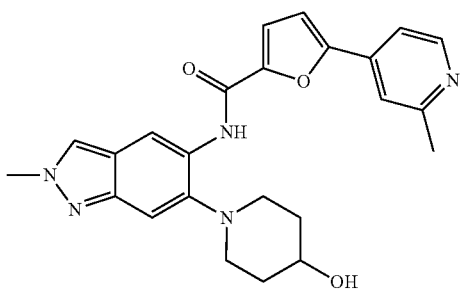 [SMILES: Cc1cc(-c2ccc(C(=O)Nc3cc4cn(C)nc4cc3N3CCC(O)CC3)o2)ccn1]

Step-1: Synthesis of N-(6-(4-((tert-butyldimethylsilyl)oxy)piperidin-1-yl)-2-methyl-2H-indazol-5-yl)-5-(2-methylpyridin-4-yl)furan-2-carboxamide Using the same reagents and conditions as described in step 7 of example 1, 6-(4-((tert-butyldimethylsilyl)oxy)piperidin-1-yl)-2-methyl-2H-indazol-5-amine (product of step 5 of example 58) (110 mg, 0.3055 mmol) was coupled with 5-(2-methylpyridin-4-yl)furan-2-carboxylic acid (intermediate 12) (74 mg, 0.366 mmol) using HATU (174 mg, 0.458 mmol) and DIPEA (0.2 mL, 1.222 mmol) in DMF (5 mL) to afford the title compound (150 mg, 94%). LCMS: m/z=546.2 (M+1)$^+$.

Step-2: Synthesis of N-(6-(4-hydroxypiperidin-1-yl)-2-methyl-2H-indazol-5-yl)-5-(2-methylpyridin-4-yl)furan-2-carboxamide Using the same reagents and conditions as described in step 7 of example 58, N-(6-(4-((tert-butyldimethylsilyl)oxy)piperidin-1-yl)-2-methyl-2H-indazol-5-yl)-5-(2-methylpyridin-4-yl)furan-2-carboxamide (100 mg, 0.1927 mmol) was deprotected using 0.1M TBAF in THF/THF (1/2 mL) at RT for 2 h to get the title compound (130 mg, 90%).

$^1$HNMR (DMSO-$d_6$, 400 MHz): δ 9.90 (s, 1H), 8.55 (s, 2H), 8.27 (s, 1H), 7.71-7.68 (m, 2H), 7.49 (s, 1H), 7.42 (s, 2H), 4.89 (s, 1H), 4.11 (s, 3H), 3.80-3.70 (s, 1H), 3.10-3.00 (m, 2H), 2.82-2.80 (t, 2H), 2.57 (s, 3H), 2.05-1.95 (m, 2H), 1.77-1.75 (m, 2H). LCMS: 100%, m/z=432.1 (M+1)$^+$. HPLC: 95.10%.

Example 68

N-(6-(3-hydroxypiperidin-1-yl)-2-methyl-2H-indazol-5-yl)-2-(2-methylpyridin-4-yl)oxazole-4-carboxamide

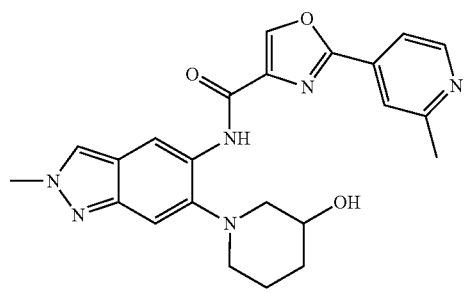

Step-1: Synthesis of 2-fluoro-4-(3-hydroxypiperidin-1-yl)-5-nitrobenzaldehyde

Using the similar reagents and conditions as described in step 1 of example 58, 2,4-difluoro-5-nitrobenzaldehyde (2.5 gm, 13.3 mmol) was substituted with piperidin-3-ol hydrochloride (2.02 gm, 14.7 mmol) using potassium carbonate (2.76 gm, 20.0 mmol) in DMF (10 mL) at 0° C. for 0.5 h to get the crude compound. The obtained crude was purified by 60-120 silica gel column chromatography and compound eluted using 10% ethyl acetate in hexane to give title compound (2.5 gm, 69.8%). LCMS: m/z=269.2 (M+1)$^+$.

Step-2: Synthesis of 4-(3-((tert-butyldimethylsilyl)oxy)piperidin-1-yl)-2-fluoro-5-nitrobenzaldehyde Using the similar reagents and conditions as described in step 2 of example 58, 2-fluoro-4-(3-hydroxypiperidin-1-yl)-5-nitrobenzaldehyde (2.5 gm, 9.32 mmol) was protected using TBDMS chloride (1.67 gm, 11.9 mmol), imidazole (1.58 mg, 23.3 mmol) and DMAP (1.258 gm, 10.2 mmol) in DMF (10 mL) at RT for 0.5 h to obtain the title compound (2.5 gm, 70.2%). LCMS: m/z=383.1 (M+1)$^+$ Step-3: Synthesis of 1-(5-nitro-1H-indazol-6-yl)azetidin-3-ol Using the similar reagents and conditions as described in step 2 of example 5, 6-(3-((tert-butyldimethylsilyl)oxy)piperidin-1-yl)-5-nitro-1H-indazole (2.5 gm, 6.54 mmol) was cyclized using hydrazine hydrate (654 mg, 13.0 mmol) in THF (10 mL) at 60° C. for 1 h to obtain the title compound (1.5 gm, 60%). LCMS: m/z=377.2 (M+1)⁺

Step-4: Synthesis of 6-(3-((tert-butyldimethylsilyl) oxy)piperidin-1-yl)-1-methyl-5-nitro-1H-indazole and 6-(3-((tert-butyldimethylsilyl)oxy)piperidin-1-yl)-2-methyl-5-nitro-2H-indazole Using the same reagents and conditions as described in step 5 of example 1, 6-(3-((tert-butyldimethylsilyl)oxy)azetidin-1-yl)-5-nitro-1H-indazole (1.5 gm, 5.84 mmol) was methylated using sodium hydride (193 mg, 8.07 mmol) and methyl iodide (2.23 mL), 15.7 mmol) in THF (20 mL) at RT for 0.5 h to get the crude product. This was purified by silica gel column chromatography and elution with 50% ethyl acetate in hexane gave 6-(3-((tert-butyldimethylsilyl)oxy) piperidin-1-yl)-1-methyl-5-nitro-1H-indazole (600 mg) and further elution gave 6-(3-((tert-butyldimethylsilyl)oxy)piperidin-1-yl)-2-methyl-5-nitro-2H-indazole (800 mg, 93.3%). LCMS: m/z=391.5 (M+1)⁺

Step-5: Synthesis of 6-(3-((tert-butyldimethylsilyl) oxy)piperidin-1-yl)-2-methyl-2H-indazol-5-amine Using the same reaction conditions as described in step 2 of example 16, 6-(3-((tert-butyldimethylsilyl)oxy)piperidin-1-yl)-2-methyl-5-nitro-2H-indazole (300 mg, 0.742 mmol) was reduced with zinc dust (386 mg, 5.94 mmol) and ammonium chloride (320 mg, 5.94 mmol) in THF/water (10/2 mL) to get the title compound (250 mg, 96.1%). LCMS: m/z=361.1 (M+1)⁺

Step-6: Synthesis of N-(6-(3-((tert-butyldimethylsilyl)oxy)piperidin-1-yl)-2-methyl-2H-indazol-5-yl)-2-(2-methylpyridin-4-yl)oxazole-4-carboxamide Using the same reaction conditions as described in step 7 of example 1, 6-(3-((tert-butyldimethylsilyl)oxy)piperidin-1-yl)-2-methyl-2H-indazol-5-amine (150 mg, 0.416 mmol) was coupled with 2-(2-methylpyridin-4-yl)oxazole-4-carboxylic acid (101 mg, 0.499 mmol) using HATU (237 mg, 0.624 mmol) and DIPEA (214 mg, 1.66 mmol) in DMF (8 mL) to get the desired compound (130 mg, 57.2%).

Step-7: Synthesis of N-(6-(3-hydroxypiperidin-1-yl)-2-methyl-2H-indazol-5-yl)-2-(2-methylpyridin-4-yl)oxazole-4-carboxamide Using the same reagents and conditions as described in step 7 of example 58, N-(6-(3-((tert-butyldimethylsilyl)oxy) piperidin-1-yl)-2-methyl-2H-indazol-5-yl)-2-(2-methylpyridin-4-yl)oxazole-4-carboxamide (130 mg, mmol) was deprotected using 0.1M TBAF in THF (1/8 mL) at RT for 0.5 h to get the title compound (70 mg, 58%).
¹HNMR (400 MHz, DMSO-d₆): δ 10.35 (s, 1H), 9.06 (s, 1H), 8.73-8.72 (d, 1H), 8.62 (s, 1H), 8.28 (s, 1H), 7.88 (s, 1H), 7.77-7.76 (d, 1H), 7.40 (s, 1H), 4.93-4.92 (d, 1H), 4.12 (s, 3H), 4.03-4.12 (m, 1H), 3.13-3.11 (m, 1H), 2.89 (s, 1H), 2.70-2.61 (m, 4H), 2.08 (s, 1H), 2.00-1.90 (m, 2H), 1.4 (s, 1H). LCMS: 95.82%, m/z=433.2 (M+1)⁺. HPLC: 96.80%.

Example 69

(R)—N-(6-(3-hydroxypiperidin-1-yl)-2-methyl-2H-indazol-5-yl)-5-(2-methylpyridin-4-yl)furan-2-carboxamide

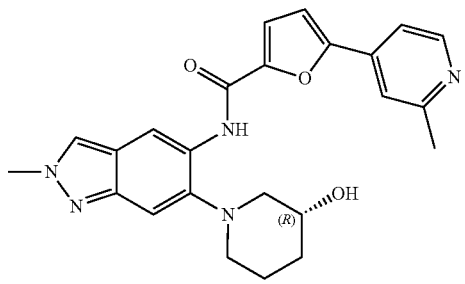

Step-1: Synthesis of (R)-2-fluoro-4-(3-hydroxypiperidin-1-yl)-5-nitrobenzaldehyde Using the similar reagents and conditions as described in step 1 of example 58, 2,4-difluoro-5-nitrobenzaldehyde (4 gm, 21.3 mmol) was substituted with (R)-piperidin-3-ol hydrochloride (3.23 gm, 23.5 mmol) using potassium carbonate (4.42 gm, 32.0 mmol) in DMF (10 mL) at 0° C. for 0.5 h to get the crude compound. The obtained crude was purified by 60-120 silica gel column chromatography and compound eluted using 10% ethyl acetate in hexane to give title compound (4 gm, 70%). LCMS: m/z=269.2 (M+1)⁺.

Step-2: Synthesis of (R)-4-(3-((tert-butyldimethylsilyl)oxy)piperidin-1-yl)-2-fluoro-5-nitrobenzaldehyde Using the similar reagents and conditions as described in step 2 of example 58, (R)-2-fluoro-4-(3-hydroxypiperidin-1-yl)-5-nitrobenzaldehyde (2.5 gm, 9.32 mmol) was protected using TBDMS chloride (1.67 gm, 11.9 mmol), imidazole (1.58 mg, 23.3 mmol) and DMAP (1.258 gm, 10.2 mmol) in DMF (10 mL) at RT for 0.5 h to obtain the title compound (2.5 gm, 70.2%). LCMS: m/z=383.1 (M+1)⁺.

Step-3: Synthesis of (R)-6-(3-((tert-butyldimethylsilyl)oxy)piperidin-1-yl)-5-nitro-1H-indazole Using the similar reagents and conditions as described in step 2 of example 5, (R)-6-(3-((tert-butyldimethylsilyl)oxy) piperidin-1-yl)-5-nitro-1H-indazole (2.5 gm, 6.54 mmol) was cyclized using hydrazine hydrate (654 mg, 13.0 mmol) in THF (10 mL) at 60° C. for 1 h to obtain the title compound (1.5 gm, 60%). LCMS: m/z=377.1 (M+1)⁺.

Step-4: Synthesis of (R)-6-(3-((tert-butyldimethylsilyl)oxy)piperidin-1-yl)-1-methyl-5-nitro-1H-indazole and (R)-6-(3-((tert-butyldimethylsilyl)oxy)piperidin-1-yl)-2-methyl-5-nitro-2H-indazole Using the same reagents and conditions as described in step 5 of example 1, (R)-6-(3-((tert-butyldimethylsilyl)oxy) piperidin-1-yl)-5-nitro-1H-indazole (1.5 gm, 3.84 mmol) was methylated using sodium hydride (193 mg, 8.07 mmol) and methyl iodide (2.23 mL, 15.7 mmol) in THF (20 mL) at RT for 0.5 h to get the crude product. This was purified by silica gel column chromatography and elution with 50% ethyl acetate in hexane gave (R)-6-(3-((tert-butyldimethylsilyl)oxy)piperidin-1-yl)-1-methyl-5-nitro-1H-indazole (600 mg) and further elution gave (R)-6-(3-((tert-butyldimethylsilyl)oxy)piperidin-1-yl)-2-methyl-5-nitro-2H-indazole (800 mg, 93.3%). LCMS: m/z=391.4 (M+1)+.

Step-5: Synthesis of (R)-6-(3-((tert-butyldimethylsilyl)oxy)piperidin-1-yl)-2-methyl-2H-indazol-5-amine Using the same reaction conditions as described in step 2 of example 16, (R)-6-(3-((tert-butyldimethylsilyl)oxy)piperidin-1-yl)-2-methyl-5-nitro-2H-indazole (300 mg, 0.742 mmol) was reduced with zinc dust (386 mg, 5.94 mmol) and ammonium chloride (320 mg, 5.94 mmol) in THF/water (10/2 mL) to get the desired product (250 mg, 96.1%). LCMS: m/z=361.1 (M+1)+.

Step-6: Synthesis of (R)—N-(6-(3-((tert-butyldimethylsilyl)oxy)piperidin-1-yl)-2-methyl-2H-indazol-5-yl)-5-(2-methylpyridin-4-yl)furan-2-carboxamide Using the same reaction conditions as described in step 7 of example 1, (R)-6-(3-((tert-butyldimethylsilyl)oxy)piperidin-1-yl)-2-methyl-2H-indazol-5-amine (150 mg, 0.416 mmol) was coupled with 5-(2-methylpyridin-4-yl)furan-2-carboxylic acid (intermediate 12) (93 mg, 0.457 mmol) using HATU (237 mg, 0.624 mmol) and DIPEA (214 mg, 1.66 mmol) in DMF (8 mL) to get the desired compound (120 mg, 54.5%). LCMS: m/z=546.3 (M+1)+.

Step-7: Synthesis of (R)—N-(6-(3-hydroxypiperidin-1-yl)-2-methyl-2H-indazol-5-yl)-5-(2-methylpyridin-4-yl)furan-2-carboxamide Using the same reagents and conditions as described in step 7 of example 58, (R)—N-(6-(3-((tert-butyldimethylsilyl)oxy)piperidin-1-yl)-2-methyl-2H-indazol-5-yl)-2-(2-methylpyridin-4-yl)oxazole-4-carboxamide (120 mg, 0.278 mmol) was deprotected using 0.1M TBAF in THF (1/8 mL) at RT for 2 h to get the title compound (50 mg, 58.5%).
$^1$HNMR (400 MHz, DMSO-$d_6$): δ 9.93 (s, 1H), 8.57-8.55 (m, 2H), 8.32-8.28 (d, 1H), 7.79 (s, 1H), 7.70-7.69 (d, 1H), 7.49-7.41 (m, 3H), 4.99 (s, 1H), 4.12 (s, 3H), 3.92 (s, 1H), 3.08-3.05 (d, 1H), 2.87 (s, 1H), 2.76 (s, 1H), 2.67 (s, 1H), 2.56 (s, 3H), 1.89 (s, 1H), 1.73 (s, 1H), 1.49 (s, 1H). LCMS: 95.77%, m/z=432.2 (M+1)+. HPLC: 94.28%.

Example 70

N-(6-(3-hydroxypiperidin-1-yl)-2-methyl-2H-indazol-5-yl)-5-(2-methylpyridin-4-yl)furan-2-carboxamide

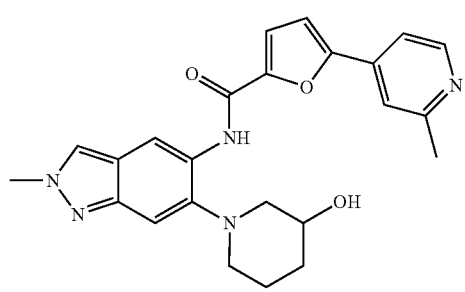 [SMILES: Cc1cc(-c2ccc(C(=O)Nc3cc4cn(C)nc4cc3N3CCCC(O)C3)o2)ccn1]

Step-1: Synthesis of N-(6-(3-((tert-butyldimethylsilyl)oxy)piperidin-1-yl)-2-methyl-2H-indazol-5-yl)-5-(2-methylpyridin-4-yl)furan-2-carboxamide Using the same reaction conditions as described in step 7 of example 1, 6-(3-((tert-butyldimethylsilyl)oxy)piperidin-1-yl)-2-methyl-2H-indazol-5-amine (product of step 5 of example 68) (150 mg, 0.416 mmol) was coupled with 5-(2-methylpyridin-4-yl)furan-2-carboxylic acid (intermediate 12) (93 mg, 0.437 mmol) using HATU (237 mg, 0.624 mmol) and DIPEA (214 mg, 1.66 mmol) in DMF (8 mL) to get the desired compound (125 mg, 56.8%). LCMS: m/z=546.2 (M+1)+.

Step-2: Synthesis of N-(6-(3-hydroxypiperidin-1-yl)-2-methyl-2H-indazol-5-yl)-5-(2-methylpyridin-4-yl)furan-2-carboxamide Using the same reagents and conditions as described in step 7 of example 58, N-(6-(3-((tert-butyldimethylsilyl)oxy)piperidin-1-yl)-2-methyl-2H-indazol-5-yl)-5-(2-methylpyridin-4-yl)furan-2-carboxamide (130 mg, 0.296 mmol) was deprotected using 0.1M TBAF in THF (1/8 mL) at RT for 0.5 h to get the title compound (40 mg, 40%).
$^1$HNMR (DMSO-$d_6$, 400 MHz): δ 9.93 (s, 1H), 8.57-8.55 (m, 2H), 8.28 (s, 1H), 7.79 (s, 1H), 7.70-7.69 (d, 1H), 7.49-7.41 (m, 3H), 5.00-4.99 (d, 1H), 4.12 (s, 3H), 3.92 (s, 1H), 3.07-3.05 (d, 1H), 2.88 (s, 1H), 2.76-2.67 (m, 2H), 2.56 (s, 3H), 1.99-1.90 (d, 2H), 1.74-1.72 (d, 1H), 1.47 (, s H1). LCMS: 97.31%, m/z=432.2 (M+1)+. HPLC: 95.57%.

Example 71

N-(6-(azepan-1-yl)-2-methyl-2H-indazol-5-yl)-2-(2-methylpyridin-4-yl)oxazole-4-carboxamide

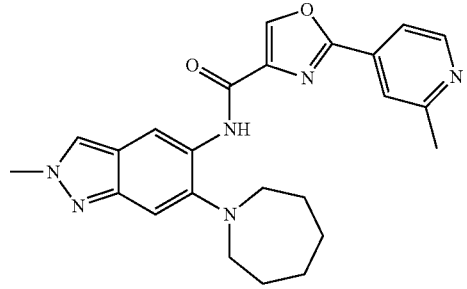 [SMILES: Cc1cc(-c2nc(C(=O)Nc3cc4cn(C)nc4cc3N3CCCCCC3)co2)ccn1]

Step-1: Synthesis of 4-(azepan-1-yl)-2-fluoro-5-nitrobenzaldehyde

Using the similar reagents and conditions as described in step 1 of example 58, 2,4-difluoro-5-nitrobenzaldehyde (2 gm, 10.6 mmol) was substituted with azepane (1.27 gm, 12 mmol) using potassium carbonate (3.68 gm, 26.7 mmol) in DMF (20 mL) at RT for 4 h to get the title compound (1.5 gm, 60%). LCMS: m/z=267.1 (M+1)+.

Step-2: Synthesis of 6-(azepan-1-yl)-5-nitro-1H-indazole

Using the similar reagents and conditions as described in step 2 of example 5, 4-(azepan-1-yl)-2-fluoro-5-nitrobenzaldehyde (1.5 gm, 5.7 mmol) was cyclized using hydrazine hydrate (0.57 gm, 11.4 mmol) in THF (20 mL) at 75° C. for 2 h to obtain the crude title compound. The obtained crude was purified by 60-120 silica gel column chromatography and compound eluted using ethyl acetate in hexane to give title compound (1 gm, 60%). LCMS: m/z=261.3 (M+1)+.

Step-3: Synthesis of 6-(azepan-1-yl)-1-methyl-5-nitro-1H-indazole 6-(azepan-1-yl)-2-methyl-5-nitro-2H-indazole Using the same reagents and conditions as described in step 5 of example 1, 6-(azepan-1-yl)-5-nitro-1H-indazole (1 gm, 3.89 mmol) was methylated using sodium hydride (372 mg, 7.78 mmol) and methyl iodide (0.5 mL, 7.7 mmol) in THF (20 mL) at RT for 0.5 h to get the crude product. This was purified by silica gel column chromatography and eluted with ethyl acetate in hexane gave 6-(azepan-1-yl)-1-methyl-5-nitro-1H-indazole (500 mg, 50%) and further elution gave 6-(azepan-1-yl)-2-methyl-5-nitro-2H-indazole (300 mg, 30%). LCMS: m/z=275.1 (M+1)+.

Step-4: Synthesis of 6-(azepan-1-yl)-2-methyl-2H-indazol-5-amine

Using the same reaction conditions as described in step 2 of example 16, 6-(azepan-1-yl)-2-methyl-5-nitro-2H-indazole (300 mg, 1.107 mmol) was reduced with zinc dust (575 mg, 8.856 mmol) and ammonium chloride (478 mg, 8.856 mmol) in THF/water (10/2 mL) to get the desired product (200 mg, 60%). LCMS: m/z=245.1 (M+1)+.

Step-5: Synthesis of N-(6-(azepan-1-yl)-2-methyl-2H-indazol-5-yl)-2-(2-methylpyridin-4-yl)oxazole-4-carboxamide Using the similar reagents and conditions as described in step 7 of example 1, 6-(azepan-1-yl)-2-methyl-2H-indazol-5-amine (120 mg, 0.4918 mmol) was coupled with 2-(2-methylpyridin-4-yl)oxazole-4-carboxylic acid (120 mg, 0.590 mmol) using HATU (280 mg, 0.737 mmol), DIPEA (0.4 mL, 1.9672 mmol) in DMF (5 mL) to get the desired compound (150 mg, 71%).
$^1$HNMR (CDCl$_3$, 400 MHz): δ 8.80 (s, 1H), 8.68-8.67 (d, 1H), 8.40 (s, 1H), 7.85-7.83 (d, 2H), 7.73-7.72 (d, 1H), 7.47 (s, 1H), 4.18 (s, 3H), 3.15 (s, 4H), 2.67 (s, 3H), 1.97 (s, 8H). LCMS: 100%, m/z=431.2 (M+1)+. HPLC: 98.46%.

Example 72

N-(6-(azepan-1-yl)-1-methyl-1H-indazol-5-yl)-2-(2-methylpyridin-4-yl)oxazole-4-carboxamide

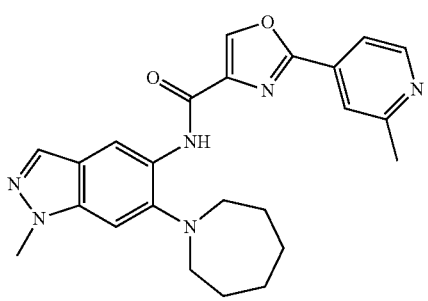 [SMILES: Cc1cc(-c2nc(C(=O)Nc3cc4cnn(C)c4cc3N3CCCCCC3)co2)ccn1]

Step-1: Synthesis of 6-(azepan-1-yl)-1-methyl-1H-indazol-5-amine

Using the same reaction conditions as described in step 2 of example 16, 6-(azepan-1-yl)-1-methyl-5-nitro-2H-indazole (product of step 3 of example 71) (500 mg, 2.214 mmol) was reduced with zinc dust (1.151 gm, 1.771 mmol) and ammonium chloride (956 mg, 1.771 mmol) in THF/water (10/2 mL) to get the desired product (300 mg, 60%). LCMS: m/z=245.1 (M+1)+.

Step-2: Synthesis of N-(6-(azepan-1-yl)-1-methyl-1H-indazol-5-yl)-2-(2-methylpyridin-4-yl)oxazole-4-carboxamide Using the similar reagents and conditions as described in step 7 of example 1, 6-(azepan-1-yl)-1-methyl-2H-indazol-5-amine (120 mg, 0.4918 mmol) was coupled with 2-(2-methylpyridin-4-yl)oxazole-4-carboxylic acid (120 mg, 0.590 mmol) using HATU (280 mg, 0.737 mmol), DIPEA (0.4 mL, 1.9672 mmol) in DMF (5 mL) to get the desired compound (150 mg, 72%).
$^1$HNMR (CDCl$_3$, 400 MHz): δ 8.90 (s, 1H), 8.69-8.67 (d, 1H), 8.42 (s, 1H), 7.93 (s, 1H), 7.84 (s, 1H), 7.74-7.72 (d, 1H), 7.19 (s, 1H), 4.04 (s, 3H), 3.17 (s, 4H), 2.67 (s, 3H), 1.98 (s, 8H). LCMS: 100%, m/z=431.1 (M+1)+. HPLC: 97.88%.

Example 73

N-(2,3-dimethyl-6-(piperidin-1-yl)-2H-indazol-5-yl)-2-(2-methylpyridin-4-yl)oxazole-4-carboxamide

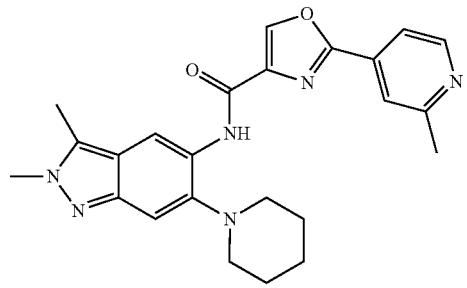 [SMILES: Cc1cc(-c2nc(C(=O)Nc3cc4c(C)n(C)nc4cc3N3CCCCC3)co2)ccn1]

Step-1: Synthesis of 6-fluoro-3-methyl-1H-indazole

Using the similar reagents and conditions as described in step 2 of example 5, 1-(2,4-difluorophenyl)ethan-1-one (2 gm, 12.8098 mmol) was cyclized using hydrazine hydrate (1.28 gm, 25.6196 mmol) in DMF (10 mL) at 120° C. for 14 h to obtain the crude product. This was purified by silica gel column chromatography and with 30% ethyl acetate in hexane to get the titled product (1.6 gm, 83.20%). LCMS: m/z=151.2 (M+1)+.

Step-2: Synthesis of 6-fluoro-3-methyl-5-nitro-1H-indazole

Using the similar reagents and conditions as described in step 1 of example 5, 6-fluoro-3-methyl-1H-indazole (1.6 gm, 10.6 mmol) was nitrated using KNO$_3$ (1.292 gm, 12.7 mmol) and sulphuric acid (20 mL) at RT for 2 h to get the title impure compound (650 mg) which was used as such for next step.

Step-3: Synthesis of 3-methyl-5-nitro-6-(piperidin-1-yl)-1H-indazole

Using the similar reagents and conditions as described in step 3 of example 1, 6-fluoro-3-methyl-5-nitro-1H-indazole (1 gm, 5.1242 mmol) was substituted using piperidine (10 mL) at 100° C. for 2 h to get the crude compound. This compound was purified by column chromatography, eluting with a gradient (80% ethyl acetate in hexane) to give the title compound (650 mg, 48.87%). LCMS: m/z=261.2 (M+1)$^+$.

Step-4: Synthesis of 1,3-dimethyl-5-nitro-6-(piperidin-1-yl)-1H-indazole and 2,3-dimethyl-5-nitro-6-(piperidin-1-yl)-2H-indazole Using the same reagents and conditions as described in step 5 of example 1, 3-methyl-5-nitro-6-(piperidin-1-yl)-1H-indazole (650 mg, 2.5 mmol) was methylated using sodium hydride (200 mg, 5 mmol) and methyl iodide (0.313 mL, 5 mmol) in THF (20 mL) at RT for 2 h to get the crude product. This was purified by silica gel column chromatography and elution with 25% ethyl acetate in hexane gave 1,3-dimethyl-5-nitro-6-(piperidin-1-yl)-1H-indazole (330 mg, 48.17%) and further elution with 80% ethyl acetate in hexane gave 2,3-dimethyl-5-nitro-6-(piperidin-1-yl)-2H-indazole (190 mg, 27.73%). LCMS: m/z=275.3 (M+1)$^+$.

Step-5: Synthesis of 2,3-dimethyl-6-(piperidin-1-yl)-2H-indazol-5-amine

Using the same reaction conditions as described in step 2 of example 16, 2,3-dimethyl-5-nitro-6-(piperidin-1-yl)-2H-indazole (190 mg, 0.6934 mmol) was reduced with zinc dust (363 mg, 5.5474 mmol) and ammonium chloride (594 mg, 11.0948 mmol) in THF/water (20/5 mL) to get the desired product (168 mg, 99.40%). LCMS: m/z=245.3 (M+1)$^+$.

Step-6: Synthesis of N-(2,3-dimethyl-6-(piperidin-1-yl)-2H-indazol-5-yl)-2-(2-methylpyridin-4-yl)oxazole-4-carboxamide Using the similar reagents and conditions as described in step 7 of example 1, 2,3-dimethyl-6-(piperidin-1-yl)-2H-indazol-5-amine (90 mg, 0.3688 mmol) was coupled with 2-(2-methylpyridin-4-yl)oxazole-4-carboxylic acid (90 mg, 0.4426 mmol) using HATU (182 mg, 0.4795 mmol) and DIPEA (0.257 mL, 1.4754 mmol) in DMF (5 mL) to get the title compound (70 mg, 43.3%).

$^1$HNMR (300 MHz, CDCl$_3$): δ 8.70-8.68 (d, 1H), 8.65 (s, 1H), 8.38 (s, 1H), 7.84 (s, 1H), 7.74-7.72 (s, 1H), 7.34 (s, 1H), 4.06 (s, 3H), 2.98 (s, 4H), 2.67 (s, 3H), 2.59 (s, 3H), 1.95 (s, 6H). LCMS: 100%, m/z=431.4 (M+1)$^+$. HPLC: 97.95%.

Example 74

N-(1,3-dimethyl-6-(piperidin-1-yl)-1H-indazol-5-yl)-2-(2-methylpyridin-4-yl)oxazole-4-carboxamide

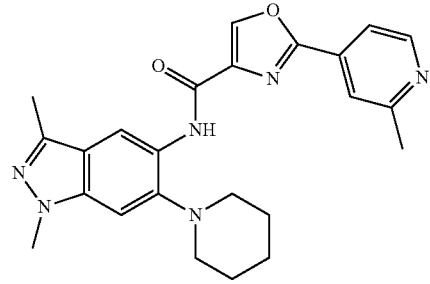 [SMILES: Cc1cc(-c2nc(C(=O)Nc3cc4c(C)nn(C)c4cc3N3CCCCC3)co2)ccn1]

Step-1: Synthesis of 1,3-dimethyl-6-(piperidin-1-yl)-1H-indazol-5-amine

Using the same reaction conditions as described in step 2 of example 16, 2,3-dimethyl-5-nitro-6-(piperidin-1-yl)-2H-indazole (product of step 4 of example 73) (330 mg, 1.2043 mmol) was reduced with zinc dust (630 mg, 9.635 mmol) and ammonium chloride (1.03 gm, 19.27 mmol) in THF/water (20/5 mL) to get the desired product (260 mg, 88.43%). LCMS: m/z=245.3 (M+1)$^+$.

Step-2: Synthesis of N-(1,3-dimethyl-6-(piperidin-1-yl)-1H-indazol-5-yl)-2-(2-methylpyridin-4-yl)oxazole-4-carboxamide Using the similar reagents and conditions as described in step 7 of example 1, 1,3-dimethyl-6-(piperidin-1-yl)-1H-indazol-5-amine (130 mg, 0.5327 mmol) was coupled with 2-(2-methylpyridin-4-yl)oxazole-4-carboxylic acid (130 mg, 0.6393 mmol) using HATU (263 mg, 0.6926 mmol) and DIPEA (0.371 mL, 2.1311 mmol) in DMF (2 mL) to get title compound (95 mg, 41.40%).

$^1$HNMR (CDCl$_3$, 300 MHz): δ 10.35 (s, 1H), 8.77 (s, 1H), 8.70-8.69 (d, 1H), 8.39 (s, 1H), 7.84 (s, 1H), 7.74-7.73 (d, 1H), 7.06 (s, 1H), 3.97 (s, 3H), 2.98 (s, 4H), 2.68 (s, 3H), 2.56 (s, 3H), 1.98-1.96 (t, 4H), 1.74 (s, 2H). LCMS: 95.42%, m/z=431.4 (M+1)$^+$. HPLC: 95.97%.

Example 75

N-(6-(4-hydroxypiperidin-1-yl)-1-(2-methoxyethyl)-1H-indazol-5-yl)-2-(2-methylpyridin-4-yl)oxazole-4-carboxamide

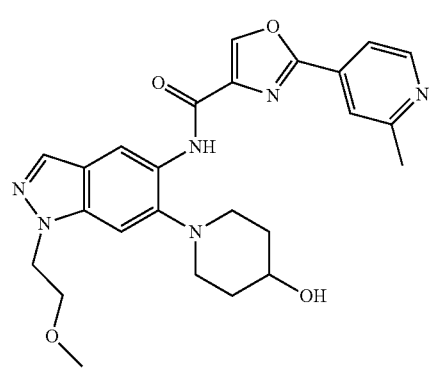 [SMILES: COCCn1ncc2cc(NC(=O)c3coc(-c4ccnc(C)c4)n3)c(N3CCC(O)CC3)cc21]

Step-1: Synthesis of 6-(4-((tert-butyldimethylsilyl)oxy)piperidin-1-yl)-1-(2-methoxyethyl)-5-nitro-1H-indazole and 6-(4-((tert-butyldimethylsilyl)oxy)piperidin-1-yl)-2-(2-methoxyethyl)-5-nitro-2H-indazole Using the same reagents and conditions as described in step 5 of example 1, 6-(4-((tert-butyldimethylsilyl)oxy)piperidin-1-yl)-5-nitro-1H-indazole (product of step 3 of example 58) (600 mg, 1.594 mmol) was alkylated using sodium hydride (58 mg, 2.393 mmol) and 1-bromo-2-methoxyethane (554 mg, 3.989 mmol) in THF (20 mL) at RT for 14 h to get the crude product. This was purified by silica gel column chromatography and elution with ethyl acetate in hexane gave the title compound 6-(4-((tert-butyldimethylsilyl)oxy)piperidin-1-yl)-1-(2-methoxyethyl)-5-nitro-1H-indazole and further elution with ethyl acetate in hexane gave the 6-(4-((tert-butyldimethylsilyl)oxy)piperidin-1-yl)-2-(2-methoxyethyl)-5-nitro-2H-indazole (450 mg, 69.23%). LCMS: m/z=435.4 (M+1)$^+$.

Step-2: Synthesis of 6-(4-((tert-butyldimethylsilyl)oxy)piperidin-1-yl)-1-(2-methoxyethyl)-1H-indazol-5-amine Using the same reaction conditions as described in step 2 of example 16, 6-(4-((tert-butyldimethylsilyl)oxy)piperidin-1-yl)-1-(2-methoxyethyl)-5-nitro-1H-indazole (270 mg, 0.622 mmol) was reduced with zinc dust (325 mg, 0.497 mmol) and ammonium chloride (532 mg, 9.953 mmol) in THF/water (10/2 mL) to get the desired crude product (230 mg). LCMS: m/z=405.2 (M+1)$^+$.

Step-3: Synthesis of N-(6-(4-((tert-butyldimethylsilyl)oxy)piperidin-1-yl)-1-(2-methoxyethyl)-1H-indazol-5-yl)-2-(2-methylpyridin-4-yl)oxazole-4-carboxamide Using the similar reagents and conditions as described in step 6 of example 5, 6-(4-((tert-butyldimethylsilyl)oxy)piperidin-1-yl)-1-(2-methoxyethyl)-1H-indazol-5-amine (230 mg, 0.569 mmol) was coupled with 2-(2-methylpyridin-4-yl)oxazole-4-carboxylic acid (174 mg, 0.8539 mmol) using HATU (281 mg, 0.74 mmol) and DIPEA (294 mg, 2.277 mmol) in DMF (5 mL) to get the desired compound (210 mg, 63.36%).

Step-4: Synthesis of N-(6-(4-hydroxypiperidin-1-yl)-1-(2-methoxyethyl)-1H-indazol-5-yl)-2-(2-methylpyridin-4-yl)oxazole-4-carboxamide Using the same reagents and conditions as described in step 7 of example 58, N-(6-(4-((tert-butyldimethylsilyl)oxy)piperidin-1-yl)-1-(2-methoxyethyl)-1H-indazol-5-yl)-2-(2-methylpyridin-4-yl)oxazole-4-carboxamide (210 mg, 0.3559 mmol) was deprotected using TBAF (140 mg, 0.533 mmol) in THF (5 mL) at RT for 0.5 h to get the title compound (90 mg, 53.25%).

$^1$HNMR (400 MHz, DMSO-d$_6$): δ 10.35 (s, 1H), 9.06 (s, 1H), 8.7 (s, 1H), 8.68 (s, 1H), 8.03 (s, 1H), 7.91 (s, 1H), 7.81-7.80 (d, 1H), 7.60 (s, 1H), 4.98 (s, 1H), 4.5 (s, 2H), 3.78-3.75 (m, 3H), 3.20 (s, 3H), 3.07-3.05 (m, 2H), 2.88-2.83 (t, 2H), 2.67 (s, 3H), 2.05 (s, 2H), 1.93-1.90 (d, 2H). LCMS: 98.72%, m/z=477.4 (M+1)$^+$. HPLC: 98.31%.

Example 76

N-(6-(4-hydroxypiperidin-1-yl)-2-(2-methoxyethyl)-2H-indazol-5-yl)-2-(2-methylpyridin-4-yl)oxazole-4-carboxamide

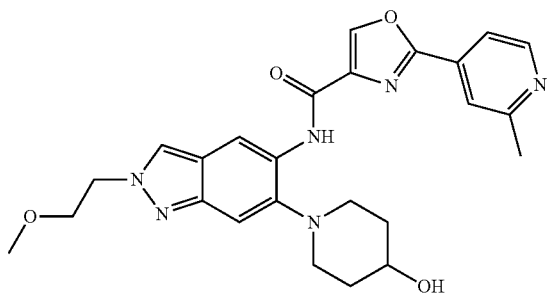 [SMILES: COCCn1cc2cc(NC(=O)c3coc(-c4ccnc(C)c4)n3)c(N3CCC(O)CC3)cc2n1]

Step-1: Synthesis of 6-(4-((tert-butyldimethylsilyl)oxy)piperidin-1-yl)-2-(2-methoxyethyl)-2H-indazol-5-amine Using the same reaction conditions as described in step 2 of example 16, 6-(4-((tert-butyldimethylsilyl)oxy)piperidin-1-yl)-2-(2-methoxyethyl)-5-nitro-2H-indazole (product of step 1 of example 75) (180 mg, 0.4147 mmol) was reduced with zinc dust (217 mg, 3.317 mmol) and ammonium chloride (354 mg, 6.635 mmol) in THF/water (10/2 mL) to get the desired crude product (150 mg).

Step-2: Synthesis of N-(6-(4-((tert-butyldimethylsilyl)oxy)piperidin-1-yl)-2-(2-methoxyethyl)-2H-indazol-5-yl)-2-(2-methylpyridin-4-yl)oxazole-4-carboxamide Using the similar reagents and conditions as described in step 6 of example 5, 6-(4-((tert-butyldimethylsilyl)oxy)piperidin-1-yl)-2-(2-methoxyethyl)-2H-indazol-5-amine (150 mg, 0.3712 mmol) was coupled with 2-(2-methylpyridin-4-yl)oxazole-4-carboxylic acid (113 mg, 0.5569 mmol) using HATU (183 mg, 0.4826 mmol) and DIPEA (191 mg, 1.485 mmol) in DMF (5 mL) to get the desired compound (115 mg, 52.38%).

Step-3: Synthesis of N-(6-(4-hydroxypiperidin-1-yl)-2-(2-methoxyethyl)-2H-indazol-5-yl)-2-(2-methylpyridin-4-yl)oxazole-4-carboxamide Using the same reagents and conditions as described in step 7 of example 58, N-(6-(4-((tert-butyldimethylsilyl)oxy)piperidin-1-yl)-2-(2-methoxyethyl)-2H-indazol-5-yl)-2-(2-methylpyridin-4-yl)oxazole-4-carboxamide (115 mg, 0.1949 mmol) was deprotected using TBAF (76 mg, 0.2923 mmol) in THF (5 mL) at RT for 0.5 h to get the title compound (40 mg, 43.47%).

$^1$HNMR (DMSO-d$_6$, 400 MHz): δ 10.44 (s, 1H), 9.05 (s, 1H), 8.69-8.67 (d, 1H), 8.63 (s, 1H), 8.30 (s, 1H), 7.92 (s, 1H), 7.81-7.80 (d, 1H), 7.42 (s, 1H), 5.0 (s, 1H), 4.52-4.51 (t, 2H), 3.81-3.79 (t, 2H), 3.22 (s, 3H), 3.01-3.00 (m, 2H), 2.85-2.83 (t, 2H), 2.61 (s, 3H), 2.03-1.93 (m, 5H). LCMS: 97.46%, m/z=477.4 (M+1)$^+$. HPLC: 95.26%.

Example 77

N-(6-(4-hydroxypiperidin-1-yl)-1-methyl-1H-indazol-5-yl)-2-(2-methylpyridin-4-yl)oxazole-4-carboxamide

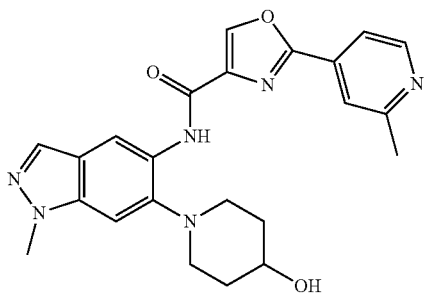 [SMILES: Cc1cc(-c2nc(C(=O)Nc3cc4cnn(C)c4cc3N3CCC(O)CC3)co2)ccn1]

Step-1: Synthesis of 6-(4-((tert-butyldimethylsilyl)oxy)piperidin-1-yl)-1-methyl-1H-indazol-5-amine Using the same reaction conditions as described in step 2 of example 16, 6-(4-((tert-butyldimethylsilyl)oxy)piperidin-1-yl)-1-methyl-5-nitro-1H-indazole (product of step 4 of example 58) (450 mg, 1.25 mmol) was reduced with zinc dust (650 mg, 10 mmol) and ammonium chloride (1.06 gm, 20 mmol) in THF/water (10/2 mL) to get the desired product (357 mg, 73.60 mmol). LCMS: m/z=361.4 (M+1)$^+$.

Step-2: Synthesis of N-(6-(4-((tert-butyldimethylsilyl)oxy)piperidin-1-yl)-1-methyl-1H-indazol-5-yl)-2-(2-methylpyridin-4-yl)oxazole-4-carboxamide Using the similar reagents and conditions as described in step 6 of example 5, 6-(4-((tert-butyldimethylsilyl)oxy)piperidin-1-yl)-1-methyl-1H-indazol-5-amine (400 mg, 1.111 mmol) was coupled with 2-(2-methylpyridin-4-yl)oxazole-4-carboxylic acid (339 mg, 1.66 mmol) using HATU (548 mg, 1.44 mmol) and DIPEA (574 mg, 4.44 mmol) in DMF (10 mL) to get the desired compound (500 mg, 83.33%). LCMS: m/z=547.4 (M+1)$^+$.

Step-3: Synthesis of N-(6-(4-hydroxypiperidin-1-yl)-1-methyl-1H-indazol-5-yl)-2-(2-methylpyridin-4-yl)oxazole-4-carboxamide Using the same reaction conditions as described in step 7 of example 58, N-(6-(4-((tert-butyldimethylsilyl)oxy)piperidin-1-yl)-1-methyl-1H-indazol-5-yl)-2-(2-methylpyridin-4-yl)oxazole-4-carboxamide (500 mg, 0.9 mmol) was deprotected using TBAF/THF (359 mg/5 mL) to get the title compound (210 mg, 53.16%).

$^1$HNMR (400 MHz, DMSO-d$_6$,): δ 10.34 (s, 1H), 9.06 (s, 1H), 8.69 (s, 2H), 8.00-7.79 (m, 3H), 7.56 (s, 1H), 4.98 (s, 1H), 4.01 (s, 3H), 3.80 (s, 1H), 3.08 (s, 2H), 2.86 (s, 2H), 2.60 (s, 3H), 2.05-1.92 (d, 4H). LCMS: 92.81%, m/z=433.3 (M+1)$^+$. HPLC: 95.70%.

Example 78

N-(6-(4-fluoropiperidin-1-yl)-1-methyl-1H-indazol-5-yl)-2-(2-methylpyridin-4-yl)oxazole-4-carboxamide

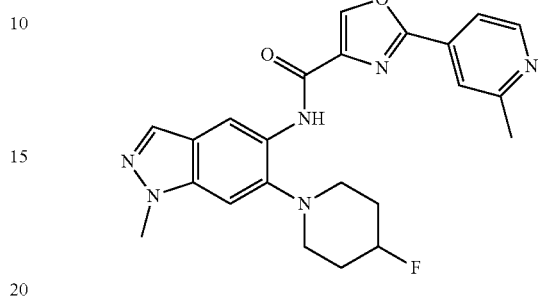

DAST (97 mg, 0.6076 mmol) was added to the cooled (−78° C.) solution of N-(6-(4-hydroxypiperidin-1-yl)-1-methyl-1H-indazol-5-yl)-2-(2-methylpyridin-4-yl)oxazole-4-carboxamide (example 77) (150 mg, 0.3472 mmol) in DCM (0.08 mL). The reaction was quenched with ice water after stirring at −78° C. for 30 min. The compound was extracted with DCM to obtain the title compound (45 mg, 30%).

$^1$HNMR (400 MHz, DMSO-d$_6$,): δ 10.30 (s, 1H), 9.08 (s, 1H), 8.70 (s, 2H), 8.02 (s, 1H), 7.84 (s, 1H), 7.75 (s, 1H), 7.61 (s, 1H), 5.05 (s, 1H), 4.95 (s, 1H), 4.02 (s, 2H), 3.12 (s, 4H), 2.95 (s, 2H), 2.66 (s, 3H), 2.16-2.10 (m, 2H). LCMS: 99.42%, m/z=435.2 (M+1)$^+$. HPLC: 98.84%.

Example 79

N-(6-(3-fluoropiperidin-1-yl)-2-methyl-2H-indazol-5-yl)-2-(2-methylpyridin-4-yl)oxazole-4-carboxamide

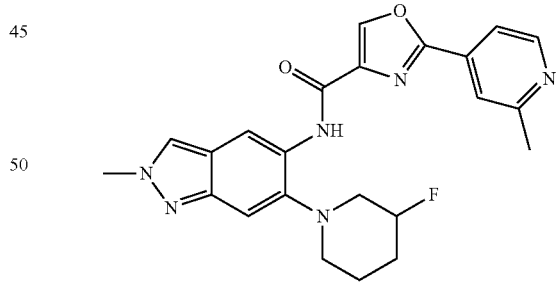

Step-1: Synthesis of 1-(2-methyl-5-nitro-2H-indazol-6-yl)piperidin-3-ol

Using the same reagents and conditions as described in step 7 of example 58, 6-(3-((tert-butyldimethylsilyl)oxy)piperidin-1-yl)-2-methyl-5-nitro-2H-indazole (product of step 4 of example 68) (900 mg, 2.30 mmol) was deprotected using 0.1M TBAF in THF (4/18 mL) at RT for 0.5 h to get the title compound (600 mg, 95.6%). LCMS: m/z=277.3 (M+1)$^+$.

Step 2: Preparation of 6-(3-fluoropiperidin-1-yl)-2-methyl-5-nitro-2H-indazole

Using the same reaction conditions as described in example 78, 1-(2-methyl-5-nitro-2H-indazol-6-yl)piperidin-3-ol (300 mg, 1.08 mmol) was fluorinated using DAST (297 mg, 1.84 mmol) in DCM (8 mL) to obtain the crude product. The obtained crude was purified by 60-120 silica gel column chromatography using 30% ethyl acetate in hexane as eluent to obtain the crude title compound (200 mg). LCMS: m/z=279.3 (M+1)$^+$.

Step-3: Synthesis of 6-(3-fluoropiperidin-1-yl)-2-methyl-2H-indazol-5-amine

Using the same reaction conditions as described in step 2 of example 16, 6-(3-fluoropiperidin-1-yl)-2-methyl-5-nitro-2H-indazole (200 mg, 0.722 mmol) was reduced with zinc dust (375 mg, 5.77 mmol) and ammonium chloride (311 mg, 5.77 mmol) in THF/water (10/4 mL) to get the title crude product (170 mg). LCMS: m/z=249.3 (M+1)$^+$.

Step-4: Synthesis of N-(6-(3-fluoropiperidin-1-yl)-2-methyl-2H-indazol-5-yl)-2-(2-methylpyridin-4-yl)oxazole-4-carboxamide Using the same reagents and conditions as described in step 6 of example 5, 6-(3-fluoropiperidin-1-yl)-2-methyl-2H-indazol-5-amine (170 mg, 0.685 mmol) was coupled with 2-(2-methylpyridin-4-yl)oxazole-4-carboxylic acid (153 mg, 0.754 mmol) using HATU (390 mg, 1.02 mmol) and DIPEA (353 mg, 2.74 mmol) in DMF (8 mL) to obtain crude product. This was purified by prep HPLC to get the title compound (40 mg, 21.45%).

$^1$HNMR (400 MHz, DMSO-d$_6$,): δ 10.40 (s, 1H), 8.72-8.70 (d, 1H), 8.64 (s, 1H), 8.29 (s, 1H), 7.90 (s, 1H), 7.78-7.77 (d, 1H), 7.47 (s, 1H), 5.10-5.00 (d, 1H), 4.12 (s, 3H), 3.10 (s, 2H), 2.90 (s, 1H), 2.90-2.80 (m, 1H), 2.59 (s, 3H), 2.20 (s, 1H), 2.10-2.00 (bs, 2H), 1.80 (s, 1H). 99.04. LCMS: 99.04%, m/z=435.3 (M+1)$^+$. HPLC: 97.96%.

Example 80

N-(6-(4-(hydroxymethyl)piperidin-1-yl)-2-methyl-2H-indazol-5-yl)-2-(2-methylpyridin-4-yl)oxazole-4-carboxamide

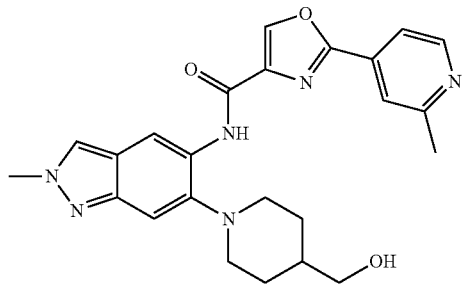 [SMILES: Cc1cc(-c2nc(C(=O)Nc3cc4cn(C)nc4cc3N3CCC(CO)CC3)co2)ccn1]

Step-1: Synthesis of 6-fluoro-1-methyl-5-nitro-1H-indazole and 6-fluoro-2-methyl-5-nitro-2H-indazole Using the same reagents and conditions as described in step 5 of example 1, 6-fluoro-5-nitro-1H-indazole (product of step 3 of example 1) (5.9 gm, 32.5 mmol) was methylated using sodium hydride (2.607 gm, 65.1 mmol) and methyl iodide (9.257 gm, 65.1 mmol) in THF (100 mL) at RT for 2 h to get the crude product. This was purified by silica gel column chromatography and elution with 20% ethyl acetate in hexane gave 6-fluoro-1-methyl-5-nitro-1H-indazole (3.5 gm, 55.02%) and further elution with 80% ethyl acetate in hexane gave 6-fluoro-2-methyl-5-nitro-2H-indazole (2.2 gm, 34.58%). LCMS: m/z=196.2 (M+1)$^+$.

Step-2: Synthesis of (1-(2-methyl-5-nitro-2H-indazol-6-yl)piperidin-4-yl)methanol Using the similar reagents and conditions as described in step 1 of example 58, 6-fluoro-2-methyl-5-nitro-2H-indazole (200 mg, 1.0248 mmol) was substituted with piperidin-4-methanol (177 mg, 1.5372 mmol) using potassium carbonate (425 mg, 3.0745 mmol) in DMF (2 mL) at 120° C. for 24 h to get the title compound (200 mg, 67.34%). LCMS: m/z=291.1 (M+1)$^+$.

Step-3: Synthesis of 6-(4-(((tert-butyldimethylsilyl)oxy)methyl)piperidin-1-yl)-2-methyl-5-nitro-2H-indazole Using the similar reagents and conditions as described in step 2 of example 58, (1-(2-methyl-5-nitro-2H-indazol-6-yl)piperidin-4-yl)methanol (200 mg, 0.68 mmol) was protected using TBDMS chloride (156 mg, 1.0332 mmol), imidazole (18 mg, 1.722 mmol) and DMAP (169 mg, 1.3776 mmol) in DMF (5 mL) at RT for 1 h to obtain the crude product. This was purified by silica gel column chromatography and elution with 40% ethyl acetate in hexane gave the title compound (202 mg, 72.66%). LCMS: m/z=405.2 (M+1)$^+$.

Step-4: Synthesis of 6-(4-(((tert-butyldimethylsilyl)oxy)methyl)piperidin-1-yl)-2-methyl-2H-indazol-5-amine Using the same reaction conditions as described in step 2 of example 16, 6-(4-(((tert-butyldimethylsilyl)oxy)methyl)piperidin-1-yl)-2-methyl-5-nitro-2H-indazole (202 mg, 0.5 mmol) was reduced with zinc dust (262 mg, 4 mmol) and ammonium chloride (428 mg, 8 mmol) in THF/water (10/2 mL) to get the desired product (170 mg, 90.90%). LCMS: m/z=375.4 (M+1)$^+$.

Step-5: Synthesis of N-(6-(4-(((tert-butyldimethylsilyl)oxy)methyl)piperidin-1-yl)-2-methyl-2H-indazol-5-yl)-2-(2-methylpyridin-4-yl)oxazole-4-carboxamide Using the similar reagents and conditions as described in step 6 of example 5, 6-(4-(((tert-butyldimethylsilyl)oxy)methyl)piperidin-1-yl)-2-methyl-2H-indazol-5-amine (170 mg, 0.4545 mmol) was coupled with 2-(2-methylpyridin-4-yl)oxazole-4-carboxylic acid (112 mg, 0.5454 mmol) using HATU (225 mg, 0.5909 mmol) and DIPEA (0.317 mL, 1.8181 mmol) in DMF (2 mL) to get the desired compound (150 mg, 59.05%). LCMS: m/z=561.3 (M+1)$^+$.

Step-6: Synthesis of N-(6-(4-(hydroxymethyl)piperidin-1-yl)-2-methyl-2H-indazol-5-yl)-2-(2-methylpyridin-4-yl)oxazole-4-carboxamide Using the same reaction conditions as described in step 8 of example 1, N-(6-(4-(((tert-butyldimethylsilyl)oxy)

methyl)piperidin-1-yl)-2-methyl-2H-indazol-5-yl)-2-(2-methylpyridin-4-yl)oxazole-4-carboxamide (150 mg, 0.2743 mmol) was deprotected using methanolic HCl (5 mL) to get the title compound (90 mg, 76.27%).

¹HNMR (400 MHz, CDCl₃,): δ 10.40 (s, 1H), 8.77 (s, 1H), 8.68-8.67 (d, 1H), 8.40 (s, 1H), 7.84-7.77 (m, 3H), 7.43 (s, 1H), 4.19 (s, 3H), 3.70 (m, 2H), 3.25-3.22 (m, 2H), 2.83-2.81 (m, 2H), 2.69 (s, 3H), 1.97 (m, 2H), 1.80 (s, 3H), 1.53-1.51 (t, 1H). LCMS: 97.74%, m/z=447.4 (M+1)⁺. HPLC: 98.57%.

Example 81

N-(6-(4-hydroxypiperidin-1-yl)-1,3-dimethyl-1H-indazol-5-yl)-2-(2-methylpyridin-4-yl)oxazole-4-carboxamide

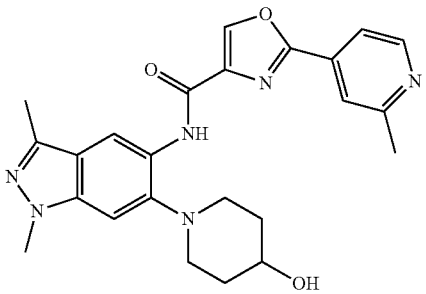 [SMILES: Cc1cc(-c2nc(C(=O)Nc3cc4c(C)nn(C)c4cc3N3CCC(O)CC3)co2)ccn1]

Step-1: Synthesis of 6-fluoro-1,3-dimethyl-5-nitro-1H-indazole and 6-fluoro-2,3-dimethyl-5-nitro-2H-indazole Using the same reagents and conditions as described in step 5 of example 1, 6-fluoro-3-methyl-5-nitro-1H-indazole (product of step 2 of example 73) (1 g, 5.12 mmol) was methylated using sodium hydride (492 mg, 10.25 mmol) and methyl iodide (1.456 g, 10.25 mmol) in THF (20 mL) at RT for 0.5 h to get the crude product. This was purified by silica gel column chromatography and elution with 25% ethyl acetate in hexane gave 6-fluoro-1,3-dimethyl-5-nitro-1H-indazole (450 mg) and further elution with 80% ethyl acetate in hexane gave 6-fluoro-2,3-dimethyl-5-nitro-2H-indazole (380 mg, 60%). LCMS: m/z=210.1 (M+1)⁺.

Step-2: Synthesis of 1-(1,3-dimethyl-5-nitro-1H-indazol-6-yl)piperidin-4-ol

Using the similar reagents and conditions as described in step 1 of example 58, 6-fluoro-1,3-dimethyl-5-nitro-1H-indazole (450 mg, 2.1531 mmol) was substituted with piperidin-4-ol (260 mg, 2.583 mmol) using potassium carbonate (891 mg, 6.45 mmol) in DMF (5 mL) at 120° C. for 14 h to get the crude compound. The obtained crude was purified by 60-120 silica gel column chromatography and compound eluted using ethyl acetate in hexane to give title compound (300 mg, 50%). LCMS: m/z=291.3 (M+1)⁺.

Step-3: Synthesis of 6-(4-((tert-butyldimethylsilyl)oxy)piperidin-1-yl)-1,3-dimethyl-5-nitro-1H-indazole Using the similar reagents and conditions as described in step 2 of example 58, 1-(1,3-dimethyl-5-nitro-1H-indazol-6-yl)piperidin-4-ol (300 mg, 1.0714 mmol) was protected using TBDMS chloride (241 mg, 1.6071 mmol), imidazole (182 mg, 2.678 mmol) and DMAP (156 mg, 1.285 mmol) in DMF (5 mL) at RT for 4 h to obtain the crude compound. The obtained crude was purified by 60-120 silica gel column chromatography and compound eluted using 20% ethyl acetate in hexane to give title compound (300 mg, 70%). LCMS: m/z=405.4 (M+1)⁺.

Step-4: Synthesis of 6-(4-((tert-butyldimethylsilyl)oxy)piperidin-1-yl)-1,3-dimethyl-1H-indazol-5-amine Using the same reaction conditions as described in step 2 of example 16, 6-(4-((tert-butyldimethylsilyl)oxy)piperidin-1-yl)-1,3-dimethyl-5-nitro-1H-indazole (300 mg, 0.7428 mmol) was reduced with zinc dust (386 mg, 5.94 mmol) and ammonium chloride (320 mg, 5.94 mmol) in THF (10 mL) to get the desired crude product (250 mg). LCMS: m/z=375.3 (M+1)⁺.

Step-5: Synthesis of N-(6-(4-((tert-butyldimethylsilyl)oxy)piperidin-1-yl)-1,3-dimethyl-1H-indazol-5-yl)-2-(2-methylpyridin-4-yl)oxazole-4-carboxamide Using the similar reagents and conditions as described in step 6 of example 5, 6-(4-((tert-butyldimethylsilyl)oxy)piperidin-1-yl)-1,3-dimethyl-1H-indazol-5-amine (250 mg, 0.6684 mmol) was coupled with 2-(2-methylpyridin-4-yl)oxazole-4-carboxylic acid (163 mg, 0.8021 mmol) using HATU (381 mg, 1.0026 mmol) and DIPEA (0.5 mL, 2.673 mmol) in DMF (5 mL) to get the desired compound (250 mg, 80%). LCMS: m/z=561.5 (M+1)⁺.

Step-6: Synthesis of N-(6-(4-hydroxypiperidin-1-yl)-1,3-dimethyl-1H-indazol-5-yl)-2-(2-methylpyridin-4-yl)oxazole-4-carboxamide Using the same reaction conditions as described in step 8 of example 1, N-(6-(4-((tert-butyldimethylsilyl)oxy)piperidin-1-yl)-1,3-dimethyl-1H-indazol-5-yl)-2-(2-methylpyridin-4-yl)oxazole-4-carboxamide (250 mg, 0.4464 mmol) was deprotected using methanolic HCl (5 mL) in methanol (5 mL) to get the title compound (160 mg, 60%).

¹HNMR (300 MHz, DMSO-d₆,): δ 10.40 (s, 1H), 8.67-8.65 (d, 1H), 8.58 (s, 1H), 7.88 (s, 1H), 7.78-7.76 (d, 1H), 7.46 (s, 1H), 5.00 (s, 1H), 3.91 (s, 3H), 3.85-3.75 (m, 1H), 3.08-3.04 (m, 2H), 2.87-2.80 (m, 2H), 2.59 (s, 3H), 2.41 (s, 3H), 2.06-2.02 (m, 2H), 1.90-1.87 (m, 2H). LCMS: 93.53%, m/z=447.4 (M+1)⁺. HPLC: 97.74%.

Example 82

N-(6-(3-(hydroxymethyl)piperidin-1-yl)-2-methyl-2H-indazol-5-yl)-2-(2-methylpyridin-4-yl)oxazole-4-carboxamide

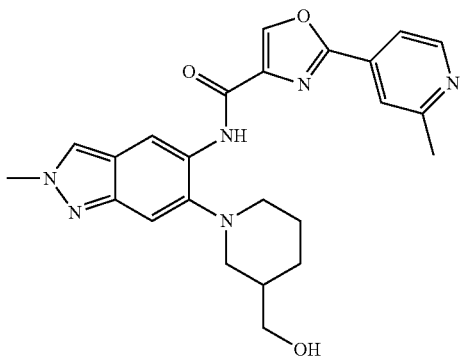 [SMILES: Cc1cc(-c2nc(C(=O)Nc3cc4cn(C)nc4cc3N3CCCC(CO)C3)co2)ccn1]

Step-1: Synthesis of (1-(2-methyl-5-nitro-2H-indazol-6-yl)piperidin-3-yl)methanol Using the similar reagents and conditions as described in step 1 of example 58, 6-fluoro-2-methyl-5-nitro-2H-indazole (product of step 1 of example 80) (200 mg, 1.0248 mmol) was substituted with piperidin-3-methanol (177 mg, 1.5372 mmol) using potassium carbonate (425 mg, 3.0745 mmol) in DMF (2 mL) at 120° C. for 24 h to get the title compound (200 mg, 67.34%). LCMS: m/z=291.2 (M+1)$^+$.

Step-2: Synthesis of 6-(3-(((tert-butyldimethylsilyl)oxy)methyl)piperidin-1-yl)-2-methyl-5-nitro-2H-indazole Using the similar reagents and conditions as described in step 2 of example 58, (1-(2-methyl-5-nitro-2H-indazol-6-yl)piperidin-3-yl)methanol (200 mg, 0.6888 mmol) was protected using TBDMS chloride (156 mg, 1.0332 mmol), imidazole (18 mg, 1.722 mmol) and DMAP (169 mg, 1.3776 mmol) in DMF (5 mL) at RT for 1 h to obtain the crude product. This was purified by silica gel column chromatography and elution with 40% ethyl acetate in hexane gave the title compound (202 mg, 72.66%). LCMS: m/z=405.2 (M+1)$^+$.

Step-3: Synthesis of 6-(3-(((tert-butyldimethylsilyl)oxy)methyl)piperidin-1-yl)-2-methyl-2H-indazol-5-amine Using the same reaction conditions as described in step 2 of example 16, 6-(3-(((tert-butyldimethylsilyl)oxy)methyl)piperidin-1-yl)-2-methyl-5-nitro-2H-indazole (202 mg, 0.5 mmol) was reduced with zinc dust (262 mg, 4 mmol) and ammonium chloride (428 mg, 8 mmol) in THF/water (10/2 mL) to get the desired product (170 mg, 90.90%). LCMS: m/z=375.4 (M+1)$^+$.

Step-4: Synthesis of N-(6-(3-(((tert-butyldimethylsilyl)oxy)methyl)piperidin-1-yl)-2-methyl-2H-indazol-5-yl)-2-(2-methylpyridin-4-yl)oxazole-4-carboxamide Using the similar reagents and conditions as described in step 6 of example 5, 6-(3-(((tert-butyldimethylsilyl)oxy)methyl)piperidin-1-yl)-2-methyl-2H-indazol-5-amine (170 mg, 0.4545 mmol) was coupled with 2-(2-methylpyridin-4-yl)oxazole-4-carboxylic acid (112 mg, 0.5454 mmol) using HATU (225 mg, 0.5909 mmol) and DIPEA (0.317 mL, 1.8181 mmol) in DMF (2 mL) to get the desired compound (150 mg, 59.05%). LCMS: m/z=561.3 (M+1)$^+$.

Step-5: Synthesis of N-(6-(3-(hydroxymethyl)piperidin-1-yl)-2-methyl-2H-indazol-5-yl)-2-(2-methylpyridin-4-yl)oxazole-4-carboxamide Using the same reaction conditions as described in step 8 of example 1, N-(6-(3-(((tert-butyldimethylsilyl)oxy)methyl)piperidin-1-yl)-2-methyl-2H-indazol-5-yl)-2-(2-methylpyridin-4-yl)oxazole-4-carboxamide (150 mg, 0.2743 mmol) was deprotected using methanolic HCl (5 mL) to get the title compound (50 mg, 42.37%).
$^1$HNMR (CDCl$_3$, 400 MHz): δ 10.4 (s, 1H), 8.75 (s, 1H), 8.69-8.67 (d, 1H), 8.39 (s, 1H), 7.82-7.81 (d, 1H), 7.71-7.70 (d, 1H), 7.42 (s, 1H), 4.17 (s, 3H), 3.80-3.60 (m, 2H), 3.40-3.30 (m, 2H), 2.68 (s, 3H), 2.40-2.30 (m, 2H), 2.10-2.00 (m, 4H). LCMS: 99.62%, m/z=447.6 (M+1)$^+$. HPLC: 99.69%.

Example 83

N-(6-(4-hydroxypiperidin-1-yl)-2,3-dimethyl-2H-indazol-5-yl)-2-(2-methylpyridin-4-yl)oxazole-4-carboxamide

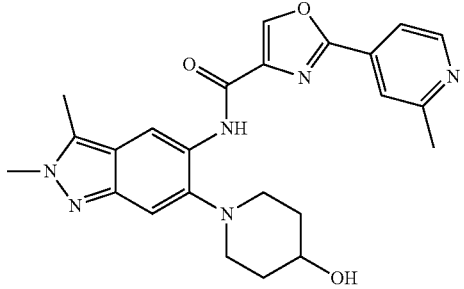 [SMILES: Cc1cc(-c2nc(C(=O)Nc3cc4c(C)n(C)nc4cc3N3CCC(O)CC3)co2)ccn1]

Step-1: Synthesis of 1-(2,3-dimethyl-5-nitro-2H-indazol-6-yl)piperidin-4-ol

Using the similar reagents and conditions as described in step 1 of example 58, 6-fluoro-2,3-dimethyl-5-nitro-2H-indazole (product of step 1 of example 81) (380 mg, 1.818 mmol) was substituted with piperidin-4-ol (220 mg, 2.181 mmol) using potassium carbonate (752 mg, 5.45 mmol) in DMF (5 mL) at 120° C. for 14 h to get the crude compound. The obtained crude was purified by 60-120 silica gel column chromatography and compound eluted using ethyl acetate in hexane to give title compound (300 mg, 40%). LCMS: m/z=291.4 (M+1)$^+$.

Step-2: Synthesis of 6-(4-(((tert-butyldimethylsilyl)oxy)piperidin-1-yl)-2,3-dimethyl-5-nitro-2H-indazole Using the similar reagents and conditions as described in step 2 of example 58, 1-(2,3-dimethyl-5-nitro-2H-indazol-6-yl)piperidin-4-ol (300 mg, 1.0714 mmol) was protected using TBDMS chloride (241 mg, 1.6071 mmol), imidazole (182 mg, 2.678 mmol) and DMAP (156 mg, 1.285 mmol) in DMF (5 mL) at RT for 4 h to obtain the crude compound. The obtained crude was purified by 60-120 silica gel column chromatography and compound eluted using ethyl acetate in hexane to give title compound (300 mg, 70%).

Step-3: Synthesis of 6-(4-((tert-butyldimethylsilyl) oxy)piperidin-1-yl)-2,3-dimethyl-2H-indazol-5-amine Using the same reaction conditions as described in step 2 of example 16, 6-(4-((tert-butyldimethylsilyl)oxy)piperidin-1-yl)-2,3-dimethyl-5-nitro-2H-indazole (300 mg, 0.7428 mmol) was reduced with zinc dust (386 mg, 5.94 mmol) and ammonium chloride (320 mg, 5.94 mmol) in THF (10 mL) to get the desired crude product (200 mg). LCMS: m/z=375.5 (M+1)$^+$.

Step-4: Synthesis of N-(6-(4-((tert-butyldimethylsilyl)oxy)piperidin-1-yl)-2,3-dimethyl-2H-indazol-5-yl)-2-(2-methylpyridin-4-yl)oxazole-4-carboxamide Using the similar reagents and conditions as described in step 6 of example 5, 6-(4-((tert-butyldimethylsilyl)oxy)piperidin-1-yl)-2,3-dimethyl-2H-indazol-5-amine (200 mg, 0.534 mmol) was coupled with 2-(2-methylpyridin-4-yl) oxazole-4-carboxylic acid (130 mg, 0.6417 mmol) using HATU (304 mg, 0.8021 mmol) and DIPEA (0.4 mL, 2.139 mmol) in DMF (5 mL) to get the desired compound (200 mg, 80%). LCMS: m/z=561.4 (M+1)$^+$.

Step-5: Synthesis of N-(6-(4-hydroxypiperidin-1-yl)-2,3-dimethyl-2H-indazol-5-yl)-2-(2-methylpyridin-4-yl)oxazole-4-carboxamide Using the same reaction conditions as described in step 8 of example 1, N-(6-(4-((tert-butyldimethylsilyl)oxy)piperidin-1-yl)-2,3-dimethyl-2H-indazol-5-yl)-2-(2-methylpyridin-4-yl)oxazole-4-carboxamide (220 mg, 0.3571) was deprotected using methanolic HCl (5 mL) in methanol (5 mL) to get the title compound (40 mg, 20%).
$^1$H NMR (400 MHz, DMSO-d$_6$): δ 10.4 (s, 1H), 8.68-8.67 (d, 1H), 8.53 (s, 1H), 7.91 (s, 1H), 7.81-7.79 (d, 1H), 7.32 (s, 1H), 4.97 (s, 1H), 4.00 (s, 3H), 3.04-3.01 (m, 3H), 2.83-2.78 (m, 2H), 2.61 (s, 3H), 2.56 (s, 3H), 2.02-2.01 (m, 2H), 1.92-1.89 (m, 2H). LCMS: 98.25%, m/z=447.3 (M+1)$^+$. HPLC: 97.10%.

Example 84

2-(2-acetamidopyridin-4-yl)-N-(2-methyl-6-(piperidin-1-yl)-2H-indazol-5-yl)oxazole-4-carboxamide

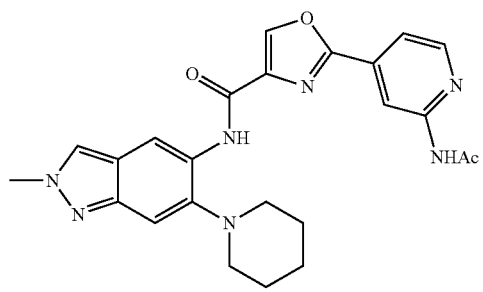 [SMILES: CC(=O)Nc1cc(-c2nc(C(=O)Nc3cc4cn(C)nc4cc3N3CCCCC3)co2)ccn1]

Using the similar reaction conditions as described in step 7 of example 1, 2-methyl-6-(piperidin-1-yl)-2H-indazol-5-amine (product of step 6 of example 1) (120 mg, 0.521 mmol), was coupled with 2-(2-acetamidopyridin-4-yl)oxazole-4-carboxylic acid (intermediate 13) (128 mg, 0.521 mmol) using HATU (209 mg, 0.782 mmol), DIPEA (209 mg, 2.08 mmol) in DMF (10 mL) to afford the title compound (55 mg, 24%).
$^1$HNMR (DMSO-d$_6$, 400 MHz): δ 10.90 (s, 1H), 10.20 (s, 1H), 8.79 (s, 1H), 8.64 (s, 1H), 8.56-8.55 (d, 1H), 8.26 (s, 1H), 7.64-7.63 (d, 1H), 7.38 (s, 1H), 4.20 (s, 3H), 2.88 (s, 4H), 2.14 (s, 3H), 1.88 (s, 4H), 1.66 (s, 2H). LCMS: 98.67%, m/z=460.3 (M-F1)$^+$. HPLC: 95.54%.

Example 85

2-(2-acetamidopyridin-4-yl)-N-(6-(3-fluoropiperidin-1-yl)-2-methyl-2H-indazol-5-yl)oxazole-4-carboxamide

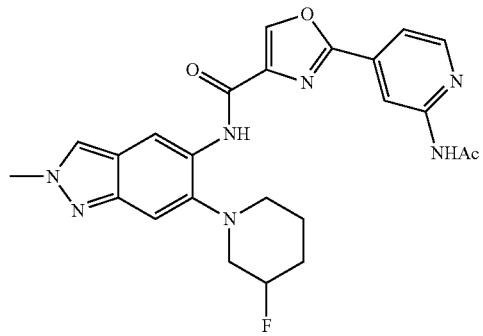 [SMILES: CC(=O)Nc1cc(-c2nc(C(=O)Nc3cc4cn(C)nc4cc3N3CCCC(F)C3)co2)ccn1]

Using the similar reagents and conditions as described in step 6 of example 5, 6-(3-fluoropiperidin-1-yl)-2-methyl-2H-indazol-5-amine (product of step 3 of example 79) (200 mg, 0.806 mmol) was coupled with 2-(2-acetamidopyridin-4-yl)oxazole-4-carboxylic acid (intermediate 13) (199 mg, 0.806 mmol) using HATU (459 mg, 1.20 mmol) and DIPEA (416 mg, 3.22 mmol) in DMF (10 mL) to obtain crude product. This was purified by prep HPLC to get the title compound (125 mg, 32.55%).
$^1$HNMR (DMSO-d$_6$, 400 MHz): δ 10.80 (s, 1H), 10.18 (s, 1H), 9.04 (s, 1H), 8.71 (s, 1H), 8.67 (s, 1H), 8.57-8.55 (d, 1H), 8.29 (s, 1H), 7.69-7.67 (m, 1H), 7.46 (s, 1H), 5.20-4.90 (m, 1H), 4.12 (s, 3H), 3.03-3.00 (m, 2H), 2.89-2.86 (m, 2H), 2.15-2.10 (m, 5H), 1.90-1.70 (m, 2H).). LCMS: 96.52%, m/z=478.2 (M+1)$^+$. HPLC: 95.00%.

Example 86

2-(2-aminopyridin-4-yl)-N-(2-methyl-6-(piperidin-1-yl)-2H-indazol-5-yl)oxazole-4-carboxamide hydrochloride

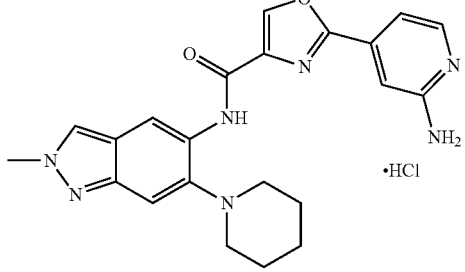

Using the similar reaction conditions as described in step 6 of example 5, 2-methyl-6-(piperidin-1-yl)-2H-indazol-5-amine (product of step 6 of example 1) (100 mg, 0.434 mmol), was coupled with 2-(2-aminopyridin-4-yl)oxazole-4-carboxylic acid (intermediate 14) (90 mg, 0.434 mmol) using HATU (247 mg, 0.6652 mmol), DIPEA (224 mg, 1.73 mmol) in DMF (8 mL) to afford the desired compound on treatment with methanolic HCl/methanol (5/5 mL) (30 mg, 62.5%).

$^1$HNMR (DMSO-$d_6$, 400 MHz): δ 10.25 (s, 1H), 9.17 (s, 1H), 8.61 (s, 1H), 8.50 (s, 2H), 8.29 (s, 1H), 8.23-8.22 (d, 1H), 7.54 (s, 1H), 7.41 (s, 1H), 7.27-7.25 (d, 1H), 4.12 (s, 3H), 2.90 (s, 4H), 1.85 (s, 4H), 1.67 (s, 2H). LCMS: 97.93%, m/z=418.4 (M+1)$^+$. HPLC: 97.62%.

Example 87

N-(6-(4-fluoropiperidin-1-yl)-1,3-dimethyl-1H-indazol-5-yl)-2-(2-methylpyridin-4-yl)oxazole-4-carboxamide

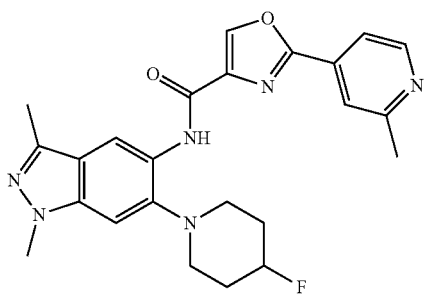 [SMILES: Cc1cc(-c2nc(C(=O)Nc3cc4c(C)nn(C)c4cc3N3CCC(F)CC3)co2)ccn1]

Using the same reaction conditions as described in example 78, N-(6-(4-hydroxypiperidin-1-yl)-1,3-dimethyl-1H-indazol-5-yl)-2-(2-methylpyridin-4-yl)oxazole-4-carboxamide (example 81) (120 mg, 0.2690 mmol) was fluorinated using DAST (0.1 mL, 0.4843 mmol) in DCM (5 mL) at −20° C. for 0.5 h to obtain the crude product. The obtained crude was purified by prep HPLC to obtain the title compound (25 mg, 20%).

$^1$HNMR (DMSO-$d_6$, 400 MHz): δ 10.23 (s, 1H), 9.18 (s, 1H), 8.87-8.86 (d, 1H), 8.59 (s, 1H), 8.13 (s, 1H), 8.03-8.01 (d, 1H), 7.54 (s, 1H), 5.07-4.90 (m, 1H), 3.94 (s, 3H), 3.16-3.12 (m, 2H), 2.96-2.92 (m, 2H), 2.71 (s, 3H), 2.44 (s, 3H), 2.32-2.14 (m, 4H). LCMS: 91.55%, m/z=449.3 (M+1)$^+$. HPLC: 98.77%.

Example 88

N-(6-(((1R,4R)-4-hydroxycyclohexyl)amino)-2-methyl-2H-indazol-5-yl)-2-(2-methylpyridin-4-yl)oxazole-4-carboxamide

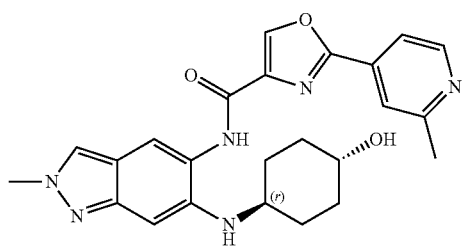 [SMILES: Cc1cc(-c2nc(C(=O)Nc3cc4cn(C)nc4cc3N[C@H]3CC[C@H](O)CC3)co2)ccn1]

Step-1: Synthesis of 2-fluoro-4-((1R,4R)-4-hydroxycyclohexyl)amino)-5-nitrobenzaldehyde Using the similar reagents and conditions as described in step 1 of example 58, 2,4-difluoro-5-nitrobenzaldehyde (4 gm, 21.3 mmol) was substituted with trans-4-aminocyclohexan-1-ol (4.293 g, 25.6 mmol) using potassium carbonate (8.869 g, 64.1 mmol) in DMF (10 mL) at RT for 10 min to get the crude compound. The obtained crude was purified by 60-120 silica gel column chromatography and compound eluted using 1-2% methanol in DCM to give title compound (3.9 g, 64.06%). LCMS: m/z=283.3 (M+1)$^+$.

Step-2: Synthesis of (1R,4R)-4-((5-nitro-1H-indazol-6-yl)amino)cyclohexan-1-ol

Using the similar reagents and conditions as described in step 2 of example 5, 4-(((1r,4r)-4-((tert-butyldimethylsilyl)oxy)cyclohexyl)amino)-2-fluoro-5-nitrobenzaldehyde (3.9 g, 13.3 mmol) was cyclized using hydrazine hydrate (1.334 g, 26.6 mmol) in THF (10 mL) at 80° C. for 4 h to get the crude compound. The obtained crude was purified by 60-120 silica gel column chromatography and compound eluted using 60% ethyl acetate in hexane to obtain the title compound (2.9 g, 76.05%).

Step-3: Synthesis of N-((1R,4R)-4-((tert-butyldimethylsilyl)oxy)cyclohexyl)-5-nitro-1H-indazol-6-amine Using the similar reagents and conditions as described in step 2 of example 58, (1R,4R)-4-((5-nitro-1H-indazol-6-yl)amino)cyclohexan-1-ol (2.9 gm, 10.5 mmol) was protected using TBDMS chloride (3.167 g, 21 mmol), imidazole (1.788 g, 26.2 mmol) and DMAP (2.567 g, 21 mmol) in DMF (10 mL) at RT for 1 h to obtain the crude product. This was purified by silica gel column chromatography and elution with 20% ethyl acetate in hexane gave title compound (3.35 g, 81.90%). LCMS: m/z=391.4 (M+1)$^+$.

Step-4: Synthesis of N-((1R,4R)-4-((tert-butyldimethylsilyl)oxy)cyclohexyl)-1-methyl-5-nitro-1H-indazol-6-amine and N-((1R,4R)-4-((tert-butyldimethylsilyl)oxy)cyclohexyl)-2-methyl-5-nitro-2H-indazol-6-amine Using the same reagents and conditions as described in step 5 of example 1, N-((1R,4R)-4-((tert-butyldimethylsilyl)oxy)cyclohexyl)-5-nitro-1H-indazol-6-amine (3.35 gm, 8.5 mmol) was methylated using sodium hydride (687 mg, 17.1 mmol) and methyl iodide (1.074 mL, 17.1 mmol) in THF (50 mL) at RT for 0.5 h to get the crude product. This was purified by silica gel column chromatography and elution with 20% ethyl acetate in hexane gave N-((1R,4R)-4-((tert-butyldimethylsilyl)oxy)cyclohexyl)-1-methyl-5-nitro-1H-indazol-6-amine (2 g) and further elution with 80% ethyl acetate in hexane gave N-((1R,4R)-4-((tert-butyldimethylsilyl)oxy)cyclohexyl)-2-methyl-5-nitro-2H-indazol-6-amine (1.2 g, 92.21%). LCMS: m/z=405.2 (M+1)$^+$.

Step-5: Synthesis of N-6-((1R,4R)-4-((tert-butyldimethylsilyl)oxy)cyclohexyl)-2-methyl-2H-indazole-5,6-diamine Using the same reaction conditions as described in step 2 of example 16, N-((1R,4R)-4-((tert-butyldimethylsilyl)oxy)cyclohexyl)-2-methyl-5-nitro-2H-indazol-6-amine (1.2 g, 2.9702 mmol) was reduced with zinc dust (1.553 g, 23.7623 mmol) and ammonium chloride (2.547 g, 47.5247 mmol) in THF/water (20/10 mL) to get the desired product (1 g, 90.09%). LCMS: m/z=375.4 (M+1)+.

Step-6: Synthesis of N-(6-(((1R,4R)-4-((tert-butyldimethylsilyl)oxy)cyclohexyl)amino)-2-methyl-2H-indazol-5-yl)-2-(2-methylpyridin-4-yl)oxazole-4-carboxamide Using the similar reagents and conditions as described in step 6 of example 5, N6-((1r,4r)-4-((tert-butyldimethylsilyl)oxy)cyclohexyl)-2-methyl-2H-indazole-5,6-diamine (200 mg, 0.534 mmol) was coupled with 2-(2-methylpyridin-4-yl)oxazole-4-carboxylic acid (141 mg, 0.695 mmol) using HATU (304 mg, 0.801 mmol) and DIPEA (275 mg, 2.136 mmol) in DMF (5 mL) to get the desired compound (120 mg, 40.1%). LCMS: m/z=561.5 (M+1)+.

Step-7: Synthesis of N-(6-(((1r,4r)-4-hydroxycyclohexyl)amino)-2-methyl-2H-indazol-5-yl)-2-(2-methylpyridin-4-yl)oxazole-4-carboxamide Using the same reagents and conditions as described in step 7 of example 58, N-(6-(((1r,4r)-4-((tert-butyldimethylsilyl)oxy)cyclohexyl)amino)-2-methyl-2H-indazol-5-yl)-2-(2-methylpyridin-4-yl)oxazole-4-carboxamide (120 mg, 0.214 mmol) was deprotected using 0.1M TBAF in THF (2/1 mL) at RT for 12 h to get the title compound (20 mg, 21%).
$^1$HNMR (CDCl$_3$, 300 MHz): δ 9.10 (s, 1H), 8.70-8.68 (d, 1H), 8.41 (s, 1H), 8.17 (s, 1H), 7.80-7.78 (d, 2H), 7.73-7.72 (d, 1H), 7.22 (s, 1H), 7.01 (s, 1H), 4.15 (s, 3H), 3.72 (s, 1H), 3.50 (s, 1H), 3.34 (s, 1H), 2.68 (s, 3H), 2.30-2.26 (m, 2H), 2.10-2.00 (m, 2H), 1.57-1.32 (m, 5H). LCMS: 98.46%, m/z=447.3 (M+1)+. HPLC: 95.23%.

Example 89

N-(6-(4-(hydroxymethyl)piperidin-1-yl)-1-methyl-1H-indazol-5-yl)-2-(2-methylpyridin-4-yl)oxazole-4-carboxamide

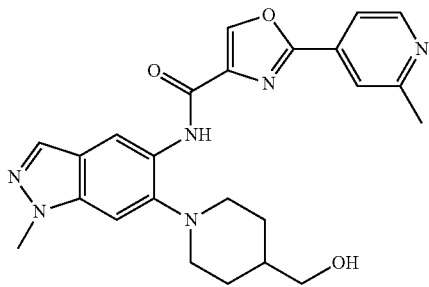 [SMILES: Cc1cc(-c2nc(C(=O)Nc3cc4cnn(C)c4cc3N3CCC(CO)CC3)co2)ccn1]

Step-1: Synthesis of (1-(1-methyl-5-nitro-1H-indazol-6-yl)piperidin-4-yl)methanol Using the similar reagents and conditions as described in step 1 of example 58, 6-fluoro-1-methyl-5-nitro-1H-indazole (product of step 1 of example 80) (500 mg, 2.562 mmol) was substituted with piperidin-4-methanol (354 mg, 3.0745 mmol) using potassium carbonate (1.061 g, 7.69 mmol) in DMF (10 mL) at 100° C. for 14 h to get the title compound (500 mg, 68%). LCMS: m/z=291.3 (M+1)+.

Step-2: Synthesis of 6-(4-(((tert-butyldimethylsilyl)oxy)methyl)piperidin-1-yl)-1-methyl-5-nitro-1H-indazole Using the similar reagents and conditions as described in step 2 of example 58, (1-(1-methyl-5-nitro-1H-indazol-6-yl)piperidin-4-yl)methanol (500 mg, 1.7241 mmol) was protected using TBDMS chloride (387 mg, 2.586 mmol), imidazole (293 mg, 4.31 mmol) and DMAP (252 mg, 2.068 mmol) in DMF (10 mL) at RT for 0.5 h to obtain the crude product. This was purified by silica gel column chromatography and elution with 20% ethyl acetate in hexane gave the title compound (500 mg, 72%). LCMS: m/z=405.4 (M+1)+.

Step-3: Synthesis of 6-(4-(((tert-butyldimethylsilyl)oxy)methyl)piperidin-1-yl)-1-methyl-1H-indazol-5-amine Using the same reaction conditions as described in step 2 of example 16, 6-(4-(((tert-butyldimethylsilyl)oxy)methyl)piperidin-1-yl)-1-methyl-5-nitro-1H-indazole (500 mg, 1.237 mmol) was reduced with zinc dust (643 mg, 9.9 mmol) and ammonium chloride (534 mg, 9.99 mmol) in THF/water (5/2 mL) to get the desired product (450 mg, 98%). LCMS: m/z=375.4 (M+1)+.

Step-4: Synthesis of N-(6-(4-(((tert-butyldimethylsilyl)oxy)methyl)piperidin-1-yl)-1-methyl-1H-indazol-5-yl)-2-(2-methylpyridin-4-yl)oxazole-4-carboxamide Using the similar reagents and conditions as described in step 7 of example 1, 6-(4-(((tert-butyldimethylsilyl)oxy)methyl)piperidin-1-yl)-1-methyl-1H-indazol-5-amine (100 mg, 0.2673 mmol) was coupled with 2-(2-methylpyridin-4-yl)oxazole-4-carboxylic acid (66 mg, 0.3208 mmol) using HATU (152 mg, 0.4010 mmol) and DIPEA (0.2 mL, 1.095 mmol) in DMF (5 mL) to get the desired compound (100 mg, 68%). LCMS: m/z=561.5 (M+1)+.

Step-5: Synthesis of N-(6-(4-(hydroxymethyl)piperidin-1-yl)-1-methyl-1H-indazol-5-yl)-2-(2-methylpyridin-4-yl)oxazole-4-carboxamide Using the same reaction conditions as described in step 8 of example 1, N-(6-(4-(((tert-butyldimethylsilyl)oxy)methyl)piperidin-1-yl)-1-methyl-1H-indazol-5-yl)-2-(2-methylpyridin-4-yl)oxazole-4-carboxamide (100 mg, 0.1785 mmol) was deprotected using methanolic HCl/methanol (1/5 mL) to get the title compound (50 mg, 69%).
$^1$HNMR (DMSO-d$_6$, 400 MHz): δ 10.22 (s, 1H), 9.07 (s, 1H), 8.73-8.69 (m, 2H), 8.01 (s, 1H), 7.83-7.82 (d, 2H), 7.56 (s, 1H), 4.68 (s, 1H), 4.03 (s, 3H), 3.47 (s, 2H), 3.14-3.11 (m, 2H), 2.85-2.80 (t, 2H), 2.61 (s, 3H), 1.92-1.90 (m, 2H), 1.70-1.65 (m, 3H). LCMS: 98.55%, m/z=447.3 (M+1)+. HPLC: 97.24%.

Example 90

2-(2-aminopyridin-4-yl)-N-(6-(4-fluoropiperidin-1-yl)-2-methyl-2H-indazol-5-yl)oxazole-4-carboxamide hydrochloride

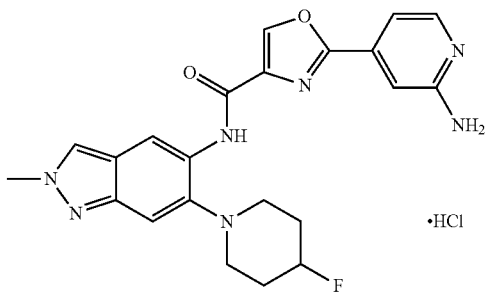 [SMILES: Cn1cc2cc(NC(=O)c3coc(-c4ccnc(N)c4)n3)c(N3CCC(F)CC3)cc2n1 ; Cl]

Step-1: Synthesis of 1-(2-methyl-5-nitro-2H-indazol-6-yl)piperidin-4-ol

Using the similar reaction conditions as described in step 8 of example 1, 6-(4-((tert-butyldimethylsilyl)oxy)piperidin-1-yl)-2-methyl-5-nitro-2H-indazole (product of step 4 of example 58) (450 mg, 1.10 mmol) was deprotected using methanolic HCl/methanol (4/8 mL) to get the title compound (300 mg, 94.40%). LCMS: m/z=277.3 (M+1)$^+$.

Step 2: Preparation of 6-(4-fluoropiperidin-1-yl)-2-methyl-5-nitro-2H-indazole Using the same reaction conditions as described in example 78, 1-(2-methyl-5-nitro-2H-indazol-6-yl)piperidin-4-ol (300 mg, 1.08 mmol) was fluorinated using DAST (262 mg, 1.63 mmol) in DCM (10 mL) to obtain the crude product. The obtained crude was purified by 60-120 silica gel column chromatography using 50% ethyl acetate in hexane as eluent to obtain the title compound (200 mg, 76.04%). LCMS: m/z=279.3 (M+1)$^+$.

Step-3: Synthesis of 6-(4-fluoropiperidin-1-yl)-2-methyl-2H-indazol-5-amine

Using the same reaction conditions as described in step 2 of example 16, 6-(4-fluoropiperidin-1-yl)-2-methyl-5-nitro-2H-indazole (200 mg, 71.9 mmol) was reduced with zinc dust (470 mg, 7.19 mmol) and ammonium chloride (384 mg, 71.9 mmol) in THF/water (15/4 mL) to get the desired crude product (160 mg, 94.11%).

Step-4: Synthesis of 2-(2-aminopyridin-4-yl)-N-(6-(4-fluoropiperidin-1-yl)-2-methyl-2H-indazol-5-yl)oxazole-4-carboxamide hydrochloride Using the similar reagents and conditions as described in step 6 of example 5, 6-(4-fluoro piperidin-1-yl)-2-methyl-2H-indazol-5-amine (80 mg, 0.322 mmol) was coupled with 2-(2-aminopyridin-4-yl)oxazole-4-carboxylic acid (intermediate 14) (73 mg, 0.354 mmol) using HATU (183 mg, 0.483 mmol) and DIPEA (166 mg, 1.90 mmol) in DMF (8 mL) to obtain crude product. This was purified by prep HPLC and treated with methanolic HCl to get the title compound (30 mg, 90.25%).

$^1$HNMR (DMSO-d$_6$, 400 MHz): δ 10.19 (s, 1H), 9.18 (s, 1H), 8.61 (s, 1H), 8.50 (s, 2H), 8.30 (s, 1H), 8.18-8.16 (d, 1H), 7.54 (s, 1H), 7.44 (s, 1H), 7.25-7.23 (d, 1H), 5.10-5.00 (m, 1H), 4.12 (s, 3H), 3.08-3.04 (m, 2H), 2.95-2.90 (m, 2H), 2.23-2.08 (m, 4H). LCMS: 97.87%, m/z=436.2 (M+1)$^+$. HPLC: 95.86%.

Example 91

N-(6-(4-fluoropiperidin-1-yl)-2-methyl-2H-indazol-5-yl)-2-(2-methylpyridin-4-yl)oxazole-4-carboxamide hydrochloride

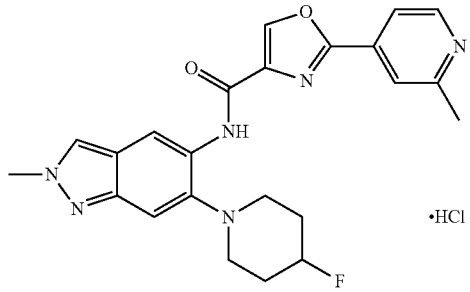

Using the same reagents and conditions as described in step 6 of example 5, 6-(4-fluoropiperidin-1-yl)-2-methyl-2H-indazol-5-amine (product of step 3 of example 90) (80 mg, 0.322 mmol) was coupled with 2-(2-methylpyridin-4-yl)oxazole-4-carboxylic acid (73 mg, 0.354 mmol) using HATU (183 mg, 0.483 mmol) and DIPEA (166 mg, 1.90 mmol) in DMF (8 mL) to obtain crude product. This was purified by prep HPLC and treated with methanolic HCl to get the title compound (30 mg, 21.42%).

$^1$HNMR (DMSO-d$_6$, 400 MHz): δ 10.33 (s, 1H), 9.20 (s, 1H), 8.87-8.86 (d, 1H), 8.62 (s, 1H), 8.30 (s, 1H), 8.13 (s, 1H), 8.03-8.02 (d, 1H), 7.45 (s, 1H), 5.10-5.00 (m, 1H), 4.12 (s, 3H), 3.08-3.06 (m, 2H), 2.95-2.90 (m, 2H), 2.72 (s, 3H), 2.33-2.14 (m, 4H). LCMS: 90.42%, m/z=435.4 (M+1)$^+$. HPLC: 98.76%.

Example 92

(S)—N-(6-(4-(hydroxymethyl)piperidin-1-yl)-2-methyl-2H-indazol-5-yl)-6-(1-(2-hydroxypropyl)-1H-pyrazol-4-yl)picolinamide

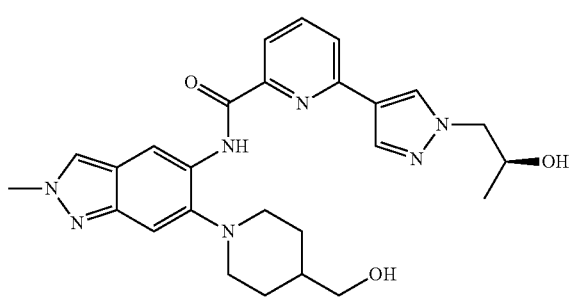 [SMILES: C[C@H](O)Cn1cc(-c2cccc(C(=O)Nc3cc4cn(C)nc4cc3N3CCC(CO)CC3)n2)cn1]

Step-1: Synthesis of 6-bromo-N-(6-(4-(((tert-butyldimethylsilyl)oxy)methyl)piperidin-1-yl)-2-methyl-2H-indazol-5-yl)picolinamide Using the same reagents and conditions as described in step 6 of example 5, 6-(4-(((tert-butyldimethylsilyl)oxy)methyl)piperidin-1-yl)-2-methyl-2H-indazol-5-amine (product of step 4 of example 80) (555 mg, 1.485 mmol) was coupled with 6-bromopicolinic acid (300 mg, 1.485 mmol) using HATU (846 mg, 2.227 mmol) and DIPEA (383 mg, 2.97 mmol) in DMF (5 mL) to obtain the desired compound (500 mg, 60.38%). LCMS: m/z=557.9 (M+1)+.

Step-2: Synthesis of N-(6-(4-(((tert-butyldimethylsilyl)oxy)methyl)piperidin-1-yl)-2-methyl-2H-indazol-5-yl)-6-(1-(tetrahydro-2H-pyran-2-yl)-1H-pyrazol-4-yl)picolinamide Using the same reagents and conditions as described in step 1 of example 6, 6-bromo-N-(6-(4-(((tert-butyldimethylsilyl)oxy)methyl)piperidin-1-yl)-2-methyl-2H-indazol-5-yl)picolinamide (450 mg, 0.820 mmol) was coupled with 1-(tetrahydro-2H-pyran-2-yl)-4-(4,4,5,5-tetramethyl-1,3,2-dioxaborolan-2-yl)-1H-pyrazole (330 mg, 1.187 mmol) using Pd(dppf)Cl$_2$ (60 mg, 0.082 mmol) and sodium carbonate (249 mg, 2.349 mmol) in DME/H$_2$O (5/1 mL) at 90° C. for 2 h to obtain title product (200 mg, 39.44%). LCMS: m/z=630.5 (M+1)+.

Step-3: Synthesis of N-(6-(4-(hydroxymethyl)piperidin-1-yl)-2-methyl-2H-indazol-5-yl)-6-(1H-pyrazol-4-yl)picolinamide hydrochloride Using the same reaction conditions as described in step 8 of example 1, N-(6-(4-(((tert-butyldimethylsilyl)oxy)methyl)piperidin-1-yl)-2-methyl-2H-indazol-5-yl)-6-(1-(tetrahydro-2H-pyran-2-yl)-1H-pyrazol-4-yl)picolinamide (180 mg, 1.06 mmol) was deprotected using methanolic HCl (2 mL) in methanol (1 mL) to get the title compound (125 mg, 89.99%). LCMS: m/z=432.4 (M+1)+.

Step-4: Synthesis of (S)—N-(6-(4-(hydroxymethyl)piperidin-1-yl)-2-methyl-2H-indazol-5-yl)-6-(1-(2-hydroxypropyl)-1H-pyrazol-4-yl)picolinamide Using the same reagents and conditions as described in example 34, N-(6-(4-(hydroxymethyl)piperidin-1-yl)-2-methyl-2H-indazol-5-yl)-6-(1H-pyrazol-4-yl)picolinamide hydrochloride (125 mg, 0.29 mmol) was substituted with (S)-2-methyloxirane (33 mg, 0.58 mmol) using sodium carbonate (184 mg, 1.74 mmol) in DMF (1 mL) at 90° C. for 16 h to get the title compound (80 mg, 56.73%).
$^1$HNMR (DMSO-d$_6$, 400 MHz): δ 10.90 (s, 1H), 8.70 (s, 1H), 8.43 (s, 1H), 8.27-8.23 (d, 2H), 8.07-8.01 (m, 2H), 7.94-7.93 (d, 1H), 5.03-5.02 (d, 1H), 4.46-4.43 (t, 1H), 4.12-4.03 (m, 6H), 3.21-3.11 (m, 4H), 2.70-2.64 (t, 2H), 1.84-1.81 (m, 2H), 1.50-1.41 (m, 3H), 1.09-1.08 (d, 3H). LCMS: 96.73%, m/z=490.4 (M+1)+. HPLC: 96.58%.

Example 93

2-(2-aminopyridin-4-yl)-N-(6-(4-hydroxypiperidin-1-yl)-2-methyl-2H-indazol-5-yl)oxazole-4-carboxamide hydrochloride

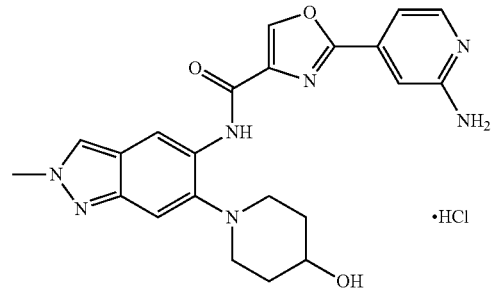 [SMILES: Cn1cc2cc(NC(=O)c3coc(-c4ccnc(N)c4)n3)c(N3CCC(O)CC3)cc2n1 ; Cl]

Step-1: Synthesis of 2-(2-aminopyridin-4-yl)-N-(6-(4-((tert-butyldimethylsilyl)oxy)piperidin-1-yl)-2-methyl-2H-indazol-5-yl)oxazole-4-carboxamide Using the same reagents and conditions as described in step 6 of example 5, 6-(4-((tert-butyldimethylsilyl)oxy)piperidin-1-yl)-2-methyl-2H-indazol-5-amine (product of step 5 of example 58) (98 mg, 0.2718 mmol) was coupled with 2-(2-aminopyridin-4-yl)oxazole-4-carboxylic acid (intermediate 14) (56 mg, 0.2718 mmol) using HATU (155 mg, 0.4077 mmol) and DIPEA (140 mg, 1.087 mmol) in DMF (5 mL) to afford the title compound (102 mg, 69%). LCMS: m/z=548.5 (M+1)+.

Step-2: Synthesis of 2-(2-aminopyridin-4-yl)-N-(6-(4-hydroxypiperidin-1-yl)-2-methyl-2H-indazol-5-yl)oxazole-4-carboxamide hydrochloride Using the same reaction conditions as described in step 8 of example 1, 2-(2-aminopyridin-4-yl)-N-(6-(4-((tert-butyldimethylsilyl)oxy)piperidin-1-yl)-2-methyl-2H-indazol-5-yl)oxazole-4-carboxamide (91 mg, 0.1603 mmol) was deprotected using methanolic HCl/methanol (2/5 mL) to get the title compound (51 mg, 65%).
$^1$HNMR (CD$_3$OD, 300 MHz): δ 8.86 (s, 1H), 8.80 (s, 1H), 8.55 (s, 1H), 8.05-8.03 (d, 1H), 7.718-7.712 (m, 1H), 7.55-7.52 (m, 2H), 4.31 (s, 3H), 4.00-3.90 (m, 1H), 3.10-3.00 (m, 2H), 2.17-2.03 (m, 4H). LCMS: 99.03%, m/z=434.15 (M+1)+. HPLC: 97.38%.

Example 94

N-(6-(4-(hydroxymethyl)piperidin-1-yl)-1-(2-methoxyethyl)-1H-indazol-5-yl)-2-(2-methylpyridin-4-yl)oxazole-4-carboxamide

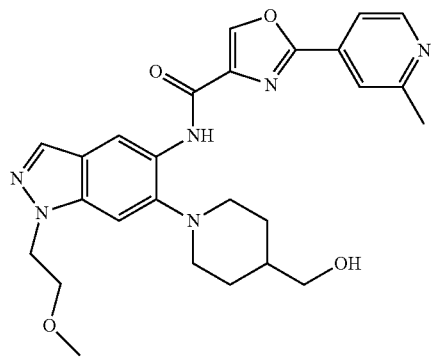 [SMILES: COCCn1ncc2cc(NC(=O)c3coc(-c4ccnc(C)c4)n3)c(N3CCC(CO)CC3)cc21]

Step-1: Synthesis of 2-fluoro-4-(4-(hydroxymethyl)piperidin-1-yl)-5-nitrobenzaldehyde Using the similar reagents and conditions as described in step 1 of example 58, 2,4-difluoro-5-nitrobenzaldehyde (10 gm, 53.48 mmol) was substituted with piperidine-4-methanol (6.76 g, 58.82 mmol) using potassium carbonate (11 g, 79.71 mmol) in DMF (100 mL) at RT for 2 h to get the title compound (14 g, 93.33%). LCMS: m/z=283.1 (M+1)$^+$.

Step-2: Synthesis of (1-(5-nitro-1H-indazol-6-yl)piperidin-4-yl)methanol

Using the similar reagents and conditions as described in step 2 of example 5, 2-fluoro-4-(4-(hydroxymethyl)piperidin-1-yl)-5-nitrobenzaldehyde (14 g, 49.64 mmol) was cyclized using 50% hydrazine hydrate (5.3 g, 99.29 mmol) in DMF (140 mL) at 60° C. for 1 h to get the title compound (12.5 g, 83.94%). LCMS: m/z=277.4 (M+1)$^+$.

Step-3: Synthesis of 6-(4-(((tert-butyldimethylsilyl)oxy)methyl)piperidin-1-yl)-5-nitro-1H-indazole Using the similar reagents and conditions as described in step 2 of example 58, (1-(5-nitro-1H-indazol-6-yl)piperidin-4-yl)methanol (11.5 gm, 41.67 mmol) was protected using TBDMS chloride (7.4 g, 50 mmol), imidazole (5.6 g, 83.34 mmol) and DMAP (6 g, 50 mmol) in DMF (100 mL) at RT for 2 h to obtain the crude product. This was purified by silica gel column chromatography and elution with 30% ethyl acetate in hexane gave title compound (14 g, 86.4%). LCMS: m/z=391.4 (M+1)$^+$.

Step-4: Synthesis of 6-(4-(((tert-butyldimethylsilyl)oxy)methyl)piperidin-1-yl)-1-(2-methoxyethyl)-5-nitro-1H-indazole and 6-(4-(((tert-butyldimethylsilyl)oxy)methyl) piperidin-1-yl)-2-(2-methoxyethyl)-5-nitro-2H-indazole Using the same reagents and conditions as described in step 5 of example 1, 6-(4-(((tert-butyldimethylsilyl)oxy)methyl)piperidin-1-yl)-5-nitro-1H-indazole (600 mg, 1.538 mmol) was alkylated using sodium hydride (120 mg, 3.076 mmol) and 1-bromo-2-methoxyethane (427 mg, 3.076 mmol) in THF (6 mL) at 70° C. for 5 h to get the crude product. This was purified by silica gel column chromatography and elution with 20% ethyl acetate in hexane gave 6-(4-(((tert-butyldimethylsilyl)oxy)methyl)piperidin-1-yl)-1-(2-methoxyethyl)-5-nitro-1H-indazole (300 mg) and further elution with ethyl acetate in hexane gave 6-(4-(((tert-butyldimethylsilyl)oxy)methyl) piperidin-1-yl)-2-(2-methoxyethyl)-5-nitro-2H-indazole (220 mg, 75.47%). LCMS: m/z=449.4 (M+1)$^+$.

Step-5: Synthesis of 6-(4-(((tert-butyldimethylsilyl)oxy)methyl)piperidin-1-yl)-1-(2-methoxyethyl)-1H-indazol-5-amine Using the same reaction conditions as described in step 2 of example 16, 6-(4-(((tert-butyldimethylsilyl)oxy)methyl)piperidin-1-yl)-1-(2-methoxyethyl)-5-nitro-1H-indazole (300 mg, 0.669 mmol) was reduced with zinc dust (342 mg, 5.357 mmol) and ammonium chloride (578 mg, 10.704 mmol) in THF/water (3/1 mL) to get the title compound (250 mg, 89.28%). LCMS: m/z=419.2 (M+1)$^+$.

Step-6: Synthesis of N-(6-(4-(((tert-butyldimethylsilyl)oxy)methyl)piperidin-1-yl)-1-(2-methoxyethyl)-1H-indazol-5-yl)-2-(2-methylpyridin-4-yl)oxazole-4-carboxamide Using the similar reagents and conditions as described in step 6 of example 5, 6-(4-(((tert-butyldimethylsilyl)oxy)methyl)piperidin-1-yl)-1-(2-methoxyethyl)-1H-indazol-5-amine (208 mg, 0.490 mmol) was coupled with 2-(2-methylpyridin-4-yl)oxazole-4-carboxylic acid (100 mg, 0.490 mmol) using HATU (279 mg, 0.735 mmol) and DIPEA (0.16 mL, 0.98 mmol) in DMF (2 mL) to get the desired compound (250 mg, 86.2%). LCMS: m/z=605.5 (M+1)$^+$.

Step-7: Synthesis of N-(6-(4-(hydroxymethyl)piperidin-1-yl)-1-(2-methoxyethyl)-1H-indazol-5-yl)-2-(2-methylpyridin-4-yl)oxazole-4-carboxamide Using the same reagents and conditions as described in step 8 of example 1, N-(6-(4-(((tert-butyldimethylsilyl)oxy)methyl)piperidin-1-yl)-1-(2-methoxyethyl)-1H-indazol-5-yl)-2-(2-methylpyridin-4-yl)oxazole-4-carboxamide (250 mg, 0.413 mmol) was deprotected using methanolic HCl/methanol (5/5 mL). This was purified by combiflash and elution with 6% methanol in DCM gave title compound (60 mg, 29.7%).
$^1$HNMR (DMSO-d$_6$, 400 MHz): δ 10.20 (s, 1H), 9.06 (s, 1H), 8.71 (s, 1H), 8.69-8.68 (d, 1H), 8.03 (s, 1H), 7.83-7.81 (d, 2H), 7.58 (s, 1H), 4.68-4.65 (t, 1H), 4.55-4.52 (t, 2H), 3.76-3.73 (t, 2H), 3.48-3.46 (t, 2H), 3.20 (s, 3H), 3.12-3.09 (d, 2H), 2.83-2.78 (t, 2H), 2.60 (s, 3H), 1.91-1.89 (d, 2H), 1.17-1.64 (m, 3H). LCMS: 99.32%, m/z=491.4 (M+1)$^+$. HPLC: 96.86%.

Example 95

(S)—N-(6-(4-(hydroxymethyl)piperidin-1-yl)-1-methyl-1H-indazol-5-yl)-6-(1-(2-hydroxypropyl)-1H-pyrazol-4-yl)picolinamide

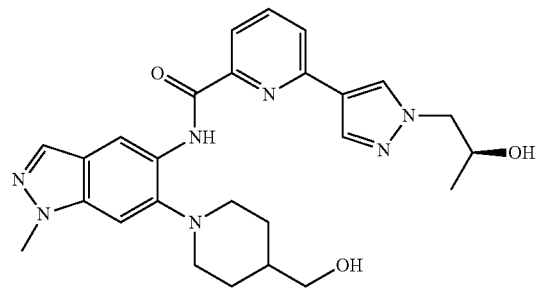 [SMILES: C[C@H](O)Cn1cc(-c2cccc(C(=O)Nc3cc4cnn(C)c4cc3N3CCC(CO)CC3)n2)cn1]

Step-1: Synthesis of 6-bromo-N-(6-(4-(((tert-butyldimethylsilyl)oxy)methyl)piperidin-1-yl)-1-methyl-1H-indazol-5-yl)picolinamide Using the similar reagents and conditions as described in step 6 of example 5, 6-(4-(((tert-butyldimethylsilyl)oxy)methyl)piperidin-1-yl)-1-methyl-1H-indazol-5-amine (product of step 3 of example 89) (180 mg, 0.495 mmol) was coupled with 6-bromopicolinic acid (100 mg, 0.495 mmol)

Step-2: Synthesis of N-(6-(4-(((tert-butyldimethylsilyl)oxy)methyl)piperidin-1-yl)-1-methyl-1H-indazol-5-yl)-6-(1-(tetrahydro-2H-pyran-2-yl)-1H-pyrazol-4-yl)picolinamide Using the same reagents and conditions as described in step 1 of example 6, 6-bromo-N-(6-(4-(((tert-butyldimethylsilyl)oxy)methyl)piperidin-1-yl)-1-methyl-1H-indazol-5-yl)picolinamide (150 mg, 0.259 mmol) was coupled with 1-(tetrahydro-2H-pyran-2-yl)-4-(4,4,5,5-tetramethyl-1,3,2-dioxaborolan-2-yl)-1H-pyrazole (110 mg, 0.395 mmol) using Pd(dppf)Cl$_2$ (19 mg, 0.025 mmol) and sodium carbonate (83 mg, 0.783 mmol) in DME/H$_2$O (5/1 mL) at 90° C. for 2 h to obtain title product (80 mg, 47.33%). LCMS: m/z=630.5 (M+1)$^+$.

Step-3: Synthesis of N-(6-(4-(hydroxymethyl)piperidin-1-yl)-1-methyl-1H-indazol-5-yl)-6-(1H-pyrazol-4-yl)picolinamide hydrochloride Using the same reaction conditions as described in step 8 of example 1, N-(6-(4-(((tert-butyldimethylsilyl)oxy)methyl)piperidin-1-yl)-1-methyl-1H-indazol-5-yl)-6-(1-(tetrahydro-2H-pyran-2-yl)-1H-pyrazol-4-yl)picolinamide (80 mg, 0.127 mmol) was deprotected using methanolic HCl (1 mL) in methanol (1 mL) to get the crude title compound (60 mg). LCMS: m/z=432.4 (M+1)$^+$.

Step-4: Synthesis of (S)—N-(6-(4-(hydroxymethyl)piperidin-1-yl)-1-methyl-1H-indazol-5-yl)-6-(1-(2-hydroxypropyl)-1H-pyrazol-4-yl)picolinamide Using the same reagents and conditions as described in example 34, N-(6-(4-(hydroxymethyl)piperidin-1-yl)-1-methyl-1H-indazol-5-yl)-6-(1H-pyrazol-4-yl)picolinamide hydrochloride (60 mg, 0.139 mmol) was substituted with (S)-2-methyloxirane (16 mg, 0.278 mmol) using sodium carbonate (73 mg, 0.6960 mmol) in DMF (1 mL) at 90° C. for 16 h to get the title compound (25 mg, 36.76%).
$^1$HNMR (CDCl$_3$, 400 MHz): δ 10.97 (s, 1H), 8.48 (s, 1H), 8.22 (s, 1H), 8.19-8.17 (d, 1H), 8.04 (s, 1H), 7.94-7.90 (m, 2H), 7.61-7.59 (d, 1H), 7.08 (s, 1H), 4.40-4.20 (m, 3H), 4.06-4.00 (m, 4H), 3.50-3.40 (m, 3H), 3.35-3.20 (m, 3H), 1.85-1.75 (m, 3H), 1.40-1.20 (m, 3H). LCMS: 97.88%, m/z=490.3 (M+1)$^+$. HPLC: 96.54%.

Step-1: Synthesis of 6-(4-(((tert-butyldimethylsilyl)oxy)methyl)piperidin-1-yl)-2-(2-methoxyethyl)-2H-indazol-5-amine Using the same reaction conditions as described in step 2 of example 16, 6-(4-(((tert-butyldimethylsilyl)oxy)methyl)piperidin-1-yl)-2-(2-methoxyethyl)-5-nitro-2H-indazole (product of step 4 of example 94) (220 mg, 0.4910 mmol) was reduced with zinc dust (251 mg, 3.928 mmol) and ammonium chloride (424 mg, 7.984 mmol) in THF/water (3/1 mL) to get the title compound (210 mg, 99.1%). LCMS: m/z=419.2 (M+1)$^+$.

Step-2: Synthesis of N-(6-(4-(((tert-butyldimethylsilyl)oxy)methyl)piperidin-1-yl)-2-(2-methoxyethyl)-2H-indazol-5-yl)-2-(2-methylpyridin-4-yl)oxazole-4-carboxamide Using the same reagents and conditions as described in step 6 of example 5, 6-(4-(((tert-butyldimethylsilyl)oxy)methyl)piperidin-1-yl)-2-(2-methoxyethyl)-2H-indazol-5-amine (208 mg, 0.490 mmol) was coupled with 2-(2-methylpyridin-4-yl)oxazole-4-carboxylic acid (100 mg, 0.490 mmol) using HATU (279 mg, 0.735 mmol) and DIPEA (0.16 mL, 0.98 mmol) in DMF (3 mL) to get the title compound (200 mg, 68.96%). LCMS: m/z=605.5 (M+1)$^+$.

Step-3: Synthesis of N-(6-(4-(hydroxymethyl)piperidin-1-yl)-2-(2-methoxyethyl)-2H-indazol-5-yl)-2-(2-methylpyridin-4-yl)oxazole-4-carboxamide Using the same reagents and conditions as described in step 8 of example 1, N-(6-(4-(((tert-butyldimethylsilyl)oxy)methyl)piperidin-1-yl)-2-(2-methoxyethyl)-2H-indazol-5-yl)-2-(2-methylpyridin-4-yl)oxazole-4-carboxamide (200 mg, 0.331 mmol) was deprotected using methanolic HCl/methanol (1/0.5 mL) This was purified by combiflash and elution with 6% methanol in DCM gave title compound (60 mg, 37.03%).
$^1$HNMR (CDCl$_3$, 400 MHz): δ 10.30 (s, 1H), 8.78 (, 1H), 8.68-8.67 (d, 1H), 8.40 (s, 1H), 7.95 (s, 1H), 7.81 (s, 1H), 7.78-7.77 (s, 1H), 7.44 (s, 1H), 4.55-4.53 (t, 2H), 3.88-3.85 (t, 2H), 3.70 (s, 2H), 2.90 (s, 3H), 3.25-3.22 (d, 2H), 3.40-3.30 (t, 2H), 2.69 (s, 3H), 2.05-1.97 (m, 2H), 1.90-1.70 (m, 3H), 1.60-1.50 (m, 1H). LCMS: 95.86%, m/z=491.4 (M+1)$^+$. HPLC: 95.33%.

Example 96

N-(6-(4-(hydroxymethyl)piperidin-1-yl)-2-(2-methoxyethyl)-2H-indazol-5-yl)-2-(2-methylpyridin-4-yl)oxazole-4-carboxamide

Example 97

N-(6-(4-(hydroxymethyl)piperidin-1-yl)-2-methyl-2H-indazol-5-yl)-2-(2-methoxypyridin-4-yl)oxazole-4-carboxamide

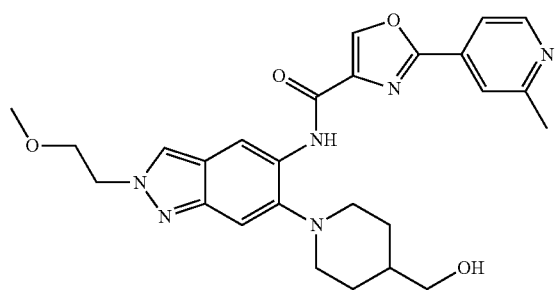

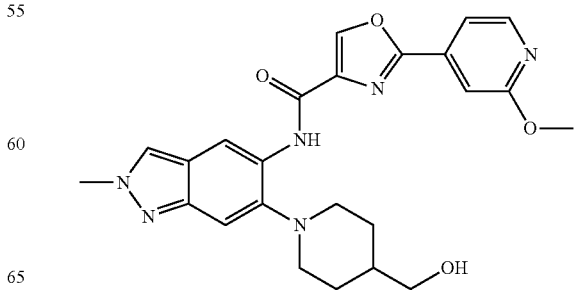

123

Step-1: Synthesis of N-(6-(4-(((tert-butyldimethylsilyl)oxy)methyl)piperidin-1-yl)-2-methyl-2H-indazol-5-yl)-2-(2-methoxypyridin-4-yl)oxazole-4-carboxamide

Using the same reagents and conditions as described in step 7 of example 1, 6-(4-(((tert-butyldimethylsilyl)oxy)methyl)piperidin-1-yl)-2-methyl-2H-indazol-5-amine (product of step 4 of example 80) (135 mg, 0.363 mmol) was coupled with 2-(2-methoxypyridin-4-yl)oxazole-4-carboxylic acid (80 mg, 0.363 mmol) using HATU (207 mg, 0.545 mmol) and DIPEA (93 mg, 0.726 mmol) in DMF (1 mL) to get the title compound (150 mg, 71%).

Step-2: Synthesis of N-(6-(4-(hydroxymethyl)piperidin-1-yl)-2-methyl-2H-indazol-5-yl)-2-(2-methoxypyridin-4-yl)oxazole-4-carboxamide

Using the same reaction conditions as described in step 7 of example 58, N-(6-(4-(((tert-butyldimethylsilyl)oxy)methyl)piperidin-1-yl)-2-methyl-2H-indazol-5-yl)-2-(2-methoxypyridin-4-yl)oxazole-4-carboxamide (150 mg, 0.26 mmol) was deprotected using TBAF/THF (1/1 mL) at RT for 2 h to get the title compound (80 mg, 66.63%).

$^1$HNMR (DMSO-$d_6$, 400 MHz): δ 10.33 (s, 1H), 9.04 (s, 1H), 8.65 (s, 1H), 8.42-8.40 (d, 1H), 8.27 (s, 1H), 7.63-7.62 (d, 1H), 7.42 (s, 1H), 7.35 (s, 1H), 4.63-4.60 (t, 1H), 4.12 (s, 3H), 3.95 (s, 3H), 3.47 (s, 2H), 3.09-3.07 (d, 2H), 2.79-2.74 (t, 2H), 1.893 (s, 2H), 1.63 (s, 3H). LCMS: 97.03%, m/z=463.2 (M+1)$^+$. HPLC: 97.28%.

Example 98

2-(2-acetamidopyridin-4-yl)-N-(6-(4-(hydroxymethyl)piperidin-1-yl)-2-methyl-2H-indazol-5-yl)oxazole-4-carboxamide

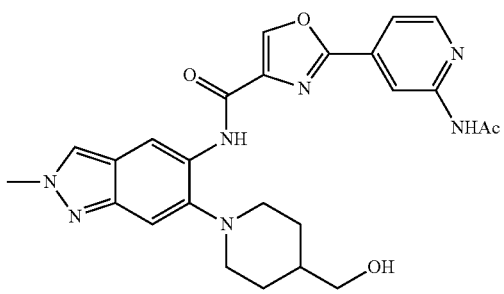 [SMILES: CC(=O)Nc1cc(-c2nc(C(=O)Nc3cc4cn(C)nc4cc3N3CCC(CO)CC3)co2)ccn1]

Step-1: Synthesis of 2-(2-acetamidopyridin-4-yl)-N-(6-(4-(((tert-butyldimethylsilyl)oxy)methyl)piperidin-1-yl)-2-methyl-2H-indazol-5-yl)oxazole-4-carboxamide

Using the same reagents and conditions as described in step 6 of example 5, 6-(4-(((tert-butyldimethylsilyl)oxy)methyl)piperidin-1-yl)-2-methyl-2H-indazol-5-amine (product of step 4 of example 80) (100 mg, 0.2673 mmol) was coupled with 2-(2-acetamidopyridin-4-yl)oxazole-4-carboxylic acid (intermediate 13) (79 mg, 0.320 mmol) using HATU (152 mg, 0.401 mmol) and DIPEA (0.2 mL, 1.0695 mmol) in DMF (5 mL) to get the desired compound (100 mg, 62%). LCMS: m/z=604.4 (M+1)$^+$.

124

Step-2: Synthesis of 2-(2-acetamidopyridin-4-yl)-N-(6-(4-(hydroxymethyl)piperidin-1-yl)-2-methyl-2H-indazol-5-yl)oxazole-4-carboxamide

Using the same reaction conditions as described in step 7 of example 58, 2-(2-acetamidopyridin-4-yl)-N-(6-(4-(((tert-butyldimethylsilyl)oxy)methyl)piperidin-1-yl)-2-methyl-2H-indazol-5-yl)oxazole-4-carboxamide (100 mg, 0.1658 mmol) was deprotected using TBAF in THF (1/4 mL) at RT for 2 h to get the title compound (20 mg, 25%).

$^1$HNMR (DMSO-$d_6$, 400 MHz): δ 10.84 (s, 1H), 10.28 (s, 1H), 9.05 (s, 1H), 8.75 (s, 1H), 8.65 (s, 1H), 8.54-8.53 (d, 1H), 8.28 (s, 1H), 7.76-7.74 (d, 1H), 7.41 (s, 1H), 4.60-4.57 (t, 1H), 4.12 (s, 3H), 3.5-3.424 (t, 2H), 3.10-3.07 (d, 2H), 2.78-2.72 (t, 2H), 2.15 (s, 3H), 2.03-2.01 (m, 1H), 1.88-1.85 (d, 2H), 1.68-1.63 (m, 2H). LCMS: 93.87%, m/z=490.4 (M+1)$^+$. HPLC: 92.72%.

Example 99

2-(2-aminopyridin-4-yl)-N-(6-(4-(hydroxymethyl)piperidin-1-yl)-1-methyl-1H-indazol-5-yl)oxazole-4-carboxamide hydrochloride

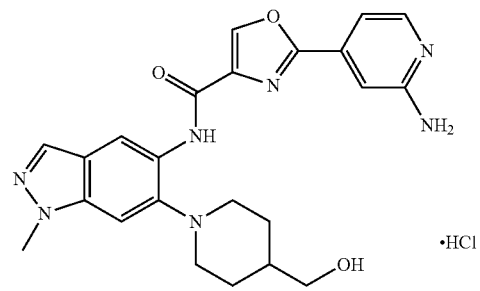 [SMILES: Cn1ncc2cc(NC(=O)c3coc(-c4ccnc(N)c4)n3)c(N3CCC(CO)CC3)cc21 ; Cl]

Step-1: Synthesis of 2-(2-aminopyridin-4-yl)-N-(6-(4-(((tert-butyldimethylsilyl)oxy)methyl)piperidin-1-yl)-1-methyl-1H-indazol-5-yl)oxazole-4-carboxamide

Using the same reagents and conditions as described in step 7 of example 1, 6-(4-(((tert-butyldimethylsilyl)oxy)methyl)piperidin-1-yl)-1-methyl-1H-indazol-5-amine (product of step 3 of example 89) (100 mg, 0.3208 mmol) was coupled with 2-(2-aminopyridin-4-yl)oxazole-4-carboxylic acid (intermediate 14) (66 mg, 0.3208 mmol) using HATU (152 mg, 0.401 mmol) and DIPEA (0.2 mL, 1.0695 mmol) in DMF (5 mL) to obtain the desired compound (100 mg, 68%). LCMS: m/z=562.4 (M+1)$^+$.

Step-2: Synthesis of 2-(2-aminopyridin-4-yl)-N-(6-(4-(hydroxymethyl)piperidin-1-yl)-1-methyl-1H-indazol-5-yl)oxazole-4-carboxamide hydrochloride

Using the same reagents and conditions as described in step 8 of example 1, 2-(2-aminopyridin-4-yl)-N-(6-(4-(((tert-butyldimethylsilyl)oxy)methyl)piperidin-1-yl)-1-methyl-1H-indazol-5-yl)oxazole-4-carboxamide (100 mg, 0.1782 mmol) was deprotected using methanolic HCl/methanol (0.5/2 mL) to get the title compound (50 mg, 64%).

$^1$H NMR (DMSO-$d_6$, 400 MHz): δ 10.15 (s, 1H), 9.17 (s, 1H), 8.73 (s, 1H), 8.40-8.20 (bs, 2H), 8.14-8.13 (d, 1H), 8.10

(s, 1H), 7.56 (s, 1H), 7.53 (s, 1H), 7.39-7.37 (dd, 1H), 4.03 (s, 3H), 3.49-3.44 (m, 3H), 3.13-3.10 (d, 2H), 2.85-2.80 (t, 2H), 1.85-1.62 (m, 5H). LCMS: 97.35%, m/z=448.4 (M+1)⁺. HPLC: 98.10%.

Example 100

2-(2-aminopyridin-4-yl)-N-(6-(4-(hydroxymethyl)piperidin-1-yl)-2-methyl-2H-indazol-5-yl)oxazole-4-carboxamide hydrochloride

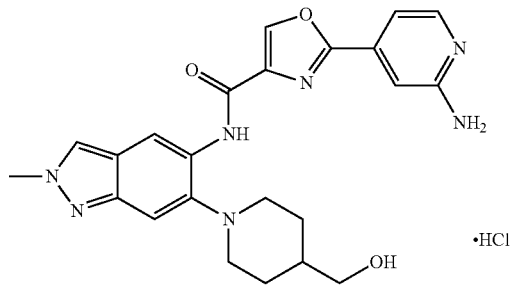 [SMILES: Cn1cc2cc(NC(=O)c3coc(-c4ccnc(N)c4)n3)c(N3CCC(CO)CC3)cc2n1 ; Cl]

Step-1: Synthesis of 2-(2-aminopyridin-4-yl)-N-(6-(4-(((tert-butyldimethylsilyl)oxy)methyl)piperidin-1-yl)-2-methyl-2H-indazol-5-yl)oxazole-4-carboxamide Using the same reagents and conditions as described in step 6 of example 5, 6-(4-(((tert-butyldimethylsilyl)oxy)methyl)piperidin-1-yl)-2-methyl-2H-indazol-5-amine (product of step 4 of example 80) (100 mg, 0.2673 mmol) was coupled with 2-(2-aminopyridin-4-yl)oxazole-4-carboxylic acid (intermediate 14) (66 mg, 0.3208 mmol) using HATU (152 mg, 0.401 mmol) and DIPEA (0.2 mL, 1.0695 mmol) in DMF (4 mL) to obtain the desired compound (100 mg, 68%). m/z=562.4 (M+1)⁺.

Step-2: Synthesis of 2-(2-aminopyridin-4-yl)-N-(6-(4-(hydroxymethyl)piperidin-1-yl)-2-methyl-2H-indazol-5-yl)oxazole-4-carboxamide hydrochloride Using the same reagents and conditions as described in step 7 of example 58, 2-(2-aminopyridin-4-yl)-N-(6-(4-(((tert-butyldimethylsilyl)oxy)methyl)piperidin-1-yl)-2-methyl-2H-indazol-5-yl)oxazole-4-carboxamide (100 mg, 0.1782 mmol) was deprotected using TBAF in THF (1/4 mL) to get the title compound (20 mg, 26%).

¹HNMR (CD₃OD, 400 MHz): δ 8.88 (s, 1H), 8.55 (s, 1H), 8.06-8.04 (d, 1H), 7.79 (s, 1H), 7.56-7.55 (d, 2H), 4.32 (s, 3H), 3.66 (s, 2H), 3.20-2.70 (m, 4H), 2.10-1.70 (m, 5H). LCMS: 99.21%, m/z=448.4 (M+1)⁺. HPLC: 95.06%.

Example 101

N-(6-(4-hydroxypiperidin-1-yl)-1-methyl-1H-indazol-5-yl)-2-(2-methoxypyridin-4-yl)oxazole-4-carboxamide

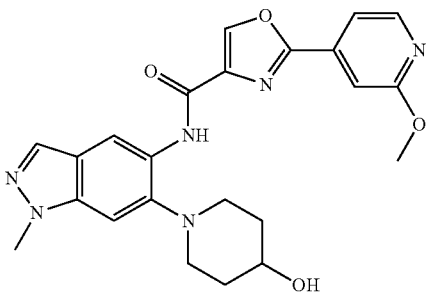 [SMILES: COc1cc(-c2nc(C(=O)Nc3cc4cnn(C)c4cc3N3CCC(O)CC3)co2)ccn1]

Step-1: Synthesis of N-(6-(4-((tert-butyldimethylsilyl)oxy)piperidin-1-yl)-1-methyl-1H-indazol-5-yl)-2-(2-methoxypyridin-4-yl)oxazole-4-carboxamide Using the same reagents and conditions as described in step 6 of example 5, 6-(4-((tert-butyldimethylsilyl)oxy)piperidin-1-yl)-1-methyl-1H-indazol-5-amine (product of step 1 of example 77) (100 mg, 0.2777 mmol) was coupled with 2-(2-methoxypyridin-4-yl)oxazole-4-carboxylic acid (74 mg, 0.333 mmol) using HATU (158 mg, 0.416 mmol) and DIPEA (0.2 mL, 1.1111 mmol) in DMF (5 mL) to get the crude product. This was purified by silica gel column chromatography and elution with 50% ethyl acetate in hexane gave title compound (120 mg, 77%). LCMS: m/z=563.4 (M+1)⁺.

Step-2: Synthesis of N-(6-(4-hydroxypiperidin-1-yl)-1-methyl-1H-indazol-5-yl)-2-(2-methoxypyridin-4-yl)oxazole-4-carboxamide Using the same reaction conditions as described in step 7 of example 58, N-(6-(4-((tert-butyldimethylsilyl)oxy)piperidin-1-yl)-1-methyl-1H-indazol-5-yl)-2-(2-methoxypyridin-4-yl)oxazole-4-carboxamide (120 mg, 0.2135 mmol) was deprotected using TBAF in THF (1/4 mL) to get the title compound (80 mg, 85%).

¹H NMR (DMSO-d₆, 400 MHz): δ 10.25 (s, 1H), 9.06 (s, 1H), 8.70 (s, 1H), 8.41-8.40 (d, 1H), 8.01 (s, 1H), 7.63-7.62 (d, 1H), 7.57 (s, 1H), 7.35 (s, 1H), 4.89 (s, 1H), 4.03 (s, 3H), 3.95 (s, 3H), 3.13-3.11 (m, 2H), 2.87-2.825 (t, 2H), 2.10-2.00 (m, 2H), 1.90-1.80 (m, 2H). LCMS: 97.79%, m/z=449.4 (M+1)⁺. HPLC: 96.81%.

Example 102

2-(2-aminopyridin-4-yl)-N-(6-(3-hydroxypiperidin-1-yl)-2-methyl-2H-indazol-5-yl)oxazole-4-carboxamide hydrochloride

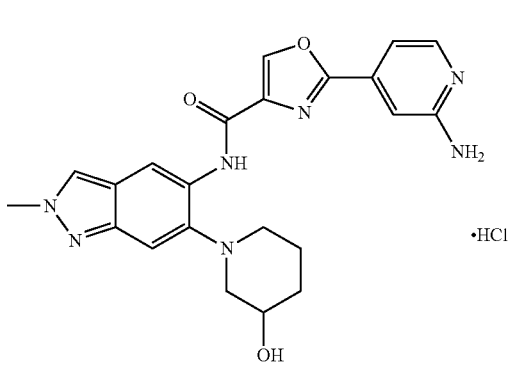 [SMILES: Cn1cc2cc(NC(=O)c3coc(-c4ccnc(N)c4)n3)c(N3CCCC(O)C3)cc2n1 ; Cl]

Step-1: Synthesis of 2-(2-aminopyridin-4-yl)-N-(6-(3-((tert-butyldimethylsilyl)oxy)piperidin-1-yl)-2-methyl-2H-indazol-5-yl)oxazole-4-carboxamide Using the same reagents and conditions as described in step 6 of example 5, 6-(3-((tert-butyldimethylsilyl)oxy)piperidin-1-yl)-2-methyl-2H-indazol-5-amine (product of step 5 of example 68) (200 mg, 0.554 mmol) was coupled with 2-(2-aminopyridin-4-yl)oxazole-4-carboxylic acid (intermediate 14) (137 mg, 0.665 mmol) using HATU (316 mg, 0.832 mmol) and DIPEA (286 mg, 2.21 mmol) in DMF (10 mL) to obtain the desired compound (100 mg, 33%). LCMS: m/z=547.8 (M+1)$^+$.

Step-2: Synthesis of 2-(2-aminopyridin-4-yl)-N-(6-(3-hydroxypiperidin-1-yl)-2-methyl-2H-indazol-5-yl)oxazole-4-carboxamide hydrochloride Using the same reagents and conditions as described in step 8 of example 1, 2-(2-aminopyridin-4-yl)-N-(6-(3-((tert-butyldimethylsilyl)oxy)piperidin-1-yl)-2-methyl-2H-indazol-5-yl)oxazole-4-carboxamide (100 mg, 0.08) was deprotected using methanolic HCl/methanol (5/5 mL to get the title compound (41 mg, 51.9%).

$^1$HNMR (DMSO-d$_6$, 400 MHz): δ 10.17 (s, 1H), 9.16 (s, 1H), 8.60 (s, 1H), 8.55-8.20 (m, 4H), 7.52 (s, 1H), 7.39 (s, 1H), 7.31-730 (d, 1H), 4.11 (s, 3H), 4.00-3.99 (m, 1H), 3.10-3.09 (m, 1H), 2.95-2.85 (m, 1H), 2.75-2.55 (m, 2H), 2.03-1.79 (m, 3H), 1.45-1.35 (m, 1H). LCMS: 98.17%, m/z=434.3 (M+1)$^+$. HPLC: 97.10%.

Example 103

2-(2-methoxypyridin-4-yl)-N-(2-methyl-6-(piperidin-1-yl)-2H-indazol-5-yl)oxazole-4-carboxamide

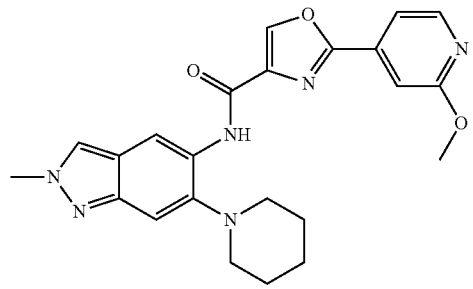 [SMILES: COc1cc(-c2nc(C(=O)Nc3cc4cn(C)nc4cc3N3CCCCC3)co2)ccn1]

Using the same reagents and conditions as described in step 7 of example 1, 2-methyl-6-(piperidin-1-yl)-2H-indazol-5-amine (product of step 6 of example 1) (90 mg, 0.391 mmol) was coupled with 2-(2-methoxypyridin-4-yl)oxazole-4-carboxylic acid (86 mg, 0.391 mmol) using HATU (223 mg, 0.586 mmol) and DIPEA (201 mg, 1.56 mmol) in DMF (8 mL) to get the title compound (60 mg, 37.5%).

$^1$HNMR (DMSO-d$_6$, 400 MHz): δ 10.40 (s, 1H), 9.06 (s, 1H), 8.63 (s, 1H), 8.46-8.45 (d, 1H), 8.28 (s, 1H), 7.57-7.55 (dd, 1H), 7.41 (s, 1H), 7.36 (s, 1H), 4.12 (s, 3H), 3.95 (s, 3H), 2.89 (s, 4H), 1.90-1.88 (t, 4H), 1.68 (s, 2H). LCMS: 99.88%, m/z=433.1 (M+1)$^+$. HPLC: 99.71%.

Example 104

2-(2-aminopyridin-4-yl)-N-(6-(3-fluoropiperidin-1-yl)-2-methyl-2H-indazol-5-yl)oxazole-4-carboxamide hydrochloride

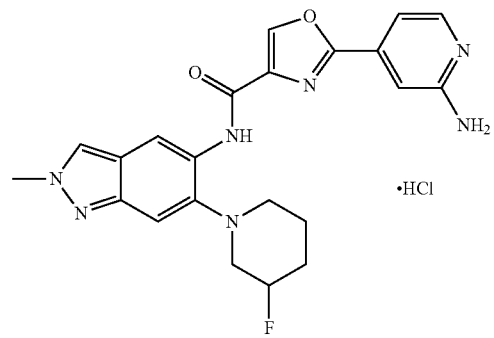 [SMILES: Cn1cc2cc(NC(=O)c3coc(-c4ccnc(N)c4)n3)c(N3CCCC(F)C3)cc2n1 ; Cl]

Using the same reagents and conditions as described in step 6 of example 5, 6-(3-fluoropiperidin-1-yl)-2-methyl-2H-indazol-5-amine (product of step 3 of example 79) (150 mg, 0.604 mmol) was coupled with 2-(2-aminopyridin-4-yl)oxazole-4-carboxylic acid (intermediate 14) (137 mg, 0.665 mmol) using HATU (344 mg, 0.905 mmol) and DIPEA (312 mg, 2.41 mmol) in DMF (10 mL) and further treated with methanolic HCl/methanol (5/5 mL) to obtain the desired compound (120 mg, 46.1%).

$^1$HNMR (DMSO-d$_6$, 400 MHz): δ 10.23 (s, 1H), 9.16 (s, 1H), 8.65 (s, 1H), 8.60-80.40 (bs, 2H), 8.31 (s, 1H), 8.23-8.21 (d, 1H), 7.52-7.48 (m, 2H), 7.35-7.33 (d, 1H), 7.04-4.93

(m, 1H), 4.13 (s, 3H), 3.30-3.11 (m, 2H), 2.85 (s, 2H), 2.12-1.78 (m, 5H). LCMS: 96.30%, m/z=436.4 (M+1)$^+$. HPLC: 94.39%.

Example 105

(R)-2-(2-aminopyridin-4-yl)-N-(6-(3-hydroxypyrrolidin-1-yl)-2-methyl-2H-indazol-5-yl)oxazole-4-carboxamide hydrochloride

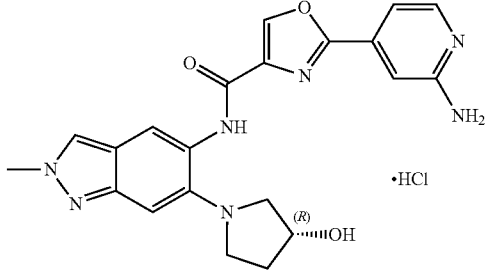

Step-1: Synthesis of (R)-2-(2-aminopyridin-4-yl)-N-(6-(3-((tert-butyldimethylsilyl)oxy)pyrrolidin-1-yl)-2-methyl-2H-indazol-5-yl)oxazole-4-carboxamide Using the same reagents and conditions as described in step 6 of example 5, (R)-6-(3-((tert-butyldimethylsilyl)oxy)pyrrolidin-1-yl)-2-methyl-2H-indazol-5-amine (product of step 3 of example 65) (100 mg, 0.2885 mmol) was coupled with 2-(2-aminopyridin-4-yl)oxazole-4-carboxylic acid (intermediate 14) (71 mg, 0.3462 mmol) using HATU (143 mg, 0.3751 mmol) and DIPEA (150 mg, 1.1542 mmol) in DMF (2 mL) to get the desired compound (100 mg crude). LCMS: m/z=534.3 (M+1)$^+$.

Step-2: Synthesis of (R)-2-(2-aminopyridin-4-yl)-N-(6-(3-hydroxypyrrolidin-1-yl)-2-methyl-2H-indazol-5-yl)oxazole-4-carboxamide hydrochloride Using the same reaction conditions as described in step 8 of example 1, (R)-2-(2-aminopyridin-4-yl)-N-(6-(3-((tert-butyldimethylsilyl)oxy)pyrrolidin-1-yl)-2-methyl-2H-indazol-5-yl)oxazole-4-carboxamide (150 mg, 0.083) was deprotected using methanolic HCl/methanol (4/3 mL), purified with prep HPLC and treated with methanolic HCl to get the title compound (20 mg, 55%).

$^1$H NMR (DMSO-d$_6$, 400 MHz): δ 9.97 (s, 1H), 9.14 (s, 1H), 8.37 (s, 1H), 8.25 (s, 1H), 8.14-8.13 (d, 1H), 7.52 (s, 1H), 7.41-7.40 (d, 1H), 7.28 (s, 1H), 4.50-4.40 (m, 1H), 4.10 (s, 3H), 3.10-2.95 (m, 3H), 2.25-2.15 (m, 2H), 2.00-1.80 (m, 2H). LCMS: 97.70%, m/z=420.3 (M+1)$^+$. HPLC: 98.60%.

Example 106

1-(1,3-dimethyl-5-(2-(2-methylpyridin-4-yl)oxazole-4-carboxamido)-1H-indazol-6-yl)piperidin-4-yl 2-methoxyacetate

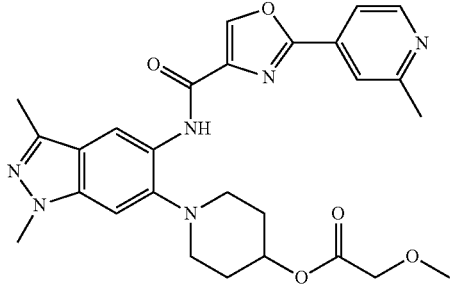 [SMILES: COCC(=O)OC1CCN(c2cc3c(cc2NC(=O)c2coc(-c4ccnc(C)c4)n2)c(C)nn3C)CC1]

To the solution of N-(6-(4-hydroxypiperidin-1-yl)-1,3-dimethyl-1H-indazol-5-yl)-2-(2-methylpyridin-4-yl)oxazole-4-carboxamide (example 81) (39 mg, 0.087 mmol) in DCM (5 mL) was added TEA (18 mg, 0.1747 mmol) and DMAP (1 mg, 0.008 mmol) and 2-methoxyacetyl chloride (14 mg, 0.1310 mmol) and stirred at RT for 16 h. Reaction mass was quenched with water and extracted with DCM to get the crude product. The obtained crude was purified by prep TLC using 6% methanol in chloroform as eluent to obtain the title compound (33 mg, 73.33%).

$^1$HNMR (CDCl$_3$, 300 MHz): δ 10.20 (s, 1H), 8.77 (s, 1H), 8.71-8.69 (d, 1H), 8.41 (s, 1H), 7.81 (s, 1H), 7.76-7.74 (d, 1H), 7.07 (s, 1H), 5.20 (s, 1H), 4.10 (s, 2H), 3.98 (s, 3H), 3.48 (s, 3H), 3.22-3.18 (m, 2H), 3.00-2.97 (m, 2H), 2.69 (s, 3H), 2.56 (s, 3H), 2.26-2.15 (m, 4H). LCMS: 93.14%, m/z=519.4 (M+1)$^+$. HPLC: 95.55%.

Example 107

N-(6-(4-hydroxypiperidin-1-yl)-2-methyl-2H-indazol-5-yl)-2-(2-methoxypyridin-4-yl)oxazole-4-carboxamide hydrochloride

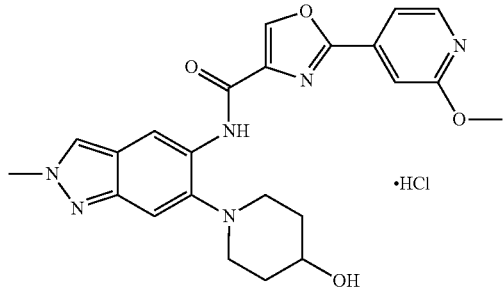

Step-1: Synthesis of N-(6-(4-((tert-butyldimethylsilyl)oxy)piperidin-1-yl)-2-methyl-2H-indazol-5-yl)-2-(2-methoxypyridin-4-yl)oxazole-4-carboxamide Using the same reagents and conditions as described in step 6 of example 5, 6-(4-((tert-butyldimethylsilyl)oxy)piperidin-1-yl)-2-methyl-2H-indazol-5-amine (product of step 5 of example 58) (100 mg, 0.277 mmol) was coupled with 2-(2-methoxypyridin-4-yl)oxazole-4-carboxylic acid (73 mg, 0.333 mmol) using HATU (137 mg, 0.361 mmol) and DIPEA (144 mg, 1.11 mmol) in DMF (5 mL) to afford the title compound (100 mg, 64.10%). LCMS: m/z=563.4 (M+1)$^+$.

Step-2: Synthesis of N-(6-(4-hydroxypiperidin-1-yl)-2-methyl-2H-indazol-5-yl)-2-(2-methoxypyridin-4-yl)oxazole-4-carboxamide hydrochloride Using the same reaction conditions as described in step 7 of example 58, N-(6-(4-((tert-butyldimethylsilyl)oxy)piperidin-1-yl)-2-methyl-2H-indazol-5-yl)-2-(2-methoxypyridin-4-yl)oxazole-4-carboxamide (100 mg, 0.1779 mmol) was deprotected using TBAF (69 mg) in THF (5 mL) to get the title compound (15 mg, 18.98%).

$^1$HNMR (DMSO-d$_6$, 400 MHz): δ 10.34 (s, 1H), 9.05 (s, 1H), 8.63 (s, 1H), 8.41-8.39 (d, 1H), 8.28 (s, 1H), 7.65-7.63 (d, 1H), 7.41-7.36 (d, 2H), 4.88 (s, 1H), 4.12 (s, 3H), 3.95 (s, 3H), 3.07-3.04 (m, 2H), 2.83-2.79 (t, 2H), 2.05-1.95 (m, 2H), 1.87-1.84 (m, 2H). LCMS: 100%, m/z=449.3 (M+1)$^+$. HPLC: 95.11%.

Example 108

N-(6-(4-aminopiperidin-1-yl)-1-(2-methoxyethyl)-1H-indazol-5-yl)-2-(2-methylpyridin-4-yl)oxazole-4-carboxamide hydrochloride

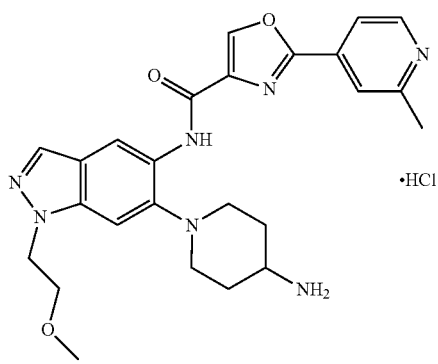 [SMILES: COCCn1ncc2cc(NC(=O)c3coc(-c4ccnc(C)c4)n3)c(N3CCC(N)CC3)cc21 ; Cl]

Step-1: Synthesis of tert-butyl (1-(5-fluoro-4-formyl-2-nitrophenyl)piperidin-4-yl)carbamate Using the similar reagents and conditions as described in step 1 of example 58, 2,4-difluoro-5-nitrobenzaldehyde (6 gm, 32.0 mmol) was substituted with tert-butyl piperidin-4-ylcarbamate (7.05 g, 35.2 mmol) using potassium carbonate (6.65 g, 48.1 mmol) in DMF (60 mL) at RT for 2 h to get the title compound (14 g, crude).

Step-2: Synthesis of tert-butyl (1-(5-nitro-1H-indazol-6-yl)piperidin-4-yl)carbamate Using the similar reagents and conditions as described in step 2 of example 5, tert-butyl (1-(5-fluoro-4-formyl-2-nitrophenyl)piperidin-4-yl)carbamate (14 g, 38.1 mmol) was cyclized using 50% hydrazine hydrate (3.81 g, 76.2 mmol) in THF (140 mL) at 60° C. for 1 h to get the title compound (15 g, crude). LCMS: m/z=362.3 (M+1)$^+$.

Step-3: Synthesis of tert-butyl (1-(1-(2-methoxyethyl)-5-nitro-1H-indazol-6-yl)piperidin-4-yl)carbamate and tert-butyl (1-(2-(2-methoxyethyl)-5-nitro-2H-indazol-6-yl)piperidin-4-yl)carbamate Using the same reagents and conditions as described in step 5 of example 1, tert-butyl (1-(5-nitro-1H-indazol-6-yl)piperidin-4-yl)carbamate (1.5 g, 4.15 mmol) was alkylated using sodium hydride (209 mg, 8.72 mmol) and 1-bromo-2-methoxyethane (1.44 g, 10.3 mmol) in THF (20 mL) at 60° C. for 5 h to get the crude product. This was purified by silica gel column chromatography and elution with 30% ethyl acetate in hexane gave tert-butyl (1-(1-(2-methoxyethyl)-5-nitro-1H-indazol-6-yl)piperidin-4-yl)carbamate (400 mg) and further elution with ethyl acetate in hexane gave tert-butyl (1-(2-(2-methoxyethyl)-5-nitro-2H-indazol-6-yl)piperidin-4-yl)carbamate (310 mg, %). LCMS: m/z=420.3 (M+1)$^+$.

Step-4: Synthesis of tert-butyl (1-(5-amino-1-(2-methoxyethyl)-1H-indazol-6-yl)piperidin-4-yl)carbamate Using the same reaction conditions as described in step 2 of example 16, tert-butyl (1-(1-(2-methoxyethyl)-5-nitro-1H-indazol-6-yl)piperidin-4-yl)carbamate (400 mg, 0.9546 mmol) was reduced with zinc dust (416 mg, 7.6372 mmol) and ammonium chloride (820 mg, 15.2736 mmol) in THF/water (12/4 mL) to get the desired product (340 mg, 91.6%). LCMS: m/z=390.4 (M+1)$^+$.

Step-5: Synthesis of tert-butyl (1-(1-(2-methoxyethyl)-5-(2-(2-methylpyridin-4-yl)oxazole-4-carboxamido)-1H-indazol-6-yl)piperidin-4-yl)carbamate Using the similar reagents and conditions as described in step 6 of example 5, tert-butyl (1-(5-amino-1-(2-methoxyethyl)-1H-indazol-6-yl)piperidin-4-yl)carbamate (350 mg, 0.8997 mmol) was coupled with 2-(2-methylpyridin-4-yl)oxazole-4-carboxylic acid (180 mg, 0.8997 mmol) using HATU (512 mg, 1.3495 mmol) and DIPEA (0.29 mL, 1.7994 mmol) in DMF (6 mL) to get the desired compound (260 mg, 50.1%). LCMS: m/z=576.5 (M+1)$^+$.

Step-6: Synthesis of N-(6-(4-aminopiperidin-1-yl)-1-(2-methoxyethyl)-1H-indazol-5-yl)-2-(2-methylpyridin-4-yl)oxazole-4-carboxamide hydrochloride Using the same reaction conditions as described in step 8 of example 1, tert-butyl (1-(1-(2-methoxyethyl)-5-(2-(2-methylpyridin-4-yl)oxazole-4-carboxamido)-1H-indazol-6-yl)piperidin-4-yl)carbamate (150 mg, mmol) was deprotected using methanolic HCl/methanol (0.5/3 mL) This was purified by prep HPLC and treated with methanolic HCl to give title compound (22 mg, 40%).

$^1$HNMR (DMSO-d$_6$, 400 MHz): δ 9.70 (s, 1H), 9.17 (s, 1H), 8.84-8.83 (d, 1H), 8.73 (s, 1H), 8.30 (s, 3H), 8.06 (s, 3H), 7.57 (s, 1H), 4.56-4.53 (t, 2H), 3.78-3.75 (t, 2H), 3.25-3.21 (m, 5H), 2.93-2.87 (t, 2H), 2.71-2.68 (m, 4H), 2.19-2.17 (m, 2H), 2.04-2.01 (m, 2H). LCMS: 96.94%, m/z=476.4 (M+1)$^+$. HPLC: 97.83%.

Example 109

N-(6-(4-aminopiperidin-1-yl)-2-methyl-2H-indazol-5-yl)-2-(2-methylpyridin-4-yl)oxazole-4-carboxamide hydrochloride

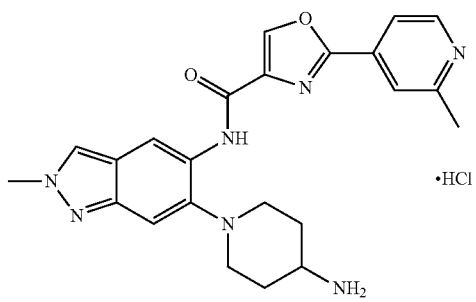

Step-1: Synthesis of tert-butyl (1-(1-methyl-5-nitro-1H-indazol-6-yl)piperidin-4-yl)carbamate and tert-butyl (1-(2-methyl-5-nitro-2H-indazol-6-yl)piperidin-4-yl)carbamate Using the same reagents and conditions as described in step 5 of example 1, tert-butyl (1-(5-nitro-1H-indazol-6-yl)piperidin-4-yl)carbamate (product of step 2 of example 108) (800 mg, 0.221 mmol) was alkylated using sodium hydride (111 mg, 4.65 mmol) and methyl iodide (1.29 g, 9.08 mmol) in THF (60 mL) at RT for 10 min to get the crude product. This was purified by silica gel column chromatography and elution with 20% ethyl acetate in hexane gave tert-butyl (1-(1-methyl-5-nitro-1H-indazol-6-yl)piperidin-4-yl)carbamate (450 mg, 54.2%) and further elution with ethyl acetate in hexane gave tert-butyl (1-(2-methyl-5-nitro-2H-indazol-6-yl)piperidin-4-yl)carbamate (200 mg, 24%).

Step-2: Synthesis of tert-butyl (1-(5-amino-2-methyl-2H-indazol-6-yl)piperidin-4-yl)carbamate Using the same reaction conditions as described in step 2 of example 16, tert-butyl (1-(2-methyl-5-nitro-2H-indazol-6-yl)piperidin-4-yl)carbamate (180 mg, 0.48 mmol) was reduced with zinc dust (313 mg, 4.8 mmol) and ammonium chloride (256 mg, 4.8 mmol) in THF/water (10/2 mL) to get the title product (150 mg, 95%).

Step-3: Synthesis of tert-butyl (1-(2-methyl-5-(2-(2-methylpyridin-4-yl)oxazole-4-carboxamido)-2H-indazol-6-yl)piperidin-4-yl)carbamate Using the similar reagents and conditions as described in step 7 of example 1, tert-butyl (1-(5-amino-2-methyl-2H-indazol-6-yl)piperidin-4-yl)carbamate (150 mg, 0.433 mmol) was coupled with 2-(2-methylpyridin-4-yl)oxazole-4-carboxylic acid (97 mg, 0.476 mmol) using HATU (247 mg, 0.65 mmol) and DIPEA (223 mg, 1.73 mmol) in DMF (10 mL) to get the title compound (140 mg, 52.7%).

Step-4: Synthesis of N-(6-(4-aminopiperidin-1-yl)-2-methyl-2H-indazol-5-yl)-2-(2-methylpyridin-4-yl)oxazole-4-carboxamide hydrochloride Using the same reagents and conditions as described in step 8 of example 1, tert-butyl (1-(2-methyl-5-(2-(2-methylpyridin-4-yl)oxazole-4-carboxamido)-2H-indazol-6-yl)piperidin-4-yl)carbamate (140 mg, 0.26 mmol) was deprotected using methanolic HCl/methanol (0.5/3 mL) to obtain title compound (100 mg, 88.4%).

$^1$HNMR (DMSO-d$_6$, 400 MHz): δ 9.79 (s, 1H), 9.22 (s, 1H), 8.93-8.92 (d, 1H), 8.70 (s, 1H), 8.39 (s, 3H), 8.31 (s, 1H), 8.22 (s, 2H), 7.45 (s, 1H), 4.13 (s, 3H), 3.31 (s, 1H), 3.21-3.18 (d, 2H), 2.90-2.85 (t, 2H), 2.78 (s, 3H), 2.18-2.16 (m, 2H), 2.09-2.03 (m, 2H). LCMS: 99.29%, m/z=432.4 (M+1)$^+$. HPLC: 94.08%.

Example 110

N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide

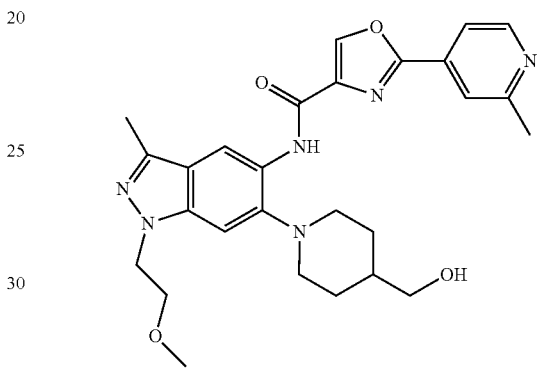

Step-1: Synthesis of 6-fluoro-1-(2-methoxyethyl)-3-methyl-5-nitro-1H-indazole and 6-fluoro-2-(2-methoxyethyl)-3-methyl-5-nitro-2H-indazole Using the same reagents and conditions as described in step 5 of example 1, 6-fluoro-3-methyl-5-nitro-1H-indazole (product of step 2 of example 73) (1 g, 5.12 mmol) was methylated using sodium hydride (492 mg, 10.25 mmol) and 1-bromo-2-methoxyethane (1 mL, 10.25 mmol) in THF (15 mL) at RT for 12 h to get the crude product. This was purified by silica gel column chromatography and elution with 50% ethyl acetate in hexane gave 6-fluoro-1-(2-methoxyethyl)-3-methyl-5-nitro-1H-indazole (500 mg, 39%) and further elution with 95% ethyl acetate in hexane gave 6-fluoro-2-(2-methoxyethyl)-3-methyl-5-nitro-2H-indazole (50 mg, 4%).

Step-2: Synthesis of (1-(1-(2-methoxyethyl)-3-methyl-5-nitro-1H-indazol-6-yl)piperidin-4-yl)methanol Using the similar reagents and conditions as described in step 1 of example 58, 6-fluoro-1-(2-methoxyethyl)-3-methyl-5-nitro-1H-indazole (500 mg, 1.96 mmol) was substituted with piperidin-4-methanol (270 mg, 2.35 mmol) using potassium carbonate (811 mg, 5.88 mmol) in DMF (5 mL) at 100° C. for 12 h to get the crude compound. The obtained crude was purified by 60-120 silica gel column chromatography and compound eluted using 50% ethyl acetate in hexane to give title compound (500 mg, 73%). LCMS: m/z=349.3 (M+1)$^+$.

Step-3: Synthesis of 6-(4-(((tert-butyldimethylsilyl)oxy)methyl)piperidin-1-yl)-1-(2-methoxyethyl)-3-methyl-5-nitro-1H-indazole Using the similar reagents and conditions as described in step 2 of example 58, (1-(1-(2-methoxyethyl)-3-methyl-5-nitro-1H-indazol-6-yl)piperidin-4-yl)methanol (500 mg, 1.47 mmol) was protected using TBDMS chloride (330 mg, 2.2 mmol), imidazole (249 mg, 3.67 mmol) and DMAP (250 mg, 1.76 mmol) in DMF (10 mL) at 0° C. for 0.5 h to obtain the title compound (500 mg, 75%). LCMS: m/z=463.4 (M+1)$^+$.

Step-4: Synthesis of 6-(4-(((tert-butyldimethylsilyl)oxy)methyl)piperidin-1-yl)-1-(2-methoxyethyl)-3-methyl-1H-indazol-5-amine Using the same reaction conditions as described in step 2 of example 16, 6-(4-(((tert-butyldimethylsilyl)oxy)methyl)piperidin-1-yl)-1-(2-methoxyethyl)-3-methyl-5-nitro-1H-indazole (500 mg, 1.0822 mmol) was reduced with zinc dust (562 mg, 8.658 mmol) and ammonium chloride (467 mg, 8.658 mmol) in THF (10 mL) to get the desired crude product (450 mg). LCMS: m/z=433.5 (M+1)$^+$.

Step-5: Synthesis of N-(6-(4-(((tert-butyldimethylsilyl)oxy)methyl)piperidin-1-yl)-1-(2-methoxyethyl)-3-methyl-1H-indazol-5-yl)-2-(2-methylpyridin-4-yl)oxazole-4-carboxamide Using the same reagents and conditions as described in step 7 of example 1, 6-(4-(((tert-butyldimethylsilyl)oxy)methyl)piperidin-1-yl)-1-(2-methoxyethyl)-3-methyl-1H-indazol-5-amine (110 mg, 0.25 mmol) was coupled with 2-(2-methylpyridin-4-yl)oxazole-4-carboxylic acid (62 mg, 0.305 mmol) using HATU (145 mg, 0.381 mmol) and DIPEA (0.2 mL, 1.01 mmol) in DMF (4 mL) to get the desired compound (110 mg, 70%). LCMS: m/z=619.5 (M+1)$^+$.

Step-6: Synthesis of N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide Using the similar reaction conditions as described in step 7 of example 58, N-(6-(4-(((tert-butyldimethylsilyl)oxy)methyl)piperidin-1-yl)-1-(2-methoxyethyl)-3-methyl-1H-indazol-5-yl)-2-(2-methylpyridin-4-yl)oxazole-4-carboxamide (110 mg, 0.1779 mmol) was deprotected using TBAF/THF (1/5 mL) to get crude product. This was purified by prep HPLC to get the title compound (62 mg, 68%).

$^1$HNMR (DMSO-d$_6$, 400 MHz): δ 10.21 (s, 1H), 9.05 (s, 1H), 8.70-8.69 (d, 1H), 8.63 (s, 1H), 7.84-7.82 (m, 2H), 7.51 (s, 1H), 4.69-4.66 (t, 1H), 4.47-4.44 (t, 2H), 3.74-3.72 (t, 2H), 3.49-3.47 (t, 2H), 3.22 (s, 3H), 3.11-3.09 (d, 2H), 2.83-2.78 (t, 2H), 2.62 (s, 3H), 2.45 (s, 3H), 1.92-1.90 (m, 2H), 1.70-1.65 (m, 3H). LCMS: 97.09%, m/z=505.4 (M+1)$^+$. HPLC: 98.87%.

Example 111

N-(6-(4-(hydroxymethyl)piperidin-1-yl)-1,3-dimethyl-1H-indazol-5-yl)-2-(2-methylpyridin-4-yl)oxazole-4-carboxamide

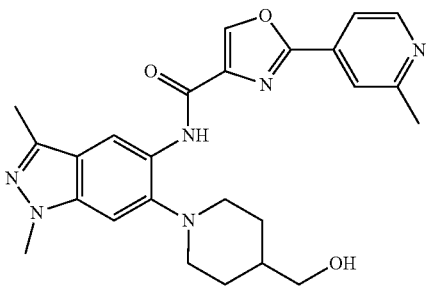 [SMILES: Cc1cc(-c2nc(C(=O)Nc3cc4c(C)nn(C)c4cc3N3CCC(CO)CC3)co2)ccn1]

Step-1: Synthesis of (1-(1,3-dimethyl-5-nitro-1H-indazol-6-yl)piperidin-4-yl)methanol Using the similar reagents and conditions as described in step 1 of example 58, 6-fluoro-1,3-dimethyl-5-nitro-1H-indazole (product of step 1 of example 81) (600 mg, 2.87 mmol) was substituted with piperidin-4-methanol (396 mg, 3.444 mmol) using potassium carbonate (188 mg, 8.612 mmol) in DMF (10 mL) at 100° C. for 14 h to get the title compound (600 mg, 72%). LCMS: m/z=305.3 (M+1)$^+$.

Step-2: Synthesis of 6-(4-(((tert-butyldimethylsilyl)oxy)methyl)piperidin-1-yl)-1,3-dimethyl-5-nitro-1H-indazole Using the similar reagents and conditions as described in step 2 of example 58, (1-(1,3-dimethyl-5-nitro-1H-indazol-6-yl)piperidin-4-yl)methanol (600 mg, 2.04 mmol) was protected using TBDMS chloride (459 mg, 3.0612 mmol), imidazole (346 mg, 5.102 mmol) and DMAP (298 mg, 2.44 mmol) in DMF (10 mL) at 0° C. for 15 min to obtain the crude compound. The obtained crude was purified by 60-120 silica gel column chromatography and compound eluted using ethyl acetate in hexane to give title compound (600 mg, 71%). LCMS: m/z=419.4 (M+1)$^+$.

Step-3: Synthesis of 6-(4-(((tert-butyldimethylsilyl)oxy)methyl)piperidin-1-yl)-1,3-dimethyl-1H-indazol-5-amine Using the same reaction conditions as described in step 2 of example 16, 6-(4-(((tert-butyldimethylsilyl)oxy)methyl)piperidin-1-yl)-1,3-dimethyl-5-nitro-1H-indazole (600 mg, 1.435 mmol) was reduced with zinc dust (746 mg, 11.483 mmol) and ammonium chloride (620 mg, 11.483 mmol) in THF (10 mL) to get the desired crude product (450 mg). LCMS: m/z=389.3 (M+1)$^+$.

Step-4: Synthesis of N-(6-(4-(((tert-butyldimethylsilyl)oxy)methyl)piperidin-1-yl)-1,3-dimethyl-1H-indazol-5-yl)-2-(2-methylpyridin-4-yl)oxazole-4-carboxamide Using the same reagents and conditions as described in step 7 of example 1, 6-(4-(((tert-butyldimethylsilyl)oxy)methyl)piperidin-1-yl)-1,3-dimethyl-1H-indazol-5-amine (110 mg, 0.283 mmol) was coupled with 2-(2-methylpyridin-4-yl)oxazole-4-carboxylic acid (69 mg, 0.3402 mmol) using HATU (161 mg, 0.4252 mmol) and DIPEA (0.2 mL, 1.1340 mmol) in DMF (5 mL) to get the desired compound (110 mg, 68%). LCMS: m/z=575.5 (M+1)+.

Step-5: Synthesis of N-(6-(4-(hydroxymethyl)piperidin-1-yl)-1,3-dimethyl-1H-indazol-5-yl)-2-(2-methylpyridin-4-yl)oxazole-4-carboxamide Using the same reaction conditions as described in step 7 of example 58, N-(6-(4-(((tert-butyldimethylsilyl)oxy)methyl)piperidin-1-yl)-1,3-dimethyl-1H-indazol-5-yl)-2-(2-methylpyridin-4-yl)oxazole-4-carboxamide (120 mg, 0.209 mmol) was deprotected using TBAF/THF (1/5 mL) to get crude product. This was purified by prep HPLC to get the title compound (30 mg, 32%).

¹HNMR (CD₃OD, 400 MHz): δ 8.71 (s, 1H), 8.68 (s, 1H), 8.65-8.64 (d, 1H), 7.95-7.92 (m, 2H), 7.37 (s, 1H), 3.97 (s, 3H), 3.64-3.62 (d, 2H), 3.24-3.21 (d, 2H), 2.93-2.87 (t, 2H), 2.69 (s, 3H), 2.53 (s, 3H), 2.03-1.99 (m, 2H), 1.86-1.78 (m, 3H). LCMS: 98.01%, m/z=461.4 (M+1)+. HPLC: 99.09%.

Example 112

2-(2-aminopyridin-4-yl)-N-(6-(4-(hydroxymethyl)piperidin-1-yl)-1,3-dimethyl-1H-indazol-5-yl)oxazole-4-carboxamide

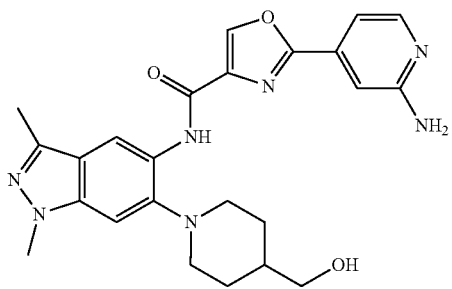 [SMILES: Cc1nn(C)c2cc(N3CCC(CO)CC3)c(NC(=O)c3coc(-c4ccnc(N)c4)n3)cc12]

Step-1: Synthesis of 2-(2-aminopyridin-4-yl)-N-(6-(4-(((tert-butyldimethylsilyl)oxy)methyl)piperidin-1-yl)-1,3-dimethyl-1H-indazol-5-yl)oxazole-4-carboxamide Using the same reagents and conditions as described in step 7 of example 1, 6-(4-(((tert-butyldimethylsilyl)oxy)methyl)piperidin-1-yl)-1,3-dimethyl-1H-indazol-5-amine (product of step 3 of example 111) (110 mg, 0.283 mmol) was coupled with 2-(2-aminopyridin-4-yl)oxazole-4-carboxylic acid (intermediate 14) (70 mg, 0.3402 mmol) using HATU (161 mg, 0.4252 mmol) and DIPEA (0.2 mL, 1.1340 mmol) in DMF (5 mL) to get the desired compound (110 mg, 68%). LCMS: m/z=576.5 (M+1)+.

Step-2: Synthesis of 2-(2-aminopyridin-4-yl)-N-(6-(4-(hydroxymethyl)piperidin-1-yl)-1,3-dimethyl-1H-indazol-5-yl)oxazole-4-carboxamide Using the same reaction conditions as described in step 7 of example 58, 2-(2-aminopyridin-4-yl)-N-(6-(4-(((tert-butyldimethylsilyl)oxy)methyl)piperidin-1-yl)-1,3-dimethyl-1H-indazol-5-yl)oxazole-4-carboxamide (110 mg, 0.173 mmol) was deprotected using TBAF/THF (1/5 mL) to get crude product. This was purified by prep HPLC to get the title compound (18 mg, 25%).

¹HNMR (DMSO-d₆, 400 MHz): δ 10.18 (s, 1H), 8.97 (s, 1H), 8.64 (s, 1H), 8.12-8.11 (d, 1H), 7.47 (s, 1H), 7.13-7.12 (d, 1H), 7.08 (s, 1H), 6.38 (s, 1H), 4.78-4.75 (t, 1H), 3.94 (s, 3H), 3.49-3.47 (t, 2H), 3.12-3.09 (d, 2H), 2.84-2.78 (t, 2H), 2.44 (s, 3H), 1.89-1.86 (m, 2H), 1.73-1.67 (m, 3H). LCMS: 100%, m/z=462.2 (M+1)+. HPLC: 98.48%.

Example 113

N-(6-(4-hydroxypiperidin-1-yl)-1-methyl-1H-indazol-5-yl)-2-(2-hydroxypyridin-4-yl)oxazole-4-carboxamide

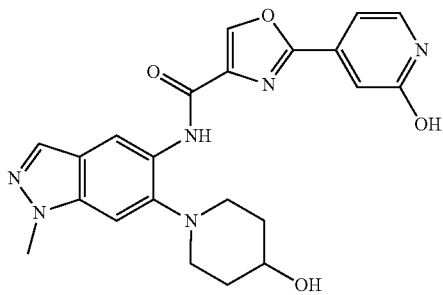 [SMILES: Cn1ncc2cc(NC(=O)c3coc(-c4ccnc(O)c4)n3)c(N3CCC(O)CC3)cc21]

Step-1: Synthesis of N-(6-(4-((tert-butyldimethylsilyl)oxy)piperidin-1-yl)-1-methyl-1H-indazol-5-yl)-2-(2-hydroxypyridin-4-yl)oxazole-4-carboxamide Using the same reagents and conditions as described in step 7 of example 1, 6-(4-((tert-butyldimethylsilyl)oxy)piperidin-1-yl)-1-methyl-1H-indazol-5-amine (product of step 1 of example 77) (70 mg, 0.339 mmol) was coupled with 2-(2-hydroxypyridin-4-yl)oxazole-4-carboxylic acid (intermediate 15) (140 mg, 0.407 mmol) using HATU (193 mg, 0.508 mmol) and DIPEA (87 mg, 0.678 mmol) in DMF (1 mL) to get the title compound (80 mg, 43%). LCMS: m/z=549.4 (M+1)+.

Step-2: Synthesis of N-(6-(4-hydroxypiperidin-1-yl)-1-methyl-1H-indazol-5-yl)-2-(2-hydroxypyridin-4-yl)oxazole-4-carboxamide Using the same reaction conditions as described in step 8 of example 1, N-(6-(4-((tert-butyldimethylsilyl)oxy)piperidin-1-yl)-1-methyl-1H-indazol-5-yl)-2-(2-hydroxypyridin-4-yl)oxazole-4-carboxamide (80 mg, 0.145 mmol) was deprotected using methanolic HCl/methanol (10.5 mL) and purified by prep HPLC to get the title compound (4 mg, 6.3%).

¹H NMR (CDCl₃, 400 MHz): δ 10.40 (s, 1H), 8.85 (s, 1H), 8.43 (s, 1H), 7.95 (s, 1H), 7.47-7.45 (d, 1H), 7.36 (s, 1H), 7.16 (s, 1H), 7.00-6.98 (m, 1H), 4.05-4.02 (m, 4H), 3.23-3.19 (m, 2H), 2.93-2.88 (t, 3H), 2.22-2.20 (m, 2H), 2.07-2.02 (m, 3H). LCMS: 100%, m/z=435.3 (M+1)+. HPLC: 98.71%.

Example 114

2-(2,6-dimethylpyridin-4-yl)-N-(6-(4-hydroxypiperidin-1-yl)-1-methyl-1H-indazol-5-yl)oxazole-4-carboxamide

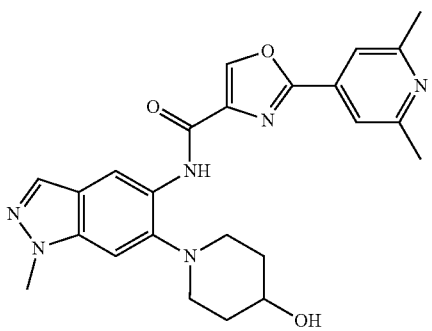 [SMILES: Cc1cc(-c2nc(C(=O)Nc3cc4cnn(C)c4cc3N3CCC(O)CC3)co2)cc(C)n1]

Step-1: Synthesis of N-(6-(4-(((tert-butyldimethylsilyl)oxy)piperidin-1-yl)-1-methyl-1H-indazol-5-yl)-2-(2,6-dimethylpyridin-4-yl)oxazole-4-carboxamide Using the same reagents and conditions as described in step 6 of example 5, 6-(4-(((tert-butyldimethylsilyl)oxy)piperidin-1-yl)-1-methyl-1H-indazol-5-amine (product of step 1 of example 77) (120 mg, 0.3666 mmol) was coupled with 2-(2,6-dimethylpyridin-4-yl)oxazole-4-carboxylic acid (intermediate 16) (70 mg, 0.333 mmol) using HATU (155 mg, 0.499 mmol) and DIPEA (76 mg, 0.666 mmol) in DMF (1 mL) to get the title compound (120 mg, 66.6%). LCMS: m/z=561.5 (M+1)$^+$.

Step-2: Synthesis of 2-(2,6-dimethylpyridin-4-yl)-N-(6-(4-hydroxypiperidin-1-yl)-1-methyl-1H-indazol-5-yl)oxazole-4-carboxamide Using the same reaction conditions as described in step 8 of example 1, N-(6-(4-(((tert-butyldimethylsilyl)oxy)piperidin-1-yl)-1-methyl-1H-indazol-5-yl)-2-(2,6-dimethylpyridin-4-yl)oxazole-4-carboxamide (120 mg, 0.214 mmol) was deprotected using methanolic HCl/methanol (1/1 mL) to get the title compound (46 mg, 47.36%).

$^1$HNMR (DMSO-$d_6$, 400 MHz): δ 10.37 (s, 1H), 9.04 (s, 1H), 8.70 (s, 1H), 8.00 (s, 1H), 7.68 (s, 2H), 7.56 (s, 1H), 5.00 (s, 1H), 4.02 (s, 3H), 3.79 (s, 1H), 3.10-3.047 (d, 2H), 2.89-2.84 (t, 2H), 2.55 (s, 6H), 2.07-2.05 (d, 2H), 1.96-1.89 (m, 2H). LCMS: 80.72%, m/z=447.4 (M+1)$^+$. HPLC: 97.70%.

Example 115

(S)—N-(6-(3-hydroxypyrrolidin-1-yl)-1-methyl-1H-indazol-5-yl)-2-(2-methylpyridin-4-yl)oxazole-4-carboxamide

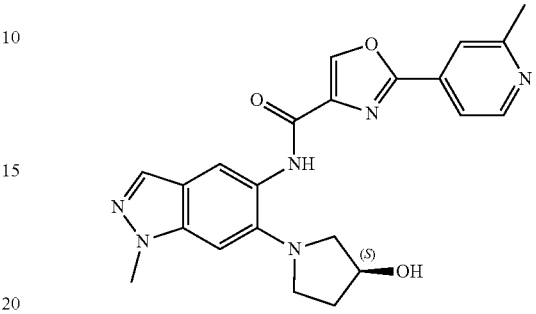

Step-1: Synthesis of (S)-1-(1-methyl-5-nitro-1H-indazol-6-yl)pyrrolidin-3-ol Using the similar reagents and conditions as described in step 1 of example 58, 6-fluoro-1-methyl-5-nitro-1H-indazole (product of step 1 of example 64) (400 mg, 2.0512 mmol) was substituted with (S)-pyrrolidin-3-ol hydrochloride (304 mg, 2.4615 mmol) using potassium carbonate (849 mg, 6.153 mmol) in DMF (10 mL) at 100° C. for 12 h to get the title compound (400 mg, 75%). m/z=263.2 (M+1)$^+$.

Step-2: Synthesis of (S)-6-(3-((tert-butyldimethylsilyl)oxy)pyrrolidin-1-yl)-1-methyl-5-nitro-1H-indazole Using the similar reagents and conditions as described in step 2 of example 58, (S)-1-(1-methyl-5-nitro-1H-indazol-6-yl)pyrrolidin-3-ol (400 mg, 1.481 mmol) was protected using TBDMS chloride (333 mg, 2.222 mmol), imidazole (251 mg, 3.703 mmol) and DMAP (216 mg, 1.37 mmol) in DMF (10 mL) at RT for 0.5 h to obtain the title compound (400 mg, 72%). LCMS: m/z=377.3 (M+1)$^+$.

Step-3: Synthesis of (S)-6-(3-((tert-butyldimethylsilyl)oxy)pyrrolidin-1-yl)-1-methyl-1H-indazol-5-amine Using the same reaction conditions as described in step 2 of example 16, (S)-6-(3-((tert-butyldimethylsilyl)oxy)pyrrolidin-1-yl)-1-methyl-5-nitro-1H-indazole (400 mg, 1.063 mmol) was reduced with zinc dust (553 mg, 8.510 mmol) and ammonium chloride (459 mg, 8.510 mmol) in THF/water (10/5 mL) to get the desired product (300 mg, 81%). LCMS: m/z=347.4 (M+1)$^+$.

Step-4: Synthesis of (S)—N-(6-(3-((tert-butyldimethylsilyl)oxy)pyrrolidin-1-yl)-1-methyl-1H-indazol-5-yl)-2-(2-methylpyridin-4-yl)oxazole-4-carboxamide Using the same reagents and conditions as described in step 6 of example 5, (S)-6-(3-((tert-butyldimethylsilyl)oxy)pyrrolidin-1-yl)-1-methyl-1H-indazol-5-amine (150 mg, 0.433 mmol) was coupled with 2-(2-methylpyridin-4-yl)oxazole-4-carboxylic acid (106 mg, 0.520 mmol) using HATU (247 mg, 0.650 mmol) and DIPEA (0.3 mL, 1.734 mmol) in DMF (5 mL) to get the desired compound (90 mg, 39%). LCMS: m/z=533.0 (M+1)$^+$.

Step-5: Synthesis of (S)—N-(6-(3-hydroxypyrrolidin-1-yl)-1-methyl-1H-indazol-5-yl)-2-(2-methylpyridin-4-yl)oxazole-4-carboxamide Using the same reaction conditions as described in step 8 of example 1, (S)—N-(6-(3-((tert-butyldimethylsilyl)oxy)pyrrolidin-1-yl)-1-methyl-1H-indazol-5-yl)-2-(2-methylpyridin-4-yl)oxazole-4-carboxamide (90 mg, 1.691 mmol) was deprotected using methanolic HCl/methanol (1/5 mL) to get the title compound (28 mg, 40%).
$^1$HNMR (CD$_3$OD, 400 MHz): δ 8.70 (s, 1H), 8.64-8.63 (d, 1H), 8.39 (s, 1H), 8.03 (s, 1H), 7.94-7.92 (m, 2H), 7.25 (s, 1H), 4.62 (s, 1H), 4.03 (s, 3H), 3.60-3.50 (m, 2H), 3.32-3.15 (m, 3H), 2.67 (s, 3H), 2.41-2.35 (m, 1H), 2.09-2.07 (m, 1H). LCMS: 97.83%, m/z=419.3 (M+1)$^+$. HPLC: 96.11%.

Example 116

N-(6-(4-hydroxypiperidin-1-yl)-1-(2-methoxyethyl)-3-methyl-1H-indazol-5-yl)-2-(2-methylpyridin-4-yl)oxazole-4-carboxamide

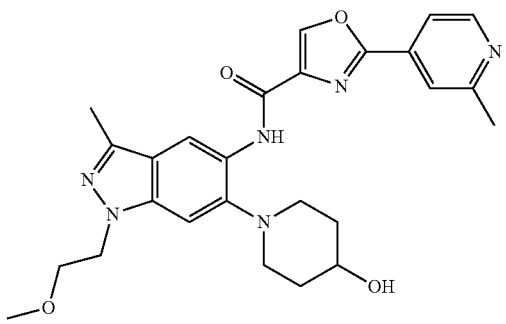

Step-1: Synthesis of 1-(1-(2-methoxyethyl)-3-methyl-5-nitro-1H-indazol-6-yl)piperidin-4-ol Using the similar reagents and conditions as described in step 1 of example 58, 6-fluoro-1-(2-methoxyethyl)-3-methyl-5-nitro-1H-indazole (product of step 1 of example 110) (350 mg, 1.372 mmol) was substituted with piperidin-4-ol (166 mg, 1.647 mmol) using potassium carbonate (568 mg, 4.117 mmol) in DMF (5 mL) at 100° C. for 12 h to get the title compound (350 mg, 76%). LCMS: m/z=335.2 (M+1)$^+$.

Step-2: Synthesis of 6-(4-((tert-butyldimethylsilyl)oxy)piperidin-1-yl)-1-(2-methoxyethyl)-3-methyl-5-nitro-1H-indazole Using the similar reagents and conditions as described in step 2 of example 58, 1-(1-(2-methoxyethyl)-3-methyl-5-nitro-1H-indazol-6-yl)piperidin-4-ol (350 mg, 1.067 mmol) was protected using TBDMS chloride (240 mg, 1.6 mmol), imidazole (181 mg, 2.667 mmol) and DMAP (156 mg, 1.280 mmol) in DMF (5 mL) at RT for 0.5 h to obtain the title compound (350 mg, 75%). LCMS: m/z=449.0 (M+1)$^+$.

Step-3: Synthesis of 6-(4-((tert-butyldimethylsilyl)oxy)piperidin-1-yl)-1-(2-methoxyethyl)-3-methyl-1H-indazol-5-amine Using the same reaction conditions as described in step 2 of example 16, 6-(4-((tert-butyldimethylsilyl)oxy)piperidin-1-yl)-1-(2-methoxyethyl)-3-methyl-5-nitro-1H-indazole (350 mg, 0.781 mmol) was reduced with zinc dust (406 mg, 6.25 mmol) and ammonium chloride (337 mg, 6.25 mmol) in THF/water (5/2 mL) to get the desired product (250 mg, 76%). LCMS: m/z=419.4 (M+1)$^+$.

Step-4: Synthesis of N-(6-(4-((tert-butyldimethylsilyl)oxy)piperidin-1-yl)-1-(2-methoxyethyl)-3-methyl-1H-indazol-5-yl)-2-(2-methylpyridin-4-yl)oxazole-4-carboxamide Using the same reagents and conditions as described in step 6 of example 5, 6-(4-((tert-butyldimethylsilyl)oxy)piperidin-1-yl)-1-(2-methoxyethyl)-3-methyl-1H-indazol-5-amine (110 mg, 0.263 mmol) was coupled with 2-(2-methylpyridin-4-yl)oxazole-4-carboxylic acid (64 mg, 0.315 mmol) using HATU (149 mg, 0.394 mmol) and DIPEA (0.2 mL, 1.00 mmol) in DMF (5 mL) to get the desired compound (110 mg, 69%).

Step-5: Synthesis of N-(6-(4-hydroxypiperidin-1-yl)-1-(2-methoxyethyl)-3-methyl-1H-indazol-5-yl)-2-(2-methylpyridin-4-yl)oxazole-4-carboxamide Using the same reaction conditions as described in step 7 of example 58, N-(6-(4-((tert-butyldimethylsilyl)oxy)piperidin-1-yl)-1-(2-methoxyethyl)-3-methyl-1H-indazol-5-yl)-2-(2-methylpyridin-4-yl)oxazole-4-carboxamide (110 mg, 0.198 mmol) was deprotected using TBAF/THF (1/4 mL) to get title compound (90 mg, 90%).
$^1$HNMR (CD$_3$OD, 400 MHz): δ 8.70 (s, 1H), 8.65-8.63 (m, 2H), 8.02 (s, 1H), 7.93-7.91 (d, 1H), 7.42 (s, 1H), 4.48-4.45 (t, 2H), 3.96-3.94 (m, 1H), 3.79-3.50 (t, 2H), 3.29 (s, 3H), 3.21-3.18 (m, 2H), 2.97-2.91 (t, 2H), 2.68 (s, 3H), 2.53 (s, 3H), 2.20-2.17 (m, 2H), 2.13-2.05 (m, 2H). LCMS: 85.24%, m/z=491.4 (M+1)$^+$. HPLC: 95.00%.

Example 117

N-(1-(2-hydroxyethyl)-6-(4-hydroxypiperidin-1-yl)-1H-indazol-5-yl)-2-(2-methylpyridin-4-yl)oxazole-4-carboxamide

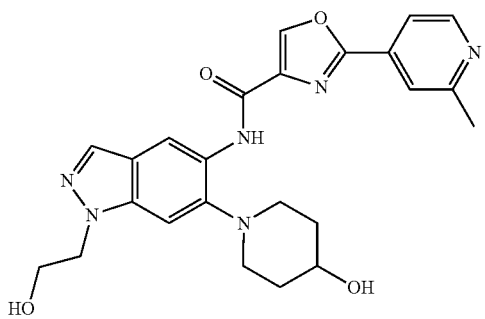 [SMILES: Cc1cc(-c2nc(C(=O)Nc3cc4cnn(CCO)c4cc3N3CCC(O)CC3)co2)ccn1]

143

Step-1: Synthesis of 1-(2-((tert-butyldimethylsilyl) oxy)ethyl)-6-(4-((tert-butyldimethylsilyl)oxy)piperidin-1-yl)-5-nitro-1H-indazole and 2-(2-((tert-butyldimethylsilyl)oxy)ethyl)-6-(4-((tert-butyldimethylsilyl)oxy)piperidin-1-yl)-5-nitro-2H-indazole Using the same reagents and conditions as described in step 5 of example 1, 6-(4-((tert-butyldimethylsilyl)oxy)piperidin-1-yl)-5-nitro-1H-indazole (1 g, 2.65 mmol) was alkylated using potassium carbonate (730 mg, 5.31 mmol) and (2-bromoethoxy)(tert-butyl)dimethylsilane (1.27 g, 5.31 mmol) in DMF (10 mL) at 100° C. for 3 h to get the crude product. This was purified by silica gel column chromatography and elution with 5% ethyl acetate in hexane gave the 1-(2-((tert-butyldimethylsilyl)oxy)ethyl)-6-(4-((tert-butyldimethylsilyl)oxy)piperidin-1-yl)-5-nitro-1H-indazole and further elution gave 2-(2-((tert-butyldimethylsilyl)oxy) ethyl)-6-(4-((tert-butyldimethylsilyl)oxy)piperidin-1-yl)-5-nitro-2H-indazole (800 mg, 57%). LCMS: m/z=535.5 (M+1)$^+$.

Step-2: Synthesis of 1-(2-((tert-butyldimethylsilyl) oxy)ethyl)-6-(4-((tert-butyldimethylsilyl)oxy)piperidin-1-yl)-1H-indazol-5-amine Using the same reaction conditions as described in step 2 of example 16, 1-(2-((tert-butyldimethylsilyl)oxy)ethyl)-6-(4-((tert-butyldimethylsilyl)oxy)piperidin-1-yl)-5-nitro-1H-indazole (250 mg, 0.468 mmol) was reduced with zinc dust (240 mg, 3.7453 mmol) and ammonium chloride (400 mg, 7.4896 mmol) in THF/water (10/3 mL) to get the desired crude product (234 mg, 99%). LCMS: m/z=505.5 (M+1)$^+$.

Step-3: Synthesis of N-(1-(2-((tert-butyldimethylsilyl)oxy)ethyl)-6-(4-((tert-butyldimethylsilyl)oxy) piperidin-1-yl)-1H-indazol-5-yl)-2-(2-methylpyridin-4-yl)oxazole-4-carboxamide Using the same reagents and conditions as described in step 6 of example 5, 1-(2-((tert-butyldimethylsilyl)oxy) ethyl)-6-(4-((tert-butyldimethylsilyl)oxy)piperidin-1-yl)-1H-indazol-5-amine (240 mg, 0.496 mmol) was coupled with 2-(2-methylpyridin-4-yl)oxazole-4-carboxylic acid (101 mg, 0.496 mmol) using HATU (280 mg, 0.744 mmol) and DIPEA (0.15 mL, 0.992 mmol) in DMF (5 mL) to get the desired compound (150 mg, 47%). LCMS: m/z=691.4 (M+1)$^+$.

Step-4: Synthesis of N-(1-(2-hydroxyethyl)-6-(4-hydroxypiperidin-1-yl)-1H-indazol-5-yl)-2-(2-methylpyridin-4-yl)oxazole-4-carboxamide Using the same reaction conditions as described in step 8 of example 1, of N-(1-(2-((tert-butyldimethylsilyl)oxy) ethyl)-6-(4-((tert-butyldimethylsilyl)oxy)piperidin-1-yl)-1H-indazol-5-yl)-2-(2-methylpyridin-4-yl)oxazole-4-carboxamide (150 mg) was deprotected using methanolic HCl/methanol (0.5/5 mL) to get the title compound (80 mg, 80%).

$^1$HNMR (DMSO-d$_6$, 400 MHz): δ 10.35 (s, 1H), 9.06 (s, 1H), 8.69-8.68 (m, 2H), 8.32 (s, 1H), 8.02 (s, 1H), 7.91 (s, 1H), 7.81-7.80 (d, 1H), 7.58 (s, 1H), 5.00-4.80 (bs, 1H), 4.42-4.40 (t, 2H), 3.81-3.78 (t, 3H), 3.10-2.87 (m, 2H), 2.85-2.83 (t, 2H), 2.87-2.83 (t, 2H), 2.61 (s, 3H), 2.08-2.04 (m, 2H), 1.95-1.90 (m, 2H). LCMS: 98.73%, m/z=463.4 (M+1)$^+$. HPLC: 95.16%.

144

Example 118

N-(6-(4-aminopiperidin-1-yl)-2-(2-methoxyethyl)-2H-indazol-5-yl)-2-(2-methylpyridin-4-yl)oxazole-4-carboxamide hydrochloride

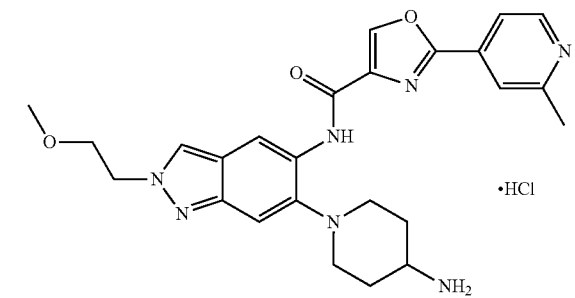

Step-1: Synthesis of tert-butyl (1-(5-amino-2-(2-methoxyethyl)-2H-indazol-6-yl)piperidin-4-yl)carbamate Using the same reaction conditions as described in step 2 of example 16, tert-butyl (1-(2-(2-methoxyethyl)-5-nitro-2H-indazol-6-yl)piperidin-4-yl)carbamate (product of step 3 of example 108) (320 mg, 0.7637 mmol) was reduced with zinc dust (397 mg, 6.1097 mmol) and ammonium chloride (660 mg, 12.2192 mmol) in THF/water (10/3 mL) to get the desired product (300 mg). LCMS: m/z=390.4 (M+1)$^+$.

Step-2: Synthesis of tert-butyl (1-(2-(2-methoxyethyl)-5-(2-(2-methylpyridin-4-yl)oxazole-4-carboxamido)-2H-indazol-6-yl)piperidin-4-yl)carbamate Using the same reagents and conditions as described in step 6 of example 5, tert-butyl (1-(5-amino-2-(2-methoxyethyl)-2H-indazol-6-yl)piperidin-4-yl)carbamate (300 mg, 0.7712 mmol) was coupled with 2-(2-methylpyridin-4-yl) oxazole-4-carboxylic acid (157 mg, 0.7712 mmol) using HATU (437 mg, 1.1568 mmol) and DIPEA (0.24 mL, 1.5424 mmol) in DMF (6 mL) to get the desired compound (169 mg, 39%). LCMS: m/z=576.4 (M+1)$^+$.

Step-3: Synthesis of N-(6-(4-aminopiperidin-1-yl)-2-(2-methoxyethyl)-2H-indazol-5-yl)-2-(2-methylpyridin-4-yl)oxazole-4-carboxamide hydrochloride Using the same reagents as described in step 8 of example 1, tert-butyl (1-(2-(2-methoxyethyl)-5-(2-(2-methylpyridin-4-yl)oxazole-4-carboxamido)-2H-indazol-6-yl)piperidin-4-yl)carbamate (160 mg) was deprotected using methanolic HCl/methanol (0.5/3 mL) to give title compound (28 mg, 57%).

$^1$HNMR (DMSO-d$_6$, 400 MHz): δ 9.78 (s, 1H), 9.13 (s, 1H), 8.80-8.79 (d, 1H), 8.69 (s, 1H), 8.32 (s, 1H), 8.21 (s, 2H), 7.98 (s, 2H), 7.45 (s, 1H), 4.54-4.52 (t, 2H), 3.81-3.79 (t, 2H), 3.22-3.16 (m, 6H), 2.90-2.84 (t, 2H), 2.67 (s, 3H), 2.18-2.15 (m, 2H), 2.01-1.96 (m, 2H). LCMS: 100%, m/z=476.2 (M+1)$^+$. HPLC: 99.23%.

Example 119

2-(2,6-dimethylpyridin-4-yl)-N-(2-methyl-6-(piperidin-1-yl)-2H-indazol-5-yl)oxazole-4-carboxamide hydrochloride

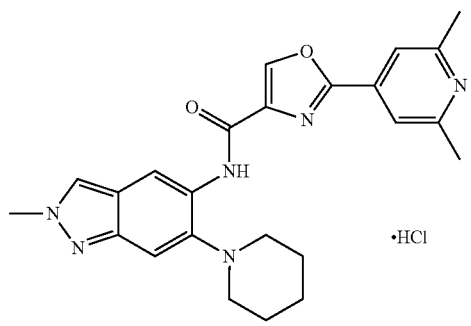

Using the same reagents and conditions as described in step 6 of example 5, 2-methyl-6-(piperidin-1-yl)-2H-indazol-5-amine (product of step 6 of example 1) (91 mg, 0.399 mol) was coupled with 2-(2,6-dimethylpyridin-4-yl)oxazole-4-carboxylic acid (intermediate 16) (70 mg, 0.333 mmol) using HATU (185 mg, 0.499 mmol) and DIPEA (86 mg, 0.666 mmol) in DMF (1 mL) and treated with methanolic HCl to get the title compound (63 mg, 58.3%).

$^1$HNMR (DMSO-$d_6$, 400 MHz): δ 10.40 (s, 1H), 9.24 (s, 1H), 8.58 (s, 1H), 8.29 (s, 1H), 8.09 (s, 2H), 7.42 (s, 1H), 4.12 (s, 3H), 2.91 (s, 4H), 2.78 (s, 6H), 1.89 (s, 4H), 1.67 (s, 2H).
LCMS: 100%, m/z=430.9 (M+1)$^+$. HPLC: 96.56%.

Example 120

2-(2-(dimethylamino)pyridin-4-yl)-N-(2-methyl-6-(piperidin-1-yl)-2H-indazol-5-yl)oxazole-4-carboxamide hydrochloride

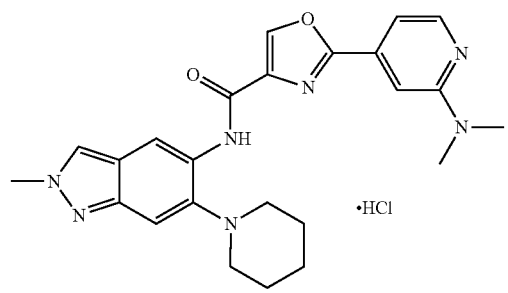

Using the similar reagents and conditions as described in step 6 of example 5, 2-methyl-6-(piperidin-1-yl)-2H-indazol-5-amine (product of step 6 of example 1) (100 mg, 0.434 mmol) was coupled with 2-(2-(dimethylamino) pyridin-4-yl) oxazole-4-carboxylic acid (intermediate 18) (122 mg 0.521 mmol) using HATU (247 mg, 0.652 mmol) and DIPEA (224 mg, 1.73 mmol) in DMF (5 mL) and further treated with methanolic HCl/methanol (5/5 mL) to obtain the desired compound (35 mg, 18.4%).

$^1$HNMR (DMSO-$d_6$, 400 MHz): δ 10.31 (s, 1H), 9.15 (s, 1H), 8.66 (s, 1H), 8.29-8.28 (d, 2H), 7.48-7.42 (d, 2H), 7.28-7.27 (d, 1H), 4.12 (s, 3H), 3.27 (s, 6H), 2.91 (bs, 4H), 1.87 (bs, 4H), 1.66 (bs, 2H). LCMS: m/z=446.4 (M+1)$^+$. HPLC: 97.65%.

Example 121

N-(6-(4-hydroxypiperidin-1-yl)-1-methyl-1H-indazol-5-yl)-2-(2-(methylamino)pyridin-4-yl)oxazole-4-carboxamide hydrochloride

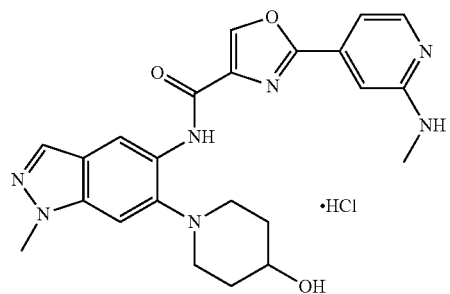 [SMILES: CNc1cc(-c2nc(C(=O)Nc3cc4cnn(C)c4cc3N3CCC(O)CC3)co2)ccn1 ; Cl]

Using the similar reagents and conditions as described in step 6 of example 5, N 6-(4-(((tert-butyldimethylsilyl)oxy) piperidin-1-yl)-1-methyl-2H-indazol-5-amine (product of step 1 of example 77) (150 mg, 0.416 mmol) was coupled with 2-(2-(methyl amino) pyridin-4-yl) oxazole-4-carboxylic acid (intermediate 17) (91.5 mg, 0.416 mmol) using HATU (237 mg, 0.624 mmol) and DIPEA (214 mg, 1.66 mmol) in DMF (5 mL) to obtain the desired compound (75 mg, 32.1%). LCMS: (M+1) and further treated with methanolic HCl/methanol (5/5 mL), for deprotection of TBDMS to get the title compound (53 mg, 82.8%).

$^1$HNMR (DMSO-$d_6$, 400 MHz): δ10.25 (s, 1H), 9.17 (s, 1H), 8.69 (s, 1H), 8.09-8.08 (d, 1H) 8.01 (s, 1H), 7.57 (s, 2H), 7.35-7.33 (d, 1H) 4.02 (s, 3H), 3.11-3.08 (m, 2H), 3.80 (m, 1bs, 1H) 3.04 (s, 3H), 2.88-2.83 (t, 2H), 2.05-2.02 (m, 2H), 1.88-1.84 (m, 2H). LCMS: m/z=448.4 (M+1)$^+$. HPLC: 94.77%

Example 122

N-(2-methyl-6-(piperidin-1-yl)-2H-indazol-5-yl)-2-(2-(methylamino)pyridin-4-yl)oxazole-4-carboxamide hydrochloride

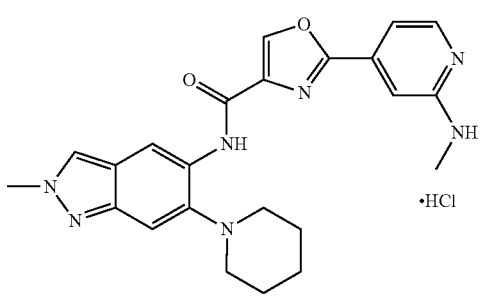 [SMILES: CNc1cc(-c2nc(C(=O)Nc3cc4cn(C)nc4cc3N3CCCCC3)co2)ccn1 ; Cl]

Using the similar reagents and conditions as described in step 6 of example 5, 2-methyl-6-(piperidin-1-yl)-2H-indazol-5-amine (product of step 6 of example 1) (85 mg, 0.37 mmol) was coupled with 2-(2-(methyl amino) pyridin-4-yl)

oxazole-4-carboxylic acid (intermediate 17) (81 mg 0.37 mmol) using HATU (210 mg, 0.55 mmol) and DIPEA (190 mg, 1.47 mmol) in DMF (5 mL) and further treated with methanolic HCl/methanol (5/5 mL) to obtain the desired compound (110 mg, 69.18%).

$^1$H NMR (DMSO-$d_6$, 400 MHz): δ 10.26 (s, 1H), 9.16 (s, 1H), 8.62 (s, 1H), 8.29 (s, 1H), 8.21-8.20 (d, 1H), 7.54 (s, 1H), 7.41 (s, 1H), 7.25-7.23 (d, 1H), 4.12 (s, 3H), 3.03 (s, 3H), 2.89 (bs, 4H), 1.85 (bs, 4H), 1.67 (bs, 2H). LCMS: m/z=432.4 (M+1)$^+$. HPLC: 97.58%.

Example 123

N-(6-(4-hydroxypiperidin-1-yl)-2-methyl-2H-indazol-5-yl)-2-(2-(methylsulfonamido) pyridin-4-yl) oxazole-4-carboxamide

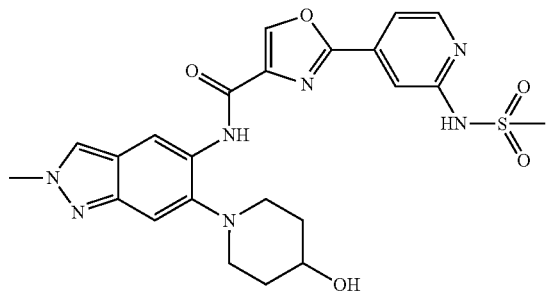

Using the same reagents and conditions as described in step 6 of example 5, 6-(4-((tert-butyldimethylsilyl)oxy)piperidin-1-yl)-2-methyl-2H-indazol-5-amine (product of step 5 of example 58) (40 mg, 0.141 mmol) was coupled with 2-(2-(methylsulfonamido) pyridin-4-yl) oxazole-4-carboxylic acid (intermediate 19) (61 mg 0.1697 mmol) using HATU (81 mg, 0.211 mmol) and DIPEA (51 mg, 0.424 mmol) in DMF (5 mL) and further treated with methanolic HCl/methanol (5/5 mL) for deprotection of TBDMS to obtain the desired compound (10 mg, 15.3%).

$^1$HNMR (DMSO-$d_6$, 400 MHz): δ 10.9 (bs, 1H) 10.33 (s, 1H), 9.05 (s, 1H), 8.61 (s, 1H), 8.54 (bs, 1H), 8.26 (s, 1H), 7.64 (s, 1H), 7.57 (s, 1H), 7.39 (s, 1H), 4.98 (bs, 1H), 4.10 (s, 3H), 3.80 (bs, 1H), 3.05-3.02 (t, 2H), 2.82-2.78 (t, 2H), 2.01 (bs, 2H), 1.87 (bs, 2H). LCMS: m/z=512.2 (M+1)$^+$. HPLC: 90.90%.

Example 124

2-(2-(dimethylamino) pyridin-4-yl)-N-(6-(4-hydroxypiperidin-1-yl)-1-methyl-1H-indazol-5-yl) oxazole-4-carboxamide

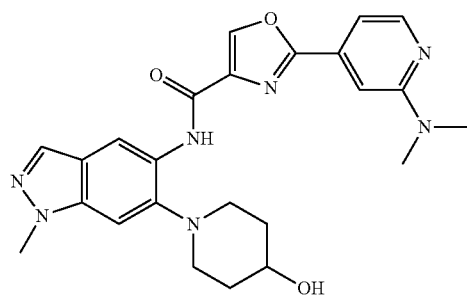 [SMILES: CN(C)c1cc(-c2nc(C(=O)Nc3cc4cnn(C)c4cc3N3CCC(O)CC3)co2)ccn1]

Using the similar reagents and conditions as described in step 6 of example 5, N 6-(4-((tert-butyldimethylsilyl)oxy) piperidin-1-yl)-1-methyl-2H-indazol-5-amine (product of step 1 of example 77) (150 mg, 0.416 mmol) was coupled with 2-(2-(dimethylamino) pyridin-4-yl) oxazole-4-carboxylic acid (Intermediate 18) (116 mg, 0.499 mmol) using HATU (237 mg, 0.624 mmol) and DIPEA (214 mg, 1.66 mmol) in DMF (5 mL) to obtain the desired compound (100 mg, 41%) and further treated with methanolic HCl/methanol (5/5 mL) for deprotection of TBDMS to get the title compound (25 mg, 31.25%).

$^1$HNMR (DMSO-$d_6$, 400 MHz): δ10.17 (s, 1H), 9.00 (s, 1H), 8.72 (s, 1H), 8.29-8.28 (d, 1H), 8.00 (s, 1H), 7.55 (s, 1H), 7.16 (s, 2H), 4.87 (s, 1H), 4.01 (s, 3H), 3.8 (bs, 1H), 3.12 (s, 6H), 3.09 (bs, 2H), 2.86-2.80 (m, 2H), 2.01 (bs, 2H), 1.86-1.82 (m, 2H). LCMS: m/z=462.20 (M+1)$^+$. HPLC: 99.01%

Example 125

N-(6-(4-(aminomethyl)piperidin-1-yl)-1-(2-methoxyethyl)-1H-indazol-5-yl)-2-(2-methylpyridin-4-yl)oxazole-4-carboxamide hydrochloride

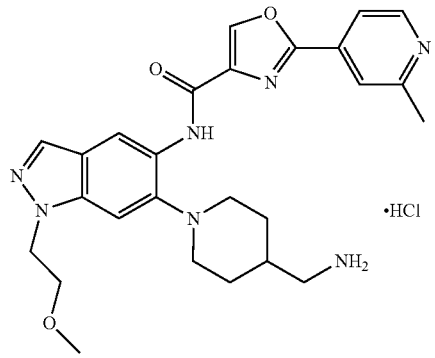 [SMILES: COCCn1ncc2cc(NC(=O)c3coc(-c4ccnc(C)c4)n3)c(N3CCC(CN)CC3)cc21 ; Cl]

Step-1: Synthesis of (1-(1-(2-methoxyethyl)-5-(2-(2-methylpyridin-4-yl) oxazole-4-carboxamido)-1H-indazol-6-yl) piperidin-4-yl) methyl methanesulfonate To a solution of N-(6-(4-(hydroxymethyl) piperidin-1-yl)-1-(2-methoxyethyl)-1H-indazol-5-yl)-2-(2-methylpyridin-4-yl) oxazole-4-carboxamide (product of step-7 of example 94) (500 mg 1.02 mmol) in DCM (10 ml) cooled to 0° C. added TEA (312 mg 3.06 mmol) followed by mesylchloride (174 mg 1.53 mmol) added, allowed to come to RT stirred for 3 hours. RM diluted with DCM washed with water dried over Na$_2$SO$_4$ and concentrated it. The crude product was purified by column chromatography using 3% methanol, in DCM to get the title compound (280 mg). LCMS: m/z=569.4 (M+1)$^+$.

Step-2: Synthesis of N-(6-(4-(azidomethyl) piperidin-1-yl)-1-(2-methoxyethyl)-1H-indazol-5-yl)-2-(2-methylpyridin-4-yl) oxazole-4-carboxamide To a solution of (1-(1-(2-methoxyethyl)-5-(2-(2-methylpyridin-4-yl) oxazole-4-carboxamido)-1H-indazol-6-yl) piperidin-4-yl) methyl methanesulfonate (280 mg, 0.49 mmol) in DMF added sodium azide (128 mg 1.97 mmol)

and heated to 60° C. for 5 hours. The reaction mixture was diluted with EtOAc washed with water dried over Na₂SO₄ and concentrated it to get the title compound. (crude: 220 mg). LCMS: m/z=516.4 (M+1)⁺.

Step-3: Synthesis of N-(6-(4-(aminomethyl) piperidin-1-yl)-1-(2-methoxyethyl)-1H-indazol-5-yl)-2-(2-methylpyridin-4-yl) oxazole-4-carboxamide hydrochloride To a solution of N-(6-(4-(azidomethyl)piperidin-1-yl)-1-(2-methoxyethyl)-1H-indazol-5-yl)-2-(2-methylpyridin-4-yl)oxazole-4-carboxamide (220 mg 0.27 mmol) in ethanol (5 ml) added Pd/C (50 mg) stirred at balloon pressure of hydrogen for 2 hours, filtered through Celite® bed taken filtrate concentrated it. The crude product was purified by prep HPLC, and further treated with Dioxane HCl/methanol (5/5 mL) to obtain the desired compound (30 mg, 63.81%).

¹HNMR (CDCl3, 300 MHz): δ10.20 (bs, 1H), 8.85 (s, 1H), 8.71-8.70 (d, 1H), 8.41 (s, 1H), 7.97 (s, 1H), 7.79-7.75 (m, 2H), 7.24 (s, 1H), 4.52-4.49 (t, 2H), 3.86-3.83 (t, 2H), 3.31 (s, 3H), 3.24-3.21 (d, 2H), 2.84-2.78 (m, 4H), 2.68 (s, 3H), 2.04-2.01 (d, 3H), 1.73-1.65 (m, 4H), (d, 1H). m/z=490.25 (M+1)⁺. HPLC: 96.59%

Example 126

2-(2,6-dimethylpyridin-4-yl)-N-(6-(4-hydroxypiperidin-1-yl)-2-methyl-2H-indazol-5-yl) oxazole-4-carboxamide

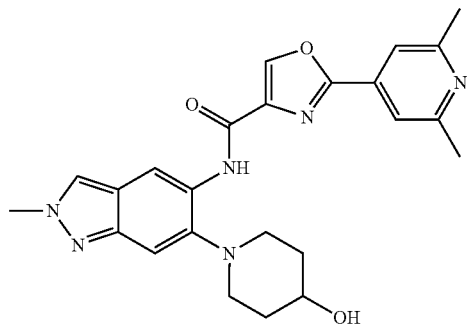

To a solution of 6-(4-((tert-butyldimethylsilyl) oxy) piperidin-1-yl)-2-methyl-2H-indazol-5-amine (product of step 5 of example 58) (250 mg 0.685 mmol) was coupled with 2-(2,6-dimethylpyridin-4-yl)oxazole-4-carboxylic acid (Intermediate 16) (120 mg, 0.571 mmol) using HATU (325 mg, 0.624 mmol) and DIPEA (178 mg, 1.14 mmol) in DMF (5 mL) to get the desired compound (200 mg, 62.69%) for deprecation of TBDMS further treated with methanolic HCl/methanol (5/5 mL), purified by Prep HPLC to get the title compound (105 mg, 66.49%).

¹HNMR (DMSO-d₆, 400 MHz): δ10.41 (s, 1H), 8.99 (s, 1H), 8.59 (s, 1H), 8.23 (s, 1H), 7.65 (bs, 2H), 7.36 (s, 1H), 4.96 (bs, 1H), 4.07 (s, 3H), 3.74 (bs, 1H), 3.02-2.99 (m, 2H), 2.81-2.76 (t, 2H), 2.51 (s, 6H) 2.01-1.99 (m, 2H), 1.91-1.71 (m, 2H). LCMS: m/z=447.2 (M+1)⁺. HPLC: 97.70%

Example 127

2-(2,6-dimethylpyridin-4-yl)-N-(6-(4-fluoropiperidin-1-yl)-2-methyl-2H-indazol-5-yl) oxazole-4-carboxamide

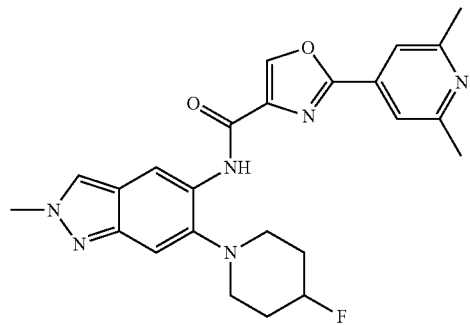

To a solution of 2-(2, 6-dimethylpyridin-4-yl)-N-(6-(4-hydroxypiperidin-1-yl)-2-methyl-2H-indazol-5-yl) oxazole-4-carboxamide (example 126) (105 mg 0.235 mmol) was fluorinated using DAST (40 mg, 0.25 mmol) in DCM (20 mL) to obtain the crude product was purified by Prep. HPLC to get the title compound (8 mg, 8.88%).

¹HNMR (CDCl3, 300 MHz): δ10.45 (S, 1H), 8.76 (s, 1H), 8.39 (s, 1H), 7.84 (s, 1H), 7.62 (bs, 2H), 7.43 (s, 1H), 4.19 (s, 3H), 3.20 (bs, 2H), 2.93 (bs, 2H), 2.63 (s, 6H), 2.33-2.22 (m, 5H). LCMS: m/z=449.4 (M+1)⁺. HPLC: 90.20%.

Example 128

Diethyl (1-(1-methyl-5-(2-(2-methylpyridin-4-yl) oxazole-4-carboxamido)-1H-indazol-6-yl)piperidin-4-yl) phosphate

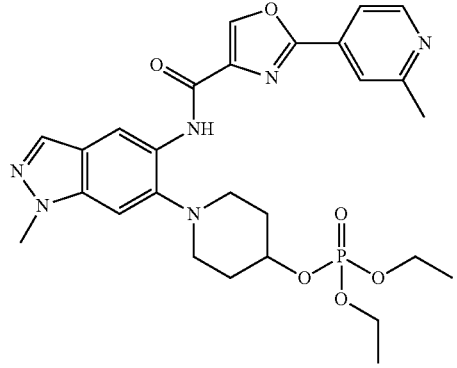 [SMILES: CCOP(=O)(OCC)OC1CCN(c2cc3c(cnn3C)cc2NC(=O)c2coc(-c3ccnc(C)c3)n2)CC1]

To a solution of 6-(4-((tert-butyldimethylsilyl)oxy)piperidin-1-yl)-1-methyl-1H-indazol-5-amine (product of step-3 of example 77) (250 mg 0.578 mmol) in pyridine (5 ml) was added diethyl chlorophosphate (0.2 ml 1.157 mmol) stirred at RT for 12 hours. Concentrated under reduced pressure completely and purified by column chromatography using 2% MeOH in DCM to get the title compound (150 mg 46%).

¹HNMR (DMSO-d₆, 400 MHz): δ10.30 (s, 1H), 9.10 (s, 1H), 8.70-8.69 (d, 2H), 8.02 (s, 1H), 7.85 (s, 1H), 7.80-7.93 (d, 1H), 7.59 (s, 1H), 4.60 (bs, 1H), 4.08-4.00 (m, 7H), 3.15-3.12 (m, 2H) 2.99-2.97 (t, 2H), 2.61 (s, 3H), 2.33-2.24

(m, 2H), 2.14-2.11 (m, 2H), 1.26-1.22 (t, 6H). LCMS: m/z=569.2 (M+1)⁺. HPLC: 95.12%.

Example 129

Diethyl ((1-(2-methyl-5-(2-(2-methylpyridin-4-yl) oxazole-4-carboxamido)-2H-indazol-6-yl) piperidin-4-yl) methyl) phosphate

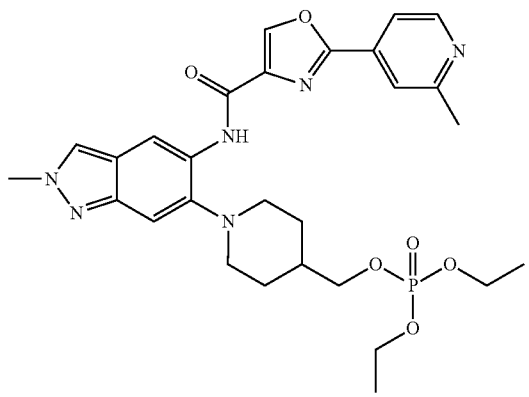 [SMILES: CCOP(=O)(OCC)OCC1CCN(c2cc3nn(C)cc3cc2NC(=O)c2coc(-c3ccnc(C)c3)n2)CC1]

To a solution of N-(6-(4-(hydroxymethyl)piperidin-1-yl)-2-methyl-2H-indazol-5-yl)-2-(2-methylpyridin-4-yl)oxazole-4-carboxamide (product of step-6 of example 80) (50 mg 0.012 mmol) in pyridine (2 ml) DCM (2 ml) was added diethyl chlorophosphate (38.6 mg 0.024 mmol) stirred at RT for 4 hours. Concentrated under reduced pressure completely and purified by column chromatography using 2% MeOH in DCM to get the title compound (40 mg 76.9%).

¹HNMR (DMSO-d₆, 400 MHz): δ10.23 (s, 1H), 9.01 (s, 1H), 8.74-8.73 (d, 1H), 8.27 (s, 1H) 8.64 (s, 1H), 7.82 (s, 1H), 7.77-7.76 (d, 1H), 7.42 (s, 1H), 4.11 (s, 1H), 4.03-3.96 (m, 6H), 3.86 (s, 1H), 3.12-3.09 (d, 2H), 2.83-2.77 (t, 2H), 2.61 (s, 3H), 1.97-1.94 (d, 2H), 1.65-1.62 (d, 2H), 1.22-1.53 (t, 6H). LCMS: m/z=583.3 (M+1)⁺. HPLC: 91.10%.

IRAK-4 Biochemical Assay

Compounds were tested for their potential to inhibit IRAK-4 enzyme in a TR-FRET assay using recombinant IRAK-4 kinase from Millipore, USA. The assay buffer was 50 mM Tris-HCl pH 7.5, 20 mM MgCl₂, 1 mM EGTA, 2 mM DTT, 3 mM MnCl₂ and 0.01% Tween 20.5 ng of IRAK-4 kinase was used for the assay. After pre-incubation of enzyme with test compound for 30 minutes at room temperature, a substrate mixture containing 100 nM Biotin Histone H3 (Millipore, USA) and 20 μM ATP (Sigma, USA) was added and the reaction was incubated for 30 min. Post incubation, the reaction was stopped by the addition of stop mix containing 40 mM EDTA, 1 nM of Europium-Anti-Phospho-Histone H3 (Ser10) antibody (Perkin Elmer, USA) and 20 nM SureLight Allophycocyanin-Streptavidin (Perkin Elmer, USA). The fluorescence emission at 615 nm and 665 nm were measured at an excitation of 340 nm and the percent inhibition was estimated from the ratio of the fluorescence intensities [(F665/F615)×10000]. The compounds were initially screened at 1 μM and 10 μM concentrations and potent compounds (>50% inhibition at 1 μM) were taken for dose response studies. The IC₅₀ values were estimated by fitting the dose-response data to sigmoidal dose response (variable slope), curve fitting program using Graphpad Prism software Version 6.01.

The compounds of the present invention were screened in the above mentioned assay and the results (IC₅₀) are summarized in the table 1. The IC₅₀ values of the compounds of examples are set forth below wherein "A" refers to an IC₅₀ value of less than 50 nM, "B" refers to IC₅₀ value ranges from 50 nM to 100 nM and "C" refers to an IC₅₀ value of greater than 100 nM.

TABLE 1

IC₅₀ values for IRAK4 activity of the selected compounds

| Group | Example No |
|-------|------------|
| A | 1-16, 18-32, 34, 38-40, 43-45, 47, 49, 52, 56-58, 60-94, 96-120, 122-123, 126 and 129. |
| B | 33, 36, 42, 46, 55 and 128. |
| C | 17, 37, 48, 50, 51, 53, 54, 59 and 95. |

We claim:

1. A compound of formula (I)

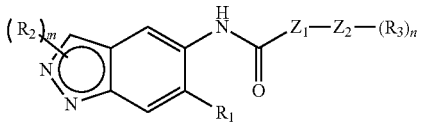

or a pharmaceutically acceptable salt thereof;

wherein $Z_1$ is an optionally substituted pyridyl, oxazolyl, or furanyl;

$Z_2$ is an optionally substituted heterocycloalkyl or optionally substituted heteroaryl selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, tetrazolyl, thienyl, triazolyl, pyrrolyl, pyridyl, pyranyl, pyrazinyl, pyridazinyl, pyrimidyl, piperazinyl, imidazolyl, oxadiazolyl, thiadiazolyl, thiazolyl, isothiazolyl, oxazolyl, furanyl and;

$R_1$ is cyano, —$NR_aR_b$ or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—CH₂—O-alkyl, —OP(O)(O-alkyl)₂ or —CH₂—OP(O)(O-alkyl)₂;

$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;

$R_3$, at each occurrence, independently is hydrogen, halogen, alkyl, haloalkyl, haloalkoxy, alkoxy, —$NR_aR_b$, hydroxyl or hydroxyalkyl;

$R_a$ is hydrogen or unsubstituted alkyl;

$R_b$ is hydrogen, unsubstituted alkyl, acyl, hydroxyalkyl, —SO₂-alkyl or optionally substituted cycloalkyl; and 'm' and 'n' are independently 1 or 2.

2. A compound of formula (IA)

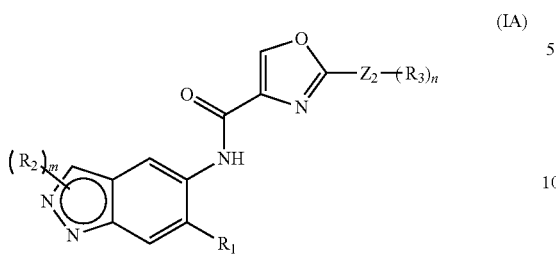

or a pharmaceutically acceptable salt thereof;
wherein
- $Z_2$ is an optionally substituted heterocycloalkyl, optionally substituted heteroaryl or a direct bond;
- $R_1$ is alkyl, cyano, $-NR_aR_b$ or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, $-OCO-CH_2-O$-alkyl, $-OP(O)(O$-alkyl$)_2$ or $-CH_2-OP(O)(O$-alkyl$)_2$;
- $R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
- $R_3$, at each occurrence, independently is hydrogen, halogen, alkyl, haloalkyl, haloalkoxy, alkoxy, $-NR_aR_b$, hydroxyl or hydroxyalkyl;
- $R_a$ is hydrogen or unsubstituted alkyl;
- $R_b$ is hydrogen, unsubstituted alkyl, acyl, hydroxyalkyl, $-SO_2$-alkyl or optionally substituted cycloalkyl; and
- 'm' and 'n' are independently 1 or 2.

3. A compound of formula (IB)

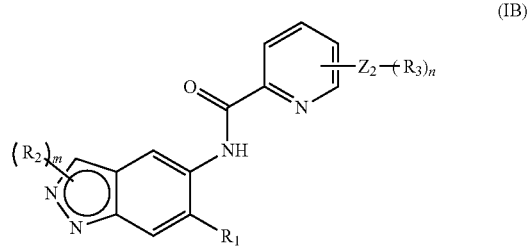

or a pharmaceutically acceptable salt thereof,
wherein
- $Z_2$ is an optionally substituted heterocycloalkyl, optionally substituted heteroaryl or a direct bond;
- $R_1$ is alkyl, cyano, $-NR_aR_b$ or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, $-OCO-CH_2-O$-alkyl, $-OP(O)(O$-alkyl$)_2$ or $-CH_2-OP(O)(O$-alkyl$)_2$;
- $R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
- $R_3$, at each occurrence, independently is hydrogen, halogen, alkyl, haloalkyl, haloalkoxy, alkoxy, $-NR_aR_b$, hydroxyl or hydroxyalkyl;
- $R_a$ is hydrogen or unsubstituted alkyl;
- $R_b$ is hydrogen, unsubstituted alkyl, acyl, hydroxyalkyl, $-SO_2$-alkyl or optionally substituted cycloalkyl; and
- 'm' and 'n' are independently 1 or 2.

4. A compound of formula (IC)

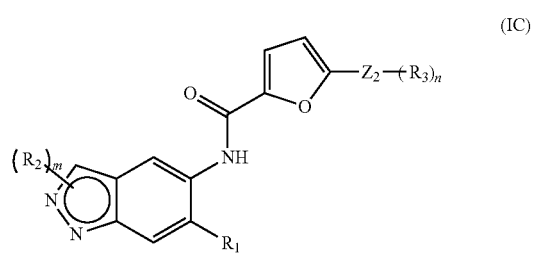

or a pharmaceutically acceptable salt thereof;
wherein
- $Z_2$ is an optionally substituted heterocycloalkyl, optionally substituted heteroaryl or a direct bond;
- $R_1$ is alkyl, cyano, $-NR_aR_b$ or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, $-OCO-CH_2-O$-alkyl, $-OP(O)(O$-alkyl$)_2$ or $-CH_2-OP(O)(O$-alkyl$)_2$;
- $R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
- $R_3$, at each occurrence, independently is hydrogen, halogen, alkyl, haloalkyl, haloalkoxy, alkoxy, $-NR_aR_b$, hydroxyl or hydroxyalkyl;
- $R_a$ is hydrogen or unsubstituted alkyl;
- $R_b$ is hydrogen, unsubstituted alkyl, acyl, hydroxyalkyl, $-SO_2$-alkyl or optionally substituted cycloalkyl; and
- 'm' and 'n' are independently 1 or 2.

5. The compound of claim 2, wherein $Z_2$ is a 5- or 6-membered heterocycloalkyl or 5- or 6-membered heteroaryl.

6. The compound of claim 3, wherein $Z_2$ is a 5- or 6-membered heterocycloalkyl or 5- or 6-membered heteroaryl.

7. The compound of claim 4, wherein $Z_2$ is a 5- or 6-membered heterocycloalkyl or 5- or 6-membered heteroaryl.

8. The compound of claim 2, wherein $Z_2$ is heterocycloalkyl or a direct bond.

9. The compound of claim 3, wherein $Z_2$ is heterocycloalkyl or a direct bond.

10. The compound of claim 4, wherein $Z_2$ is heterocycloalkyl or a direct bond.

11. The compound of claim 2, wherein $Z_2$ is azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, tetrazolyl, thienyl, triazolyl, pyrrolyl, pyridyl, pyranyl, pyrazinyl, pyridazinyl, pyrimidyl, piperazinyl, imidazolyl, oxadiazolyl, thiadiazolyl, thiazolyl, isothiazolyl, oxazolyl, furanyl or pyrazolyl.

12. The compound of claim 3, wherein $Z_2$ is azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, tetrazolyl, thienyl, triazolyl, pyrrolyl, pyridyl, pyranyl, pyrazinyl, pyridazinyl, pyrimidyl, piperazinyl, imidazolyl, oxadiazolyl, thiadiazolyl, thiazolyl, isothiazolyl, oxazolyl, furanyl or pyrazolyl.

13. The compound of claim 4, wherein $Z_2$ is azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, tetrazolyl, thienyl, triazolyl, pyrrolyl, pyridyl, pyranyl, pyrazinyl, pyridazinyl, pyrimidyl, piperazinyl, imidazolyl, oxadiazolyl, thiadiazolyl, thiazolyl, isothiazolyl, oxazolyl, furanyl or pyrazolyl.

14. The compound of claim 2, wherein $Z_2$ is pyridyl, pyrazolyl, pyrrolidinyl, or a direct bond.

15. The compound of claim 3, wherein $Z_2$ is pyridyl, pyrazolyl, pyrrolidinyl, or a direct bond.

16. The compound of claim 4, wherein $Z_2$ is pyridyl, pyrazolyl, pyrrolidinyl, or a direct bond.

17. The compound of claim 2, wherein $Z_2$ is a direct bond.

18. The compound of claim 3, wherein $Z_2$ is a direct bond.

19. The compound of claim 4, wherein $Z_2$ is a direct bond.

20. The compound according to claim 2, wherein $R_1$ is selected from cyano, cycloalkyl, —$NR_aR_b$, aryl, and heterocyclyl.

21. The compound according to claim 3, wherein $R_1$ is selected from cyano, cycloalkyl, —$NR_aR_b$, aryl, and heterocyclyl.

22. The compound according to claim 4, wherein $R_1$ is selected from cyano, cycloalkyl, —$NR_aR_b$, aryl, and heterocyclyl.

23. The compound according to claim 1, wherein $R_1$ is selected from cyano, cycloalkyl, aryl, and heterocyclyl.

24. The compound of claim 1, wherein $R_1$ is selected from cyclopropyl, cyclohexyl, piperidinyl, and morpholinyl.

25. The compound according to claim 1, wherein $R_1$ is optionally substituted heterocyclyl; wherein the substituent is halogen, hydroxyl, hydroxyalkyl or amino.

26. The compound according to claim 25, wherein $R_1$ is optionally substituted azetidinyl, piperidinyl, morpholinyl, pyrrolidinyl or azepanyl.

27. The compound of claim 1, wherein $R_1$ is optionally substituted piperidinyl or morpholinyl.

28. The compound according to claim 1, wherein $R_1$ is optionally substituted phenyl; wherein the substituent is halogen.

29. The compound according to claim 2, wherein $R_1$ is optionally substituted phenyl; wherein the substituent is halogen.

30. The compound of claim 1, wherein $R_1$ is cyano or cycloalkyl.

31. The compound of claim 1, wherein $R_1$ is cyclopropyl or cyclohexyl.

32. The compound of claim 1, wherein $R_1$ is —$NR_aR_b$; $R_a$ is hydrogen; $R_b$ is optionally substituted cycloalkyl; wherein the substituent is hydroxyl.

33. The compound of claim 29, wherein $R_2$ is optionally substituted alkyl and the substituent is alkoxy.

34. The compound of claim 1, wherein $R_2$ is cyclopropyl or cyclopentyl.

35. The compound of claim 29, wherein $R_2$ is cyclopropyl or cyclopentyl.

36. The compound of claim 2, wherein $R_3$ is hydrogen, halogen, alkyl, alkoxy, —$NR_aR_b$, hydroxyl or hydroxyalkyl.

37. The compound of claim 3, wherein $R_3$ is hydrogen, halogen, alkyl, alkoxy, —$NR_aR_b$, hydroxyl or hydroxyalkyl.

38. The compound of claim 4, wherein $R_3$ is hydrogen, halogen, alkyl, alkoxy, —$NR_aR_b$, hydroxyl or hydroxyalkyl.

39. The compound of claim 33, wherein $R_3$ is selected from hydrogen, alkyl and —$NR_aR_b$.

40. The compound of claim 39, wherein $R_3$ is H.

41. A compound selected from:

| Example No | IUPAC Name |
|---|---|
| 1. | N-(2-methyl-6-(piperidin-1-yl)-2H-indazol-5-yl)-6-(1H-pyrazol-4-yl) picolinamide; |
| 2. | N-(2-methyl-6-(piperidin-1-yl)-2H-indazol-5-yl)-2-(2-methylpyridin-4-yl) oxazole-4-carboxamide; |
| 3. | N-(1-methyl-6-(piperidin-1-yl)-1H-indazol-5-yl)-2-(2-methylpyridin-4-yl) oxazole-4-carboxamide; |
| 4. | N-(2-cyclopentyl-6-(piperidin-1-yl)-2H-indazol-5-yl)-2-(2-methylpyridin-4-yl) oxazole-4-carboxamide; |
| 5. | N-(6-cyano-2-cyclopentyl-2H-indazol-5-yl)-2-(2-methylpyridin-4-yl) oxazole-4-carboxamide; |
| 6. | N-(2-cyclopentyl-6-cyclopropyl-2H-indazol-5-yl)-2-(2-methylpyridin-4-yl) oxazole-4-carboxamide; |
| 7. | N-(2-cyclopentyl-6-cyclopropyl-2H-indazol-5-yl)-6-(1H-pyrazol-4-yl) picolinamide; |
| 8. | N-(2-cyclopentyl-6-morpholino-2H-indazol-5-yl)-2-(2-methylpyridin-4-yl) oxazole-4-carboxamide; |
| 9. | 6'-amino-N-(2-cyclopentyl-6-morpholino-2H-indazol-5-yl)-[2,3'-bipyridine]-6-carboxamide 2,2,2-trifluoroacetate; |
| 10. | N-(6-(3-fluorophenyl)-2-methyl-2H-indazol-5-yl)-2-(2-methylpyridin-4-yl)oxazole-4-carboxamide; |
| 11. | N-(6-cyclohexyl-2-methyl-2H-indazol-5-yl)-2-(2-methylpyridin-4-yl)oxazole-4-carboxamide hydrochloride; |
| 12. | 6'-fluoro-N-(2-methyl-6-(piperidin-1-yl)-2H-indazol-5-yl)-[2,3'-bipyridine]-6-carboxamide hydrochloride; |
| 13. | N-(6-cyclohexyl-2-methyl-2H-indazol-5-yl)-6-(1H-pyrazol-4-yl)picolinamide hydrochloride; |
| 14. | 2'-fluoro-N-(2-methyl-6-(piperidin-1-yl)-2H-indazol-5-yl)-[2,3'-bipyridine]-6-carboxamide; |
| 15. | 2-(2-chloropyridin-4-yl)-N-(2-methyl-6-(piperidin-1-yl)-2H-indazol-5-yl)oxazole-4-carboxamide hydrochloride; |
| 16. | N-(6-cyclopropyl-2-methyl-2H-indazol-5-yl)-2-(2-methylpyridin-4-yl)oxazole-4-carboxamide hydrochloride; |
| 17. | N-(1-cyclopentyl-6-cyclopropyl-1H-indazol-5-yl)-6-(1-methyl-1H-pyrazol-4-yl)picolinamide; |
| 18. | N-(2-cyclopentyl-6-cyclopropyl-2H-indazol-5-yl)-6-(1-methyl-1H-pyrazol-4-yl)picolinamide; |
| 19. | 6-(1-methyl-1H-pyrazol-4-yl)-N-(2-methyl-6-(piperidin-1-yl)-2H-indazol-5-yl)picolinamide; |
| 20. | N-(2-cyclopentyl-6-cyclopropyl-2H-indazol-5-yl)-2-(6-methoxypyridin-3-yl)oxazole-4-carboxamide; |
| 21. | 2-(6-methoxypyridin-3-yl)-N-(2-methyl-6-(piperidin-1-yl)-2H-indazol-5-yl)oxazole-4-carboxamide; |
| 22. | N-(2-methyl-6-(piperidin-1-yl)-2H-indazol-5-yl)-2-(3-methylpyridin-4-yl)oxazole-4-carboxamide; |
| 23. | 6-bromo-N-(2-methyl-6-(piperidin-1-yl)-2H-indazol-5-yl)picolinamide; |
| 24. | 6-chloro-5-methyl-N-(2-methyl-6-(piperidin-1-yl)-2H-indazol-5-yl)picolinamide |
| 25. | N-(2-methyl-6-(piperidin-1-yl)-2H-indazol-5-yl)-2-(6-methylpyridin-3-yl)oxazole-4-carboxamide; |
| 26. | N-(2-cyclopentyl-6-cyclopropyl-2H-indazol-5-yl)-2-(2-methylpyridin-3-yl)oxazole-4-carboxamide; |
| 27. | N-(2-cyclopentyl-6-cyclopropyl-2H-indazol-5-yl)-2-(3-methylpyridin-4-yl)oxazole-4-carboxamide; |
| 28. | N-(2-cyclopentyl-6-cyclopropyl-2H-indazol-5-yl)-2-(6-methylpyridin-3-yl)oxazole-4-carboxamide; |
| 29. | 6'-amino-3-methyl-N-(2-methyl-6-(piperidin-1-yl)-2H-indazol-5-yl)-[2,3'-bipyridine]-6-carboxamide hydrochloride; |
| 30. | 5-methyl-6-(1-methyl-1H-pyrazol-4-yl)-N-(2-methyl-6-(piperidin-1-yl)-2H-indazol-5-yl)picolinamide; |
| 31. | N-(1-cyclopropyl-6-(piperidin-1-yl)-1H-indazol-5-yl)-2-(2-methylpyridin-4-yl)oxazole-4-carboxamide hydrochloride; |
| 32. | 2-(2-hydroxypyridin-3-yl)-N-(2-methyl-6-(piperidin-1-yl)-2H-indazol-5-yl)oxazole-4-carboxamide; |
| 33. | (S)-6-(3-aminopyrrolidin-1-yl)-N-(2-methyl-6-(piperidin-1-yl)-2H-indazol-5-yl)picolinamide 2,2,2-trifluoroacetate; |

| Example No | IUPAC Name |
|---|---|
| 34. | (S)-6-(1-(2-hydroxypropyl)-1H-pyrazol-4-yl)-N-(2-methyl-6-(piperidin-1-yl)-2H-indazol-5-yl)picolinamide; |
| 35. | N-(1,6-dicyclopropyl-1H-indazol-5-yl)-2-(6-methoxypyridin-3-yl)oxazole-4-carboxamide; |
| 36. | N-(1,6-dicyclopropyl-1H-indazol-5-yl)-2-(2-methylpyridin-4-yl)oxazole-4-carboxamide hydrochloride; |
| 37. | (S)-N-(6-cyclopropyl-1-methyl-1H-indazol-5-yl)-6-(3-hydroxypyrrolidin-1-yl)picolinamide; |
| 38. | (R)-6-(3-hydroxypyrrolidin-1-yl)-N-(2-methyl-6-(piperidin-1-yl)-2H-indazol-5-yl)picolinamide; |
| 39. | (S)-6-(3-hydroxypyrrolidin-1-yl)-N-(2-methyl-6-(piperidin-1-yl)-2H-indazol-5-yl)picolinamide; |
| 40. | 6-(3-hydroxypyrrolidin-1-yl)-N-(2-methyl-6-(piperidin-1-yl)-2H-indazol-5-yl)picolinamide; |
| 41. | (S)-6-(3-aminopyrrolidin-1-yl)-N-(6-cyclopropyl-1-methyl-1H-indazol-5-yl)picolinamide; |
| 42. | (R)-6-(3-aminopyrrolidin-1-yl)-N-(2-methyl-6-(piperidin-1-yl)-2H-indazol-5-yl)picolinamide; |
| 43. | (R)-6-(1-(2-hydroxypropyl)-1H-pyrazol-4-yl)-N-(2-methyl-6-(piperidin-1-yl)-2H-indazol-5-yl)picolinamide; |
| 44. | (S)-2-(3-aminopyrrolidin-1-yl)-N-(2-methyl-6-(piperidin-1-yl)-2H-indazol-5-yl)oxazole-4-carboxamide; |
| 45. | N-(6-cyclopropyl-1-methyl-1H-indazol-5-yl)-2-(2-methylpyridin-4-yl)oxazole-4-carboxamide; |
| 46. | (S)-N-(6-cyclopropyl-1-methyl-1H-indazol-5-yl)-6-(1-(2-hydroxypropyl)-1H-pyrazol-4-yl)picolinamide; |
| 47. | (S)-N-(6-cyclopropyl-2-methyl-2H-indazol-5-yl)-6-(1-(2-hydroxypropyl)-1H-pyrazol-4-yl)picolinamide; |
| 48. | (S)-6-(3-aminopyrrolidin-1-yl)-N-(6-cyclopropyl-2-methyl-2H-indazol-5-yl)picolinamide; |
| 49. | (S)-N-(6-cyclopropyl-2-methyl-2H-indazol-5-yl)-6-(3-hydroxypyrrolidin-1-yl)picolinamide; |
| 50. | (S)-N-(6-cyclopropyl-1-methyl-1H-indazol-5-yl)-2-(3-hydroxypyrrolidin-1-yl)oxazole-4-carboxamide; |
| 51. | (S)-2-(3-aminopyrrolidin-1-yl)-N-(6-cyclopropyl-1-methyl-1H-indazol-5-yl)oxazole-4-carboxamide; |
| 52. | (S)-2-(3-hydroxypyrrolidin-1-yl)-N-(2-methyl-6-(piperidin-1-yl)-2H-indazol-5-yl)oxazole-4-carboxamide; |
| 53. | (S)-N-(6-cyclopropyl-1-methyl-1H-indazol-5-yl)-2-(1-(2-hydroxypropyl)-1H-pyrazol-4-yl)oxazole-4-carboxamide; |
| 54. | (S)-2-(3-aminopyrrolidin-1-yl)-N-(6-cyclopropyl-2-methyl-2H-indazol-5-yl)oxazole-4-carboxamide; |
| 55. | (S)-N-(6-cyclopropyl-2-methyl-2H-indazol-5-yl)-2-(3-hydroxypyrrolidin-1-yl)oxazole-4-carboxamide; |
| 56. | (S)-6-(1-(2-hydroxypropyl)-1H-pyrazol-4-yl)-N-(2-methyl-6-(piperidin-1-yl)-2H-indazol-5-yl)picolinamide; |
| 57. | 6-((2-hydroxypropyl)amino)-N-(2-methyl-6-(piperidin-1-yl)-2H-indazol-5-yl)picolinamide; |
| 58. | N-(6-(4-hydroxypiperidin-1-yl)-2-methyl-2H-indazol-5-yl)-2-(2-methylpyridin-4-yl)oxazole-4-carboxamide; |
| 59. | N-(6-(azetidin-1-yl)-1-methyl-1H-indazol-5-yl)-2-(2-methylpyridin-4-yl)oxazole-4-carboxamide; |
| 60. | N-(6-(azetidin-1-yl)-2-methyl-2H-indazol-5-yl)-2-(2-methylpyridin-4-yl)oxazole-4-carboxamide; |
| 61. | N-(6-(3-hydroxyazetidin-1-yl)-2-methyl-2H-indazol-5-yl)-2-(2-methylpyridin-4-yl)oxazole-4-carboxamide; |
| 62. | N-(1-methyl-6-(pyrrolidin-1-yl)-1H-indazol-5-yl)-2-(2-methylpyridin-4-yl)oxazole-4-carboxamide; |
| 63. | N-(2-methyl-6-(pyrrolidin-1-yl)-2H-indazol-5-yl)-2-(2-methylpyridin-4-yl)oxazole-4-carboxamide; |
| 64. | (S)-N-(6-(3-hydroxypyrrolidin-1-yl)-2-methyl-2H-indazol-5-yl)-2-(2-methylpyridin-4-yl)oxazole-4-carboxamide; |
| 65. | (R)-N-(6-(3-hydroxypyrrolidin-1-yl)-2-methyl-2H-indazol-5-yl)-2-(2-methylpyridin-4-yl)oxazole-4-carboxamide; |
| 66. | N-(2-methyl-6-(piperidin-1-yl)-2H-indazol-5-yl)-5-(2-methylpyridin-4-yl)furan-2-carboxamide; |
| 67. | N-(6-(4-hydroxypiperidin-1-yl)-2-methyl-2H-indazol-5-yl)-5-(2-methylpyridin-4-yl)furan-2-carboxamide; |
| 68. | N-(6-(3-hydroxypiperidin-1-yl)-2-methyl-2H-indazol-5-yl)-2-(2-methylpyridin-4-yl)oxazole-4-carboxamide; |
| 69. | (R)-N-(6-(3-hydroxypiperidin-1-yl)-2-methyl-2H-indazol-5-yl)-5-(2-methylpyridin-4-yl)furan-2-carboxamide; |
| 70. | N-(6-(3-hydroxypiperidin-1-yl)-2-methyl-2H-indazol-5-yl)-5-(2-methylpyridin-4-yl)furan-2-carboxamide; |
| 71. | N-(6-(azepan-1-yl)-2-methyl-2H-indazol-5-yl)-2-(2-methylpyridin-4-yl)oxazole-4-carboxamide; |
| 72. | N-(6-(azepan-1-yl)-1-methyl-1H-indazol-5-yl)-2-(2-methylpyridin-4-yl)oxazole-4-carboxamide; |
| 73. | N-(2,3-dimethyl-6-(piperidin-1-yl)-2H-indazol-5-yl)-2-(2-methylpyridin-4-yl)oxazole-4-carboxamide; |
| 74. | N-(1,3-dimethyl-6-(piperidin-1-yl)-1H-indazol-5-yl)-2-(2-methylpyridin-4-yl)oxazole-4-carboxamide; |
| 75. | N-(6-(4-hydroxypiperidin-1-yl)-1-(2-methoxyethyl)-1H-indazol-5-yl)-2-(2-methylpyridin-4-yl)oxazole-4-carboxamide; |
| 76. | N-(6-(4-hydroxypiperidin-1-yl)-2-(2-methoxyethyl)-2H-indazol-5-yl)-2-(2-methylpyridin-4-yl)oxazole-4-carboxamide; |
| 77. | N-(6-(4-hydroxypiperidin-1-yl)-1-methyl-1H-indazol-5-yl)-2-(2-methylpyridin-4-yl)oxazole-4-carboxamide; |
| 78. | N-(6-(4-fluoropiperidin-1-yl)-1-methyl-1H-indazol-5-yl)-2-(2-methylpyridin-4-yl)oxazole-4-carboxamide; |
| 79. | N-(6-(3-fluoropiperidin-1-yl)-2-methyl-2H-indazol-5-yl)-2-(2-methylpyridin-4-yl)oxazole-4-carboxamide; |
| 80. | N-(6-(4-(hydroxymethyl)piperidin-1-yl)-2-methyl-2H-indazol-5-yl)-2-(2-methylpyridin-4-yl)oxazole-4-carboxamide; |
| 81. | N-(6-(4-hydroxypiperidin-1-yl)-1,3-dimethyl-1H-indazol-5-yl)-2-(2-methylpyridin-4-yl)oxazole-4-carboxamide; |
| 82. | N-(6-(3-(hydroxymethyl)piperidin-1-yl)-2-methyl-2H-indazol-5-yl)-2-(2-methylpyridin-4-yl)oxazole-4-carboxamide; |
| 83. | N-(6-(4-(hydroxymethyl)piperidin-1-yl)-2,3-dimethyl-2H-indazol-5-yl)-2-(2-methylpyridin-4-yl)oxazole-4-carboxamide; |
| 84. | 2-(2-acetamidopyridin-4-yl)-N-(2-methyl-6-(piperidin-1-yl)-2H-indazol-5-yl)oxazole-4-carboxamide; |
| 85. | 2-(2-acetamidopyridin-4-yl)-N-(6-(3-fluoropiperidin-1-yl)-2-methyl-2H-indazol-5-yl)oxazole-4-carboxamide; |
| 86. | 2-(2-aminopyridin-4-yl)-N-(2-methyl-6-(piperidin-1-yl)-2H-indazol-5-yl)oxazole-4-carboxamide hydrochloride; |
| 87. | N-(6-(4-fluoropiperidin-1-yl)-1,3-dimethyl-1H-indazol-5-yl)-2-(2-methylpyridin-4-yl)oxazole-4-carboxamide; |
| 88. | N-(6-(((1R,4R)-4-hydroxycyclohexyl)amino)-2-methyl-2H-indazol-5-yl)-2-(2-methylpyridin-4-yl)oxazole-4-carboxamide; |
| 89. | N-(6-(4-(hydroxymethyl)piperidin-1-yl)-1-methyl-1H-indazol-5-yl)-2-(2-methylpyridin-4-yl)oxazole-4-carboxamide; |
| 90. | 2-(2-aminopyridin-4-yl)-N-(6-(4-fluoropiperidin-1-yl)-2-methyl-2H-indazol-5-yl)oxazole-4-carboxamide hydrochloride; |
| 91. | N-(6-(4-fluoropiperidin-1-yl)-2-methyl-2H-indazol-5-yl)-2-(2-methylpyridin-4-yl)oxazole-4-carboxamide hydrochloride; |
| 92. | (S)-N-(6-(4-(hydroxymethyl)piperidin-1-yl)-2-methyl-2H-indazol-5-yl)-6-(1-(2-hydroxypropyl)-1H-pyrazol-4-yl)picolinamide; |
| 93. | 2-(2-aminopyridin-4-yl)-N-(6-(4-hydroxypiperidin-1-yl)-2-methyl-2H-indazol-5-yl)oxazole-4-carboxamide hydrochloride; |
| 94. | N-(6-(4-(hydroxymethyl)piperidin-1-yl)-1-(2-methoxyethyl)-1H-indazol-5-yl)-2-(2-methylpyridin-4-yl)oxazole-4-carboxamide; |
| 95. | (S)-N-(6-(4-(hydroxymethyl)piperidin-1-yl)-1-methyl-1H-indazol-5-yl)-6-(1-(2-hydroxypropyl)-1H-pyrazol-4-yl)picolinamide; |
| 96. | N-(6-(4-(hydroxymethyl)piperidin-1-yl)-2-(2-methoxyethyl)-2H-indazol-5-yl)-2-(2-methylpyridin-4-yl)oxazole-4-carboxamide; |
| 97. | N-(6-(4-(hydroxymethyl)piperidin-1-yl)-2-methyl-2H-indazol-5-yl)-2-(2-methoxypyridin-4-yl)oxazole-4-carboxamide; |
| 98. | 2-(2-acetamidopyridin-4-yl)-N-(6-(4-(hydroxymethyl)piperidin-1-yl)-2-methyl-2H-indazol-5-yl)oxazole-4-carboxamide; |
| 99. | 2-(2-aminopyridin-4-yl)-N-(6-(4-(hydroxymethyl)piperidin-1-yl)-1-methyl-1H-indazol-5-yl)oxazole-4-carboxamide hydrochloride; |
| 100. | 2-(2-aminopyridin-4-yl)-N-(6-(4-(hydroxymethyl)piperidin-1-yl)-2-methyl-2H-indazol-5-yl)oxazole-4-carboxamide hydrochloride; |
| 101. | N-(6-(4-hydroxypiperidin-1-yl)-1-methyl-1H-indazol-5-yl)-2-(2-methoxypyridin-4-yl)oxazole-4-carboxamide; |
| 102. | 2-(2-aminopyridin-4-yl)-N-(6-(3-hydroxypiperidin-1-yl)-2-methyl-2H-indazol-5-yl)oxazole-4-carboxamide hydrochloride; |
| 103. | 2-(2-methoxypyridin-4-yl)-N-(2-methyl-6-(piperidin-1-yl)-2H-indazol-5-yl)oxazole-4-carboxamide; |

| Example No | IUPAC Name |
|---|---|
| 104. | 2-(2-aminopyridin-4-yl)-N-(6-(3-fluoropiperidin-1-yl)-2-methyl-2H-indazol-5-yl)oxazole-4-carboxamide hydrochloride; |
| 105. | (R)-2-(2-aminopyridin-4-yl)-N-(6-(3-hydroxypyrrolidin-1-yl)-2-methyl-2H-indazol-5-yl)oxazole-4-carboxamide hydrochloride; |
| 106. | 1-(1,3-dimethyl-5-(2-(2-methylpyridin-4-yl)oxazole-4-carboxamido)-1H-indazol-6-yl)piperidin-4-yl 2-methoxyacetate; |
| 107. | N-(6-(4-hydroxypiperidin-1-yl)-2-methyl-2H-indazol-5-yl)-2-(2-methoxypyridin-4-yl)oxazole-4-carboxamide hydrochloride; |
| 108. | N-(6-(4-aminopiperidin-1-yl)-1-(2-methoxyethyl)-1H-indazol-5-yl)-2-(2-methylpyridin-4-yl)oxazole-4-carboxamide hydrochloride; |
| 109. | N-(6-(4-aminopiperidin-1-yl)-2-methyl-2H-indazol-5-yl)-2-(2-methylpyridin-4-yl)oxazole-4-carboxamide hydrochloride; |
| 110. | N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide; |
| 111. | N-(6-(4-(hydroxymethyl)piperidin-1-yl)-1,3-dimethyl-1H-indazol-5-yl)-2-(2-methylpyridin-4-yl)oxazole-4-carboxamide; |
| 112. | 2-(2-aminopyridin-4-yl)-N-(6-(4-(hydroxymethyl)piperidin-1-yl)-1,3-dimethyl-1H-indazol-5-yl)oxazole-4-carboxamide; |
| 113. | N-(6-(4-hydroxypiperidin-1-yl)-1-methyl-1H-indazol-5-yl)-2-(2-hydroxypyridin-4-yl)oxazole-4-carboxamide; |
| 114. | 2-(2,6-dimethylpyridin-4-yl)-N-(6-(4-hydroxypiperidin-1-yl)-1-methyl-1H-indazol-5-yl)oxazole-4-carboxamide; |
| 115. | (S)-N-(6-(3-hydroxypyrrolidin-1-yl)-1-methyl-1H-indazol-5-yl)-2-(2-methylpyridin-4-yl)oxazole-4-carboxamide; |
| 116. | N-(6-(4-hydroxypiperidin-1-yl)-1-(2-methoxyethyl)-3-methyl-1H-indazol-5-yl)-2-(2-methylpyridin-4-yl)oxazole-4-carboxamide; |
| 117. | N-(1-(2-hydroxyethyl)-6-(4-hydroxypiperidin-1-yl)-1H-indazol-5-yl)-2-(2-methylpyridin-4-yl)oxazole-4-carboxamide; |
| 118. | N-(6-(4-aminopiperidin-1-yl)-2-(2-methoxyethyl)-2H-indazol-5-yl)-2-(2-methylpyridin-4-yl)oxazole-4-carboxamide hydrochloride; |
| 119. | 2-(2,6-dimethylpyridin-4-yl)-N-(2-methyl-6-(piperidin-1-yl)-2H-indazol-5-yl)oxazole-4-carboxamide hydrochloride; |
| 120. | 2-(2-(dimethylamino)pyridin-4-yl)-N-(2-methyl-6-(piperidin-1-yl)-2H-indazol-5-yl)oxazole-4-carboxamide; |
| 121. | N-(6-(4-hydroxypiperidin-1-yl)-1-methyl-1H-indazol-5-yl)-2-(2-(methylamino)pyridin-4-yl)oxazole-4-carboxamide; |
| 122. | N-(2-methyl-6-(piperidin-1-yl)-2H-indazol-5-yl)-2-(2-(methylamino)pyridin-4-yl)oxazole-4-carboxamide; |
| 123. | N-(6-(4-hydroxypiperidin-1-yl)-2-methyl-2H-indazol-5-yl)-2-(2-(methylsulfonamido) pyridin-4-yl) oxazole-4-carboxamide; |
| 124. | 2-(2-(dimethylamino) pyridin-4-yl)-N-(6-(4-hydroxypiperidin-1-yl)-1-methyl-1H-indazol-5-yl) oxazole-4-carboxamide; |
| 125. | N-(6-(4-(aminomethyl)piperidin-1-yl)-1-(2-methoxyethyl)-1H-indazol-5-yl)-2-(2-methylpyridin-4-yl)oxazole-4-carboxamide; |
| 126. | 2-(2,6-dimethylpyridin-4-yl)-N-(6-(4-hydroxypiperidin-1-yl)-2-methyl-2H-indazol-5-yl) oxazole-4-carboxamide; |
| 127. | 2-(2,6-dimethylpyridin-4-yl)-N-(6-(4-fluoropiperidin-1-yl)-2-methyl-2H-indazol-5-yl) oxazole-4-carboxamide; |
| 128. | Diethyl (1-(2-methyl-5-(2-(2-methylpyridin-4-yl)oxazole-4-carboxamido)-1H-indazol-6-yl)piperidin-4-yl) phosphate; and |
| 129. | Diethyl ((1-(2-methyl-5-(2-(2-methylpyridin-4-yl) oxazole-4-carboxamido)-2H-indazol-6-yl) piperidin-4-yl) methyl) phosphate; | or a pharmaceutically acceptable salt thereof.

42. A pharmaceutical composition comprising at least one compound according to claim 1, or a pharmaceutically acceptable salt thereof, and a pharmaceutically acceptable carrier or excipient.

\* \* \* \* \*